United States Patent
Wong et al.

(10) Patent No.: US 6,465,629 B1
(45) Date of Patent: Oct. 15, 2002

(54) BRG1 IS A TUMOR SUPPRESSOR THAT IS MUTATED IN PROSTATE AND OTHER CANCER TYPES

(75) Inventors: Alexander K. C. Wong; Sean V. Tavtigian; David H. F. Teng, all of Salt Lake City, UT (US)

(73) Assignee: Myriad Genetics, Inc., Salt Lake City, UT (US)

(*) Notice: Subject to any disclaimer, the term of this patent is extended or adjusted under 35 U.S.C. 154(b) by 0 days.

(21) Appl. No.: 09/535,008

(22) Filed: Mar. 23, 2000

Related U.S. Application Data

(60) Provisional application No. 60/125,806, filed on Mar. 23, 1999.

(51) Int. Cl.$^7$ ............................................. C07H 21/04
(52) U.S. Cl. ................................................... 536/23.1
(58) Field of Search ......................................... 536/23.1

(56) References Cited

U.S. PATENT DOCUMENTS

| | | | |
|---|---|---|---|
| 5,658,784 A | * 8/1997 | Eckner et al. | 435/325 |
| 6,069,231 A | * 5/2000 | Huang | 530/327 |
| 6,180,612 B1 | * 1/2001 | Hockensmith et al. | 514/25 |

OTHER PUBLICATIONS

LeBlay, K. et al. "Antigenic polymorphism of the lipopolysaccharides from human and animal isolates of *Bordetella bronchiseptica*", Microbiology, 1997; 143:1433–1441.

Schofield, J. et al. "Expression of *Drosophila trithorax*-group homologues in chick embryos", *Mechanisms of Development*, 1999; 80:115–118.

Database Pir 63 on Genbank, Gencore Version 4.5. Accession No. S45252, Chiba et al. "Two Human Homologues of Saccharomyces Cerevisiae SW12/SNF2 and Drosophila Brahm", Sequence search, Nucleic Acids Res. 1994; 22:1815–1820.

Bourachot, B. et al. "The Activity of Mammalian brm/SNF2α Is Dependent on a High–Mobility–Group Protein I/Y–Like DNA Binding Domain", *Molecular and Cellular Biology*, Jun. 1999; 19(6):3931–3939.

Dunaief, J. L. et al. "The Retinoblastoma Protein and BRG1 Form a Complex and Cooperate to Induce Cell Cycle Arrest", *Cell*, Oct. 7, 1994; 79:119–130.

Gao, A. C. et al. "Suppression of the Tumorigenicity of Prostatic Cancer Cells by Gene(s) Located on Human Chromosome 19p13.1–13.2", *The Prostate*, 1999; 38:46–54.

Ichinose, H. et al. "Ligand–dependent interaction between the estrogen receptor and the human homologues of SW12/SNF2", *Gene*, 1997; 188:95–100.

Khavari, P.A. et al. "BRG1 contains a conserved domain of the SW12/SNF2 family necessary for normal mitotic growth and transcription", *Nature*, Nov. 11, 1993; 366:170–174.

Muchardt, C. et al. "The hbrm and BRG–1 proteins, components of the human SNF/SWI complex, are phosphorylated and excluded from the condensed chromosomes during mitosis", *The EMBO Journal*, 1996; 15(13):3394–3402.

Murphy, D.J. et al. "Human SWI–SNF Component BRG1 Represses Transcription of the c–fos Gene", *Molecular and Cellular Biology*, Apr. 1999; 19(4):2724–2733.

Neish, A.S. et al. "Factors associated with the mammalian RNA polymerase II holoenzyme", *Nucleic Acids Research*, 1998: 26(3):847–853.

Randazzo, F.M. et al. "brg1: A Putative Murine Homologue of the *Drosophila brahma* Gene, a Homeotic Gene Regulator", *Developmental Biology*, 1994; 161:229–242.

Reyes, J.C. et al. "Altered control of cellular proliferation in the absence of mammalian brahma (SNF2α)", *The EMBO Journal*, 1998; 17(23):6979–6991.

Shanahan, F. et al. "Cyclin E Associates with BAF155 and BRG1, Components of the Mammalian SWI–SNF Complex, and Alters the Ability of BRG1 to Induce Growth Arrest", *Molecular and Cellular Biology*, Feb. 1999; 19(2):1460–1469.

Sumi–Ichinose, C. et al. "SNF2β–BRG1 Is Essential for the Viability of F9 Murine Embryonal Carcinoma Cells", *Molecular and Cellular Biology*, Oct. 1997, 17(10):5976–5986.

* cited by examiner

*Primary Examiner*—Stephanie W. Zitomer
(74) *Attorney, Agent, or Firm*—Rothwell, Figg, Ernst & Manbeck

(57) ABSTRACT

The present invention relates to the relation of the BRG1 gene (also called SNF2α) to human cancers and its use in the diagnosis and prognosis of human cancer. The invention also relates to the therapy of human cancers which have a mutation in the BRG1 gene, including gene therapy, protein replacement therapy and protein mimetics. Finally, the invention relates to the screening of drugs for cancer therapy.

5 Claims, No Drawings

SEQUENCE LISTING

<160> NUMBER OF SEQ ID NOS: 77

<210> SEQ ID NO 1
<211> LENGTH: 5471
<212> TYPE: DNA
<213> ORGANISM: Homo sapiens
<220> FEATURE:
<221> NAME/KEY: CDS

```
<222> LOCATION: (75)..(5015)
<220> FEATURE:
<221> NAME/KEY: conflict
<222> LOCATION: (1780)
<223> OTHER INFORMATION: GenBank Accession No. U29175 shows a C at this
      position (position 1784 in GenBank) rather than
      the G shown here.
<220> FEATURE:
<221> NAME/KEY: allele
<222> LOCATION: (26)
<223> OTHER INFORMATION: Polymorphism of either T or C in this noncoding
      region.
<220> FEATURE:
<221> NAME/KEY: allele
<222> LOCATION: (1583)
<223> OTHER INFORMATION: Polymorphism of A or G resulting in a silent
      mutation.
<220> FEATURE:
<221> NAME/KEY: allele
<222> LOCATION: (1598)
<223> OTHER INFORMATION: Polymorphism of T or C resulting in a silent
      mutation.
<220> FEATURE:
<221> NAME/KEY: allele
<222> LOCATION: (1892)
<223> OTHER INFORMATION: Polymorphism of A or G resulting in a silent
      mutation.

<400> SEQUENCE: 1
ggcgggggag gcgccgggaa gtcgatggcg ccggcggctc ctgcaggagg ccactgtctg    60
cagctcccgt gaag atg tcc act cca gac cca ccc ctg ggc gga act cct     110
              Met Ser Thr Pro Asp Pro Pro Leu Gly Gly Thr Pro
                1               5                  10 cgg cca ggt cct tcc ccg ggc cct ggc cct tcc cct gga gcc atg ctg    158
Arg Pro Gly Pro Ser Pro Gly Pro Gly Pro Ser Pro Gly Ala Met Leu
        15                  20                  25 ggc cct agc ccg ggt ccc tcg ccg ggc tcc gcc cac agc atg atg ggg    206
Gly Pro Ser Pro Gly Pro Ser Pro Gly Ser Ala His Ser Met Met Gly
30                  35                  40 ccc agc cca ggg ccg ccc tca gca gga cac ccc atc ccc acc cag ggg    254
Pro Ser Pro Gly Pro Pro Ser Ala Gly His Pro Ile Pro Thr Gln Gly
45                  50                  55                  60 cct gga ggg tac cct cag gac aac atg cac cag atg cac aag ccc atg    302
Pro Gly Gly Tyr Pro Gln Asp Asn Met His Gln Met His Lys Pro Met
                65                  70                  75 gag tcc atg cat gag aag ggc atg tcg gac gac ccg cgc tac aac cag    350
Glu Ser Met His Glu Lys Gly Met Ser Asp Asp Pro Arg Tyr Asn Gln
        80                  85                  90 atg aaa gga atg ggg atg cgg tca ggg ggc cat gct ggg atg ggg ccc    398
Met Lys Gly Met Gly Met Arg Ser Gly Gly His Ala Gly Met Gly Pro
95                  100                 105 ccg ccc agc ccc atg gac cag cac tcc caa ggt tac ccc tcg ccc ctg    446
Pro Pro Ser Pro Met Asp Gln His Ser Gln Gly Tyr Pro Ser Pro Leu
    110                 115                 120 ggt ggc tct gag cat gcc tct agt cca gtt cca gcc agt ggc ccg tct    494
Gly Gly Ser Glu His Ala Ser Ser Pro Val Pro Ala Ser Gly Pro Ser
125                 130                 135                 140 tcg ggg ccc cag atg tct tcc ggg cca gga ggt gcc ccg ctg gat ggt    542
Ser Gly Pro Gln Met Ser Ser Gly Pro Gly Gly Ala Pro Leu Asp Gly
                145                 150                 155 gct gac ccc cag gcc ttg ggg cag cag aac cgg ggc cca acc cca ttt    590
Ala Asp Pro Gln Ala Leu Gly Gln Gln Asn Arg Gly Pro Thr Pro Phe
            160                 165                 170 aac cag aac cag ctg cac cag ctc aga gct cag atc atg gcc tac aag    638
Asn Gln Asn Gln Leu His Gln Leu Arg Ala Gln Ile Met Ala Tyr Lys
        175                 180                 185
```

```
atg ctg gcc agg ggg cag ccc ctc ccc gac cac ctg cag atg gcg gtg       686
Met Leu Ala Arg Gly Gln Pro Leu Pro Asp His Leu Gln Met Ala Val
    190                 195                 200 cag ggc aag cgg ccg atg ccc ggg atg cag cag cag atg cca acg cta       734
Gln Gly Lys Arg Pro Met Pro Gly Met Gln Gln Gln Met Pro Thr Leu
205                 210                 215                 220 cct cca ccc tcg gtg tcc gca aca gga ccc ggc cct ggc cct ggc cct       782
Pro Pro Pro Ser Val Ser Ala Thr Gly Pro Gly Pro Gly Pro Gly Pro
                225                 230                 235 ggc ccc ggc ccg ggt ccc ggc ccg gca cct cca aat tac agc agg cct       830
Gly Pro Gly Pro Gly Pro Gly Pro Ala Pro Pro Asn Tyr Ser Arg Pro
            240                 245                 250 cat ggt atg gga ggg ccc aac atg cct ccc cca gga ccc tcg ggc gtg       878
His Gly Met Gly Gly Pro Asn Met Pro Pro Pro Gly Pro Ser Gly Val
        255                 260                 265 ccc ccc ggg atg cca ggc cag cct cct gga ggg cct ccc aag ccc tgg       926
Pro Pro Gly Met Pro Gly Gln Pro Pro Gly Gly Pro Pro Lys Pro Trp
    270                 275                 280 cct gaa gga ccc atg gcg aat gct gct gcc ccc acg agc acc cct cag       974
Pro Glu Gly Pro Met Ala Asn Ala Ala Ala Pro Thr Ser Thr Pro Gln
285                 290                 295                 300 aag ctg att ccc ccg cag cca acg ggc cgc cct tcc ccc gcg ccc cct      1022
Lys Leu Ile Pro Pro Gln Pro Thr Gly Arg Pro Ser Pro Ala Pro Pro
                305                 310                 315 gcc gtc cca ccc gcc gcc tcg ccc gtg atg cca ccg cag acc cag tcc      1070
Ala Val Pro Pro Ala Ala Ser Pro Val Met Pro Pro Gln Thr Gln Ser
            320                 325                 330 ccc ggg cag ccg gcc cag ccc gcg ccc atg gtg cca ctg cac cag aag      1118
Pro Gly Gln Pro Ala Gln Pro Ala Pro Met Val Pro Leu His Gln Lys
        335                 340                 345 cag agc cgc atc acc ccc atc cag aag ccg cgg ggc ctc gac cct gtg      1166
Gln Ser Arg Ile Thr Pro Ile Gln Lys Pro Arg Gly Leu Asp Pro Val
    350                 355                 360 gag atc ctg cag gag cgc gag tac agg ctg cag gct cgc atc gca cac      1214
Glu Ile Leu Gln Glu Arg Glu Tyr Arg Leu Gln Ala Arg Ile Ala His
365                 370                 375                 380 cga att cag gaa ctt gaa aac ctt ccc ggg tcc ctg gcc ggg gat ttg      1262
Arg Ile Gln Glu Leu Glu Asn Leu Pro Gly Ser Leu Ala Gly Asp Leu
                385                 390                 395 cga acc aaa gcg acc att gag ctc aag gcc ctc agg ctg ctg aac ttc      1310
Arg Thr Lys Ala Thr Ile Glu Leu Lys Ala Leu Arg Leu Leu Asn Phe
            400                 405                 410 cag agg cag ctg cgc cag gag gtg gtg gtg tgc atg cgg agg gac aca      1358
Gln Arg Gln Leu Arg Gln Glu Val Val Val Cys Met Arg Arg Asp Thr
        415                 420                 425 gcg ctg gag aca gcc ctc aat gct aag gcc tac aag cgc agc aag cgc      1406
Ala Leu Glu Thr Ala Leu Asn Ala Lys Ala Tyr Lys Arg Ser Lys Arg
    430                 435                 440 cag tcc ctg cgc gag gcc cgc atc act gag aag ctg gag aag cag cag      1454
Gln Ser Leu Arg Glu Ala Arg Ile Thr Glu Lys Leu Glu Lys Gln Gln
445                 450                 455                 460 aag atc gag cag gag cgc aag cgc cgg cag aag cac cag gaa tac ctc      1502
Lys Ile Glu Gln Glu Arg Lys Arg Arg Gln Lys His Gln Glu Tyr Leu
                465                 470                 475 aat agc att ctc cag cat gcc aag gat ttc aag gaa tat cac aga tcc      1550
Asn Ser Ile Leu Gln His Ala Lys Asp Phe Lys Glu Tyr His Arg Ser
            480                 485                 490 gtc aca ggc aaa atc cag aag ctg acc aag gca gtg gcc acg tac cat      1598
Val Thr Gly Lys Ile Gln Lys Leu Thr Lys Ala Val Ala Thr Tyr His
```

|   |   |
|---|---|
| gcc aac acg gag cgg gag cag aag aaa gag aac gag cgg atc gag aag<br>Ala Asn Thr Glu Arg Glu Gln Lys Lys Glu Asn Glu Arg Ile Glu Lys<br>510                                515                          520 | 1646 |
| gag cgc atg cgg agg ctc atg gct gaa gat gag gag ggg tac cgc aag<br>Glu Arg Met Arg Arg Leu Met Ala Glu Asp Glu Glu Gly Tyr Arg Lys<br>525                              530                          535                        540 | 1694 |
| ctc atc gac cag aag aag gac aag cgc ctg gcc tac ctc ttg cag cag<br>Leu Ile Asp Gln Lys Lys Asp Lys Arg Leu Ala Tyr Leu Leu Gln Gln<br>                                  545                          550                          555 | 1742 |
| aca gac gag tac gtg gct aac ctc acg gag ctg gtg cgg cag cac aag<br>Thr Asp Glu Tyr Val Ala Asn Leu Thr Glu Leu Val Arg Gln His Lys<br>                          560                          565                          570 | 1790 |
| gct gcc cag gtc gcc aag gag aaa aag aag aaa aag aaa aag aag aag<br>Ala Ala Gln Val Ala Lys Glu Lys Lys Lys Lys Lys Lys Lys Lys Lys<br>                        575                          580                          585 | 1838 |
| gca gaa aat gca gaa gga cag acg cct gcc att ggg ccg gat ggc gag<br>Ala Glu Asn Ala Glu Gly Gln Thr Pro Ala Ile Gly Pro Asp Gly Glu<br>590                                595                          600 | 1886 |
| cct cta gac gag acc agc cag atg agc gac ctc ccg gtg aag gtg atc<br>Pro Leu Asp Glu Thr Ser Gln Met Ser Asp Leu Pro Val Lys Val Ile<br>605                              610                          615                        620 | 1934 |
| cac gtg gag agt ggg aag atc ctc aca ggc aca gat gcc ccc aaa gcc<br>His Val Glu Ser Gly Lys Ile Leu Thr Gly Thr Asp Ala Pro Lys Ala<br>                        625                          630                        635 | 1982 |
| ggg cag ctg gag gcc tgg ctc gag atg aac ccg ggg tat gaa gta gct<br>Gly Gln Leu Glu Ala Trp Leu Glu Met Asn Pro Gly Tyr Glu Val Ala<br>                          640                          645                        650 | 2030 |
| ccg agg tct gat agt gaa gaa agt ggc tca gaa gaa gag gaa gag gag<br>Pro Arg Ser Asp Ser Glu Glu Ser Gly Ser Glu Glu Glu Glu Glu Glu<br>                        655                          660                        665 | 2078 |
| gag gag gaa gag cag ccg cag gca gca cag cct ccc acc ctg ccc gtg<br>Glu Glu Glu Glu Gln Pro Gln Ala Ala Gln Pro Pro Thr Leu Pro Val<br>                        670                          675                        680 | 2126 |
| gag gag aag aag aag att cca gat cca gac agc gat gac gtc tct gag<br>Glu Glu Lys Lys Lys Ile Pro Asp Pro Asp Ser Asp Asp Val Ser Glu<br>685                              690                          695                        700 | 2174 |
| gtg gac gcg cgg cac atc att gag aat gcc aag caa gat gtc gat gat<br>Val Asp Ala Arg His Ile Ile Glu Asn Ala Lys Gln Asp Val Asp Asp<br>                        705                          710                        715 | 2222 |
| gaa tat ggc gtg tcc cag gcc ctt gca cgt ggc ctg cag tcc tac tat<br>Glu Tyr Gly Val Ser Gln Ala Leu Ala Arg Gly Leu Gln Ser Tyr Tyr<br>                        720                          725                        730 | 2270 |
| gcc gtg gcc cat gct gtc act gag aga gtg gac aag cag tca gcg ctt<br>Ala Val Ala His Ala Val Thr Glu Arg Val Asp Lys Gln Ser Ala Leu<br>735                              740                          745 | 2318 |
| atg gtc aat ggt gtc ctc aaa cag tac cag atc aaa ggt ttg gag tgg<br>Met Val Asn Gly Val Leu Lys Gln Tyr Gln Ile Lys Gly Leu Glu Trp<br>          750                          755                          760 | 2366 |
| ctg gtg tcc ctg tac aac aac aac ctg aac ggc atc ctg gcc gac gag<br>Leu Val Ser Leu Tyr Asn Asn Asn Leu Asn Gly Ile Leu Ala Asp Glu<br>765                              770                          775                        780 | 2414 |
| atg ggc ctg ggg aag acc atc cag acc atc gcg ctc atc acg tac ctc<br>Met Gly Leu Gly Lys Thr Ile Gln Thr Ile Ala Leu Ile Thr Tyr Leu<br>                        785                          790                        795 | 2462 |
| atg gag cac aaa cgc atc aat ggg ccc ttc ctc atc atc gtg cct ctc<br>Met Glu His Lys Arg Ile Asn Gly Pro Phe Leu Ile Ile Val Pro Leu<br>          800                          805                          810 | 2510 |
| tca acg ctg tcc aac tgg gcg tac gag ttt gac aag tgg gcc ccc tcc | 2558 |

```
Ser Thr Leu Ser Asn Trp Ala Tyr Glu Phe Asp Lys Trp Ala Pro Ser
        815                 820                 825 gtg gtg aag gtg tct tac aag gga tcc cca gca gca aga cgg gcc ttt     2606
Val Val Lys Val Ser Tyr Lys Gly Ser Pro Ala Ala Arg Arg Ala Phe
830                 835                 840 gtc ccc cag ctc cgg agt ggg aag ttc aac gtc ttg ctg acg acg tac     2654
Val Pro Gln Leu Arg Ser Gly Lys Phe Asn Val Leu Leu Thr Thr Tyr
845                 850                 855                 860 gag tac atc atc aaa gac aag cac atc ctc gcc aag atc cgt tgg aag     2702
Glu Tyr Ile Ile Lys Asp Lys His Ile Leu Ala Lys Ile Arg Trp Lys
                865                 870                 875 tac atg att gtg gac gaa ggt cac cgc atg aag aac cac cac tgc aag     2750
Tyr Met Ile Val Asp Glu Gly His Arg Met Lys Asn His His Cys Lys
            880                 885                 890 ctg acg cag gtg ctc aac acg cac tat gtg gca ccc cgc cgc ctg ctg     2798
Leu Thr Gln Val Leu Asn Thr His Tyr Val Ala Pro Arg Arg Leu Leu
        895                 900                 905 ctg acg ggc aca ccg ctg cag aac aag ctt ccc gag ctc tgg gcg ctg     2846
Leu Thr Gly Thr Pro Leu Gln Asn Lys Leu Pro Glu Leu Trp Ala Leu
    910                 915                 920 ctc aac ttc ctg ctg ccc acc atc ttc aag agc tgc agc acc ttc gag     2894
Leu Asn Phe Leu Leu Pro Thr Ile Phe Lys Ser Cys Ser Thr Phe Glu
925                 930                 935                 940 cag tgg ttt aac gca ccc ttt gcc atg acc ggg gaa aag gtg gac ctg     2942
Gln Trp Phe Asn Ala Pro Phe Ala Met Thr Gly Glu Lys Val Asp Leu
                945                 950                 955 aat gag gag gaa acc att ctc atc atc cgg cgt ctc cac aaa gtg ctg     2990
Asn Glu Glu Glu Thr Ile Leu Ile Ile Arg Arg Leu His Lys Val Leu
            960                 965                 970 cgg ccc ttc ttg ctc cga cga ctc aag aag gaa gtc gag gcc cag ttg     3038
Arg Pro Phe Leu Leu Arg Arg Leu Lys Lys Glu Val Glu Ala Gln Leu
        975                 980                 985 ccc gaa aag gtg gag tac gtc atc aag tgc gac atg tct gcg ctg cag     3086
Pro Glu Lys Val Glu Tyr Val Ile Lys Cys Asp Met Ser Ala Leu Gln
    990                 995                 1000 cga gtg ctc tac cgc cac atg cag gcc aag ggc gtg ctg ctg act gat    3134
Arg Val Leu Tyr Arg His Met Gln Ala Lys Gly Val Leu Leu Thr Asp
1005                1010                1015                1020 ggc tcc gag aag gac aag aag ggc aaa ggc ggc acc aag acc ctg atg    3182
Gly Ser Glu Lys Asp Lys Lys Gly Lys Gly Gly Thr Lys Thr Leu Met
                1025                1030                1035 aac acc atc atg cag ctg cgg aag atc tgc aac cac ccc tac atg ttc    3230
Asn Thr Ile Met Gln Leu Arg Lys Ile Cys Asn His Pro Tyr Met Phe
            1040                1045                1050 cag cac atc gag gag tcc ttt tcc gag cac ttg ggg ttc act ggc ggc    3278
Gln His Ile Glu Glu Ser Phe Ser Glu His Leu Gly Phe Thr Gly Gly
        1055                1060                1065 att gtc caa ggg ctg gac ctg tac cga gcc tcg ggt aaa ttt gag ctt    3326
Ile Val Gln Gly Leu Asp Leu Tyr Arg Ala Ser Gly Lys Phe Glu Leu
    1070                1075                1080 ctt gat aga att ctt ccc aaa ctc cga gca acc aac cac aaa gtg ctg    3374
Leu Asp Arg Ile Leu Pro Lys Leu Arg Ala Thr Asn His Lys Val Leu
1085                1090                1095                1100 ctg ttc tgc caa atg acc tcc ctc atg acc atc atg gaa gat tac ttt    3422
Leu Phe Cys Gln Met Thr Ser Leu Met Thr Ile Met Glu Asp Tyr Phe
                1105                1110                1115 gcg tat cgc ggc ttt aaa tac ctc agg ctt gat gga acc acg aag gcg    3470
Ala Tyr Arg Gly Phe Lys Tyr Leu Arg Leu Asp Gly Thr Thr Lys Ala
            1120                1125                1130
```

-continued

| | |
|---|---|
| gag gac cgg ggc atg ctg ctg aaa acc ttc aac gag ccc ggc tct gag<br>Glu Asp Arg Gly Met Leu Leu Lys Thr Phe Asn Glu Pro Gly Ser Glu<br>    1135                    1140                    1145 | 3518 |
| tac ttc atc ttc ctg ctc agc acc cgg gct ggg ggg ctc ggc ctg aac<br>Tyr Phe Ile Phe Leu Leu Ser Thr Arg Ala Gly Gly Leu Gly Leu Asn<br>    1150                    1155                    1160 | 3566 |
| ctc cag tcg gca gac act gtg atc att ttt gac agc gac tgg aat cct<br>Leu Gln Ser Ala Asp Thr Val Ile Ile Phe Asp Ser Asp Trp Asn Pro<br>1165                    1170                    1175                    1180 | 3614 |
| cac cag gac ctg caa gcg cag gac cga gcc cac cgc atc ggg cag cag<br>His Gln Asp Leu Gln Ala Gln Asp Arg Ala His Arg Ile Gly Gln Gln<br>                1185                    1190                    1195 | 3662 |
| aac gag gtg cgt gtg ctc cgc ctc tgc acc gtc aac agc gtg gag gag<br>Asn Glu Val Arg Val Leu Arg Leu Cys Thr Val Asn Ser Val Glu Glu<br>    1200                    1205                    1210 | 3710 |
| aag atc cta gct gca gcc aag tac aag ctc aac gtg gac cag aag gtg<br>Lys Ile Leu Ala Ala Ala Lys Tyr Lys Leu Asn Val Asp Gln Lys Val<br>                1215                    1220                    1225 | 3758 |
| atc cag gcc ggc atg ttc gac cag aag tcc tcc agc cat gag cgg cgc<br>Ile Gln Ala Gly Met Phe Asp Gln Lys Ser Ser Ser His Glu Arg Arg<br>    1230                    1235                    1240 | 3806 |
| gcc ttc ctg cag gcc atc ctg gag cac gag gag cag gat gag agc aga<br>Ala Phe Leu Gln Ala Ile Leu Glu His Glu Glu Gln Asp Glu Ser Arg<br>1245                    1250                    1255                    1260 | 3854 |
| cac tgc agc acg ggc agc ggc agt gcc agc ttc gcc cac act gcc cct<br>His Cys Ser Thr Gly Ser Gly Ser Ala Ser Phe Ala His Thr Ala Pro<br>                1265                    1270                    1275 | 3902 |
| ccg cca gcg ggc gtc aac ccc gac ttg gag gag cca cct cta aag gag<br>Pro Pro Ala Gly Val Asn Pro Asp Leu Glu Glu Pro Pro Leu Lys Glu<br>    1280                    1285                    1290 | 3950 |
| gaa gac gag gtg ccc gac gac gag acc gtc aac cag atg atc gcc cgg<br>Glu Asp Glu Val Pro Asp Asp Glu Thr Val Asn Gln Met Ile Ala Arg<br>                1295                    1300                    1305 | 3998 |
| cac gag gag gag ttt gat ctg ttc atg cgc atg gac ctg gac cgc agg<br>His Glu Glu Glu Phe Asp Leu Phe Met Arg Met Asp Leu Asp Arg Arg<br>    1310                    1315                    1320 | 4046 |
| cgc gag gag gcc cgc aac ccc aag cgg aag ccg cgc ctc atg gag gag<br>Arg Glu Glu Ala Arg Asn Pro Lys Arg Lys Pro Arg Leu Met Glu Glu<br>1325                    1330                    1335                    1340 | 4094 |
| gac gag ctc ccc tcg tgg atc atc aag gac gac gcg gag gtg gag cgg<br>Asp Glu Leu Pro Ser Trp Ile Ile Lys Asp Asp Ala Glu Val Glu Arg<br>                1345                    1350                    1355 | 4142 |
| ctg acc tgt gag gag gag gag gag aag atg ttc ggc cgt ggc tcc cgc<br>Leu Thr Cys Glu Glu Glu Glu Glu Lys Met Phe Gly Arg Gly Ser Arg<br>    1360                    1365                    1370 | 4190 |
| cac cgc aag gag gtg gac tac agc gac tca ctg acg gag aag cag tgg<br>His Arg Lys Glu Val Asp Tyr Ser Asp Ser Leu Thr Glu Lys Gln Trp<br>                1375                    1380                    1385 | 4238 |
| ctc aag gcc atc gag gag ggc acg ctg gag gag atc gaa gag gag gtc<br>Leu Lys Ala Ile Glu Glu Gly Thr Leu Glu Glu Ile Glu Glu Glu Val<br>    1390                    1395                    1400 | 4286 |
| cgg cag aag aaa tca tca cgg aag cgc aag cga gac agc gac gcc ggc<br>Arg Gln Lys Lys Ser Ser Arg Lys Arg Lys Arg Asp Ser Asp Ala Gly<br>1405                    1410                    1415                    1420 | 4334 |
| tcc tcc acc ccg acc acc agc acc cgc agc cgc gac aag gac gac gag<br>Ser Ser Thr Pro Thr Thr Ser Thr Arg Ser Arg Asp Lys Asp Asp Glu<br>                1425                    1430                    1435 | 4382 |
| agc aag aag cag aag aag cgc ggg cgg ccg cct gcc gag aaa ctc tcc<br>Ser Lys Lys Gln Lys Lys Arg Gly Arg Pro Pro Ala Glu Lys Leu Ser<br>    1440                    1445                    1450 | 4430 |

-continued

```
cct aac cca ccc aac ctc acc aag aag atg aag aag att gtg gat gcc       4478
Pro Asn Pro Pro Asn Leu Thr Lys Lys Met Lys Lys Ile Val Asp Ala
        1455                1460                1465 gtg atc aag tac aag gac agc agc agt gga cgt cag ctc agc gag gtc       4526
Val Ile Lys Tyr Lys Asp Ser Ser Ser Gly Arg Gln Leu Ser Glu Val
    1470                1475                1480 ttc atc cag ctg ccc tcg cga aag gag ctg ccc gag tac tac gag ctc       4574
Phe Ile Gln Leu Pro Ser Arg Lys Glu Leu Pro Glu Tyr Tyr Glu Leu
1485                1490                1495                1500 atc cgc aag ccc gtg gac ttc aag aag ata aag gag cgc att cgc aac       4622
Ile Arg Lys Pro Val Asp Phe Lys Lys Ile Lys Glu Arg Ile Arg Asn
                1505                1510                1515 cac aag tac cgc agc ctc aac gac cta gag aag gac gtc atg ctc ctg       4670
His Lys Tyr Arg Ser Leu Asn Asp Leu Glu Lys Asp Val Met Leu Leu
            1520                1525                1530 tgc cag aac gca cag acc ttc aac ctg gag ggc tcc ctg atc tat gaa       4718
Cys Gln Asn Ala Gln Thr Phe Asn Leu Glu Gly Ser Leu Ile Tyr Glu
        1535                1540                1545 gac tcc atc gtc ttg cag tcg gtc ttc acc agc gtg cgg cag aaa atc       4766
Asp Ser Ile Val Leu Gln Ser Val Phe Thr Ser Val Arg Gln Lys Ile
    1550                1555                1560 gag aag gag gat gac agt gaa ggc gag gag agt gag gag gag gaa gag       4814
Glu Lys Glu Asp Asp Ser Glu Gly Glu Glu Ser Glu Glu Glu Glu Glu
1565                1570                1575                1580 ggc gag gag gaa ggc tcc gaa tcc gaa tct cgg tcc gtc aaa gtg aag       4862
Gly Glu Glu Glu Gly Ser Glu Ser Glu Ser Arg Ser Val Lys Val Lys
                1585                1590                1595 atc aag ctt ggc cgg aag gag aag gca cag gac cgg ctg aag ggc ggc       4910
Ile Lys Leu Gly Arg Lys Glu Lys Ala Gln Asp Arg Leu Lys Gly Gly
            1600                1605                1610 cgg cgg cgg ccg agc cga ggg tcc cga gcc aag ccg gtc gtg agt gac       4958
Arg Arg Arg Pro Ser Arg Gly Ser Arg Ala Lys Pro Val Val Ser Asp
        1615                1620                1625 gat gac agt gag gag gaa caa gag gag gac cgc tca gga agt ggc agc       5006
Asp Asp Ser Glu Glu Glu Gln Glu Glu Asp Arg Ser Gly Ser Gly Ser
    1630                1635                1640 gaa gaa gac tgagccccga cattccagtc tcgaccccga gcccctcgtt              5055
Glu Glu Asp
1645 ccagagctga gatggcatag gccttagcag taacgggtag cagcagatgt agtttcagac    5115 ttggagtaaa actgtataaa caaaagaatc ttccatattt atacagcaga gaagctgtag    5175 gactgtttgt gactggccct gtcctggcat cagtagcatc tgtaacagca ttaactgtct    5235 taaagagaga gagagagaat tccgaattgg ggaacacacg atacctgttt ttcttttccg    5295 ttgctggcag tactgttgcg ccgcagtttg gagtcactgt agttaagtgt ggatgcatgt    5355 gcgtcaccgt ccactcctcc tactgtattt tattggacag gtcagactcg ccgggggccc    5415 ggcgagggta tgtcagtgtc actggatgtc aaacagtaat aaattaaacc aacaac        5471
```

<210> SEQ ID NO 2
<211> LENGTH: 1647
<212> TYPE: PRT
<213> ORGANISM: Homo sapiens

<400> SEQUENCE: 2

```
Met Ser Thr Pro Asp Pro Pro Leu Gly Gly Thr Pro Arg Pro Gly Pro
 1               5                  10                  15

Ser Pro Gly Pro Gly Pro Ser Pro Gly Ala Met Leu Gly Pro Ser Pro
```

-continued

```
                20                  25                  30
Gly Pro Ser Pro Gly Ser Ala His Ser Met Met Gly Pro Ser Pro Gly
                35                  40                  45
Pro Pro Ser Ala Gly His Pro Ile Pro Thr Gln Gly Pro Gly Gly Tyr
        50                  55                  60
Pro Gln Asp Asn Met His Gln Met His Lys Pro Met Glu Ser Met His
65                  70                  75                  80
Glu Lys Gly Met Ser Asp Asp Pro Arg Tyr Asn Gln Met Lys Gly Met
                85                  90                  95
Gly Met Arg Ser Gly Gly His Ala Gly Met Gly Pro Pro Ser Pro
            100                 105                 110
Met Asp Gln His Ser Gln Gly Tyr Pro Ser Pro Leu Gly Gly Ser Glu
            115                 120                 125
His Ala Ser Ser Pro Val Pro Ala Ser Gly Pro Ser Ser Gly Pro Gln
        130                 135                 140
Met Ser Ser Gly Pro Gly Gly Ala Pro Leu Asp Gly Ala Asp Pro Gln
145                 150                 155                 160
Ala Leu Gly Gln Gln Asn Arg Gly Pro Thr Pro Phe Asn Gln Asn Gln
                165                 170                 175
Leu His Gln Leu Arg Ala Gln Ile Met Ala Tyr Lys Met Leu Ala Arg
            180                 185                 190
Gly Gln Pro Leu Pro Asp His Leu Gln Met Ala Val Gln Gly Lys Arg
        195                 200                 205
Pro Met Pro Gly Met Gln Gln Gln Met Pro Thr Leu Pro Pro Pro Ser
    210                 215                 220
Val Ser Ala Thr Gly Pro Gly Pro Gly Pro Gly Pro Gly Pro Gly Pro
225                 230                 235                 240
Gly Pro Gly Pro Ala Pro Pro Asn Tyr Ser Arg Pro His Gly Met Gly
                245                 250                 255
Gly Pro Asn Met Pro Pro Pro Gly Pro Ser Gly Val Pro Pro Gly Met
            260                 265                 270
Pro Gly Gln Pro Pro Gly Gly Pro Pro Lys Pro Trp Pro Glu Gly Pro
        275                 280                 285
Met Ala Asn Ala Ala Ala Pro Thr Ser Thr Pro Gln Lys Leu Ile Pro
    290                 295                 300
Pro Gln Pro Thr Gly Arg Pro Ser Pro Ala Pro Pro Ala Val Pro Pro
305                 310                 315                 320
Ala Ala Ser Pro Val Met Pro Pro Gln Thr Gln Ser Pro Gly Gln Pro
                325                 330                 335
Ala Gln Pro Ala Pro Met Val Pro Leu His Gln Lys Gln Ser Arg Ile
            340                 345                 350
Thr Pro Ile Gln Lys Pro Arg Gly Leu Asp Pro Val Glu Ile Leu Gln
        355                 360                 365
Glu Arg Glu Tyr Arg Leu Gln Ala Arg Ile Ala His Arg Ile Gln Glu
    370                 375                 380
Leu Glu Asn Leu Pro Gly Ser Leu Ala Gly Asp Leu Arg Thr Lys Ala
385                 390                 395                 400
Thr Ile Glu Leu Lys Ala Leu Arg Leu Leu Asn Phe Gln Arg Gln Leu
                405                 410                 415
Arg Gln Glu Val Val Val Cys Met Arg Arg Asp Thr Ala Leu Glu Thr
            420                 425                 430
Ala Leu Asn Ala Lys Ala Tyr Lys Arg Ser Lys Arg Gln Ser Leu Arg
        435                 440                 445
```

-continued

```
Glu Ala Arg Ile Thr Glu Lys Leu Glu Lys Gln Gln Lys Ile Glu Gln
    450                 455                 460
Glu Arg Lys Arg Arg Gln Lys His Gln Glu Tyr Leu Asn Ser Ile Leu
465                 470                 475                 480
Gln His Ala Lys Asp Phe Lys Glu Tyr His Arg Ser Val Thr Gly Lys
                485                 490                 495
Ile Gln Lys Leu Thr Lys Ala Val Ala Thr Tyr His Ala Asn Thr Glu
            500                 505                 510
Arg Glu Gln Lys Lys Glu Asn Glu Arg Ile Glu Lys Glu Arg Met Arg
        515                 520                 525
Arg Leu Met Ala Glu Asp Glu Glu Gly Tyr Arg Lys Leu Ile Asp Gln
    530                 535                 540
Lys Lys Asp Lys Arg Leu Ala Tyr Leu Leu Gln Gln Thr Asp Glu Tyr
545                 550                 555                 560
Val Ala Asn Leu Thr Glu Leu Val Arg Gln His Lys Ala Ala Gln Val
                565                 570                 575
Ala Lys Glu Lys Lys Lys Lys Lys Lys Lys Lys Lys Ala Glu Asn Ala
            580                 585                 590
Glu Gly Gln Thr Pro Ala Ile Gly Pro Asp Gly Glu Pro Leu Asp Glu
        595                 600                 605
Thr Ser Gln Met Ser Asp Leu Pro Val Lys Val Ile His Val Glu Ser
    610                 615                 620
Gly Lys Ile Leu Thr Gly Thr Asp Ala Pro Lys Ala Gly Gln Leu Glu
625                 630                 635                 640
Ala Trp Leu Glu Met Asn Pro Gly Tyr Glu Val Ala Pro Arg Ser Asp
                645                 650                 655
Ser Glu Glu Ser Gly Ser Glu Glu Glu Glu Glu Glu Glu Glu Glu Glu
            660                 665                 670
Gln Pro Gln Ala Ala Gln Pro Pro Thr Leu Pro Val Glu Glu Lys Lys
        675                 680                 685
Lys Ile Pro Asp Pro Asp Ser Asp Asp Val Ser Glu Val Asp Ala Arg
    690                 695                 700
His Ile Ile Glu Asn Ala Lys Gln Asp Val Asp Asp Glu Tyr Gly Val
705                 710                 715                 720
Ser Gln Ala Leu Ala Arg Gly Leu Gln Ser Tyr Tyr Ala Val Ala His
                725                 730                 735
Ala Val Thr Glu Arg Val Asp Lys Gln Ser Ala Leu Met Val Asn Gly
            740                 745                 750
Val Leu Lys Gln Tyr Gln Ile Lys Gly Leu Glu Trp Leu Val Ser Leu
        755                 760                 765
Tyr Asn Asn Asn Leu Asn Gly Ile Leu Ala Asp Glu Met Gly Leu Gly
    770                 775                 780
Lys Thr Ile Gln Thr Ile Ala Leu Ile Thr Tyr Leu Met Glu His Lys
785                 790                 795                 800
Arg Ile Asn Gly Pro Phe Leu Ile Ile Val Pro Leu Ser Thr Leu Ser
                805                 810                 815
Asn Trp Ala Tyr Glu Phe Asp Lys Trp Ala Pro Ser Val Val Lys Val
            820                 825                 830
Ser Tyr Lys Gly Ser Pro Ala Ala Arg Arg Ala Phe Val Pro Gln Leu
        835                 840                 845
Arg Ser Gly Lys Phe Asn Val Leu Leu Thr Thr Tyr Glu Tyr Ile Ile
    850                 855                 860
```

-continued

```
Lys Asp Lys His Ile Leu Ala Lys Ile Arg Trp Lys Tyr Met Ile Val
865                 870                 875                 880

Asp Glu Gly His Arg Met Lys Asn His Cys Lys Leu Thr Gln Val
            885                 890                 895

Leu Asn Thr His Tyr Val Ala Pro Arg Leu Leu Leu Thr Gly Thr
        900                 905                 910

Pro Leu Gln Asn Lys Leu Pro Glu Leu Trp Ala Leu Leu Asn Phe Leu
    915                 920                 925

Leu Pro Thr Ile Phe Lys Ser Cys Ser Thr Phe Glu Gln Trp Phe Asn
    930                 935                 940

Ala Pro Phe Ala Met Thr Gly Glu Lys Val Asp Leu Asn Glu Glu Glu
945                 950                 955                 960

Thr Ile Leu Ile Ile Arg Arg Leu His Lys Val Leu Arg Pro Phe Leu
                965                 970                 975

Leu Arg Arg Leu Lys Lys Glu Val Glu Ala Gln Leu Pro Glu Lys Val
            980                 985                 990

Glu Tyr Val Ile Lys Cys Asp Met Ser Ala Leu Gln Arg Val Leu Tyr
        995                 1000                1005

Arg His Met Gln Ala Lys Gly Val Leu Leu Thr Asp Gly Ser Glu Lys
    1010                1015                1020

Asp Lys Lys Gly Lys Gly Thr Lys Thr Leu Met Asn Thr Ile Met
025                 1030                1035                1040

Gln Leu Arg Lys Ile Cys Asn His Pro Tyr Met Phe Gln His Ile Glu
            1045                1050                1055

Glu Ser Phe Ser Glu His Leu Gly Phe Thr Gly Gly Ile Val Gln Gly
        1060                1065                1070

Leu Asp Leu Tyr Arg Ala Ser Gly Lys Phe Glu Leu Leu Asp Arg Ile
    1075                1080                1085

Leu Pro Lys Leu Arg Ala Thr Asn His Lys Val Leu Leu Phe Cys Gln
    1090                1095                1100

Met Thr Ser Leu Met Thr Ile Met Glu Asp Tyr Phe Ala Tyr Arg Gly
105                 1110                1115                1120

Phe Lys Tyr Leu Arg Leu Asp Gly Thr Thr Lys Ala Glu Asp Arg Gly
            1125                1130                1135

Met Leu Leu Lys Thr Phe Asn Glu Pro Gly Ser Glu Tyr Phe Ile Phe
        1140                1145                1150

Leu Leu Ser Thr Arg Ala Gly Gly Leu Gly Leu Asn Leu Gln Ser Ala
    1155                1160                1165

Asp Thr Val Ile Ile Phe Asp Ser Asp Trp Asn Pro His Gln Asp Leu
    1170                1175                1180

Gln Ala Gln Asp Arg Ala His Arg Ile Gly Gln Gln Asn Glu Val Arg
185                 1190                1195                1200

Val Leu Arg Leu Cys Thr Val Asn Ser Val Glu Glu Lys Ile Leu Ala
            1205                1210                1215

Ala Ala Lys Tyr Lys Leu Asn Val Asp Gln Lys Val Ile Gln Ala Gly
        1220                1225                1230

Met Phe Asp Gln Lys Ser Ser Ser His Glu Arg Arg Ala Phe Leu Gln
    1235                1240                1245

Ala Ile Leu Glu His Glu Glu Gln Asp Glu Ser Arg His Cys Ser Thr
    1250                1255                1260

Gly Ser Gly Ser Ala Ser Phe Ala His Thr Ala Pro Pro Ala Gly
265                 1270                1275                1280

Val Asn Pro Asp Leu Glu Glu Pro Pro Leu Lys Glu Glu Asp Glu Val
```

```
                    1285                1290                1295

Pro Asp Asp Glu Thr Val Asn Gln Met Ile Ala Arg His Glu Glu
                1300                1305                1310

Phe Asp Leu Phe Met Arg Met Asp Leu Asp Arg Arg Glu Glu Ala
            1315                1320                1325

Arg Asn Pro Lys Arg Lys Pro Arg Leu Met Glu Glu Asp Glu Leu Pro
        1330                1335                1340

Ser Trp Ile Ile Lys Asp Asp Ala Glu Val Glu Arg Leu Thr Cys Glu
345                 1350                1355                1360

Glu Glu Glu Glu Lys Met Phe Gly Arg Gly Ser Arg His Arg Lys Glu
                1365                1370                1375

Val Asp Tyr Ser Asp Ser Leu Thr Glu Lys Gln Trp Leu Lys Ala Ile
            1380                1385                1390

Glu Glu Gly Thr Leu Glu Glu Ile Glu Glu Val Arg Gln Lys Lys
        1395                1400                1405

Ser Ser Arg Lys Arg Lys Arg Asp Ser Asp Ala Gly Ser Ser Thr Pro
    1410                1415                1420

Thr Thr Ser Thr Arg Ser Arg Asp Lys Asp Asp Glu Ser Lys Lys Gln
425                 1430                1435                1440

Lys Lys Arg Gly Arg Pro Pro Ala Glu Lys Leu Ser Pro Asn Pro Pro
            1445                1450                1455

Asn Leu Thr Lys Lys Met Lys Lys Ile Val Asp Ala Val Ile Lys Tyr
        1460                1465                1470

Lys Asp Ser Ser Ser Gly Arg Gln Leu Ser Glu Val Phe Ile Gln Leu
    1475                1480                1485

Pro Ser Arg Lys Glu Leu Pro Glu Tyr Tyr Glu Leu Ile Arg Lys Pro
    1490                1495                1500

Val Asp Phe Lys Lys Ile Lys Glu Arg Ile Arg Asn His Lys Tyr Arg
505                 1510                1515                1520

Ser Leu Asn Asp Leu Glu Lys Asp Val Met Leu Leu Cys Gln Asn Ala
                1525                1530                1535

Gln Thr Phe Asn Leu Glu Gly Ser Leu Ile Tyr Glu Asp Ser Ile Val
            1540                1545                1550

Leu Gln Ser Val Phe Thr Ser Val Arg Gln Lys Ile Glu Lys Glu Asp
        1555                1560                1565

Asp Ser Glu Gly Glu Glu Ser Glu Glu Glu Glu Gly Glu Glu Glu
    1570                1575                1580

Gly Ser Glu Ser Glu Ser Arg Ser Val Lys Val Lys Ile Lys Leu Gly
585                 1590                1595                1600

Arg Lys Glu Lys Ala Gln Asp Arg Leu Lys Gly Gly Arg Arg Arg Pro
            1605                1610                1615

Ser Arg Gly Ser Arg Ala Lys Pro Val Val Ser Asp Asp Asp Ser Glu
        1620                1625                1630

Glu Glu Gln Glu Glu Asp Arg Ser Gly Ser Gly Ser Glu Glu Asp
    1635                1640                1645

<210> SEQ ID NO 3
<211> LENGTH: 63
<212> TYPE: DNA
<213> ORGANISM: Artificial Sequence
<220> FEATURE:
<223> OTHER INFORMATION: Description of Artificial Sequence:Hypothetical
      sequence to illustrate percent homology

<400> SEQUENCE: 3
```

-continued accgtagcta cgtacgtata tagaaagggc gcgatcgtcg tcgcgtatga cgacttagca    60
tgc    63

<210> SEQ ID NO 4
<211> LENGTH: 130
<212> TYPE: DNA
<213> ORGANISM: Artificial Sequence
<220> FEATURE:
<223> OTHER INFORMATION: Description of Artificial Sequence:Hypothetical
      sequence to illustrate percent homology

<400> SEQUENCE: 4
accggtagct acgtacgtta tttagaaagg ggtgtgtgtg tgtgtgtaaa ccggggtttt    60
cgggatcgtc cgtcgcgtat gacgacttag ccatgcacgg tatatcgtat taggactagc   120
gattgactag    130

<210> SEQ ID NO 5
<211> LENGTH: 21
<212> TYPE: DNA
<213> ORGANISM: Homo sapiens
<220> FEATURE:
<223> OTHER INFORMATION: Description of Artificial Sequence:Hypothetical
      sequence to illustrate percent homology

<400> SEQUENCE: 5
actgtctgca gctcccgtga a    21

<210> SEQ ID NO 6
<211> LENGTH: 21
<212> TYPE: DNA
<213> ORGANISM: Homo sapiens

<400> SEQUENCE: 6
cagcatggct ccaggggaag g    21

<210> SEQ ID NO 7
<211> LENGTH: 22
<212> TYPE: DNA
<213> ORGANISM: Homo sapiens

<400> SEQUENCE: 7
agatccgttg gaagtacatg at    22

<210> SEQ ID NO 8
<211> LENGTH: 22
<212> TYPE: DNA
<213> ORGANISM: Homo sapiens

<400> SEQUENCE: 8
ggtgccacat agtgcgtgtt ga    22

<210> SEQ ID NO 9
<211> LENGTH: 20
<212> TYPE: DNA
<213> ORGANISM: Homo sapiens

<400> SEQUENCE: 9
gcagtgccag cttcgcccac    20

<210> SEQ ID NO 10
<211> LENGTH: 20
<212> TYPE: DNA
<213> ORGANISM: Homo sapiens

```
<400> SEQUENCE: 10
tcatctggtt gacggtctcg                                                   20

<210> SEQ ID NO 11
<211> LENGTH: 20
<212> TYPE: DNA
<213> ORGANISM: Homo sapiens

<400> SEQUENCE: 11
cgagaaggag gatgacagtg                                                   20

<210> SEQ ID NO 12
<211> LENGTH: 22
<212> TYPE: DNA
<213> ORGANISM: Homo sapiens

<400> SEQUENCE: 12
ttgatcttca ctttgacgga cc                                                22

<210> SEQ ID NO 13
<211> LENGTH: 20
<212> TYPE: DNA
<213> ORGANISM: Homo sapiens

<400> SEQUENCE: 13
cggaaggaga aggcacagga                                                   20

<210> SEQ ID NO 14
<211> LENGTH: 20
<212> TYPE: DNA
<213> ORGANISM: Homo sapiens

<400> SEQUENCE: 14
ctcctcactg tcatcgtcac                                                   20

<210> SEQ ID NO 15
<211> LENGTH: 20
<212> TYPE: DNA
<213> ORGANISM: Homo sapiens

<400> SEQUENCE: 15
cccgacattc cagtctcgac                                                   20

<210> SEQ ID NO 16
<211> LENGTH: 20
<212> TYPE: DNA
<213> ORGANISM: Homo sapiens

<400> SEQUENCE: 16
acagatgcta ctgatgccag                                                   20

<210> SEQ ID NO 17
<211> LENGTH: 373
<212> TYPE: DNA
<213> ORGANISM: Homo sapiens
<220> FEATURE:
<221> NAME/KEY: misc_feature
<222> LOCATION: (1)..(99)
<223> OTHER INFORMATION: Intron flanking 5' end of exon 10.
<220> FEATURE:
<221> NAME/KEY: misc_feature
<222> LOCATION: (100)..(267)
<223> OTHER INFORMATION: Exon 10.
<220> FEATURE:
```

```
<221> NAME/KEY: misc_feature
<222> LOCATION: (268)..(373)
<223> OTHER INFORMATION: Intron flanking 3' end of exon 10.
<220> FEATURE:
<221> NAME/KEY: misc_feature
<222> LOCATION: (239)..(307)
<223> OTHER INFORMATION: Deleted in TSU-pr1.

<400> SEQUENCE: 17
tacgcgtgcc ctcagtgcgc ttctggattg actggccatg ggtgctcaca gacatgcaca      60
ttgtgccacc acattgcagt aaccccatg cttttgtagg ctgaagatga ggaggggtac      120
cgcaagctca tcgaccagaa gaaggacaag cgcctggcct acctcttgca gcagacagac     180
gagtacgtgg ctaacctcac ggagctggtg cggcagcaca aggctgccca ggtcgccaag     240
gagaaaaaga agaaaaagaa aaagaaggtg tgctgggcct ggcatggtgc ccgccgcggg     300
tgggatggga gcagccgtct tcacgtgtgt ggcctcagcc ttgtgggtca gggcctgacc     360
gtgtctctct cta                                                       373

<210> SEQ ID NO 18
<211> LENGTH: 21
<212> TYPE: DNA
<213> ORGANISM: Homo sapiens

<400> SEQUENCE: 18
cagaagctga ttcccccgca g                                                21

<210> SEQ ID NO 19
<211> LENGTH: 22
<212> TYPE: DNA
<213> ORGANISM: Homo sapiens

<400> SEQUENCE: 19
agcagcactt tgtggttggt tg                                               22

<210> SEQ ID NO 20
<211> LENGTH: 38
<212> TYPE: DNA
<213> ORGANISM: Homo sapiens

<400> SEQUENCE: 20
gttttcccag tcacgacggc cacgtaccat gccaacac                              38

<210> SEQ ID NO 21
<211> LENGTH: 39
<212> TYPE: DNA
<213> ORGANISM: Homo sapiens

<400> SEQUENCE: 21
aggaaacagc tatgaccatg ctggtctcgt ctagaggct                             39

<210> SEQ ID NO 22
<211> LENGTH: 20
<212> TYPE: DNA
<213> ORGANISM: Homo sapiens

<400> SEQUENCE: 22
agccctggcc tgaaggaccc                                                  20

<210> SEQ ID NO 23
<211> LENGTH: 20
<212> TYPE: DNA
<213> ORGANISM: Homo sapiens
```

```
<400> SEQUENCE: 23
cgctgactgc ttgtccactc                                             20

<210> SEQ ID NO 24
<211> LENGTH: 38
<212> TYPE: DNA
<213> ORGANISM: Homo sapiens

<400> SEQUENCE: 24
gttttcccag tcacgacgtc tccagcatgc caaggatt                         38

<210> SEQ ID NO 25
<211> LENGTH: 39
<212> TYPE: DNA
<213> ORGANISM: Homo sapiens

<400> SEQUENCE: 25
aggaaacagc tatgaccatg gcgtctgtcc ttctgcatt                        39

<210> SEQ ID NO 26
<211> LENGTH: 21
<212> TYPE: DNA
<213> ORGANISM: Homo sapiens

<400> SEQUENCE: 26
ggtggcacgg cacccgcgtg a                                           21

<210> SEQ ID NO 27
<211> LENGTH: 22
<212> TYPE: DNA
<213> ORGANISM: Homo sapiens

<400> SEQUENCE: 27
tacgcgtgcc ctcagtgcgc tt                                          22

<210> SEQ ID NO 28
<211> LENGTH: 23
<212> TYPE: DNA
<213> ORGANISM: Homo sapiens

<400> SEQUENCE: 28
tctgcatttt ctgccttctg gaa                                         23

<210> SEQ ID NO 29
<211> LENGTH: 21
<212> TYPE: DNA
<213> ORGANISM: Homo sapiens

<400> SEQUENCE: 29
tagagagaga cacggtcagg c                                           21

<210> SEQ ID NO 30
<211> LENGTH: 645
<212> TYPE: DNA
<213> ORGANISM: Homo sapiens

<400> SEQUENCE: 30 caccccgtc cgcccaggga cgggcgcgca cgcgcgccgg gagcggaagg gcgggctggc   60
gcgcgcacga ggccgggcag gcggcggaag ctggagaggc cgccgcggtg ctgaggggga  120
ggggagccgg cgagcgcgcg cgcagcgggg gcgcgggtgg cgcgcgtgtg tgtgaagggg  180
```

-continued

| | |
|---|---|
| gggcggtggc cgaggcgggc gggcgcgcgc gcgaggcttc ccctcgtttg gcggcggcgg | 240 |
| cggcttcttt gtttcgtgaa gagaagcgag acgcccattc tgccccggc cccgcgcgga | 300 |
| ggggcggggg aggcgccggg aagtcgacgg cgccggcggc tcctggtaag gaacgcgggc | 360 |
| cgcgggggca gcgcggcgcg gggccgggga gggcggtttg aatggagccg gggcgccgag | 420 |
| gggggagggg gctgccggcg cgccctgtgc ggggccgggg tacggcggcg cccgagggtc | 480 |
| aagaagccca gccggcagcc gcgcgcgtgg ggaaggccac agtgtcgcga ggccgtggca | 540 |
| gcggcggccc ccgcggagcg gcggggtggg tgggggggccc gggccgcgtg gaggccgcgc | 600 |
| gatcctctcc gcgcgcgctc tcgccgggt cgccggacaa agctc | 645 |

<210> SEQ ID NO 31
<211> LENGTH: 854
<212> TYPE: DNA
<213> ORGANISM: Homo sapiens

<400> SEQUENCE: 31

| | |
|---|---|
| ccctgagaca ccctctgccg tgatcaggaa tatggcagga gcccctgaag gcccctgtgg | 60 |
| ggcagtgctt gtctgtgagc gtggcccacc ccttcctggg tagactgact gatcttgtgt | 120 |
| gcctgagatg taggacttcc tctgagagtg atcatggaga aacggtttgg gtggctggtg | 180 |
| gggaaggtac tggcttcctg tgggatgtag attctgatgt gaccgtatga ttgtcccttg | 240 |
| ctatccctgt cctgcctcgc ccttggtcat gaaccccaga ctgaccagga ctgtcttcca | 300 |
| gcaggaggcc actgtctgca gctcccgtga agatgtccac tccagaccca ccctgggcg | 360 |
| gaactcctcg gccaggtcct tccccggggcc ctggcccttc ccctggagcc atgctgggcc | 420 |
| ctagcccggg tccctcgccg ggctccgccc acagcatgat ggggcccagc ccagggccgc | 480 |
| cctcagcagg acaccccatc cccacccagg ggcctggagg gtaccctcag acaacatgc | 540 |
| accagatgca caaggtaggg atccctgtgc ccgcctcgca cctgcggcct ctgcccacta | 600 |
| gggctgcagg cagcctctgg accgagggcc ttacttggag gatgggggga agccttcttg | 660 |
| ttggaggtgt cctgccttgg ctcagccccc taccccaggg cccacggcca tgaacagaag | 720 |
| gttcagctcg tcagacccca gcctgtgctg gcgcatgatc tgggccccgc gggcacctgc | 780 |
| cccaccgttt cccgctcccct tgctttctgc atgtgaaatt tgggaatatc actacaaagt | 840 |
| tttcttttgg taat | 854 |

<210> SEQ ID NO 32
<211> LENGTH: 735
<212> TYPE: DNA
<213> ORGANISM: Homo sapiens

<400> SEQUENCE: 32

| | |
|---|---|
| aggtgacatt tctaagtgtc acgggccaca ggaggtcccg ggtggtagaa gatgaggatt | 60 |
| gcttgaccac agtctcccat atgctcgtgc tccactgggc gacatttatt ttgtgtacct | 120 |
| gtctcgaggc ctaagtaggt gtcagaacct tgccttggag tcatgctggg gactggggag | 180 |
| atgcgcgtca tcttcgggtg gctgttctcg gtgccctcga gcttctctcg ggcagcgcat | 240 |
| agctgcgctg ccacctcacg ttccacatgc tgaccctgcc ttgccatggt ccctctcgca | 300 |
| gcccatggag tccatgcatg agaagggcat gtcggacgac ccgcgctaca accagatgaa | 360 |
| aggaatgggg atgcggtcag ggggccatgc tgggatgggg cccccgccca gcccatgga | 420 |
| ccagcactcc caaggtacag aactgcgttc cttcctgcct tgtgtttgtc atactccaga | 480 |
| gtcctcagat cattttcctc ccctgggttc ccacaggatg gattcaggga gtacctagga | 540 |

```
tgatgtagcc gggtgggtgg cccgccacag agagctgtct ggcatggcgt ggctggtgct    600
ctgttctggc cacctcgtct cggagcagcc ctggaagggg aaatgctggt tggggggcag    660
accatgttca gcatgggtga tagaggaggg ctgtgcaggg cagcagcccc gtgccaccca    720
ggaacttact ggaaa                                                     735
```

<210> SEQ ID NO 33
<211> LENGTH: 1417
<212> TYPE: DNA
<213> ORGANISM: Homo sapiens

<400> SEQUENCE: 33

```
atgtggaccc cgcctgtgga caggcaggcg gaagccggga gagagccgtg atttcatgca     60
caggttctca gcattaacca gaagcacctt actgagacgt gggccaaacc aaatccacca    120
ggtcggctgc tgggctgagg tgccttcagc atgtgccctc caggtgcccc tggttgactc    180
aagagaagga tgccatttgg ctgtgccctg tctcagagta ggagctggtg taggggggaag   240 aggctgtaaa aatcacagac atatgctgcc gagtgaccag tgggctgacc tttctctgca    300
ggttacccct cgcccctggg tggctctgag catgcctcta gtccagttcc agccagtggc    360
ccgtcttcgg ggccccagat gtcttccggg ccaggaggtg cccgctggga tggtgctgac    420
ccccaggcct tggggcagca gaaccggggc ccaacccccat ttaaccagaa ccagctgcac   480
cagctcagag ctcagatcat ggcctacaag atgctggcca gggggcagcc cctcccccgac  540 cacctgcaga tggcggtgca gggcaagcgg ccgatgcccg ggatgcagca gcagatgcca   600
acgctacctc caccctcggt gtccgcaaca ggacccggcc ctggccctgg ccctggcccc   660
ggcccgggtc ccggcccggc acctccaaat tacagcaggc ctcatggtaa gactggctgc   720
cctggccctc aggtgtctca gagcgaatgg ctggggcgtg ggtggcgggg tggacagacc   780
gtgctctgtt gccgactggg ttccccggtt tgggattgca cgggcccata ctgcacttct    840
gggtgctcgg gtggtggggg cagctaaatg ctgcttcccc agctcccgc ttcccctggg     900 gccgctggtt aataggtgta tctgctgtgt ccctggagc cagggctgcc cacggggctg     960
ggcgcaggca taaacctggg acgcactgtt ttctcttttg tttctcccta catgtaggta   1020
tgggagggcc caacatgcct cccccaggac cctcgggcgt gccccccggg atgccaggcc   1080
agcctcctgg agggcctccc aagccctggc ctgaaggtga gctccctctt ctatggtggt  1140
gcacccgtgc ccttactccc catctcaagc ttgggtcctt gagatgagct ttgtcaggga  1200 gaaaggccg agggtggtca ggctgaactg cagcctgtac ttttcttgtg gtggtccccg   1260
ggtctcccct gtagccagtc agttcccaaa ggctgtcgtt catccctcct ctgacagctt  1320
gtggccttca cccagtccct gagccctgta tatgtaattg ctcagtaagt gctgcaggct  1380
cccatctgtt gggctcaaag aggcagtggg actcatt                            1417
```

<210> SEQ ID NO 34
<211> LENGTH: 861
<212> TYPE: DNA
<213> ORGANISM: Homo sapiens

<400> SEQUENCE: 34

```
ggatttagtt ggcactagga ggagatgaca ggaaatgctg ccatagagcc acagacagaa     60
caaaaaggcc ttgggagcct ggggctggcc ccagtggagg gtgtgaagga cgagggtgag   120
gctgagatct ggaggaggtt ggagcccaag gcaggtgtga aggacacccc tgggtgaaag   180
```

```
gtgggagatg ggcggggtct gcctgtcccc agtgcctcaa gcagctcagc agctttccat    240
ttccagcccg ggatgggccc cagagctcaa catgacgccc tggccccttg ccttctccca    300
ggacccatgg cgaatgctgc tgcccccacg agcacccctc agaagctgat tcccccgcag    360
ccaacgggcc gcccttcccc cgcgcccccct gccgtccccac ccgccgcctc gcccgtgatg   420
```

```
ccaccgcaga cccagtcccc cgggcagccg gcccagcccg cgcccatggt gccactgcac    480
cagaagcaga gccgcatcac ccccatccag aagccgcggg gcctcgaccc tgtggagatc    540
ctgcaggagc gcgagtacag gtgagggcgg ggccagttg ccaaggtcac tgccctgtgt     600
cccccatgtc ccctggggga agccactcaa ctttctcccc cactctagca aacagtgccc    660
tgtgcccacc actgccactt ggcctacacc tccttcctca cctccctgct cccaccctgg    720
ctgcggtctg tttcccacac agcagtttga gttctctctc tttttttttt tttgagacgg    780
agtttcactc ttgttgccca cgctggagtg caatggcaca atctcggttc actgcaacct    840
gcatctcctg gcttcaagcg a                                               861

<210> SEQ ID NO 35
<211> LENGTH: 729
<212> TYPE: DNA
<213> ORGANISM: Homo sapiens

<400> SEQUENCE: 35
cagagctgca tgaaaacctt ggcccgcctg acgccagaac ctggctcaca ccactgaaaa     60
ggcatgacct gggcgcgtct atcaggaatc ttgtttgctg tcccctgagg cccggtcctg    120
aggagtgccc cgggctatct ccctctctgc tgtgccctgc ggccagcatc ctcttctgag    180
gcatctcttg cctcatgact agtgcctgcc tctctcgagg gatgggtccc ctgcagctcc    240
agctgtaact gggtgccctg gcaaccctct caccgccttt gctccttgtc tctgctccca    300
ggctgcaggc tcgcatcgca caccgaattc aggaacttga aaaccttccc gggtccctgg    360
ccggggattt gcgaaccaaa gcgaccattg agctcaaggc cctcaggctg ctgaacttcc    420
agaggcaggt gggtgctggc atggccgcag ctttccgaaa agggccttg tcaccaacac     480 tgctgctaag gctccaaata cggcttgcct ggctagtatt acacctgcct gggctgtgaa    540
aagcagccgt ggccatccat gggcactcaa tcactgcaga gccttcctct tacggcctgc    600
gcagtgctgg ggacgtggac ctcactaccc taaagcactt gccgcctcaa agcagacttg    660
tatgggcttc tttcttcctt tccctttccc tttttttttt ttttttggaaa cagtcttgct    720 ctatcacct                                                             729

<210> SEQ ID NO 36
<211> LENGTH: 776
<212> TYPE: DNA
<213> ORGANISM: Homo sapiens

<400> SEQUENCE: 36
cacacccagc caagagtgtt atacttctga atgactccta agacgtgtgt gtggtagagg     60
ggaggcaagc tggaggtccg agaggacccc ctggatagat gtccagaagt gatcaccttc    120
tgtcctgtgc tcgccctgcc cggggcacc tgctagacgt cccctgcaca cacggactgg     180
gtgtgtaagg cacttacaat gctcctttag cggtgaagca tgtgacatca ccatacgtgt    240
ttgtcattgt ggatgccaca gagctgtgca gtgcgcgggc ttgtcctctt ccctcctaca    300
gctgcgccag gaggtggtgg tgtgcatgcg gagggacaca gcgctggaga cagccctcaa    360
tgctaaggcc tacaagcgca gcaagcgcca gtccctgcgc gaggcccgca tcactgagaa    420
```

```
gctggagaag cagcagaaga tcgagcagga gcgcaagcgc cggcagaagc accaggtacg    480
ctccggtggc cccaaggccc tgcagcccgc ccacctggct gcctggcttg tccagcggtt    540
gccacggggc tgtgtttgct ttgttcctaa acatgctgct tgtctctctc ttttgctcat    600
tgtaacagta ttctaggtac tgagagtgta ttggtgtaaa acccaatgg  tagggagaag    660
atagtgatga atccacgcg  tagcacgtct ggaaggtgat agggcacaaa gaaaaatcaa    720
gccaggatag agaggaagga acgggctgtt gtagaactga tgttggggga gttctt       776
```

<210> SEQ ID NO 37
<211> LENGTH: 776
<212> TYPE: DNA
<213> ORGANISM: Homo sapiens

<400> SEQUENCE: 37

```
ttaccatggt ctcgatctcc tgacctcatg atccgcccgc ctcagcctcc caaagtgctg     60
ggattacagg catgagccac tgtgcccagc ctaattttt  ttatttttat ttttagtaga   120
gacggggttt caccgtgtta gccaggatga tctcgatctc ctgacctcgt gatccaccca   180
cctcagcctc ccaaagtgct gggattacag gccaatattc taggttttaa acaagccttg   240
cggggagatg tgtccaccat gctgctgaag ggtcagcctc tcttttgtg  ctttcctgca   300
ggaatacctc aatagcattc tccagcatgc caaggatttc aaggaatatc acagatccgt   360
cacaggcaaa atccagaagc tgaccaaggc agtggccacg taccatgcca acacggagcg   420
ggagcagaag aaagagaacg agcggatcga agggagcgc  atgcggaggc tcatggtatg   480
gtcctgcctt cttgacgtgc gctcttctac atgtgtagct ggtactgcgg gctccagggg   540
tcactcccca gggttacgcc aaggcatttc acagctcgga gttagaggtg ggacagaggg   600
aaaagagcag gcgcgggctt gggagtcagt cctgggctcg gatatttgct gatctctctg   660
atcatcagaa tgactgtgtg acctcaggcc acttagccgg ctcctctgcc ttctctggaa   720
aatggaggtg gtgccccctt ccctcgttct gtgagagcca ggtggtgtga tccaga       776
```

<210> SEQ ID NO 38
<211> LENGTH: 934
<212> TYPE: DNA
<213> ORGANISM: Homo sapiens

<400> SEQUENCE: 38

```
gagagaaggc ttcgggtttg gggtgtattt cgtggacaga gtgggtagga ctggctcatg     60
gcctctgtaa atggctgctg gcgggactgt ctgcctagcg ggtgcccttg gaacctagcc    120
cttggtgggt tttgaggaaa tgattcctga atgaggagtc gattgccgtg tgaagggctg    180
gtggcacggc acccgcgtga gctacgcgtg ccctcagtgc gcttctggat tgactggcca    240
tgggtgctca cagacatgca cattgtgcca ccacattgca gtaaccccca tgcttttgta    300
ggctgaagat gaggagggt  accgcaagct catcgaccag aagaaggaca agcgcctggc    360
ctacctcttg cagcagacag acgagtacgt ggctaacctc acggagctgg tcggcagca    420
caaggctgcc caggtcgcca aggagaaaaa gaagaaaaag aaaagaagg  tgtgctgggc    480
ctggcatggt gcccgccgcg ggtgggatgg agcagccgt  cttcacgtgt gtggcctcag    540
ccttgtgggt cagggcctga ccgtgtctct ctctatttcc agaaggcaga aaatgcagaa    600
ggacagacgc ctgccattgg gccggatggc gaggtgagga agcagggttt cttgtggaag    660
tatcaagcta gccctaaggc gttggtctgt ttcagacttt aaaacctgtg ttcttttaaa    720
```

-continued

| | |
|---|---|
| attacgaaca atgatatgtg atgatggtga gaatcccagg gtgtcctctg acgcccatcc | 780 |
| cacccgaccc cacatcccac atgttgtgtt ttcttccaga cctttttcta tgcatgtgcc | 840 |
| acaggattca tctttcaggt tttactttgt tgtaacgtcc gacttacagg agaggtgcaa | 900 |
| gaaccgtcca gagatgtcct gtgtgttctt cacc | 934 |

<210> SEQ ID NO 39
<211> LENGTH: 971
<212> TYPE: DNA
<213> ORGANISM: Homo sapiens

<400> SEQUENCE: 39

| | |
|---|---|
| ggttgtagtg agccgagagc cgagatcacg ccactgcact ctagcctggg tgacagagcg | 60 |
| agactccgtc tcaaaaaaaa aaaaaaaaa aaaagaagaa acaagtgtca gccaaggttg | 120 |
| atgggttata tattttact ggattactga gtatacagtt tacgcatttt cccaccactg | 180 |
| gccatgtttg cctgccattt tctgtgcaaa cagttgagtg ggtgcttccc accttggcct | 240 |
| ctgtaagtgt ttggtctgga ggccctgcaa cctcagtgtc acacgaatga ctcttttca | 300 |
| gcctctggac gagaccagcc agatgagcga cctcccggtg aaggtgatcc acgtggagag | 360 |
| tgggaagatc ctcacaggca cagatgcccc caaagccggg cagctggagg cctggctcga | 420 |
| gatgaacccg gggtgagttg ggccttgcat tccagatgca gtggggatcc aagtcctcgg | 480 |
| tgggccttgt tccagggagg tggcagccag gagcaatttt acttctgttt gaattcccgg | 540 |
| caggtttggt agggaaagtg aattctgctg gctctgagca gatttgtatg aaagccctta | 600 |
| catttttct aggtatgaag tagctccgag gtctgatagt gaagaaagtg gctcagaaga | 660 |
| agaggaagag gtaagagtgc atttcctggc tttcaaggct ctcagtgccc actggcagtg | 720 |
| acttccaccc tgtgtgttgt gaccgtctcc tgccctggct gggcatcttg tggggcaggg | 780 |
| aacagcaggg cccaggcctg cccgaagtcg gtgcttaga gctgtcctat ccaatagggc | 840 |
| agcttctggc gacatgtgac catttccatt ttaaattaaa tcagtcacat tacataaaat | 900 |
| ttaagactca ttttctcttt cacactggct gcatttcagg tgcttggcat cccttatctg | 960 |
| ggaatggtct g | 971 |

<210> SEQ ID NO 40
<211> LENGTH: 724
<212> TYPE: DNA
<213> ORGANISM: Homo sapiens

<400> SEQUENCE: 40

| | |
|---|---|
| tgtggtggtg catagctgta gttctagctg ctggggaggc tgaggcagga tgattgcttg | 60 |
| agctgaggag ttcaaagcca tctgggcaac atcctgagac tcccatatat taaaaaaaat | 120 |
| aataataaat acataatttt aaaacaaaga tgtaaataat aaacagcaca cattccagga | 180 |
| taggtagagg gggtgagggc tgtaagaaga tcacttgctt ctgagactgt tctccccatg | 240 |
| ggagtcccgt cccccctctc tgggggatga actgaggtga catgggcttg tctcttggta | 300 |
| ggaggaggag gaagagcagc cgcaggcagc acagcctccc accctgcccg tggaggagaa | 360 |
| gaagaagatt ccagatccag acagcgatga cgtctctgag gtggacgcgc ggcacatcat | 420 |
| tgagtaaggg gtcccgacac aggttgttct gtgccagctt cctgtgaggt ggcgctggtg | 480 |
| ggagtggcta gaatcccagc catccctagc tgacattcag cactgtccag ccagctgcta | 540 |
| ctgtggaact acagagacca aatttattta cttcacattt catgtatttt atagggattt | 600 |
| aatagagcaa ttgcattcgc atggttcacc atatgcttac gaggtacagt caggtgtgcg | 660 |

```
ggagaagccc tcctcacccc gttctctgct ccccggctcc ctcccttttcc actaccctcc    720 ctgg                                                                  724
```

<210> SEQ ID NO 41
<211> LENGTH: 753
<212> TYPE: DNA
<213> ORGANISM: Homo sapiens

<400> SEQUENCE: 41

```
cctcccaaag tgttgaaatt acaggcgtga gccaccacgc ccatcagagt gacagaattc     60
ttgtactgtg gtggtgcaat caggacccag agctcccagg agtccagtct ggacccctca    120
ggcttagtgc gggctgccct gcctggcctc acactgtccg gctgcacctc tatgtgtctt    180
acagtgctgg ccacaggtca ttcagcagaa agggccactc cgcagagctt gtgtcaggag    240
ccagcacatt gtcacagata ggaatgtgtg tccttacccg gcacctccat ctcactccca    300
ggaatgccaa gcaagatgtc gatgatgaat atggcgtgtc ccaggccctt gcacgtggcc    360
tgcagtccta ctatgccgtg gcccatgctg tcactgagag agtggacaag cagtcagcgc    420
ttatggtcaa tggtgtcctc aaacagtacc aggtgaggta gggggtgggg aggccaccgc    480
cacgtagctg cctcggtgca ggtgttccca ggtggtgcgg gcttcagacc tcaggcagac    540
ctgagttcac cttttgctct ttgtgggcaa tgcactcttc ccctctgagc ctcggtttcc    600
ccatgtgtaa agcagagatg tggtctggta ggttagctgc caggaggacg tgcaacagca    660
gaaagtcagt gtctactggg tgcccgatgt gccaggcaga gtgggagcga tttgcactcc    720
agtggcctca cagaggagac ggggccacct gag                                 753
```

<210> SEQ ID NO 42
<211> LENGTH: 766
<212> TYPE: DNA
<213> ORGANISM: Homo sapiens

<400> SEQUENCE: 42

```
atggacaggc agacaatgta acaggtggga gtgagctgtt gagatgtgta ttagaaatgt     60
cacacgtgtc catcgttcgc acagtcatcc tgcagcttca cagacgttat tgctaaggat    120
gaggctaagc gataaagaat cagtttggtt cagaggaaaa atccgtggta aaggcagtag    180
agggtgggat gtggcttagg cagaactcgt ggctggcggt gtcttgactc tctgaagtgg    240
gaggaccctc tggtgtccga cccggccttc agtcctggcg tggccgcatc tgtccttgca    300
gatcaaaggt ttggagtggc tggtgtccct gtacaacaac aacctgaacg gcatcctggc    360
cgacgagatg ggcctgggga agaccatcca gaccatcgcg ctcatcacgt acctcatgga    420
gcacaaacgc atcaatgggc ccttcctcat catcgtgcct ctctcgtgag tacccgctgc    480
cagcaacatc ccacacgccg ctcacacgct cctgtgtttg tttcctaagt ttgccgcagt    540
agaataccac aaacgaggtg gcttaattac agaaatttgt tttcctggag gccagaagtc    600
cagggtcaag gtgtagcagg ttgcttcctc ctgaggcctc tcttcctgct tgcagggata    660
cgtgcttaca tgtatctcac tgtgtcttca catggtcctt cctctgtgcg tgtctgtgtc    720
ctcatctctt cttcttagaa ggacatgggt caggttggat gagggt                   766
```

<210> SEQ ID NO 43
<211> LENGTH: 669
<212> TYPE: DNA
<213> ORGANISM: Homo sapiens

```
<400> SEQUENCE: 43
ccagccctgg cagcattgtt tctgtccccc atcacatctc tgtgtcccta cttctcactc    60
taaagggcct tgccctcttt tcccagtggc ctcccttctg tcctctgagg cagagccctt   120
cacgtcctcg ccagtctctc ttcctccctc cctccctcag ctgccctaaa cacagtttct   180
ctgcccactc ggagggctgt ggccatgttg gcctcgcccc tgacagccag tggctatggg   240
tttgcacagt gagccattga tgagagaccg gcacttgact ctcatttcct tgttccatca   300
gaacgctgtc caactgggcg tacgagtttg acaagtgggc cccctccgtg gtgaaggtgt   360
cttacaaggt aggtcacagc cactgaggtt tcctctcttg ctacggaggt gcaggcggtg   420
gtgggcagga cgtccacaca tacctctgga cagtgaacct gagaatgctg ggtctccagt   480
cgcatggagt ctccaggaca gcctggaact ccagtcacat ggatccggga gtttggactg   540
ggcagggaca gggcagatta gctcactggg gaggagacag gagtgagcat ggtggccagc   600
actcagaggc cagctcaggc gcctgagatg gggacccagg aagaggggag cctgtcagcc   660
accaggaat                                                           669

<210> SEQ ID NO 44
<211> LENGTH: 713
<212> TYPE: DNA
<213> ORGANISM: Homo sapiens

<400> SEQUENCE: 44
cccaggaaga ggggagcctg tcagccacca ggaatgtgca gatggcggtg caggctgcgt    60
ggttccctca ggccccggcc gccgctggcc tgcactgctt cctcttcccc ctgcagcgcg   120
tgttctgcgt ggtgaggtct ggggacgcgc agcggccct gccagcccct ttccccacta   180
cccctgtgag gacgagccct cccgccgtgt cactgggcag ttgcaggggg tgcctgtgcc   240
cctcttgcca cctggccacc cggctccaaa agccgagctg tgcatcctgc ttcccttgca   300
gggatcccca gcagcaagac gggcctttgt ccccagctc cggagtggga agttcaacgt   360
cttgctgacg acgtacgagt acatcatcaa agacaagcac atcctcgcca aggtaacgtg   420
tccctgtggg aaatgccagg ccatgggccg agtgctcaca cgtgggtcac gctgcccgtc   480
tcctccaaag cccctacaag tttcttcccg gagtccacc tgcatgtgcg tgaagacagc   540
tgccctgtgt aggggaaagg cctaggtggg ggcgacctca ggtttacctc cctaactgtc   600
tccaggcagg ccctgagtca ggcccagaag ctggggccat ctacacagca tgcgctctgc   660
ctcctctcgg gccttctgcc cagagagcct cagcaccaag gcgtctcctg acc          713

<210> SEQ ID NO 45
<211> LENGTH: 845
<212> TYPE: DNA
<213> ORGANISM: Homo sapiens

<400> SEQUENCE: 45
gtagattcat atgtgtgatt ttgcagggaa gccagattgc ttttttgcaa tttgcattgt    60
tcacctgcca atagtcatgg ggtcacgggc ctgtctctgc ccaaggcttg caagaggcta   120
cgttgtgtgg ctccaactcg gtgagtcagc cccggggcag gacgtcaggc ctgtgctctc   180
cacccagctg cgctcttcca cctggagcct tcctggctgt gggcgcagag tgggagatt   240
ctccccatgt gccgggccac ctgctgcccc ctgccctgat tgcccactct ggggcccgca   300
gatccgttgg aagtacatga ttgtggacga aggtcaccgc atgaagaacc accactgcaa   360
gctgacgcag gtgctcaaca cgcactatgt ggcaccccgc cgcctgctgc tgacgggcac   420
```

```
accgctgcag aacaagcttc ccgagctctg ggcgctgctc aacttcctgc tgcccaccat    480
cttcaagagc tgcagcacct tcgagcagtg gtttaacgca ccctttgcca tgaccgggga    540
aaaggtgggt ttgcccagct gtgcccatgc tgacggttcc agtgcggct ggctttgctg     600 gttggaacgt gttgagcacc agctacagct ggctgggcct gtgctgggtg cctggtgaga    660
gtctgcatct gcatggagca ggggagccct ggaacccaag gctggggcag ccacaagggc    720
cccaggggag cagggcagag gtcatggtgg tgaatctcgg aatgctcggg gcgtctctga    780
ccctatgctc caggtgcaga gtggatggtg aggaagatgg ccctgaggca gctgtgggac    840
cgcaa                                                                845
```

<210> SEQ ID NO 46
<211> LENGTH: 716
<212> TYPE: DNA
<213> ORGANISM: Homo sapiens

<400> SEQUENCE: 46

```
agcagcatgc ccgctgccgg gggtctttct ggtgaggcac agggagcaga gtgctctggg     60
tactgcggtt ccatgtccca ggaattacat ggagggaacc agatcctcac agtttcctaa    120
ggaagagggt gccctgcctg ctcccagaa agcataaagc aggctgaaaa gccacgtgcc     180
aagggcaaga tcaccccagg ggaccccgtc caccctgtcc ccacatccgc accttctagt    240
gagacctctg tcgccctcct ttggaggtaa cgcttgcttc tcctgtcttg ggggcttcca    300
ggtggacctg aatgaggagg aaaccattct catcatccgg cgtctccaca agtgctgcg    360 gcccttcttg ctccgacgac tcaagaagga agtcgaggcc cagttgcccg aaaaggtgat    420
ggagttttga ggggagccac cagtgaagca gcctcacgtg ggggctttct ccagggctgg    480
gcgtgctcag ggcctctccc cacagtccca ggcctgccct ggtcaatcca gcttgggggt    540
ggcgatgacg ccactgggtc tgtaaagccc tgtgctgctg ttgtagggat tgaaaagcac    600
tcataggctc acatagctca caataggtta gagcacaaaa tcccacttcc tgtcaggggg    660
ccaggtgcct gtgcgggctc tcctggccac atcaggaggg gccgtgggct tggggt        716
```

<210> SEQ ID NO 47
<211> LENGTH: 710
<212> TYPE: DNA
<213> ORGANISM: Homo sapiens

<400> SEQUENCE: 47

```
ccccggctgc agttgtccct cttggctctt tgtttcctgg ctggctgtag agaggccccc     60
agaagatggc tgggggggccc tttctggccc agtaaccctc tggtatctct gcctggtgct    120
tcctctcatt gcccaggtct cccctcttct ccccagctgt gagggtctcc tcacccacac    180
cccagtgtgc tctggtcaga gctcatatga cagggccgag ggggtcagag ctgggttcgg    240
atggggggag tcaggcctca agccaccttg ggccctcgtg agcattatgt gtcccctgca    300
ggtggagtac gtcatcaagt gcgacatgtc tgcgctgcag cgagtgctct accgccacat    360
gcaggccaag ggcgtgctgc tgactgatgg ctccgagaag acaagaagg tgggccccag     420 agtcccccaa ctgcattccc cactgggtgt ccaaggccgg cagcgtggca ggcagagcag    480
agcgtgctct gaccatcggg tcatgatctg gtcatgatcc ccagggcatc tggccagccc    540
tggttatgat ggctggtggc ttgtgtcagg acacactgac tcagctgcca gtggcttctc    600
ctttgcctat gaaacactgg ctccttctgc aattggcagc ctgggcccag cactaacccc    660
```

-continued agcagggtta gagtgttcta gaatgccccc cttctctgtt attaagtgaa        710

<210> SEQ ID NO 48
<211> LENGTH: 689
<212> TYPE: DNA
<213> ORGANISM: Homo sapiens

<400> SEQUENCE: 48
atcacaaagc atcggggact ctgcctcagc cctttgccag tcttgtttcc gtcccgtcct    60
gctggccctg tccctgccat ctgccctctg ctgtgccagg cagtcatttg tttcccaggg   120
cttgttgggg gcctccgggc ctccagcctg ccatctcctc actcccaatt gctgtgccaa   180
aagccactct tccccactag agcgtcccca tggcccttct cccaacaccc acccatccac   240
caagcccacc ccaccccagg agggcaagac cccatttggg tccctctcat ctgccttcca   300
gggcaaaggc ggcaccaaga ccctgatgaa caccatcatg cagctgcgga agatctgcaa   360 ccaccctac atgttccagc acatcgaggt gagcccgccg cggctgggac ggctcaggcc   420
ctgctgtctg ctgagctcct aggcagagct ggcttctcct cgacagctct ttaaaaacag   480
actcgaatat tttcattagg taatgcctgt acatctgtct ctcatttggt cttcgcttca   540
ccagtgctta cgggaagaat cccagcagtt agggcgcaac gtgcgatagg aatatagggc   600
cctgaaagct tgccctcaga gagcaggagc gtttggagac ttctctgggg atgtgtcccc   660
ccacagtggg gtcctgctgc gtctctttg                                     689

<210> SEQ ID NO 49
<211> LENGTH: 649
<212> TYPE: DNA
<213> ORGANISM: Homo sapiens

<400> SEQUENCE: 49
ctggggctgt ctcagcaccc tgagcgtggc tgtggcccca tgacgtcctc gtgcattcag    60
ggtgtgaaga gtgctgtatg ggatgtcctt tccttcgttg gaggagtgtg agggaaagga   120
tgtcagtgga ctaagaaaga tggttttggc atctgtgtct ggtctcagag ccgccgtggg   180
cccgtgccga gcacacagtg tggggctttt gtcctctgag cacgagcggt gtgtgcggac   240
cgcagcgggg cccggtggcc tgctcctgcc tgtcactgac ccctctctcc ttgccttgca   300
ggagtccttt tccgagcact tggggttcac tggcggcatt gtccaagggt gagaagcttc   360
ccaactggat ggggtgggca ggtggtccac ccagaggttt tctgtcgttt tgttggcttt   420
attgctgctg ttatgttgtc caatttcaaa ggcagaaaat tagaaaatac agaagaatcc   480
aaagcaaata atacaaatct tttttttttt tttttttga ggtggagttt tgctcttgtt   540
gcccaggctg gagtgcagtg acacaatctc ggctcactgc aacctctgcc tcctgggttc   600
aaatgattct cctgcctcag cctcccgagt agctgggatt accggcacc               649

<210> SEQ ID NO 50
<211> LENGTH: 769
<212> TYPE: DNA
<213> ORGANISM: Homo sapiens

<400> SEQUENCE: 50
cgtgttgtgc cggccatgtg actcacagct cctctcattt tcatgagtgt ctgggtttga    60
cgagaaatac atgtgccacc ctggtgatac gcctccccag cgagggtggc cgggcttatt   120
tcagttgggg gaaatggctt tgctgaagct ttgggtgggg gacgtctgct taggatgcat   180
gtctgtgccc ttgaacccgg cgcctggcct ggaggcgggc gatgcacctc ctgccttacc   240

```
tgcctgcagg gttccaggtt taacatcctg cgccttctct cctgcctcct ccacactcca    300
ggctggacct gtaccgagcc tcgggtaaat ttgagcttct tgatagaatt cttcccaaac    360
tccgagcaac caaccacaaa gtgctgctgt tctgccaaat gacctccctc atgaccatca    420
tggaagatta ctttgcgtat cgcggcttta aatacctcag gcttgatggt gagtatgagc    480
cagtgaggcg tttcttacag ggttttgttg ttgtggctgc cacagaagct cctcactggc    540
attccctcct gtgaggcagg gtgaggccca ggcgctctgg tccagtggc cagagtgggc    600 ctagccacag gctgagcatc ttgggcactc ggcactggga caggccgtgg attggacgcc    660
gggtgtcctg actcctaggc tgacagtctt tccacgacaa tgctgggcgc actggggaag    720
gggtgccctg tgcactttta gctggaagtg acagaattcc ataccatgt     769

<210> SEQ ID NO 51
<211> LENGTH: 766
<212> TYPE: DNA
<213> ORGANISM: Homo sapiens

<400> SEQUENCE: 51
cgctgtggcc tagctgtggg ctgggtgctg gactctgtgc tccaggccca cctcctctag     60
ttctcccagc ggggcctgtt ttcatttctg ggatgtgtgg agagacgttt tgtggtgaaa    120
cactggaaat ccagttattc gccagtggcc cacaggcccg tgtggagagt gcggagccag    180
ggatctgggg atgctggcag gtgctgatcc tgctcctgct ctcagaagca ggtgttcctt    240
ggtgtcccca ctctacccct gaggtcaccc cgctgaccct gttctcctct gtgcccgtca    300
ggaaccacga aggcggagga ccggggcatg ctgctgaaaa ccttcaacga gcccggctct    360
gagtacttca tcttcctgct cagcacccgg gctggggggc tcggcctgaa cctccagtcg    420
gcagacactg tgatcatttt tgacagcgac tggaatcctc accaggtaaa agcgggccgg    480
gccccaggtc gaggagaagg aaggggtgc ctgcaaaacc tcgaggagac ggccctggct    540
tgagggtcct ccagcctcct ccacattgtc ttggacccca ggagccggga ggagctgcac    600
ccatatctcc ataggtcatc aggagagaaa gaggcgggt cctcctgttt cccaaaatac    660
aaacagcctt tccctctgat tgggaaagca gtgtataagc catccgtcgg tttggttttt    720
cttaaatctt ggaatggcac ccatgaggag gtggaaagta tcctga                  766

<210> SEQ ID NO 52
<211> LENGTH: 1513
<212> TYPE: DNA
<213> ORGANISM: Homo sapiens

<400> SEQUENCE: 52
agctgcttga gaatataatc ccctgggggg ttggtgcttt cttcccgaat atctgtgggg     60
tcccaataag gtagaaggtg gcacttctgg aggaacgtga tgagagtccc cttcccccga    120
gggacacatg gcggcccagg ctccaccagc tctgttttca tgcggcggca ggtcaggctg    180
ggcagaattg tcaggccgag ggtggcacgc acagcacacc tctccagcta gtgtcagagg    240
ccaccttccc ttttatgacc tcctgggctc ctttgggact gactggcacc tcttccccca    300
ggacctgcaa gcgcaggacc gagcccaccg catcgggcag cagaacgagg tgcgtgtgct    360
ccgcctctgc accgtcaaca gcgtggagga aagatccta gctgcagcca agtacaagct    420
caacgtggac cagaaggtga tccaggccgg catgttcgac cagaagtcct ccagccatga    480
gcggcgcgcc ttcctgcagg ccatcctgga gcacgaggag caggatgagg tgagcccagc    540
```

-continued

| | |
|---|---|
| accggcccg acccctcccc agcgtgaatg gtggacgcgt gagcggcttt cattttttgtt | 600 |
| tttttaccctt ttttgcactc ttattttttt tgcatccctt tggagtaaag ggagtgtggg | 660 |
| ctgaacggaa agaggatgag tacttgcttt ttctttgaag tggtttttt ttctaaactg | 720 |
| ctggtgaaag acgccggatt gacagccctg gagactgaag tcctctattt atccacagag | 780 |
| cagacactgc agcacgggca gcggcagtgc agcttcgcc cacactgccc ctccgccagc | 840 |
| gggcgtcaac cccgacttgg aggagccacc tctaaaggtg agagggtag ttcagtctcc | 900 |
| atgcccattc aatcctcggc ttctcggctg agacggccag caagggccct ggtcccacgg | 960 |
| agcgtgcgtg tgcgtgtgcg tgtgtgtgcc tttcgctgcc gtgtgggtcc ccatccaccg | 1020 |
| cagccgtgcc gggaccacca gctcattccc acggacgccg ccgctcgcct ctgagctcgg | 1080 |
| ccgccgccca ccccggcccc tcctcagcgg cactgacagt ttgcaatctt ataggaggaa | 1140 |
| gacgaggtgc ccgacgacga gaccgtcaac cagatgatcg cccggcacga ggaggagttt | 1200 |
| gatctgttca tggtaagcgc tgcaggctgg atgggggcagt tcaggcatcc cactctgctg | 1260 |
| ccaccaggag caaagcagac gtcctagtgc ccatggtggt atccctagca ggtcagggag | 1320 |
| ccagggacag ctcacagtgc agcccactcc cacctccaga ctgacccgtc ttccaccccc | 1380 |
| agtctcctga ggatggcatc ggagggcgag atgcacaccc agccttctgc atgtgacccg | 1440 |
| agacctgccc caccagctct gttttctaac gggctctcca gggcttcatg cactccctttt | 1500 |
| cagagggagt tcg | 1513 |

<210> SEQ ID NO 53
<211> LENGTH: 821
<212> TYPE: DNA
<213> ORGANISM: Homo sapiens

<400> SEQUENCE: 53

| | |
|---|---|
| tcatgcctcc accaacgctg ggccacgcag ctgctgcccc cctgctgggg tctgcagccc | 60 |
| tcttgtgcaa ccttccatct tttcgagttt cctctgcctc ctgaggcaga gcctctagtc | 120 |
| agggtctgac ggagccaggc caggtcagcc actgaaaaat cgagagctac tgtttaactc | 180 |
| tcgcagcagc gtggagcccc acgggcagag aaaggccctt ctgaactctc ggtgttctgg | 240 |
| ctctagcgtg cccctggtgc ctgcatgctg atgcctctcc cgttgcctcc ctgcccacca | 300 |
| gcgcatggac ctggaccgca ggcgcgagga ggcccgcaac cccaagcgga agccgcgcct | 360 |
| catggaggag gacgagctcc cctcgtggat catcaaggac gacgcggagg tggagcggct | 420 |
| gacctgtgag gaggaggagg agaagatgtt cggccgtggc tcccgccacc gcaaggaggt | 480 |
| ggactacagc gactcactga cggagaagca gtggctcaag gtacatgctg gagaggccca | 540 |
| gcagctgccg caggccagcg ccaggcaggg ctggggagac aaagggccca ccgccaggac | 600 |
| tcaggcctgg gtccaaaatg cttttccttgg gccactcctg gccaggctcc gcaggcagcc | 660 |
| gagagccttc cgatgtgggc cagggatggt caggtccttt tggctctgcc ttggaatgca | 720 |
| agaaggaccc acggttcctg agcagctcaa aacctgctgc tggttatggt tggtcttttca | 780 |
| agtaaaaggg tttacctctt cccgaggtta aaaatcatgt t | 821 |

<210> SEQ ID NO 54
<211> LENGTH: 160
<212> TYPE: DNA
<213> ORGANISM: Homo sapiens

<400> SEQUENCE: 54

| | |
|---|---|
| aaacactaaa cagacattaa aaaattttgt tgtagaaaat tacaggaaaa gatatccatg | 60 |

| | |
|---|---|
| acacagccag cagtgtggca cgtgggctac aattccagcg tggccttcag ttctgcacac | 120 |
| gtgcgtcaaa ggtggggaga gttctggtgg tgggtggcgc | 160 |

<210> SEQ ID NO 55
<211> LENGTH: 856
<212> TYPE: DNA
<213> ORGANISM: Homo sapiens

<400> SEQUENCE: 55

| | |
|---|---|
| agcacgttct tttctgtaca gagaagatag ttcttttttt ttggtcaaga aattcaacca | 60 |
| ttagtttttt aaagacaagc ttgggtgggg tgcctgctgg gggcagtgct ggtctttcac | 120 |
| tgcagcccag gcacccttg agagtcccag tgtgtgttat gccccgagcc agtcaagctg | 180 |
| aagggagagc gggtgcgggg gccctcctcc gtgtcccagc ccggcccctg ggattgcgtc | 240 |
| gcggcctctg cttgtcgacc tgggtgctgg ctgtcctatt ttactactat tgaccctgaa | 300 |
| ggccatcgag gagggcacgc tggaggagat cgaagaggag gtccggcaga agaaatcatc | 360 |
| acggaagcgc aagcgagaca gcgacgccgg ctcctccacc ccgaccacca gcacccgcag | 420 |
| ccgcgacaag gacgacgaga gcaagaagca gaagaagcgc gggcggccgc ctgccgagaa | 480 |
| actctcccct aacccaccca acctcaccaa gaagatgaag aagattgtgg atgccgtgat | 540 |
| caagtacaag gacaggtaag cgaggaggcg gggagggcgg gggctgtagg ggtccccgtg | 600 |
| ggagcaggcc tggcatctgc actctgactc tgcacactca ggcttgggcc gctcactctt | 660 |
| tcactcatcc acaaacactg actgaatctc tgtgtctttg agcctggccc tgaggaacat | 720 |
| gctttctgga acagggaagc acacatgtat ctgcggtgat gagagggaat gtcacatgtg | 780 |
| gtcgagagga gaggcagggg tgcgggtctc ggagaagggg acattgcagc agagccttga | 840 |
| gagaggggag gttggg | 856 |

<210> SEQ ID NO 56
<211> LENGTH: 1237
<212> TYPE: DNA
<213> ORGANISM: Homo sapiens

<400> SEQUENCE: 56

| | |
|---|---|
| tagcctggca tggtggtgca cgactgtaaa aaatcccagt gactccaaag gctgaggcag | 60 |
| gagaatctcc tgaacctggg aggtggaggt tgcagtgagc cgagatcgca ccattgcact | 120 |
| ccagcctggg cagcaagagc gaaactccgt ctcaaaaaaa aaaaagcgc atgtgcaaga | 180 |
| aatagctcct gagctgagtt ggaatttctc atccttaaac aatgtgggaa cctgctgagg | 240 |
| tgggtgggg gctcccgggt gggcggactc ggggtgata gccgccggtt ctgccttgca | 300 |
| gcagcagtgg acgtcagctc agcgaggtct tcatccagct gccctcgcga aaggagctgc | 360 |
| ccgagtacta cgagctcatc cgcaagcccg tggacttcaa gaagataaag gtaaccctga | 420 |
| cgttgtacct gcgccccgca tgtgcccgga ggggagtctg acccaggggc accccatct | 480 |
| gagagctgtg tgtgtgggc agaatgacca gaaaccacct aggcggtgcc ttgggctacc | 540 |
| tggttaggga cctggtcgtg ggcttttggg gttccttgta agggttgggg gtgtcctgag | 600 |
| ggatgtcagt gggcagtcgg tgttgggtgt tccttcaagg tcccactcac ttagtgctgg | 660 |
| gcctcagtca tgcagttccc atgcctagtg agccaggtta ccgaggctgg cgcttcggcc | 720 |
| acatcctcat aggcacgagg aatcctagcc cgtggggtct ccagcacaca gccaggcctg | 780 |
| cgggcaggcg aggcggggtc ctgaggtaag acctgctcct cccgtccact gcaggagcgc | 840 |

-continued

| | |
|---|---|
| attcgcaacc acaagtaccg cagcctcaac gacctagaga aggacgtcat gctcctgtgc | 900 |
| cagaacgcac agaccttcaa cctggagggc tccctggtga gggcaccgct ggggttggg | 960 |
| gatgggccac tcccacagct gggctttgac ccaacccgcc cctccttccc ttctgaattg | 1020 |
| atgggttaaa aacaagtccc gctagctgtg gtggttcgtg cctgtaatcc cagcactttg | 1080 |
| ggaggccaag gcgggaggat cacttgagac caggagttca cgaccagcct gggcaacata | 1140 |
| acaagaccct gtctttaaaa aaaaaaaga aaaattaaa aatttccaac ttgggatatt | 1200 |
| ttagcaatta caaaagcagt atgtatttac cgaagaa | 1237 |

<210> SEQ ID NO 57
<211> LENGTH: 1037
<212> TYPE: DNA
<213> ORGANISM: Homo sapiens

<400> SEQUENCE: 57

| | |
|---|---|
| attgcagacc tcagagattg tgcagaagga gggaggcacc tgcagctatt cccaaaccag | 60 |
| tgtgcctgac cttcaccct ggagcatttc agaagtctga tgctcgggcc cctatggagg | 120 |
| aagattatgg agagggcctt ccaccctggg tgggctgaag ccccgacccg ctgaggctcg | 180 |
| cattggccac tgatcagctg tccaggggca acacagggct ggggctgggg ctggggccag | 240 |
| ggccgggcag gcagccctcc agtcgggccc atccactcaa gcccctggtg tctctgccca | 300 |
| gatctatgaa gactccatcg tcttgcagtc ggtcttcacc agcgtgcggc agaaaatcga | 360 |
| gaaggaggat gacagtgaag gcgaggagag tgaggaggag gaagagggcg aggaggaagg | 420 |
| ctccgaatcc gaatgtgagt cccggggggg ttcaggacgc cggggttcac gctggcccga | 480 |
| gagcccccaa ggccccagct tttcacagcc ctcccggctc ccagacgccc cttgctgtgg | 540 |
| gggtgctgca ttcccagagc tcaaggctgt cttttccctcc cggtcccctc cagctcggtc | 600 |
| cgtcaaagtg aagatcaagc ttggccggaa ggagaaggca caggaccggc tgaagggcgg | 660 |
| ccggcggcgg ccgagccgag ggtcccgagc caagccggtc gtgagtgacg atgacagtga | 720 |
| ggaggaacaa gaggaggtga ggccgggccc ccgagcaggc agagctggca tgtggcagga | 780 |
| ggcatcccgg ggccctgatg ggacagccct gtgggcggt gctcccacgc ccccacgctg | 840 |
| caggtgggaa agctgaggct tgacctgcca tggctgaccc caggtcacac agccagtatg | 900 |
| tggcagggct gccactcaaa gccaagcctg tgtgaccccg gaaccagctc tcagtacccg | 960 |
| tgggtgtctg gggactgggg gacacgtgag tcctcaggac aggcagcagg cggtcccagg | 1020 |
| gcaccagggc tcctggg | 1037 |

<210> SEQ ID NO 58
<211> LENGTH: 859
<212> TYPE: DNA
<213> ORGANISM: Homo sapiens

<400> SEQUENCE: 58

| | |
|---|---|
| ctcctgcctc agcctcccaa gtagctggga ctacaggcgc cgccaccac gcccggctaa | 60 |
| tttttttgtat ttttttagtag agacggggtt tcaccgtgtt agccaggatg gtctcgatct | 120 |
| cctgacctcg tgatccgccc gccttggcct tccaaagtgc tgggattacg ggcgtgagcc | 180 |
| accgtgcccg gcccacatca gtgttttctt gagcaagttt atttaaagtt tggcaggtcc | 240 |
| ctggcaaggt gccctggcag gggtggccaa cgcacactct ctcctcctgt ccctctccca | 300 |
| ggaccgctca ggaagtggca gcgaagaaga ctgagccccg acattccagt ctcgaccccg | 360 |
| agcccctcgt tccagagctg agatggcata ggccttagca gtaacgggta gcagcagatg | 420 |

```
tagtttcaga cttggagtaa aactgtataa acaaaagaat cttccatatt tatacagcag    480
agaagctgta ggactgtttg tgactggccc tgtcctggca tcagtagcat ctgtaacagc    540
attaactgtc ttaaagagag agagagagaa ttccgaattg gggaacacac gatacctgtt    600
tttcttttcc gttgctggca gtactgttgc ccgcagttt ggagtcactg tagttaagtg     660
tggatgcatg tgcgtcaccg tccactcctc ctactgtatt ttattggaca ggtcagactc    720
gccgggggcc cggcgagggt atgtcagtgt cactggatgt caaacagtaa taaattaaac    780
caacaacaaa acgcacagcc ttgcctgcag gtggacttgt gcctggctcc caccgtttct    840
gccagcagga gtggcgggg                                                  859

<210> SEQ ID NO 59
<211> LENGTH: 96
<212> TYPE: DNA
<213> ORGANISM: Homo sapiens

<400> SEQUENCE: 59
aaaattacag gaaaagatat ccatgacaca gccagcagtg tggcacgtgg gctacaattc     60
cagcgtggcc ttcagttctg cacacgtgcg tcaaag                               96

<210> SEQ ID NO 60
<211> LENGTH: 5386
<212> TYPE: DNA
<213> ORGANISM: Homo sapiens
<220> FEATURE:
<221> NAME/KEY: CDS
<222> LOCATION: (75)..(1805)

<400> SEQUENCE: 60 ggcggggag gcgccgggaa gtcgatggcg ccggcggctc ctgcaggagg ccactgtctg      60
cagctcccgt gaag atg tcc act cca gac cca ccc ctg ggc gga act cct     110
              Met Ser Thr Pro Asp Pro Pro Leu Gly Gly Thr Pro
                1               5                  10 cgg cca ggt cct tcc ccg ggc cct ggc cct tcc cct gga gcc atg ctg     158
Arg Pro Gly Pro Ser Pro Gly Pro Gly Pro Ser Pro Gly Ala Met Leu
        15                  20                  25 ggc cct agc ccg ggt ccc tcg ccg ggc tcc gcc cac agc atg atg ggg     206
Gly Pro Ser Pro Gly Pro Ser Pro Gly Ser Ala His Ser Met Met Gly
    30                  35                  40 ccc agc cca ggg ccg ccc tca gca gga cac ccc atc ccc acc cag ggg     254
Pro Ser Pro Gly Pro Pro Ser Ala Gly His Pro Ile Pro Thr Gln Gly
45                  50                  55                  60 cct gga ggg tac cct cag gac aac atg cac cag atg cac aag ccc atg     302
Pro Gly Gly Tyr Pro Gln Asp Asn Met His Gln Met His Lys Pro Met
                65                  70                  75 gag tcc atg cat gag aag ggc atg tcg gac gac ccg cgc tac aac cag     350
Glu Ser Met His Glu Lys Gly Met Ser Asp Asp Pro Arg Tyr Asn Gln
            80                  85                  90 atg aaa gga atg ggg atg cgg tca ggg ggc cat gct ggg atg ggg ccc     398
Met Lys Gly Met Gly Met Arg Ser Gly Gly His Ala Gly Met Gly Pro
        95                  100                 105 ccg ccc agc ccc atg gac cag cac tcc caa ggt tac ccc tcg ccc ctg     446
Pro Pro Ser Pro Met Asp Gln His Ser Gln Gly Tyr Pro Ser Pro Leu
    110                 115                 120 ggt ggc tct gag cat gcc tct agt cca gtt cca gcc agt ggc ccg tct     494
Gly Gly Ser Glu His Ala Ser Ser Pro Val Pro Ala Ser Gly Pro Ser
125                 130                 135                 140 tcg ggg ccc cag atg tct tcc ggg cca gga ggt gcc ccg ctg gat ggt     542
```

```
Ser Gly Pro Gln Met Ser Ser Gly Pro Gly Ala Pro Leu Asp Gly
                145                 150                 155 gct gac ccc cag gcc ttg ggg cag cag aac cgg ggc cca acc cca ttt        590
Ala Asp Pro Gln Ala Leu Gly Gln Gln Asn Arg Gly Pro Thr Pro Phe
                160                 165                 170 aac cag aac cag ctg cac cag ctc aga gct cag atc atg gcc tac aag        638
Asn Gln Asn Gln Leu His Gln Leu Arg Ala Gln Ile Met Ala Tyr Lys
                175                 180                 185 atg ctg gcc agg ggg cag ccc ctc ccc gac cac ctg cag atg gcg gtg        686
Met Leu Ala Arg Gly Gln Pro Leu Pro Asp His Leu Gln Met Ala Val
            190                 195                 200 cag ggc aag cgg ccg atg ccc ggg atg cag cag cag atg cca acg cta        734
Gln Gly Lys Arg Pro Met Pro Gly Met Gln Gln Gln Met Pro Thr Leu
205                 210                 215                 220 cct cca ccc tcg gtg tcc gca aca gga ccc ggc cct ggc cct ggc cct        782
Pro Pro Pro Ser Val Ser Ala Thr Gly Pro Gly Pro Gly Pro Gly Pro
                225                 230                 235 ggc ccc ggc ccg ggt ccc ggc ccg gca cct cca aat tac agc agg cct        830
Gly Pro Gly Pro Gly Pro Gly Pro Ala Pro Pro Asn Tyr Ser Arg Pro
                240                 245                 250 cat ggt atg gga ggg ccc aac atg cct ccc cca gga ccc tcg ggc gtg        878
His Gly Met Gly Gly Pro Asn Met Pro Pro Pro Gly Pro Ser Gly Val
            255                 260                 265 ccc ccc ggg atg cca ggc cag cct cct gga ggg cct ccc aag ccc tgg        926
Pro Pro Gly Met Pro Gly Gln Pro Pro Gly Gly Pro Pro Lys Pro Trp
            270                 275                 280 cct gaa gga ccc atg gcg aat gct gct gcc ccc acg agc acc cct cag        974
Pro Glu Gly Pro Met Ala Asn Ala Ala Ala Pro Thr Ser Thr Pro Gln
285                 290                 295                 300 aag ctg att ccc ccg cag cca acg ggc cgc cct tcc ccc gcg ccc cct       1022
Lys Leu Ile Pro Pro Gln Pro Thr Gly Arg Pro Ser Pro Ala Pro Pro
                305                 310                 315 gcc gtc cca ccc gcc gcc tcg ccc gtg atg cca ccg cag acc cag tcc       1070
Ala Val Pro Pro Ala Ala Ser Pro Val Met Pro Pro Gln Thr Gln Ser
                320                 325                 330 ccc ggg cag ccg gcc cag ccc gcg ccc atg gtg cca ctg cac cag aag       1118
Pro Gly Gln Pro Ala Gln Pro Ala Pro Met Val Pro Leu His Gln Lys
            335                 340                 345 cag agc cgc atc acc ccc atc cag aag ccg cgg ggc ctc gac cct gtg       1166
Gln Ser Arg Ile Thr Pro Ile Gln Lys Pro Arg Gly Leu Asp Pro Val
350                 355                 360 gag atc ctg cag gag cgc gag tac agg ctg cag gct cgc atc gca cac       1214
Glu Ile Leu Gln Glu Arg Glu Tyr Arg Leu Gln Ala Arg Ile Ala His
365                 370                 375                 380 cga att cag gaa ctt gaa aac ctt ccc ggg tcc ctg gcc ggg gat ttg       1262
Arg Ile Gln Glu Leu Glu Asn Leu Pro Gly Ser Leu Ala Gly Asp Leu
                385                 390                 395 cga acc aaa gcg acc att gag ctc aag gcc ctc agg ctg ctg aac ttc       1310
Arg Thr Lys Ala Thr Ile Glu Leu Lys Ala Leu Arg Leu Leu Asn Phe
                400                 405                 410 cag agg cag ctg cgc cag gag gtg gtg gtg tgc atg cgg agg gac aca       1358
Gln Arg Gln Leu Arg Gln Glu Val Val Val Cys Met Arg Arg Asp Thr
                415                 420                 425 gcg ctg gag aca gcc ctc aat gct aag gcc tac aag cgc agc aag cgc       1406
Ala Leu Glu Thr Ala Leu Asn Ala Lys Ala Tyr Lys Arg Ser Lys Arg
430                 435                 440 cag tcc ctg cgc gag gcc cgc atc act gag aag ctg gag aag cag cag       1454
Gln Ser Leu Arg Glu Ala Arg Ile Thr Glu Lys Leu Glu Lys Gln Gln
445                 450                 455                 460
```

-continued

```
aag atc gag cag gag cgc aag cgc cgg cag aag cac cag gaa tac ctc     1502
Lys Ile Glu Gln Glu Arg Lys Arg Arg Gln Lys His Gln Glu Tyr Leu
            465                 470                 475 aat agc att ctc cag cat gcc aag gat ttc aag gaa tat cac aga tcc     1550
Asn Ser Ile Leu Gln His Ala Lys Asp Phe Lys Glu Tyr His Arg Ser
        480                 485                 490 gtc aca ggc aaa atc cag aag ctg acc aag gca gtg gcc acg tac cat     1598
Val Thr Gly Lys Ile Gln Lys Leu Thr Lys Ala Val Ala Thr Tyr His
    495                 500                 505 gcc aac acg gag cgg gag cag aag aaa gag aac gag cgg atc gag aag     1646
Ala Asn Thr Glu Arg Glu Gln Lys Lys Glu Asn Glu Arg Ile Glu Lys
510                 515                 520 gag cgc atg cgg agg ctc atg gct gaa gat gag gag ggg tac cgc aag     1694
Glu Arg Met Arg Arg Leu Met Ala Glu Asp Glu Glu Gly Tyr Arg Lys
525                 530                 535                 540 ctc atc gac cag aag aag gac aag cgc ctg gcc tac ctc ttg cag cag     1742
Leu Ile Asp Gln Lys Lys Asp Lys Arg Leu Ala Tyr Leu Leu Gln Gln
                545                 550                 555 aca gac gaa agg cag aaa atg cag aag gac aga cgc ctg cca ttg ggc     1790
Thr Asp Glu Arg Gln Lys Met Gln Lys Asp Arg Arg Leu Pro Leu Gly
            560                 565                 570 cgg atg gcg agc ctc tagacgagac cagccagatg agcgacctcc cggtgaaggt     1845
Arg Met Ala Ser Leu
            575 gatccacgtg gagagtggga agatcctcac aggcacagat gcccccaaag ccgggcagct    1905 ggaggcctgg ctcgagatga acccggggta tgaagtagcc ccgaggtctg atagtgaaga    1965 aagtggctca gaagaagagg aagaggagga ggaggaagag cagccgcagg cagcacagcc    2025 tcccaccctg cccgtggagg agaagaagaa gattccagat ccagacagcg atgacgtctc    2085 tgaggtggac gcgcggcaca tcattgagaa tgccaagcaa gatgtcgatg atgaatatgg    2145 cgtgtcccag gcccttgcac gtggcctgca gtcctactat gccgtggccc atgctgtcac    2205 tgagagagtg gacaagcagt cagcgcttat ggtcaatggt gtcctcaaac agtaccagat    2265 caaaggtttg gagtggctgg tgtccctgta caacaacaac ctgaacggca tcctggccga    2325 cgagatgggc ctggggaaga ccatccagac catcgcgctc atcacgtacc tcatggagca    2385 caaacgcatc aatgggccct tcctcatcat cgtgcctctc tcaacgctgt ccaactgggc    2445 gtacgagttt gacaagtggg cccccctccgt ggtgaaggtg tcttacaagg gatccccagc    2505 agcaagacgg gcctttgtcc cccagctccg gagtgggaag ttcaacgtct tgctgacgac    2565 gtacgagtac atcatcaaag acaagcacat cctcgccaag atccgttgga agtacatgat    2625 tgtggacgaa ggtcaccgca tgaagaacca ccactgcaag ctgacgcagg tgctcaacac    2685 gcactatgtg gcaccccgcc gcctgctgct gacgggcaca ccgctgcaga caagcttcc    2745 cgagctctgg gcgctgctca acttcctgct gcccaccatc ttcaagagct gcagcacctt    2805 cgagcagtgg tttaacgcac cctttgccat gaccggggaa aaggtggacc tgaatgagga    2865 ggaaaccatt ctcatcatcc ggcgtctcca caaagtgctg cggcccttct tgctccgacg    2925 actcaagaag gaagtcgagg cccagttgcc cgaaaaggtg gagtacgtca tcaagtgcga    2985 catgtctgcg ctgcagcgag tgctctaccc ccacatgcag gccaagggcg tgctgctgac    3045 tgatggctcc gagaaggaca agaagggcaa aggcggcacc aagaccctga tgaacaccat    3105 catgcagctg cggaagatct gcaaccaccc ctacatgttc cagcacatcg aggagtcctt    3165 ttccgagcac ttggggttca ctggcggcat tgtccaaggg ctggacctgt accgagcctc    3225 gggtaaattt gagcttcttg atagaattct tcccaaactc cgagcaacca accacaaagt    3285
```

```
gctgctgttc tgccaaatga cctccctcat gaccatcatg aagattact  ttgcgtatcg    3345 cggctttaaa tacctcaggc ttgatggaac cacgaaggcg gaggaccggg gcatgctgct    3405
gaaaaccttc aacgagcccg gctctgagta cttcatcttc ctgctcagca cccgggctgg    3465
ggggctcggc ctgaacctcc agtcggcaga cactgtgatc attttgaca  gcgactggaa    3525 tcctcaccag gacctgcaag cgcaggaccg agcccaccgc atcgggcagc agaacgaggt    3585
gcgtgtgctc cgcctctgca ccgtcaacag cgtggaggag aagatcctag ctgcagccaa    3645
gtacaagctc aacgtggacc agaaggtgat ccaggccggc atgttcgacc agaagtcctc    3705
cagccatgag cggcgcgcct tcctgcaggc catcctggag cacgaggagc aggatgagag    3765
cagacactgc agcacgggca gcggcagtgc cagcttcgcc cacactgccc ctccgccagc    3825
gggcgtcaac cccgacttgg aggagccacc tctaaaggag gaagacgagg tgcccgacga    3885
cgagaccgtc aaccagatga tcgcccggca cgaggaggag tttgatctgt tcatgcgcat    3945
ggacctggac cgcaggcgcg aggaggcccg caaccccaag cggaagccgc gcctcatgga    4005
ggaggacgag ctcccctcgt ggatcatcaa ggacgacgcg gaggtggagc ggctgacctg    4065
tgaggaggag gaggagaaga tgttcggccg tggctcccgc caccgcaagg aggtggacta    4125
cagcgactca ctgacggaga gcagtggct  caaggccatc gaggagggca cgctggagga    4185
gatcgaagag gaggtccggc agaagaaatc atcacggaag cgcaagcgag acagcgacgc    4245
cggctcctcc accccgacca ccagcacccg cagccgcgac aaggacgacg agagcaagaa    4305
gcagaagaag cgcgggcggc cgcctgccga gaaactctcc cctaacccac caacctcac    4365 caagaagatg aagaagattg tggatgccgt gatcaagtac aaggacagca gcagtggacg    4425
tcagctcagc gaggtcttca tccagctgcc ctcgcgaaag gagctgcccg agtactacga    4485
gctcatccgc aagcccgtgg acttcaagaa gataaaggag cgcattcgca accacaagta    4545
ccgcagcctc aacgacctag agaaggacgt catgctcctg tgccagaacg cacagacctt    4605
caacctggag ggctccctga tctatgaaga ctccatcgtc ttgcagtcgg tcttcaccag    4665
cgtgcggcag aaaatcgaga aggaggatga cagtgaaggc gaggagagtg aggaggagga    4725
agagggcgag gaggaaggct ccgaatccga atctcggtcc gtcaaagtga agatcaagct    4785
tggccggaag gagaaggcac aggaccggct gaagggcggc cggcggcggc cgagccgagg    4845
gtcccgagcc aagccggtcg tgagtgacga tgacagtgag gaggaacaag aggaggaccg    4905
ctcaggaagt ggcagcgaag aagactgagc cccgacattc cagtctcgac cccgagcccc    4965
tcgttccaga gctgagatgg catagggcctt agcagtaacg ggtagcagca gatgtagttt    5025
cagacttgga gtaaaactgt ataaacaaaa gaatcttcca tatttataca gcagagaagc    5085
tgtaggactg tttgtgactg gccctgtcct ggcatcagta gcatctgtaa cagcattaac    5145
tgtcttaaag agagagagag agaattccga attggggaac acacgatacc tgtttttctt    5205
ttccgttgct ggcagtactg ttgcgccgca gtttggagtc actgtagtta agtgtggatg    5265
catgtgcgtc accgtccact cctcctactg tatttattg  gacaggtcag actcgccggg    5325
ggcccggcga gggtatgtca gtgtcactgg atgtcaaaca gtaataaatt aaaccaacaa    5385
c                                                                    5386
```

<210> SEQ ID NO 61
<211> LENGTH: 577
<212> TYPE: PRT
<213> ORGANISM: Homo sapiens

<400> SEQUENCE: 61

-continued

```
Met Ser Thr Pro Asp Pro Pro Leu Gly Gly Thr Pro Arg Pro Gly Pro
 1               5                  10                 15
Ser Pro Gly Pro Gly Pro Ser Pro Gly Ala Met Leu Gly Pro Ser Pro
             20                  25                  30
Gly Pro Ser Pro Gly Ser Ala His Ser Met Met Gly Pro Ser Pro Gly
             35                  40                  45
Pro Pro Ser Ala Gly His Pro Ile Pro Thr Gln Gly Pro Gly Gly Tyr
     50                  55                  60
Pro Gln Asp Asn Met His Gln Met His Lys Pro Met Glu Ser Met His
 65                  70                  75                  80
Glu Lys Gly Met Ser Asp Asp Pro Arg Tyr Asn Gln Met Lys Gly Met
                 85                  90                  95
Gly Met Arg Ser Gly Gly His Ala Gly Met Gly Pro Pro Ser Pro
             100                 105                 110
Met Asp Gln His Ser Gln Gly Tyr Pro Ser Pro Leu Gly Gly Ser Glu
             115                 120                 125
His Ala Ser Ser Pro Val Pro Ala Ser Gly Pro Ser Ser Gly Pro Gln
         130                 135                 140
Met Ser Ser Gly Pro Gly Gly Ala Pro Leu Asp Gly Ala Asp Pro Gln
145                 150                 155                 160
Ala Leu Gly Gln Gln Asn Arg Gly Pro Thr Pro Phe Asn Gln Asn Gln
                 165                 170                 175
Leu His Gln Leu Arg Ala Gln Ile Met Ala Tyr Lys Met Leu Ala Arg
             180                 185                 190
Gly Gln Pro Leu Pro Asp His Leu Gln Met Ala Val Gln Gly Lys Arg
             195                 200                 205
Pro Met Pro Gly Met Gln Gln Gln Met Pro Thr Leu Pro Pro Pro Ser
         210                 215                 220
Val Ser Ala Thr Gly Pro Gly Pro Gly Pro Gly Pro Gly Pro Gly Pro
225                 230                 235                 240
Gly Pro Gly Pro Ala Pro Pro Asn Tyr Ser Arg Pro His Gly Met Gly
             245                 250                 255
Gly Pro Asn Met Pro Pro Gly Pro Ser Gly Val Pro Pro Gly Met
         260                 265                 270
Pro Gly Gln Pro Pro Gly Gly Pro Pro Lys Pro Trp Pro Glu Gly Pro
     275                 280                 285
Met Ala Asn Ala Ala Ala Pro Thr Ser Thr Pro Gln Lys Leu Ile Pro
     290                 295                 300
Pro Gln Pro Thr Gly Arg Pro Ser Pro Ala Pro Pro Ala Val Pro Pro
305                 310                 315                 320
Ala Ala Ser Pro Val Met Pro Pro Gln Thr Gln Ser Pro Gly Gln Pro
                 325                 330                 335
Ala Gln Pro Ala Pro Met Val Pro Leu His Gln Lys Gln Ser Arg Ile
             340                 345                 350
Thr Pro Ile Gln Lys Pro Arg Gly Leu Asp Pro Val Glu Ile Leu Gln
             355                 360                 365
Glu Arg Glu Tyr Arg Leu Gln Ala Arg Ile Ala His Arg Ile Gln Glu
     370                 375                 380
Leu Glu Asn Leu Pro Gly Ser Leu Ala Gly Asp Leu Arg Thr Lys Ala
385                 390                 395                 400
Thr Ile Glu Leu Lys Ala Leu Arg Leu Leu Asn Phe Gln Arg Gln Leu
                 405                 410                 415
```

-continued

```
Arg Gln Glu Val Val Cys Met Arg Arg Asp Thr Ala Leu Glu Thr
            420                 425                 430
Ala Leu Asn Ala Lys Ala Tyr Lys Arg Ser Lys Arg Gln Ser Leu Arg
        435                 440                 445
Glu Ala Arg Ile Thr Glu Lys Leu Glu Lys Gln Gln Lys Ile Glu Gln
    450                 455                 460
Glu Arg Lys Arg Gln Lys His Gln Glu Tyr Leu Asn Ser Ile Leu
465                 470                 475                 480
Gln His Ala Lys Asp Phe Lys Glu Tyr His Arg Ser Val Thr Gly Lys
                485                 490                 495
Ile Gln Lys Leu Thr Lys Ala Val Ala Thr Tyr His Ala Asn Thr Glu
            500                 505                 510
Arg Glu Gln Lys Lys Glu Asn Glu Arg Ile Glu Lys Glu Arg Met Arg
        515                 520                 525
Arg Leu Met Ala Glu Asp Glu Glu Gly Tyr Arg Lys Leu Ile Asp Gln
    530                 535                 540
Lys Lys Asp Lys Arg Leu Ala Tyr Leu Leu Gln Gln Thr Asp Glu Arg
545                 550                 555                 560
Gln Lys Met Gln Lys Asp Arg Arg Leu Pro Leu Gly Arg Met Ala Ser
                565                 570                 575
Leu
```

<210> SEQ ID NO 62
<211> LENGTH: 5471
<212> TYPE: DNA
<213> ORGANISM: Homo sapiens
<220> FEATURE:
<221> NAME/KEY: CDS
<222> LOCATION: (75)..(1703)

<400> SEQUENCE: 62

```
ggcgggggag gcgccgggaa gtcgatggcg ccggcggctc ctgcaggagg ccactgtctg       60
cagctcccgt gaag atg tcc act cca gac cca ccc ctg ggc gga act cct       110
              Met Ser Thr Pro Asp Pro Pro Leu Gly Gly Thr Pro
                1               5                   10 cgg cca ggt cct tcc ccg ggc cct ggc cct tcc cct gga gcc atg ctg       158
Arg Pro Gly Pro Ser Pro Gly Pro Gly Pro Ser Pro Gly Ala Met Leu
         15                  20                  25 ggc cct agc ccg ggt ccc tcg ccg ggc tcc gcc cac agc atg atg ggg       206
Gly Pro Ser Pro Gly Pro Ser Pro Gly Ser Ala His Ser Met Met Gly
     30                  35                  40 ccc agc cca ggg ccg ccc tca gca gga cac ccc atc ccc acc cag ggg       254
Pro Ser Pro Gly Pro Pro Ser Ala Gly His Pro Ile Pro Thr Gln Gly
 45                  50                  55                  60 cct gga ggg tac cct cag gac aac atg cac cag atg cac aag ccc atg       302
Pro Gly Gly Tyr Pro Gln Asp Asn Met His Gln Met His Lys Pro Met
                 65                  70                  75 gag tcc atg cat gag aag ggc atg tcg gac gac ccg cgc tac aac cag       350
Glu Ser Met His Glu Lys Gly Met Ser Asp Asp Pro Arg Tyr Asn Gln
             80                  85                  90 atg aaa gga atg ggg atg cgg tca ggg ggc cat gct ggg atg ggg ccc       398
Met Lys Gly Met Gly Met Arg Ser Gly Gly His Ala Gly Met Gly Pro
         95                 100                 105 ccg ccc agc ccc atg gac cag cac tcc caa ggt tac ccc tcg ccc ctg       446
Pro Pro Ser Pro Met Asp Gln His Ser Gln Gly Tyr Pro Ser Pro Leu
    110                 115                 120 ggt ggc tct gag cat gcc tct agt cca gtt cca gcc agt ggc ccg tct       494
Gly Gly Ser Glu His Ala Ser Ser Pro Val Pro Ala Ser Gly Pro Ser
```

-continued

```
              125                 130                 135                 140
tcg ggg ccc cag atg tct tcc ggg cca gga ggt gcc ccg ctg gat ggt           542
Ser Gly Pro Gln Met Ser Ser Gly Pro Gly Gly Ala Pro Leu Asp Gly
                        145                 150                 155 gct gac ccc cag gcc ttg ggg cag cag aac cgg ggc cca acc cca ttt           590
Ala Asp Pro Gln Ala Leu Gly Gln Gln Asn Arg Gly Pro Thr Pro Phe
                160                 165                 170 aac cag aac cag ctg cac cag ctc aga gct cag atc atg gcc tac aag           638
Asn Gln Asn Gln Leu His Gln Leu Arg Ala Gln Ile Met Ala Tyr Lys
                175                 180                 185 atg ctg gcc agg ggg cag ccc ctc ccc gac cac ctg cag atg gcg gtg           686
Met Leu Ala Arg Gly Gln Pro Leu Pro Asp His Leu Gln Met Ala Val
            190                 195                 200 cag ggc aag cgg ccg atg ccc ggg atg cag cag cag atg cca acg cta           734
Gln Gly Lys Arg Pro Met Pro Gly Met Gln Gln Gln Met Pro Thr Leu
205                 210                 215                 220 cct cca ccc tcg gtg tcc gca aca gga ccc ggc cct ggc cct ggc cct           782
Pro Pro Pro Ser Val Ser Ala Thr Gly Pro Gly Pro Gly Pro Gly Pro
                        225                 230                 235 ggc ccc ggc ccg ggt ccc ggc ccg gca cct cca aat tac agc agg cct           830
Gly Pro Gly Pro Gly Pro Gly Pro Ala Pro Pro Asn Tyr Ser Arg Pro
                240                 245                 250 cat ggt atg gga ggg ccc aac atg cct ccc cca gga ccc tcg ggc gtg           878
His Gly Met Gly Gly Pro Asn Met Pro Pro Pro Gly Pro Ser Gly Val
                255                 260                 265 ccc ccc ggg atg cca ggc cag cct cct gga ggg cct ccc aag ccc tgg           926
Pro Pro Gly Met Pro Gly Gln Pro Pro Gly Gly Pro Pro Lys Pro Trp
            270                 275                 280 cct gaa gga ccc atg gcg aat gct gct gcc ccc acg agc acc cct cag           974
Pro Glu Gly Pro Met Ala Asn Ala Ala Ala Pro Thr Ser Thr Pro Gln
285                 290                 295                 300 aag ctg att ccc ccg cag cca acg ggc cgc cct tcc ccc gcg ccc cct          1022
Lys Leu Ile Pro Pro Gln Pro Thr Gly Arg Pro Ser Pro Ala Pro Pro
                        305                 310                 315 gcc gtc cca ccc gcc gcc tcg ccc gtg atg cca ccg cag acc cag tcc          1070
Ala Val Pro Pro Ala Ala Ser Pro Val Met Pro Pro Gln Thr Gln Ser
                320                 325                 330 ccc ggg cag ccg gcc cag ccc gcg ccc atg gtg cca ctg cac cag aag          1118
Pro Gly Gln Pro Ala Gln Pro Ala Pro Met Val Pro Leu His Gln Lys
                335                 340                 345 cag agc cgc atc acc ccc atc cag aag ccg cgg ggc ctc gac cct gtg          1166
Gln Ser Arg Ile Thr Pro Ile Gln Lys Pro Arg Gly Leu Asp Pro Val
            350                 355                 360 gag atc ctg cag gag cgc gag tac agg ctg cag gct cgc atc gca cac          1214
Glu Ile Leu Gln Glu Arg Glu Tyr Arg Leu Gln Ala Arg Ile Ala His
365                 370                 375                 380 cga att cag gaa ctt gaa aac ctt ccc ggg tcc ctg gcc ggg gat ttg          1262
Arg Ile Gln Glu Leu Glu Asn Leu Pro Gly Ser Leu Ala Gly Asp Leu
                        385                 390                 395 cga acc aaa gcg acc att gag ctc aag gcc ctc agg ctg ctg aac ttc          1310
Arg Thr Lys Ala Thr Ile Glu Leu Lys Ala Leu Arg Leu Leu Asn Phe
                400                 405                 410 cag agg cag ctg cgc cag gag gtg gtg gtg tgc atg cgg agg gac aca          1358
Gln Arg Gln Leu Arg Gln Glu Val Val Val Cys Met Arg Arg Asp Thr
            415                 420                 425 gcg ctg gag aca gcc ctc aat gct aag gcc tac aag cgc agc aag cgc          1406
Ala Leu Glu Thr Ala Leu Asn Ala Lys Ala Tyr Lys Arg Ser Lys Arg
430                 435                 440 cag tcc ctg cgc gag gcc cgc atc act gag aag ctg gag aag cag cag          1454
```

```
Gln Ser Leu Arg Glu Ala Arg Ile Thr Glu Lys Leu Glu Lys Gln Gln
445                 450                 455                 460 aag atc gag cag gag cgc aag cgc cgg cag aag cac cag gaa tac ctc        1502
Lys Ile Glu Gln Glu Arg Lys Arg Arg Gln Lys His Gln Glu Tyr Leu
                465                 470                 475 aat agc att ctc cag cat gcc aag gat ttc aag gaa tat cac aga tcc        1550
Asn Ser Ile Leu Gln His Ala Lys Asp Phe Lys Glu Tyr His Arg Ser
            480                 485                 490 gtc aca ggc aaa atc cag aag ctg acc aag gca gtg gcc acg tac cat        1598
Val Thr Gly Lys Ile Gln Lys Leu Thr Lys Ala Val Ala Thr Tyr His
        495                 500                 505 gcc aac acg gag cgg gag cag aag aaa gag aac gag cgg atc gag aag        1646
Ala Asn Thr Glu Arg Glu Gln Lys Lys Glu Asn Glu Arg Ile Glu Lys
    510                 515                 520 gag cgc atg cgg agg ctc atg gct gaa gat gag gag ggg tac cgc aag        1694
Glu Arg Met Arg Arg Leu Met Ala Glu Asp Glu Glu Gly Tyr Arg Lys
525                 530                 535                 540 ctc atc gac tagaagaagg acaagcgcct ggcctacctc ttgcagcaga               1743
Leu Ile Asp cagacgagta cgtggctaac ctcacggagc tggtgcggca gcacaaggct gcccaggtcg     1803
ccaaggagaa aaagaagaaa aagaaaaaga agaaggcaga aaatgcagaa ggacagacgc     1863
ctgccattgg gccggatggc gagcctctag acgagaccag ccagatgagc gacctcccgg     1923
tgaaggtgat ccacgtggag agtgggaaga tcctcacagg cacagatgcc cccaaagccg     1983
ggcagctgga ggcctggctc gagatgaacc cggggtatga agtagctccg aggtctgata     2043
gtgaagaaag tggctcagaa gaagaggaag aggaggagga ggaagagcag ccgcaggcag     2103
cacagcctcc caccctgccc gtggaggaga agaagaagat tccagatcca gacagcgatg     2163
acgtctctga ggtggacgcg cggcacatca ttgagaatgc caagcaagat gtcgatgatg     2223
aatatggcgt gtcccaggcc cttgcacgtg gcctgcagtc ctactatgcc gtggcccatg     2283
ctgtcactga gagagtggac aagcagtcag cgcttatggt caatggtgtc ctcaaacagt     2343
accagatcaa aggtttggag tggctggtgt ccctgtacaa caacaacctg aacggcatcc     2403
tggccgacga gatgggcctg ggaagaccga tccagaccat cgcgctcatc acgtacctca     2463
tggagcacaa acgcatcaat gggcccttcc tcatcatcgt gcctctctca acgctgtcca     2523
actgggcgta cgagtttgac aagtgggccc cctccgtggt gaaggtgtct tacaagggat     2583
ccccagcagc aagacgggcc tttgtccccc agctccggag tgggaagttc aacgtcttgc     2643
tgacgacgta cgagtacatc atcaaagaca gcacatcct cgccaagatc cgttggaagt     2703
acatgattgt ggacgaaggt caccgcatga agaaccacca ctgcaagctg acgcaggtgc     2763
tcaacacgca ctatgtggca ccccgccgcc tgctgctgac gggcacaccg ctgcagaaca     2823
agcttcccga gctctgggcg ctgctcaact tcctgctgcc accatcttc aagagctgca     2883 gcaccttcga gcagtggttt aacgcaccct tgccatgac cggggaaaag gtggacctga     2943
atgaggagga aaccattctc atcatccggc gtctccacaa agtgctgcgg cccttcttgc     3003
tccgacgact caagaaggaa gtcgaggccc agttgcccga aaaggtggag tacgtcatca     3063
agtgcgacat gtctgcgctg cagcgagtgc tctaccgcca catgcaggcc aagggcgtgc     3123
tgctgactga tggctccgag aaggacaaga agggcaaagg cggcaccaag accctgatga     3183
acaccatcat gcagctgcgg aagatctgca accaccccta catgttccag cacatcgagg     3243 agtcctttc cgagcacttg gggttcactg gcggcattgt ccagggctg gacctgtacc     3303 gagcctcggg taaatttgag cttcttgata gaattcttcc caaactccga gcaaccaacc     3363
```

```
acaaagtgct gctgttctgc caaatgacct ccctcatgac catcatggaa gattactttg   3423
cgtatcgcgg cttaaaatac ctcaggcttg atggaaccac gaaggcggag gaccggggca   3483
tgctgctgaa aaccttcaac gagcccggct ctgagtactt catcttcctg ctcagcaccc   3543
gggctggggg gctcggcctg aacctccagt cggcagacac tgtgatcatt tttgacagcg   3603
actggaatcc tcaccaggac ctgcaagcgc aggaccgagc ccaccgcatc gggcagcaga   3663
acgaggtgcg tgtgctccgc ctctgcaccg tcaacagcgt ggaggagaag atcctagctg   3723
cagccaagta caagctcaac gtggaccaga aggtgatcca ggccgcatg ttcgaccaga    3783 agtcctccag ccatgagcgg cgcgccttcc tgcaggccat cctggagcac gaggagcagg   3843
atgagagcag acactgcagc acgggcagcg gcagtgccag cttcgcccac actgcccctc   3903
cgccagcggg cgtcaacccc gacttggagg agccacctct aaaggaggaa gacgaggtgc   3963
ccgacgacga gaccgtcaac cagatgatcg cccggcacga ggaggagttt gatctgttca   4023
tgcgcatgga cctggaccgc aggcgcgagg aggcccgcaa ccccaagcgg aagccgcgcc   4083
tcatggagga ggacgagctc ccctcgtgga tcatcaagga cgacgcggag gtggagcggc   4143
tgacctgtga ggaggaggag gagaagatgt tcggccgtgg ctcccgccac cgcaaggagg   4203
tggactacag cgactcactg acggagaagc agtggctcaa ggccatcgag gagggcacgc   4263
tggaggagat cgaagaggag gtccggcaga agaaatcatc acggaagcgc aagcgagaca   4323
gcgacgccgg ctcctccacc ccgaccacca gcacccgcag ccgcgacaag gacgacgaga   4383
gcaagaagca gaagaagcgc gggcggccgc ctgccgagaa actctcccct aacccaccca   4443
acctcaccaa gaagatgaag aagattgtgg atgccgtgat caagtacaag gacagcagca   4503
gtggacgtca gctcagcgag gtcttcatcc agctgccctc gcgaaaggag ctgcccgagt   4563
actacgagct catccgcaag cccgtggact caagaagat aaaggagcgc attcgcaacc    4623
acaagtaccg cagcctcaac gacctagaga aggacgtcat gctcctgtgc cagaacgcac   4683 agacccttcaa cctggaggc tccctgatct atgaagactc catcgtcttg cagtcggtct    4743
tcaccagcgt gcggcagaaa atcgagaagg aggatgacag tgaaggcgag gagagtgagg   4803
aggaggaaga gggcgaggag gaaggctccg aatccgaatc tcggtccgtc aaagtgaaga   4863
tcaagcttgg ccggaaggag aaggcacagg accggctgaa gggcggccgg cggcggccga   4923
gccgagggtc ccgagccaag ccggtcgtga gtgacgatga cagtgaggag gaacaagagg   4983
aggaccgctc aggaagtggc agcgaagaag actgagcccc gacattccag tctcgacccc   5043 gagccctcg ttccagagct gagatggcat aggccttagc agtaacgggt agcagcagat     5103
gtagtttcag acttggagta aaactgtata aacaaaagaa tcttccatat ttatacagca   5163
gagaagctgt aggactgttt gtgactggcc ctgtcctggc atcagtagca tctgtaacag   5223
cattaactgt cttaaagaga gagagagaga attccgaatt ggggaacaca cgatacctgt   5283 tttctttc cgttgctggc agtactgttg cgccgcagtt tggagtcact gtagttaagt      5343
gtggatgcat gtgcgtcacc gtccactcct cctactgtat tttattggac aggtcagact   5403 cgccggggc ccggcgaggg tatgtcagtg tcactggatg tcaaacagta ataaattaaa     5463
ccaacaac                                                            5471
```

<210> SEQ ID NO 63
<211> LENGTH: 543
<212> TYPE: PRT
<213> ORGANISM: Homo sapiens -continued

```
<400> SEQUENCE: 63

Met Ser Thr Pro Asp Pro Pro Leu Gly Gly Thr Pro Arg Pro Gly Pro
 1               5                  10                  15

Ser Pro Gly Pro Gly Pro Ser Pro Gly Ala Met Leu Gly Pro Ser Pro
                20                  25                  30

Gly Pro Ser Pro Gly Ser Ala His Ser Met Met Gly Pro Ser Pro Gly
            35                  40                  45

Pro Pro Ser Ala Gly His Pro Ile Pro Thr Gln Gly Pro Gly Gly Tyr
        50                  55                  60

Pro Gln Asp Asn Met His Gln Met His Lys Pro Met Glu Ser Met His
65                  70                  75                  80

Glu Lys Gly Met Ser Asp Asp Pro Arg Tyr Asn Gln Met Lys Gly Met
                85                  90                  95

Gly Met Arg Ser Gly Gly His Ala Gly Met Gly Pro Pro Ser Pro
            100                 105                 110

Met Asp Gln His Ser Gln Gly Tyr Pro Ser Pro Leu Gly Gly Ser Glu
            115                 120                 125

His Ala Ser Ser Pro Val Pro Ala Ser Gly Pro Ser Ser Gly Pro Gln
        130                 135                 140

Met Ser Ser Gly Pro Gly Gly Ala Pro Leu Asp Gly Ala Asp Pro Gln
145                 150                 155                 160

Ala Leu Gly Gln Gln Asn Arg Gly Pro Thr Pro Phe Asn Gln Asn Gln
                165                 170                 175

Leu His Gln Leu Arg Ala Gln Ile Met Ala Tyr Lys Met Leu Ala Arg
            180                 185                 190

Gly Gln Pro Leu Pro Asp His Leu Gln Met Ala Val Gln Gly Lys Arg
        195                 200                 205

Pro Met Pro Gly Met Gln Gln Gln Met Pro Thr Leu Pro Pro Pro Ser
210                 215                 220

Val Ser Ala Thr Gly Pro Gly Pro Gly Pro Gly Pro Gly Pro Gly Pro
225                 230                 235                 240

Gly Pro Gly Pro Ala Pro Pro Asn Tyr Ser Arg Pro His Gly Met Gly
                245                 250                 255

Gly Pro Asn Met Pro Pro Pro Gly Pro Ser Gly Val Pro Pro Gly Met
            260                 265                 270

Pro Gly Gln Pro Pro Gly Gly Pro Pro Lys Pro Trp Pro Glu Gly Pro
        275                 280                 285

Met Ala Asn Ala Ala Pro Thr Ser Thr Pro Gln Lys Leu Ile Pro
290                 295                 300

Pro Gln Pro Thr Gly Arg Pro Ser Pro Ala Pro Pro Ala Val Pro Pro
305                 310                 315                 320

Ala Ala Ser Pro Val Met Pro Pro Gln Thr Gln Ser Pro Gly Gln Pro
                325                 330                 335

Ala Gln Pro Ala Pro Met Val Pro Leu His Gln Lys Gln Ser Arg Ile
            340                 345                 350

Thr Pro Ile Gln Lys Pro Arg Gly Leu Asp Pro Val Glu Ile Leu Gln
        355                 360                 365

Glu Arg Glu Tyr Arg Leu Gln Ala Arg Ile Ala His Arg Ile Gln Glu
    370                 375                 380

Leu Glu Asn Leu Pro Gly Ser Leu Ala Gly Asp Leu Arg Thr Lys Ala
385                 390                 395                 400

Thr Ile Glu Leu Lys Ala Leu Arg Leu Leu Asn Phe Gln Arg Gln Leu
                405                 410                 415
```

```
Arg Gln Glu Val Val Cys Met Arg Arg Asp Thr Ala Leu Glu Thr
            420             425             430

Ala Leu Asn Ala Lys Ala Tyr Lys Arg Ser Lys Arg Gln Ser Leu Arg
        435             440             445

Glu Ala Arg Ile Thr Glu Lys Leu Glu Lys Gln Gln Lys Ile Glu Gln
    450             455             460

Glu Arg Lys Arg Arg Gln Lys His Gln Glu Tyr Leu Asn Ser Ile Leu
465             470             475             480

Gln His Ala Lys Asp Phe Lys Glu Tyr His Arg Ser Val Thr Gly Lys
            485             490             495

Ile Gln Lys Leu Thr Lys Ala Val Ala Thr Tyr His Ala Asn Thr Glu
            500             505             510

Arg Glu Gln Lys Lys Glu Asn Glu Arg Ile Glu Lys Glu Arg Met Arg
        515             520             525

Arg Leu Met Ala Glu Asp Glu Glu Gly Tyr Arg Lys Leu Ile Asp
        530             535             540

<210> SEQ ID NO 64
<211> LENGTH: 5567
<212> TYPE: DNA
<213> ORGANISM: Homo sapiens
<220> FEATURE:
<221> NAME/KEY: CDS
<222> LOCATION: (75)..(5111)
<220> FEATURE:
<221> NAME/KEY: conflict
<222> LOCATION: (1780)
<223> OTHER INFORMATION: GenBank Accession No. U29175 shows a C at this
      position (position 1784 in BenBank) rather than
      the G shown here.
<220> FEATURE:
<221> NAME/KEY: allele
<222> LOCATION: (26)
<223> OTHER INFORMATION: Polymorphism of either T or C in this noncoding
      region.
<220> FEATURE:
<221> NAME/KEY: allele
<222> LOCATION: (1583)
<223> OTHER INFORMATION: Polymorphism of A or G resulting in a silent
      mutation.
<220> FEATURE:
<221> NAME/KEY: allele
<222> LOCATION: (1598)
<223> OTHER INFORMATION: Polymorphism of T or C resulting in a silent
      mutation.
<220> FEATURE:
<221> NAME/KEY: allele
<222> LOCATION: (1892)
<223> OTHER INFORMATION: Polymorphism of A or G resulting in a silent
      mutation.
<220> FEATURE:
<221> NAME/KEY: misc_feature
<222> LOCATION: (4245)..(4340)
<223> OTHER INFORMATION: 96 basepair insertion compared to SEQ ID NO:1
      as a result of alternate splicing.

<400> SEQUENCE: 64
ggcgggggag gcgccgggaa gtcgatggcg ccggcggctc ctgcaggagg ccactgtctg      60
cagctcccgt gaag atg tcc act cca gac cca ccc ctg ggc gga act cct     110
              Met Ser Thr Pro Asp Pro Pro Leu Gly Gly Thr Pro
                1               5                  10 cgg cca ggt cct tcc ccg ggc cct ggc cct tcc cct gga gcc atg ctg     158
Arg Pro Gly Pro Ser Pro Gly Pro Gly Pro Ser Pro Gly Ala Met Leu
        15                  20                  25 ggc cct agc ccg ggt ccc tcg ccg ggc tcc gcc cac agc atg atg ggg     206
Gly Pro Ser Pro Gly Pro Ser Pro Gly Ser Ala His Ser Met Met Gly
```

```
                30                    35                    40
ccc agc cca ggg ccg ccc tca gca gga cac ccc atc ccc acc cag ggg        254
Pro Ser Pro Gly Pro Pro Ser Ala Gly His Pro Ile Pro Thr Gln Gly
 45                  50                  55                  60 cct gga ggg tac cct cag gac aac atg cac cag atg cac aag ccc atg        302
Pro Gly Gly Tyr Pro Gln Asp Asn Met His Gln Met His Lys Pro Met
                 65                  70                  75 gag tcc atg cat gag aag ggc atg tcg gac gac ccg cgc tac aac cag        350
Glu Ser Met His Glu Lys Gly Met Ser Asp Asp Pro Arg Tyr Asn Gln
             80                  85                  90 atg aaa gga atg ggg atg cgg tca ggg ggc cat gct ggg atg ggg ccc        398
Met Lys Gly Met Gly Met Arg Ser Gly Gly His Ala Gly Met Gly Pro
         95                 100                 105 ccg ccc agc ccc atg gac cag cac tcc caa ggt tac ccc tcg ccc ctg        446
Pro Pro Ser Pro Met Asp Gln His Ser Gln Gly Tyr Pro Ser Pro Leu
    110                 115                 120 ggt ggc tct gag cat gcc tct agt cca gtt cca gcc agt ggc ccg tct        494
Gly Gly Ser Glu His Ala Ser Ser Pro Val Pro Ala Ser Gly Pro Ser
125                 130                 135                 140 tcg ggg ccc cag atg tct tcc ggg cca gga ggt gcc ccg ctg gat ggt        542
Ser Gly Pro Gln Met Ser Ser Gly Pro Gly Gly Ala Pro Leu Asp Gly
                145                 150                 155 gct gac ccc cag gcc ttg ggg cag cag aac cgg ggc cca acc cca ttt        590
Ala Asp Pro Gln Ala Leu Gly Gln Gln Asn Arg Gly Pro Thr Pro Phe
            160                 165                 170 aac cag aac cag ctg cac cag ctc aga gct cag atc atg gcc tac aag        638
Asn Gln Asn Gln Leu His Gln Leu Arg Ala Gln Ile Met Ala Tyr Lys
        175                 180                 185 atg ctg gcc agg ggg cag ccc ctc ccc gac cac ctg cag atg gcg gtg        686
Met Leu Ala Arg Gly Gln Pro Leu Pro Asp His Leu Gln Met Ala Val
    190                 195                 200 cag ggc aag cgg ccg atg ccc ggg atg cag cag cag atg cca acg cta        734
Gln Gly Lys Arg Pro Met Pro Gly Met Gln Gln Gln Met Pro Thr Leu
205                 210                 215                 220 cct cca ccc tcg gtg tcc gca aca gga ccc ggc cct ggc cct ggc cct        782
Pro Pro Pro Ser Val Ser Ala Thr Gly Pro Gly Pro Gly Pro Gly Pro
                225                 230                 235 ggc ccc ggc ccg ggt ccc ggc ccg gca cct cca aat tac agc agg cct        830
Gly Pro Gly Pro Gly Pro Gly Pro Ala Pro Pro Asn Tyr Ser Arg Pro
            240                 245                 250 cat ggt atg gga ggg ccc aac atg cct ccc cca gga ccc tcg ggc gtg        878
His Gly Met Gly Gly Pro Asn Met Pro Pro Pro Gly Pro Ser Gly Val
        255                 260                 265 ccc ccc ggg atg cca ggc cag cct cct gga ggg cct ccc aag ccc tgg        926
Pro Pro Gly Met Pro Gly Gln Pro Pro Gly Gly Pro Pro Lys Pro Trp
    270                 275                 280 cct gaa gga ccc atg gcg aat gct gct gcc ccc acg agc acc cct cag        974
Pro Glu Gly Pro Met Ala Asn Ala Ala Ala Pro Thr Ser Thr Pro Gln
285                 290                 295                 300 aag ctg att ccc ccg cag cca acg ggc cgc cct tcc ccc gcg ccc cct        1022
Lys Leu Ile Pro Pro Gln Pro Thr Gly Arg Pro Ser Pro Ala Pro Pro
                305                 310                 315 gcc gtc cca ccc gcc gcc tcg ccc gtg atg cca ccg cag acc cag tcc        1070
Ala Val Pro Pro Ala Ala Ser Pro Val Met Pro Pro Gln Thr Gln Ser
            320                 325                 330 ccc ggg cag ccg gcc cag ccc gcg ccc atg gtg cca ctg cac cag aag        1118
Pro Gly Gln Pro Ala Gln Pro Ala Pro Met Val Pro Leu His Gln Lys
        335                 340                 345 cag agc cgc atc acc ccc atc cag aag ccg cgg ggc ctc gac cct gtg        1166
```

```
                                                                    -continued Gln Ser Arg Ile Thr Pro Ile Gln Lys Pro Arg Gly Leu Asp Pro Val
    350                 355                 360 gag atc ctg cag gag cgc gag tac agg ctg cag gct cgc atc gca cac       1214
Glu Ile Leu Gln Glu Arg Glu Tyr Arg Leu Gln Ala Arg Ile Ala His
365                 370                 375                 380 cga att cag gaa ctt gaa aac ctt ccc ggg tcc ctg gcc ggg gat ttg       1262
Arg Ile Gln Glu Leu Glu Asn Leu Pro Gly Ser Leu Ala Gly Asp Leu
                385                 390                 395 cga acc aaa gcg acc att gag ctc aag gcc ctc agg ctg ctc aac ttc       1310
Arg Thr Lys Ala Thr Ile Glu Leu Lys Ala Leu Arg Leu Leu Asn Phe
            400                 405                 410 cag agg cag ctg cgc cag gag gtg gtg gtg tgc atg cgg agg gac aca       1358
Gln Arg Gln Leu Arg Gln Glu Val Val Val Cys Met Arg Arg Asp Thr
        415                 420                 425 gcg ctg gag aca gcc ctc aat gct aag gcc tac aag cgc agc aag cgc       1406
Ala Leu Glu Thr Ala Leu Asn Ala Lys Ala Tyr Lys Arg Ser Lys Arg
    430                 435                 440 cag tcc ctg cgc gag gcc cgc atc act gag aag ctg gag aag cag cag       1454
Gln Ser Leu Arg Glu Ala Arg Ile Thr Glu Lys Leu Glu Lys Gln Gln
445                 450                 455                 460 aag atc gag cag gag cgc aag cgc cgg cag aag cac cag gaa tac ctc       1502
Lys Ile Glu Gln Glu Arg Lys Arg Arg Gln Lys His Gln Glu Tyr Leu
                465                 470                 475 aat agc att ctc cag cat gcc aag gat ttc aag gaa tat cac aga tcc       1550
Asn Ser Ile Leu Gln His Ala Lys Asp Phe Lys Glu Tyr His Arg Ser
            480                 485                 490 gtc aca ggc aaa atc cag aag ctg acc aag gca gtg gcc acg tac cat       1598
Val Thr Gly Lys Ile Gln Lys Leu Thr Lys Ala Val Ala Thr Tyr His
        495                 500                 505 gcc aac acg gag cgg gag cag aag aaa gag aac gag cgg atc gag aag       1646
Ala Asn Thr Glu Arg Glu Gln Lys Lys Glu Asn Glu Arg Ile Glu Lys
    510                 515                 520 gag cgc atg cgg agg ctc atg gct gaa gat gag gag ggg tac cgc aag       1694
Glu Arg Met Arg Arg Leu Met Ala Glu Asp Glu Glu Gly Tyr Arg Lys
525                 530                 535                 540 ctc atc gac cag aag aag gac aag cgc ctg gcc tac ctc ttg cag cag       1742
Leu Ile Asp Gln Lys Lys Asp Lys Arg Leu Ala Tyr Leu Leu Gln Gln
                545                 550                 555 aca gac gag tac gtg gct aac ctc acg gag ctg gtg cgg cag cac aag       1790
Thr Asp Glu Tyr Val Ala Asn Leu Thr Glu Leu Val Arg Gln His Lys
            560                 565                 570 gct gcc cag gtc gcc aag gag aaa aag aag aaa aag aaa aag aag aag       1838
Ala Ala Gln Val Ala Lys Glu Lys Lys Lys Lys Lys Lys Lys Lys Lys
        575                 580                 585 gca gaa aat gca gaa gga cag acg cct gcc att ggg ccg gat ggc gag       1886
Ala Glu Asn Ala Glu Gly Gln Thr Pro Ala Ile Gly Pro Asp Gly Glu
    590                 595                 600 cct cta gac gag acc agc cag atg agc gac ctc ccg gtg aag gtg atc       1934
Pro Leu Asp Glu Thr Ser Gln Met Ser Asp Leu Pro Val Lys Val Ile
605                 610                 615                 620 cac gtg gag agt ggg aag atc ctc aca ggc aca gat gcc ccc aaa gcc       1982
His Val Glu Ser Gly Lys Ile Leu Thr Gly Thr Asp Ala Pro Lys Ala
                625                 630                 635 ggg cag ctg gag gcc tgg ctc gag atg aac ccg ggg tat gaa gta gct       2030
Gly Gln Leu Glu Ala Trp Leu Glu Met Asn Pro Gly Tyr Glu Val Ala
            640                 645                 650 ccg agg tct gat agt gaa gaa agt ggc tca gaa gaa gag gaa gag gag       2078
Pro Arg Ser Asp Ser Glu Glu Ser Gly Ser Glu Glu Glu Glu Glu Glu
        655                 660                 665
```

```
                                                            -continued gag gag gaa gag cag ccg cag gca gca cag cct ccc acc ctg ccc gtg      2126
Glu Glu Glu Glu Gln Pro Gln Ala Ala Gln Pro Pro Thr Leu Pro Val
        670                 675                 680 gag gag aag aag aag att cca gat cca gac agc gat gac gtc tct gag      2174
Glu Glu Lys Lys Lys Ile Pro Asp Pro Asp Ser Asp Asp Val Ser Glu
685                 690                 695                 700 gtg gac gcg cgg cac atc att gag aat gcc aag caa gat gtc gat gat      2222
Val Asp Ala Arg His Ile Ile Glu Asn Ala Lys Gln Asp Val Asp Asp
                705                 710                 715 gaa tat ggc gtg tcc cag gcc ctt gca cgt ggc ctg cag tcc tac tat      2270
Glu Tyr Gly Val Ser Gln Ala Leu Ala Arg Gly Leu Gln Ser Tyr Tyr
        720                 725                 730 gcc gtg gcc cat gct gtc act gag aga gtg gac aag cag tca gcg ctt      2318
Ala Val Ala His Ala Val Thr Glu Arg Val Asp Lys Gln Ser Ala Leu
            735                 740                 745 atg gtc aat ggt gtc ctc aaa cag tac cag atc aaa ggt ttg gag tgg      2366
Met Val Asn Gly Val Leu Lys Gln Tyr Gln Ile Lys Gly Leu Glu Trp
750                 755                 760 ctg gtg tcc ctg tac aac aac aac ctg aac ggc atc ctg gcc gac gag      2414
Leu Val Ser Leu Tyr Asn Asn Asn Leu Asn Gly Ile Leu Ala Asp Glu
765                 770                 775                 780 atg ggc ctg ggg aag acc atc cag acc atc gcg ctc atc acg tac ctc      2462
Met Gly Leu Gly Lys Thr Ile Gln Thr Ile Ala Leu Ile Thr Tyr Leu
                785                 790                 795 atg gag cac aaa cgc atc aat ggg ccc ttc ctc atc atc gtg cct ctc      2510
Met Glu His Lys Arg Ile Asn Gly Pro Phe Leu Ile Ile Val Pro Leu
        800                 805                 810 tca acg ctg tcc aac tgg gcg tac gag ttt gac aag tgg gcc ccc tcc      2558
Ser Thr Leu Ser Asn Trp Ala Tyr Glu Phe Asp Lys Trp Ala Pro Ser
            815                 820                 825 gtg gtg aag gtg tct tac aag gga tcc cca gca gca aga cgg gcc ttt      2606
Val Val Lys Val Ser Tyr Lys Gly Ser Pro Ala Ala Arg Arg Ala Phe
830                 835                 840 gtc ccc cag ctc cgg agt ggg aag ttc aac gtc ttg ctg acg acg tac      2654
Val Pro Gln Leu Arg Ser Gly Lys Phe Asn Val Leu Leu Thr Thr Tyr
845                 850                 855                 860 gag tac atc atc aaa gac aag cac atc ctc gcc aag atc cgt tgg aag      2702
Glu Tyr Ile Ile Lys Asp Lys His Ile Leu Ala Lys Ile Arg Trp Lys
                865                 870                 875 tac atg att gtg gac gaa ggt cac cgc atg aag aac cac cac tgc aag      2750
Tyr Met Ile Val Asp Glu Gly His Arg Met Lys Asn His His Cys Lys
        880                 885                 890 ctg acg cag gtg ctc aac acg cac tat gtg gca ccc cgc cgc ctg ctg      2798
Leu Thr Gln Val Leu Asn Thr His Tyr Val Ala Pro Arg Arg Leu Leu
            895                 900                 905 ctg acg ggc aca ccg ctg cag aac aag ctt ccc gag ctc tgg gcg ctg      2846
Leu Thr Gly Thr Pro Leu Gln Asn Lys Leu Pro Glu Leu Trp Ala Leu
910                 915                 920 ctc aac ttc ctg ctg ccc acc atc ttc aag agc tgc agc acc ttc gag      2894
Leu Asn Phe Leu Leu Pro Thr Ile Phe Lys Ser Cys Ser Thr Phe Glu
925                 930                 935                 940 cag tgg ttt aac gca ccc ttt gcc atg acc ggg gaa aag gtg gac ctg      2942
Gln Trp Phe Asn Ala Pro Phe Ala Met Thr Gly Glu Lys Val Asp Leu
                945                 950                 955 aat gag gag gaa acc att ctc atc atc cgg cgt ctc cac aaa gtg ctg      2990
Asn Glu Glu Glu Thr Ile Leu Ile Ile Arg Arg Leu His Lys Val Leu
        960                 965                 970 cgg ccc ttc ttg ctc cga cga ctc aag aag gaa gtc gag gcc cag ttg      3038
Arg Pro Phe Leu Leu Arg Arg Leu Lys Lys Glu Val Glu Ala Gln Leu
            975                 980                 985
```

```
ccc gaa aag gtg gag tac gtc atc aag tgc gac atg tct gcg ctg cag      3086
Pro Glu Lys Val Glu Tyr Val Ile Lys Cys Asp Met Ser Ala Leu Gln
    990                 995                 1000 cga gtg ctc tac cgc cac atg cag gcc aag ggc gtg ctg ctg act gat      3134
Arg Val Leu Tyr Arg His Met Gln Ala Lys Gly Val Leu Leu Thr Asp
1005                1010                 1015                1020 ggc tcc gag aag gac aag aag ggc aaa ggc ggc acc aag acc ctg atg      3182
Gly Ser Glu Lys Asp Lys Lys Gly Lys Gly Gly Thr Lys Thr Leu Met
                1025                1030                1035 aac acc atc atg cag ctg cgg aag atc tgc aac cac ccc tac atg ttc      3230
Asn Thr Ile Met Gln Leu Arg Lys Ile Cys Asn His Pro Tyr Met Phe
            1040                1045                1050 cag cac atc gag gag tcc ttt tcc gag cac ttg ggg ttc act ggc ggc      3278
Gln His Ile Glu Glu Ser Phe Ser Glu His Leu Gly Phe Thr Gly Gly
        1055                1060                1065 att gtc caa ggg ctg gac ctg tac cga gcc tcg ggt aaa ttt gag ctt      3326
Ile Val Gln Gly Leu Asp Leu Tyr Arg Ala Ser Gly Lys Phe Glu Leu
    1070                1075                1080 ctt gat aga att ctt ccc aaa ctc cga gca acc aac cac aaa gtg ctg      3374
Leu Asp Arg Ile Leu Pro Lys Leu Arg Ala Thr Asn His Lys Val Leu
1085                1090                1095                1100 ctg ttc tgc caa atg acc tcc ctc atg acc atc atg gaa gat tac ttt      3422
Leu Phe Cys Gln Met Thr Ser Leu Met Thr Ile Met Glu Asp Tyr Phe
                1105                1110                1115 gcg tat cgc ggc ttt aaa tac ctc agg ctt gat gga acc acg aag gcg      3470
Ala Tyr Arg Gly Phe Lys Tyr Leu Arg Leu Asp Gly Thr Thr Lys Ala
            1120                1125                1130 gag gac cgg ggc atg ctg ctg aaa acc ttc aac gag ccc ggc tct gag      3518
Glu Asp Arg Gly Met Leu Leu Lys Thr Phe Asn Glu Pro Gly Ser Glu
        1135                1140                1145 tac ttc atc ttc ctg ctc agc acc cgg gct ggg ggg ctc ggc ctg aac      3566
Tyr Phe Ile Phe Leu Leu Ser Thr Arg Ala Gly Gly Leu Gly Leu Asn
    1150                1155                1160 ctc cag tcg gca gac act gtg atc att ttt gac agc gac tgg aat cct      3614
Leu Gln Ser Ala Asp Thr Val Ile Ile Phe Asp Ser Asp Trp Asn Pro
1165                1170                1175                1180 cac cag gac ctg caa gcg cag gac cga gcc cac cgc atc ggg cag cag      3662
His Gln Asp Leu Gln Ala Gln Asp Arg Ala His Arg Ile Gly Gln Gln
                1185                1190                1195 aac gag gtg cgt gtg ctc cgc ctc tgc acc gtc aac agc gtg gag gag      3710
Asn Glu Val Arg Val Leu Arg Leu Cys Thr Val Asn Ser Val Glu Glu
            1200                1205                1210 aag atc cta gct gca gcc aag tac aag ctc aac gtg gac cag aag gtg      3758
Lys Ile Leu Ala Ala Ala Lys Tyr Lys Leu Asn Val Asp Gln Lys Val
        1215                1220                1225 atc cag gcc ggc atg ttc gac cag aag tcc tcc agc cat gag cgg cgc      3806
Ile Gln Ala Gly Met Phe Asp Gln Lys Ser Ser Ser His Glu Arg Arg
    1230                1235                1240 gcc ttc ctg cag gcc atc ctg gag cac gag gag cag gat gag agc aga      3854
Ala Phe Leu Gln Ala Ile Leu Glu His Glu Glu Gln Asp Glu Ser Arg
1245                1250                1255                1260 cac tgc agc acg ggc agc ggc agt gcc agc ttc gcc cac act gcc cct      3902
His Cys Ser Thr Gly Ser Gly Ser Ala Ser Phe Ala His Thr Ala Pro
                1265                1270                1275 ccg cca gcg ggc gtc aac ccc gac ttg gag gag cca cct cta aag gag      3950
Pro Pro Ala Gly Val Asn Pro Asp Leu Glu Glu Pro Pro Leu Lys Glu
            1280                1285                1290 gaa gac gag gtg ccc gac gac gag acc gtc aac cag atg atc gcc cgg      3998
Glu Asp Glu Val Pro Asp Asp Glu Thr Val Asn Gln Met Ile Ala Arg
```

-continued

```
           1295                1300                1305
cac gag gag gag ttt gat ctg ttc atg cgc atg gac ctg gac cgc agg    4046
His Glu Glu Glu Phe Asp Leu Phe Met Arg Met Asp Leu Asp Arg Arg
   1310                1315                1320 cgc gag gag gcc cgc aac ccc aag cgg aag ccg cgc ctc atg gag gag    4094
Arg Glu Glu Ala Arg Asn Pro Lys Arg Lys Pro Arg Leu Met Glu Glu
1325                1330                1335                1340 gac gag ctc ccc tcg tgg atc atc aag gac gac gcg gag gtg gag cgg    4142
Asp Glu Leu Pro Ser Trp Ile Ile Lys Asp Asp Ala Glu Val Glu Arg
           1345                1350                1355 ctg acc tgt gag gag gag gag gag aag atg ttc ggc cgt ggc tcc cgc    4190
Leu Thr Cys Glu Glu Glu Glu Glu Lys Met Phe Gly Arg Gly Ser Arg
       1360                1365                1370 cac cgc aag gag gtg gac tac agc gac tca ctg acg gag aag cag tgg    4238
His Arg Lys Glu Val Asp Tyr Ser Asp Ser Leu Thr Glu Lys Gln Trp
   1375                1380                1385 ctc aag aaa att aca gga aaa gat atc cat gac aca gcc agc agt gtg    4286
Leu Lys Lys Ile Thr Gly Lys Asp Ile His Asp Thr Ala Ser Ser Val
1390                1395                1400 gca cgt ggg cta caa ttc cag cgt ggc ctt cag ttc tgc aca cgt gcg    4334
Ala Arg Gly Leu Gln Phe Gln Arg Gly Leu Gln Phe Cys Thr Arg Ala
1405                1410                1415                1420 tca aag gcc atc gag gag ggc acg ctg gag gag atc gaa gag gag gtc    4382
Ser Lys Ala Ile Glu Glu Gly Thr Leu Glu Glu Ile Glu Glu Glu Val
           1425                1430                1435 cgg cag aag aaa tca tca cgg aag cgc aag cga gac agc gac gcc ggc    4430
Arg Gln Lys Lys Ser Ser Arg Lys Arg Lys Arg Asp Ser Asp Ala Gly
       1440                1445                1450 tcc tcc acc ccg acc acc agc acc cgc agc cgc gac aag gac gac gag    4478
Ser Ser Thr Pro Thr Thr Ser Thr Arg Ser Arg Asp Lys Asp Asp Glu
   1455                1460                1465 agc aag aag cag aag aag cgc ggg cgg ccg cct gcc gag aaa ctc tcc    4526
Ser Lys Lys Gln Lys Lys Arg Gly Arg Pro Pro Ala Glu Lys Leu Ser
1470                1475                1480 cct aac cca ccc aac ctc acc aag aag atg aag aag att gtg gat gcc    4574
Pro Asn Pro Pro Asn Leu Thr Lys Lys Met Lys Lys Ile Val Asp Ala
1485                1490                1495                1500 gtg atc aag tac aag gac agc agc agt gga cgt cag ctc agc gag gtc    4622
Val Ile Lys Tyr Lys Asp Ser Ser Ser Gly Arg Gln Leu Ser Glu Val
           1505                1510                1515 ttc atc cag ctg ccc tcg cga aag gag ctg ccc gag tac tac gag ctc    4670
Phe Ile Gln Leu Pro Ser Arg Lys Glu Leu Pro Glu Tyr Tyr Glu Leu
       1520                1525                1530 atc cgc aag ccc gtg gac ttc aag aag ata aag gag cgc att cgc aac    4718
Ile Arg Lys Pro Val Asp Phe Lys Lys Ile Lys Glu Arg Ile Arg Asn
   1535                1540                1545 cac aag tac cgc agc ctc aac gac cta gag aag gac gtc atg ctc ctg    4766
His Lys Tyr Arg Ser Leu Asn Asp Leu Glu Lys Asp Val Met Leu Leu
1550                1555                1560 tgc cag aac gca cag acc ttc aac ctg gag ggc tcc ctg atc tat gaa    4814
Cys Gln Asn Ala Gln Thr Phe Asn Leu Glu Gly Ser Leu Ile Tyr Glu
1565                1570                1575                1580 gac tcc atc gtc ttg cag tcg gtc ttc acc agc gtg cgg cag aaa atc    4862
Asp Ser Ile Val Leu Gln Ser Val Phe Thr Ser Val Arg Gln Lys Ile
           1585                1590                1595 gag aag gag gat gac agt gaa ggc gag gag agt gag gag gag gaa gag    4910
Glu Lys Glu Asp Asp Ser Glu Gly Glu Glu Ser Glu Glu Glu Glu Glu
       1600                1605                1610 ggc gag gag gaa ggc tcc gaa tcc gaa tct cgg tcc gtc aaa gtg aag    4958
```

-continued

```
Gly Glu Glu Glu Gly Ser Glu Ser Glu Ser Arg Ser Val Lys Val Lys
        1615                1620                1625 atc aag ctt ggc cgg aag gag aag gca cag gac cgg ctg aag ggc ggc      5006
Ile Lys Leu Gly Arg Lys Glu Lys Ala Gln Asp Arg Leu Lys Gly Gly
        1630                1635                1640 cgg cgg cgg ccg agc cga ggg tcc cga gcc aag ccg gtc gtg agt gac      5054
Arg Arg Arg Pro Ser Arg Gly Ser Arg Ala Lys Pro Val Val Ser Asp
1645                1650                1655                1660 gat gac agt gag gag gaa caa gag gag gac cgc tca gga agt ggc agc      5102
Asp Asp Ser Glu Glu Glu Gln Glu Glu Asp Arg Ser Gly Ser Gly Ser
                1665                1670                1675 gaa gaa gac tgagcccga cattccagtc tcgaccccga gccctcgtt                5151
Glu Glu Asp ccagagctga gatggcatag gccttagcag taacgggtag cagcagatgt agtttcagac    5211
ttggagtaaa actgtataaa caaaagaatc ttccatattt atacagcaga gaagctgtag    5271
gactgtttgt gactggccct gtcctggcat cagtagcatc tgtaacagca ttaactgtct    5331
taaagagaga gagagagaat tccgaattgg ggaacacacg atacctgttt ttcttttccg    5391
ttgctggcag tactgttgcg ccgcagtttg gagtcactgt agttaagtgt ggatgcatgt    5451
gcgtcaccgt ccactcctcc tactgtattt tattggacag gtcagactcg ccggggggccc   5511 ggcgagggta tgtcagtgtc actggatgtc aaacagtaat aaattaaacc aacaac        5567
```

<210> SEQ ID NO 65
<211> LENGTH: 1679
<212> TYPE: PRT
<213> ORGANISM: Homo sapiens

<400> SEQUENCE: 65

```
Met Ser Thr Pro Asp Pro Pro Leu Gly Gly Thr Pro Arg Pro Gly Pro
1               5                   10                  15

Ser Pro Gly Pro Gly Pro Ser Pro Gly Ala Met Leu Gly Pro Ser Pro
            20                  25                  30

Gly Pro Ser Pro Gly Ser Ala His Ser Met Met Gly Pro Ser Pro Gly
        35                  40                  45

Pro Pro Ser Ala Gly His Pro Ile Pro Thr Gln Gly Pro Gly Gly Tyr
    50                  55                  60

Pro Gln Asp Asn Met His Gln Met His Lys Pro Met Glu Ser Met His
65                  70                  75                  80

Glu Lys Gly Met Ser Asp Asp Pro Arg Tyr Asn Gln Met Lys Gly Met
                85                  90                  95

Gly Met Arg Ser Gly Gly His Ala Gly Met Gly Pro Pro Pro Ser Pro
            100                 105                 110

Met Asp Gln His Ser Gln Gly Tyr Pro Ser Pro Leu Gly Gly Ser Glu
        115                 120                 125

His Ala Ser Ser Pro Val Pro Ala Ser Gly Pro Ser Ser Gly Pro Gln
    130                 135                 140

Met Ser Ser Gly Pro Gly Gly Ala Pro Leu Asp Gly Ala Asp Pro Gln
145                 150                 155                 160

Ala Leu Gly Gln Gln Asn Arg Gly Pro Thr Pro Phe Asn Gln Asn Gln
                165                 170                 175

Leu His Gln Leu Arg Ala Gln Ile Met Ala Tyr Lys Met Leu Ala Arg
            180                 185                 190

Gly Gln Pro Leu Pro Asp His Leu Gln Met Ala Val Gln Gly Lys Arg
        195                 200                 205
```

-continued

```
Pro Met Pro Gly Met Gln Gln Met Pro Thr Leu Pro Pro Ser
    210                 215                 220
Val Ser Ala Thr Gly Pro Gly Pro Gly Pro Gly Pro Gly Pro
225                 230                 235                 240
Gly Pro Gly Pro Ala Pro Pro Asn Tyr Ser Arg Pro His Gly Met Gly
                245                 250                 255
Gly Pro Asn Met Pro Pro Gly Pro Ser Gly Val Pro Pro Gly Met
            260                 265                 270
Pro Gly Gln Pro Pro Gly Gly Pro Pro Lys Pro Trp Pro Glu Gly Pro
        275                 280                 285
Met Ala Asn Ala Ala Ala Pro Thr Ser Thr Pro Gln Lys Leu Ile Pro
    290                 295                 300
Pro Gln Pro Thr Gly Arg Pro Ser Pro Ala Pro Pro Ala Val Pro Pro
305                 310                 315                 320
Ala Ala Ser Pro Val Met Pro Pro Gln Thr Gln Ser Pro Gly Gln Pro
                325                 330                 335
Ala Gln Pro Ala Pro Met Val Pro Leu His Gln Lys Gln Ser Arg Ile
            340                 345                 350
Thr Pro Ile Gln Lys Pro Arg Gly Leu Asp Pro Val Glu Ile Leu Gln
        355                 360                 365
Glu Arg Glu Tyr Arg Leu Gln Ala Arg Ile Ala His Arg Ile Gln Glu
    370                 375                 380
Leu Glu Asn Leu Pro Gly Ser Leu Ala Gly Asp Leu Arg Thr Lys Ala
385                 390                 395                 400
Thr Ile Glu Leu Lys Ala Leu Arg Leu Leu Asn Phe Gln Arg Gln Leu
                405                 410                 415
Arg Gln Glu Val Val Val Cys Met Arg Arg Asp Thr Ala Leu Glu Thr
            420                 425                 430
Ala Leu Asn Ala Lys Ala Tyr Lys Arg Ser Lys Arg Gln Ser Leu Arg
        435                 440                 445
Glu Ala Arg Ile Thr Glu Lys Leu Glu Lys Gln Gln Lys Ile Glu Gln
    450                 455                 460
Glu Arg Lys Arg Arg Gln Lys His Gln Glu Tyr Leu Asn Ser Ile Leu
465                 470                 475                 480
Gln His Ala Lys Asp Phe Lys Glu Tyr His Arg Ser Val Thr Gly Lys
                485                 490                 495
Ile Gln Lys Leu Thr Lys Ala Val Ala Thr Tyr His Ala Asn Thr Glu
            500                 505                 510
Arg Glu Gln Lys Lys Glu Asn Glu Arg Ile Glu Lys Glu Arg Met Arg
        515                 520                 525
Arg Leu Met Ala Glu Asp Glu Glu Gly Tyr Arg Lys Leu Ile Asp Gln
    530                 535                 540
Lys Lys Asp Lys Arg Leu Ala Tyr Leu Leu Gln Gln Thr Asp Glu Tyr
545                 550                 555                 560
Val Ala Asn Leu Thr Glu Leu Val Arg Gln His Lys Ala Ala Gln Val
                565                 570                 575
Ala Lys Glu Lys Lys Lys Lys Lys Lys Lys Lys Ala Glu Asn Ala
            580                 585                 590
Glu Gly Gln Thr Pro Ala Ile Gly Pro Asp Gly Glu Pro Leu Asp Glu
        595                 600                 605
Thr Ser Gln Met Ser Asp Leu Pro Val Lys Val Ile His Val Glu Ser
    610                 615                 620
Gly Lys Ile Leu Thr Gly Thr Asp Ala Pro Lys Ala Gly Gln Leu Glu
```

-continued

```
          625                 630                 635                 640
Ala Trp Leu Glu Met Asn Pro Gly Tyr Glu Val Ala Pro Arg Ser Asp
                    645                 650                 655
Ser Glu Glu Ser Gly Ser Glu Glu Glu Glu Glu Glu Glu Glu Glu Glu
                    660                 665                 670
Gln Pro Gln Ala Ala Gln Pro Pro Thr Leu Pro Val Glu Glu Lys Lys
                    675                 680                 685
Lys Ile Pro Asp Pro Asp Ser Asp Val Ser Glu Val Asp Ala Arg
    690                 695                 700
His Ile Ile Glu Asn Ala Lys Gln Asp Val Asp Asp Glu Tyr Gly Val
705                 710                 715                 720
Ser Gln Ala Leu Ala Arg Gly Leu Gln Ser Tyr Tyr Ala Val Ala His
                    725                 730                 735
Ala Val Thr Glu Arg Val Asp Lys Gln Ser Ala Leu Met Val Asn Gly
                    740                 745                 750
Val Leu Lys Gln Tyr Gln Ile Lys Gly Leu Glu Trp Leu Val Ser Leu
                    755                 760                 765
Tyr Asn Asn Asn Leu Asn Gly Ile Leu Ala Asp Glu Met Gly Leu Gly
                    770                 775                 780
Lys Thr Ile Gln Thr Ile Ala Leu Ile Thr Tyr Leu Met Glu His Lys
785                 790                 795                 800
Arg Ile Asn Gly Pro Phe Leu Ile Ile Val Pro Leu Ser Thr Leu Ser
                    805                 810                 815
Asn Trp Ala Tyr Glu Phe Asp Lys Trp Ala Pro Ser Val Val Lys Val
                    820                 825                 830
Ser Tyr Lys Gly Ser Pro Ala Ala Arg Arg Ala Phe Val Pro Gln Leu
                    835                 840                 845
Arg Ser Gly Lys Phe Asn Val Leu Leu Thr Thr Tyr Glu Tyr Ile Ile
                    850                 855                 860
Lys Asp Lys His Ile Leu Ala Lys Ile Arg Trp Lys Tyr Met Ile Val
865                 870                 875                 880
Asp Glu Gly His Arg Met Lys Asn His His Cys Lys Leu Thr Gln Val
                    885                 890                 895
Leu Asn Thr His Tyr Val Ala Pro Arg Arg Leu Leu Leu Thr Gly Thr
                    900                 905                 910
Pro Leu Gln Asn Lys Leu Pro Glu Leu Trp Ala Leu Leu Asn Phe Leu
                    915                 920                 925
Leu Pro Thr Ile Phe Lys Ser Cys Ser Thr Phe Glu Gln Trp Phe Asn
                    930                 935                 940
Ala Pro Phe Ala Met Thr Gly Glu Lys Val Asp Leu Asn Glu Glu Glu
945                 950                 955                 960
Thr Ile Leu Ile Ile Arg Arg Leu His Lys Val Leu Arg Pro Phe Leu
                    965                 970                 975
Leu Arg Arg Leu Lys Lys Glu Val Glu Ala Gln Leu Pro Glu Lys Val
                    980                 985                 990
Glu Tyr Val Ile Lys Cys Asp Met Ser Ala Leu Gln Arg Val Leu Tyr
                    995                 1000                1005
Arg His Met Gln Ala Lys Gly Val Leu Leu Thr Asp Gly Ser Glu Lys
    1010                1015                1020
Asp Lys Lys Gly Lys Gly Gly Thr Lys Thr Leu Met Asn Thr Ile Met
025                 1030                1035                1040
Gln Leu Arg Lys Ile Cys Asn His Pro Tyr Met Phe Gln His Ile Glu
                    1045                1050                1055
```

-continued

Glu Ser Phe Ser Glu His Leu Gly Phe Thr Gly Gly Ile Val Gln Gly
                1060                1065                1070

Leu Asp Leu Tyr Arg Ala Ser Gly Lys Phe Glu Leu Leu Asp Arg Ile
        1075                1080                1085

Leu Pro Lys Leu Arg Ala Thr Asn His Lys Val Leu Leu Phe Cys Gln
    1090                1095                1100

Met Thr Ser Leu Met Thr Ile Met Glu Asp Tyr Phe Ala Tyr Arg Gly
105                 1110                1115                1120

Phe Lys Tyr Leu Arg Leu Asp Gly Thr Thr Lys Ala Glu Asp Arg Gly
            1125                1130                1135

Met Leu Leu Lys Thr Phe Asn Glu Pro Gly Ser Glu Tyr Phe Ile Phe
        1140                1145                1150

Leu Leu Ser Thr Arg Ala Gly Gly Leu Gly Leu Asn Leu Gln Ser Ala
    1155                1160                1165

Asp Thr Val Ile Ile Phe Asp Ser Asp Trp Asn Pro His Gln Asp Leu
    1170                1175                1180

Gln Ala Gln Asp Arg Ala His Arg Ile Gly Gln Gln Asn Glu Val Arg
185                 1190                1195                1200

Val Leu Arg Leu Cys Thr Val Asn Ser Val Glu Glu Lys Ile Leu Ala
            1205                1210                1215

Ala Ala Lys Tyr Lys Leu Asn Val Asp Gln Lys Val Ile Gln Ala Gly
        1220                1225                1230

Met Phe Asp Gln Lys Ser Ser His Glu Arg Arg Ala Phe Leu Gln
    1235                1240                1245

Ala Ile Leu Glu His Glu Glu Gln Asp Glu Ser Arg His Cys Ser Thr
    1250                1255                1260

Gly Ser Gly Ser Ala Ser Phe Ala His Thr Ala Pro Pro Ala Gly
265                 1270                1275                1280

Val Asn Pro Asp Leu Glu Glu Pro Pro Leu Lys Glu Glu Asp Glu Val
            1285                1290                1295

Pro Asp Asp Glu Thr Val Asn Gln Met Ile Ala Arg His Glu Glu Glu
        1300                1305                1310

Phe Asp Leu Phe Met Arg Met Asp Leu Asp Arg Arg Arg Glu Glu Ala
    1315                1320                1325

Arg Asn Pro Lys Arg Lys Pro Arg Leu Met Glu Glu Asp Glu Leu Pro
    1330                1335                1340

Ser Trp Ile Ile Lys Asp Asp Ala Glu Val Glu Arg Leu Thr Cys Glu
345                 1350                1355                1360

Glu Glu Glu Glu Lys Met Phe Gly Arg Gly Ser Arg His Arg Lys Glu
            1365                1370                1375

Val Asp Tyr Ser Asp Ser Leu Thr Glu Lys Gln Trp Leu Lys Lys Ile
        1380                1385                1390

Thr Gly Lys Asp Ile His Asp Thr Ala Ser Ser Val Ala Arg Gly Leu
    1395                1400                1405

Gln Phe Gln Arg Gly Leu Gln Phe Cys Thr Arg Ala Ser Lys Ala Ile
    1410                1415                1420

Glu Glu Gly Thr Leu Glu Glu Ile Glu Glu Val Arg Gln Lys Lys
425                 1430                1435                1440

Ser Ser Arg Lys Arg Lys Arg Asp Ser Asp Ala Gly Ser Ser Thr Pro
            1445                1450                1455

Thr Thr Ser Thr Arg Ser Arg Asp Lys Asp Asp Glu Ser Lys Lys Gln
        1460                1465                1470

-continued

```
Lys Lys Arg Gly Arg Pro Pro Ala Glu Lys Leu Ser Pro Asn Pro Pro
    1475                1480                1485

Asn Leu Thr Lys Lys Met Lys Lys Ile Val Asp Ala Val Ile Lys Tyr
1490                1495                1500

Lys Asp Ser Ser Ser Gly Arg Gln Leu Ser Glu Val Phe Ile Gln Leu
505                 1510                1515                1520

Pro Ser Arg Lys Glu Leu Pro Gly Tyr Tyr Glu Leu Ile Arg Lys Pro
        1525                1530                1535

Val Asp Phe Lys Lys Ile Lys Glu Arg Ile Arg Asn His Lys Tyr Arg
        1540                1545                1550

Ser Leu Asn Asp Leu Glu Lys Asp Val Met Leu Leu Cys Gln Asn Ala
        1555                1560                1565

Gln Thr Phe Asn Leu Glu Gly Ser Leu Ile Tyr Glu Asp Ser Ile Val
    1570                1575                1580

Leu Gln Ser Val Phe Thr Ser Val Arg Gln Lys Ile Glu Lys Glu Asp
585                 1590                1595                1600

Asp Ser Glu Gly Glu Glu Ser Glu Glu Glu Glu Gly Glu Glu Glu
            1605                1610                1615

Gly Ser Glu Ser Glu Ser Arg Ser Val Lys Val Lys Ile Lys Leu Gly
            1620                1625                1630

Arg Lys Glu Lys Ala Gln Asp Arg Leu Lys Gly Gly Arg Arg Arg Pro
        1635                1640                1645

Ser Arg Gly Ser Arg Ala Lys Pro Val Val Ser Asp Asp Asp Ser Glu
    1650                1655                1660

Glu Glu Gln Glu Glu Asp Arg Ser Gly Ser Gly Ser Glu Glu Asp
665                 1670                1675
```

<210> SEQ ID NO 66
<211> LENGTH: 5468
<212> TYPE: DNA
<213> ORGANISM: Homo sapiens
<220> FEATURE:
<221> NAME/KEY: CDS
<222> LOCATION: (75)..(5012)
<220> FEATURE:
<221> NAME/KEY: conflict
<222> LOCATION: (1780)
<223> OTHER INFORMATION: GenBank Accession No. U29175 shows a C at this
      position (position 1784 in GenBank) rather than
      the G shown here.
<220> FEATURE:
<221> NAME/KEY: allele
<222> LOCATION: (26)
<223> OTHER INFORMATION: Polymorphism of either T or C in this noncoding
      region.
<220> FEATURE:
<221> NAME/KEY: allele
<222> LOCATION: (1583)
<223> OTHER INFORMATION: Polymorphism of A or G resulting in a silent
      mutation.
<220> FEATURE:
<221> NAME/KEY: allele
<222> LOCATION: (1598)
<223> OTHER INFORMATION: Polymorphism of T or C resulting in a silent
      mutation.
<220> FEATURE:
<221> NAME/KEY: allele
<222> LOCATION: (1892)
<223> OTHER INFORMATION: Polymorphism of A or G resulting in a silent
      mutation.
<220> FEATURE:
<221> NAME/KEY: misc_feature
<222> LOCATION: (4498)..(4499)
<223> OTHER INFORMATION: A CAG is missing between these bases as compared
      to SEQ ID NO:1.

```
<400> SEQUENCE: 66
ggcgggggag gcgccgggaa gtcgatggcg ccggcggctc ctgcaggagg ccactgtctg      60
cagctcccgt gaag atg tcc act cca gac cca ccc ctg ggc gga act cct       110
              Met Ser Thr Pro Asp Pro Pro Leu Gly Gly Thr Pro
                1               5                   10 cgg cca ggt cct tcc ccg ggc cct ggc cct tcc cct gga gcc atg ctg       158
Arg Pro Gly Pro Ser Pro Gly Pro Gly Pro Ser Pro Gly Ala Met Leu
         15                  20                  25 ggc cct agc ccg ggt ccc tcg ccg ggc tcc gcc cac agc atg atg ggg       206
Gly Pro Ser Pro Gly Pro Ser Pro Gly Ser Ala His Ser Met Met Gly
     30                  35                  40 ccc agc cca ggg ccg ccc tca gca gga cac ccc atc ccc acc cag ggg       254
Pro Ser Pro Gly Pro Pro Ser Ala Gly His Pro Ile Pro Thr Gln Gly
 45                  50                  55                  60 cct gga ggg tac cct cag gac aac atg cac cag atg cac aag ccc atg       302
Pro Gly Gly Tyr Pro Gln Asp Asn Met His Gln Met His Lys Pro Met
                 65                  70                  75 gag tcc atg cat gag aag ggc atg tcg gac gac ccg cgc tac aac cag       350
Glu Ser Met His Glu Lys Gly Met Ser Asp Asp Pro Arg Tyr Asn Gln
             80                  85                  90 atg aaa gga atg ggg atg cgg tca ggg ggc cat gct ggg atg ggg ccc       398
Met Lys Gly Met Gly Met Arg Ser Gly Gly His Ala Gly Met Gly Pro
         95                  100                 105 ccg ccc agc ccc atg gac cag cac tcc caa ggt tac ccc tcg ccc ctg       446
Pro Pro Ser Pro Met Asp Gln His Ser Gln Gly Tyr Pro Ser Pro Leu
     110                 115                 120 ggt ggc tct gag cat gcc tct agt cca gtt cca gcc agt ggc ccg tct       494
Gly Gly Ser Glu His Ala Ser Ser Pro Val Pro Ala Ser Gly Pro Ser
125                 130                 135                 140 tcg ggg ccc cag atg tct tcc ggg cca gga ggt gcc ccg ctg gat ggt       542
Ser Gly Pro Gln Met Ser Ser Gly Pro Gly Gly Ala Pro Leu Asp Gly
                145                 150                 155 gct gac ccc cag gcc ttg ggg cag cag aac cgg ggc cca acc cca ttt       590
Ala Asp Pro Gln Ala Leu Gly Gln Gln Asn Arg Gly Pro Thr Pro Phe
             160                 165                 170 aac cag aac cag ctg cac cag ctc aga gct cag atc atg gcc tac aag       638
Asn Gln Asn Gln Leu His Gln Leu Arg Ala Gln Ile Met Ala Tyr Lys
         175                 180                 185 atg ctg gcc agg ggg cag ccc ctc ccc gac cac ctg cag atg gcg gtg       686
Met Leu Ala Arg Gly Gln Pro Leu Pro Asp His Leu Gln Met Ala Val
     190                 195                 200 cag ggc aag cgg ccg atg ccc ggg atg cag cag cag atg cca acg cta       734
Gln Gly Lys Arg Pro Met Pro Gly Met Gln Gln Gln Met Pro Thr Leu
205                 210                 215                 220 cct cca ccc tcg gtg tcc gca aca gga ccc ggc cct ggc cct ggc cct       782
Pro Pro Pro Ser Val Ser Ala Thr Gly Pro Gly Pro Gly Pro Gly Pro
                225                 230                 235 ggc ccc ggc ccg ggt ccc ggc ccg gca cct cca aat tac agc agg cct       830
Gly Pro Gly Pro Gly Pro Gly Pro Ala Pro Pro Asn Tyr Ser Arg Pro
             240                 245                 250 cat ggt atg gga ggg ccc aac atg cct ccc cca gga ccc tcg ggc gtg       878
His Gly Met Gly Gly Pro Asn Met Pro Pro Pro Gly Pro Ser Gly Val
         255                 260                 265 ccc ccc ggg atg cca ggc cag cct cct gga ggg cct ccc aag ccc tgg       926
Pro Pro Gly Met Pro Gly Gln Pro Pro Gly Gly Pro Pro Lys Pro Trp
     270                 275                 280 cct gaa gga ccc atg gcg aat gct gct gcc ccc acg agc acc cct cag       974
Pro Glu Gly Pro Met Ala Asn Ala Ala Ala Pro Thr Ser Thr Pro Gln
285                 290                 295                 300
```

```
aag ctg att ccc ccg cag cca acg ggc cgc cct tcc ccc gcg ccc cct      1022
Lys Leu Ile Pro Pro Gln Pro Thr Gly Arg Pro Ser Pro Ala Pro Pro
                305                 310                 315 gcc gtc cca ccc gcc gcc tcg ccc gtg atg cca ccg cag acc cag tcc      1070
Ala Val Pro Pro Ala Ala Ser Pro Val Met Pro Pro Gln Thr Gln Ser
            320                 325                 330 ccc ggg cag ccg gcc cag ccc gcg ccc atg gtg cca ctg cac cag aag      1118
Pro Gly Gln Pro Ala Gln Pro Ala Pro Met Val Pro Leu His Gln Lys
        335                 340                 345 cag agc cgc atc acc ccc atc cag aag ccg cgg ggc ctc gac cct gtg      1166
Gln Ser Arg Ile Thr Pro Ile Gln Lys Pro Arg Gly Leu Asp Pro Val
    350                 355                 360 gag atc ctg cag gag cgc gag tac agg ctg cag gct cgc atc gca cac      1214
Glu Ile Leu Gln Glu Arg Glu Tyr Arg Leu Gln Ala Arg Ile Ala His
365                 370                 375                 380 cga att cag gaa ctt gaa aac ctt ccc ggg tcc ctg gcc ggg gat ttg      1262
Arg Ile Gln Glu Leu Glu Asn Leu Pro Gly Ser Leu Ala Gly Asp Leu
                385                 390                 395 cga acc aaa gcg acc att gag ctc aag gcc ctc agg ctg ctg aac ttc      1310
Arg Thr Lys Ala Thr Ile Glu Leu Lys Ala Leu Arg Leu Leu Asn Phe
            400                 405                 410 cag agg cag ctg cgc cag gag gtg gtg gtg tgc atg cgg agg gac aca      1358
Gln Arg Gln Leu Arg Gln Glu Val Val Val Cys Met Arg Arg Asp Thr
        415                 420                 425 gcg ctg gag aca gcc ctc aat gct aag gcc tac aag cgc agc aag cgc      1406
Ala Leu Glu Thr Ala Leu Asn Ala Lys Ala Tyr Lys Arg Ser Lys Arg
    430                 435                 440 cag tcc ctg cgc gag gcc cgc atc act gag aag ctg gag aag cag cag      1454
Gln Ser Leu Arg Glu Ala Arg Ile Thr Glu Lys Leu Glu Lys Gln Gln
445                 450                 455                 460 aag atc gag cag gag cgc aag cgc cgg cag aag cac cag gaa tac ctc      1502
Lys Ile Glu Gln Glu Arg Lys Arg Arg Gln Lys His Gln Glu Tyr Leu
                465                 470                 475 aat agc att ctc cag cat gcc aag gat ttc aag gaa tat cac aga tcc      1550
Asn Ser Ile Leu Gln His Ala Lys Asp Phe Lys Glu Tyr His Arg Ser
            480                 485                 490 gtc aca ggc aaa atc cag aag ctg acc aag gca gtg gcc acg tac cat      1598
Val Thr Gly Lys Ile Gln Lys Leu Thr Lys Ala Val Ala Thr Tyr His
        495                 500                 505 gcc aac acg gag cgg gag cag aag aaa gag aac gag cgg atc gag aag      1646
Ala Asn Thr Glu Arg Glu Gln Lys Lys Glu Asn Glu Arg Ile Glu Lys
    510                 515                 520 gag cgc atg cgg agg ctc atg gct gaa gat gag gag ggg tac cgc aag      1694
Glu Arg Met Arg Arg Leu Met Ala Glu Asp Glu Glu Gly Tyr Arg Lys
525                 530                 535                 540 ctc atc gac cag aag aag gac aag cgc ctg gcc tac ctc ttg cag cag      1742
Leu Ile Asp Gln Lys Lys Asp Lys Arg Leu Ala Tyr Leu Leu Gln Gln
                545                 550                 555 aca gac gag tac gtg gct aac ctc acg gag ctg gtg cgg cag cac aag      1790
Thr Asp Glu Tyr Val Ala Asn Leu Thr Glu Leu Val Arg Gln His Lys
            560                 565                 570 gct gcc cag gtc gcc aag gag aaa aag aag aaa aag aaa aag aag aag      1838
Ala Ala Gln Val Ala Lys Glu Lys Lys Lys Lys Lys Lys Lys Lys Lys
        575                 580                 585 gca gaa aat gca gaa gga cag acg cct gcc att ggg ccg gat ggc gag      1886
Ala Glu Asn Ala Glu Gly Gln Thr Pro Ala Ile Gly Pro Asp Gly Glu
    590                 595                 600 cct cta gac gag acc agc cag atg agc gac ctc ccg gtg aag gtg atc      1934
Pro Leu Asp Glu Thr Ser Gln Met Ser Asp Leu Pro Val Lys Val Ile
```

```
                605                 610                 615                 620 cac gtg gag agt ggg aag atc ctc aca ggc aca gat gcc ccc aaa gcc         1982
His Val Glu Ser Gly Lys Ile Leu Thr Gly Thr Asp Ala Pro Lys Ala
                    625                 630                 635 ggg cag ctg gag gcc tgg ctc gag atg aac ccg ggg tat gaa gta gct         2030
Gly Gln Leu Glu Ala Trp Leu Glu Met Asn Pro Gly Tyr Glu Val Ala
        640                 645                 650 ccg agg tct gat agt gaa gaa agt ggc tca gaa gaa gag gaa gag gag         2078
Pro Arg Ser Asp Ser Glu Glu Ser Gly Ser Glu Glu Glu Glu Glu Glu
            655                 660                 665 gag gag gaa gag cag ccg cag gca gca cag cct ccc acc ctg ccc gtg         2126
Glu Glu Glu Glu Gln Pro Gln Ala Ala Gln Pro Pro Thr Leu Pro Val
        670                 675                 680 gag gag aag aag aag att cca gat cca gac agc gat gac gtc tct gag         2174
Glu Glu Lys Lys Lys Ile Pro Asp Pro Asp Ser Asp Asp Val Ser Glu
685                 690                 695                 700 gtg gac gcg cgg cac atc att gag aat gcc aag caa gat gtc gat gat         2222
Val Asp Ala Arg His Ile Ile Glu Asn Ala Lys Gln Asp Val Asp Asp
                705                 710                 715 gaa tat ggc gtg tcc cag gcc ctt gca cgt ggc ctg cag tcc tac tat         2270
Glu Tyr Gly Val Ser Gln Ala Leu Ala Arg Gly Leu Gln Ser Tyr Tyr
            720                 725                 730 gcc gtg gcc cat gct gtc act gag aga gtg gac aag cag tca gcg ctt         2318
Ala Val Ala His Ala Val Thr Glu Arg Val Asp Lys Gln Ser Ala Leu
        735                 740                 745 atg gtc aat ggt gtc ctc aaa cag tac cag atc aaa ggt ttg gag tgg         2366
Met Val Asn Gly Val Leu Lys Gln Tyr Gln Ile Lys Gly Leu Glu Trp
            750                 755                 760 ctg gtg tcc ctg tac aac aac aac ctg aac ggc atc ctg gcc gac gag         2414
Leu Val Ser Leu Tyr Asn Asn Asn Leu Asn Gly Ile Leu Ala Asp Glu
765                 770                 775                 780 atg ggc ctg ggg aag acc atc cag acc atc gcg ctc atc acg tac ctc         2462
Met Gly Leu Gly Lys Thr Ile Gln Thr Ile Ala Leu Ile Thr Tyr Leu
                785                 790                 795 atg gag cac aaa cgc atc aat ggg ccc ttc ctc atc atc gtg cct ctc         2510
Met Glu His Lys Arg Ile Asn Gly Pro Phe Leu Ile Ile Val Pro Leu
            800                 805                 810 tca acg ctg tcc aac tgg gcg tac gag ttt gac aag tgg gcc ccc tcc         2558
Ser Thr Leu Ser Asn Trp Ala Tyr Glu Phe Asp Lys Trp Ala Pro Ser
        815                 820                 825 gtg gtg aag gtg tct tac aag gga tcc cca gca gca aga cgg gcc ttt         2606
Val Val Lys Val Ser Tyr Lys Gly Ser Pro Ala Ala Arg Arg Ala Phe
        830                 835                 840 gtc ccc cag ctc cgg agt ggg aag ttc aac gtc ttg ctg acg acg tac         2654
Val Pro Gln Leu Arg Ser Gly Lys Phe Asn Val Leu Leu Thr Thr Tyr
845                 850                 855                 860 gag tac atc atc aaa gac aag cac atc ctc gcc aag atc cgt tgg aag         2702
Glu Tyr Ile Ile Lys Asp Lys His Ile Leu Ala Lys Ile Arg Trp Lys
                865                 870                 875 tac atg att gtg gac gaa ggt cac cgc atg aag aac cac cac tgc aag         2750
Tyr Met Ile Val Asp Glu Gly His Arg Met Lys Asn His His Cys Lys
            880                 885                 890 ctg acg cag gtg ctc aac acg cac tat gtg gca ccc cgc cgc ctg ctg         2798
Leu Thr Gln Val Leu Asn Thr His Tyr Val Ala Pro Arg Arg Leu Leu
        895                 900                 905 ctg acg ggc aca ccg ctg cag aac aag ctt ccc gag ctc tgg gcg ctg         2846
Leu Thr Gly Thr Pro Leu Gln Asn Lys Leu Pro Glu Leu Trp Ala Leu
        910                 915                 920 ctc aac ttc ctg ctg ccc acc atc ttc aag agc tgc agc acc ttc gag         2894
```

```
                                                          -continued

Leu Asn Phe Leu Leu Pro Thr Ile Phe Lys Ser Cys Ser Thr Phe Glu
925                 930                 935                 940 cag tgg ttt aac gca ccc ttt gcc atg acc ggg gaa aag gtg gac ctg    2942
Gln Trp Phe Asn Ala Pro Phe Ala Met Thr Gly Glu Lys Val Asp Leu
                945                 950                 955 aat gag gag gaa acc att ctc atc atc cgg cgt ctc cac aaa gtg ctg    2990
Asn Glu Glu Glu Thr Ile Leu Ile Ile Arg Arg Leu His Lys Val Leu
            960                 965                 970 cgg ccc ttc ttg ctc cga cga ctc aag aag gaa gtc gag gcc cag ttg    3038
Arg Pro Phe Leu Leu Arg Arg Leu Lys Lys Glu Val Glu Ala Gln Leu
        975                 980                 985 ccc gaa aag gtg gag tac gtc atc aag tgc gac atg tct gcg ctg cag    3086
Pro Glu Lys Val Glu Tyr Val Ile Lys Cys Asp Met Ser Ala Leu Gln
    990                 995                 1000 cga gtg ctc tac cgc cac atg cag gcc aag ggc gtg ctg ctg act gat    3134
Arg Val Leu Tyr Arg His Met Gln Ala Lys Gly Val Leu Leu Thr Asp
1005                 1010                 1015                 1020 ggc tcc gag aag gac aag aag ggc aaa ggc ggc acc aag acc ctg atg    3182
Gly Ser Glu Lys Asp Lys Lys Gly Lys Gly Gly Thr Lys Thr Leu Met
                1025                 1030                 1035 aac acc atc atg cag ctg cgg aag atc tgc aac cac ccc tac atg ttc    3230
Asn Thr Ile Met Gln Leu Arg Lys Ile Cys Asn His Pro Tyr Met Phe
            1040                 1045                 1050 cag cac atc gag gag tcc ttt tcc gag cac ttg ggg ttc act ggc ggc    3278
Gln His Ile Glu Glu Ser Phe Ser Glu His Leu Gly Phe Thr Gly Gly
        1055                 1060                 1065 att gtc caa ggg ctg gac ctg tac cga gcc tcg ggt aaa ttt gag ctt    3326
Ile Val Gln Gly Leu Asp Leu Tyr Arg Ala Ser Gly Lys Phe Glu Leu
    1070                 1075                 1080 ctt gat aga att ctt ccc aaa ctc cga gca acc aac cac aaa gtg ctg    3374
Leu Asp Arg Ile Leu Pro Lys Leu Arg Ala Thr Asn His Lys Val Leu
1085                 1090                 1095                 1100 ctg ttc tgc caa atg acc tcc ctc atg acc atc atg gaa gat tac ttt    3422
Leu Phe Cys Gln Met Thr Ser Leu Met Thr Ile Met Glu Asp Tyr Phe
                1105                 1110                 1115 gcg tat cgc ggc ttt aaa tac ctc agg ctt gat gga acc acg aag gcg    3470
Ala Tyr Arg Gly Phe Lys Tyr Leu Arg Leu Asp Gly Thr Thr Lys Ala
            1120                 1125                 1130 gag gac cgg ggc atg ctg ctg aaa acc ttc aac gag ccc ggc tct gag    3518
Glu Asp Arg Gly Met Leu Leu Lys Thr Phe Asn Glu Pro Gly Ser Glu
        1135                 1140                 1145 tac ttc atc ttc ctg ctc agc acc cgg gct ggg ggg ctc ggc ctg aac    3566
Tyr Phe Ile Phe Leu Leu Ser Thr Arg Ala Gly Gly Leu Gly Leu Asn
    1150                 1155                 1160 ctc cag tcg gca gac act gtg atc att ttt gac agc gac tgg aat cct    3614
Leu Gln Ser Ala Asp Thr Val Ile Ile Phe Asp Ser Asp Trp Asn Pro
1165                 1170                 1175                 1180 cac cag gac ctg caa gcg cag gac cga gcc cac cgc atc ggg cag cag    3662
His Gln Asp Leu Gln Ala Gln Asp Arg Ala His Arg Ile Gly Gln Gln
                1185                 1190                 1195 aac gag gtg cgt gtg ctc cgc ctc tgc acc gtc aac agc gtg gag gag    3710
Asn Glu Val Arg Val Leu Arg Leu Cys Thr Val Asn Ser Val Glu Glu
            1200                 1205                 1210 aag atc cta gct gca gcc aag tac aag ctc aac gtg gac cag aag gtg    3758
Lys Ile Leu Ala Ala Ala Lys Tyr Lys Leu Asn Val Asp Gln Lys Val
        1215                 1220                 1225 atc cag gcc ggc atg ttc gac cag aag tcc tcc agc cat gag cgg cgc    3806
Ile Gln Ala Gly Met Phe Asp Gln Lys Ser Ser Ser His Glu Arg Arg
    1230                 1235                 1240
```

-continued

| | |
|---|---|
| gcc ttc ctg cag gcc atc ctg gag cac gag gag cag gat gag agc aga<br>Ala Phe Leu Gln Ala Ile Leu Glu His Glu Glu Gln Asp Glu Ser Arg<br>1245                       1250                    1255                    1260 | 3854 |
| cac tgc agc acg ggc agc ggc agt gcc agc ttc gcc cac act gcc cct<br>His Cys Ser Thr Gly Ser Gly Ser Ala Ser Phe Ala His Thr Ala Pro<br>               1265                    1270                    1275 | 3902 |
| ccg cca gcg ggc gtc aac ccc gac ttg gag gag cca cct cta aag gag<br>Pro Pro Ala Gly Val Asn Pro Asp Leu Glu Glu Pro Pro Leu Lys Glu<br>          1280                    1285                    1290 | 3950 |
| gaa gac gag gtg ccc gac gac gag acc gtc aac cag atg atc gcc cgg<br>Glu Asp Glu Val Pro Asp Asp Glu Thr Val Asn Gln Met Ile Ala Arg<br>1295                       1300                    1305 | 3998 |
| cac gag gag gag ttt gat ctg ttc atg cgc atg gac ctg gac cgc agg<br>His Glu Glu Glu Phe Asp Leu Phe Met Arg Met Asp Leu Asp Arg Arg<br>               1310                    1315                    1320 | 4046 |
| cgc gag gag gcc cgc aac ccc aag cgg aag ccg cgc ctc atg gag gag<br>Arg Glu Glu Ala Arg Asn Pro Lys Arg Lys Pro Arg Leu Met Glu Glu<br>1325                       1330                    1335                    1340 | 4094 |
| gac gag ctc ccc tcg tgg atc atc aag gac gac gcg gag gtg gag cgg<br>Asp Glu Leu Pro Ser Trp Ile Ile Lys Asp Asp Ala Glu Val Glu Arg<br>               1345                    1350                    1355 | 4142 |
| ctg acc tgt gag gag gag gag gag aag atg ttc ggc cgt ggc tcc cgc<br>Leu Thr Cys Glu Glu Glu Glu Glu Lys Met Phe Gly Arg Gly Ser Arg<br>          1360                    1365                    1370 | 4190 |
| cac cgc aag gag gtg gac tac agc gac tca ctg acg gag aag cag tgg<br>His Arg Lys Glu Val Asp Tyr Ser Asp Ser Leu Thr Glu Lys Gln Trp<br>1375                       1380                    1385 | 4238 |
| ctc aag gcc atc gag gag ggc acg ctg gag gag atc gaa gag gag gtc<br>Leu Lys Ala Ile Glu Glu Gly Thr Leu Glu Glu Ile Glu Glu Glu Val<br>               1390                    1395                    1400 | 4286 |
| cgg cag aag aaa tca tca cgg aag cgc aag cga gac agc gac gcc ggc<br>Arg Gln Lys Lys Ser Ser Arg Lys Arg Lys Arg Asp Ser Asp Ala Gly<br>1405                       1410                    1415                    1420 | 4334 |
| tcc tcc acc ccg acc acc agc acc cgc agc cgc gac aag gac gac gag<br>Ser Ser Thr Pro Thr Thr Ser Thr Arg Ser Arg Asp Lys Asp Asp Glu<br>               1425                    1430                    1435 | 4382 |
| agc aag aag cag aag aag cgc ggg cgg ccg cct gcc gag aaa ctc tcc<br>Ser Lys Lys Gln Lys Lys Arg Gly Arg Pro Pro Ala Glu Lys Leu Ser<br>          1440                    1445                    1450 | 4430 |
| cct aac cca ccc aac ctc acc aag aag atg aag aag att gtg gat gcc<br>Pro Asn Pro Pro Asn Leu Thr Lys Lys Met Lys Lys Ile Val Asp Ala<br>1455                       1460                    1465 | 4478 |
| gtg atc aag tac aag gac agc agt gga cgt cag ctc agc gag gtc ttc<br>Val Ile Lys Tyr Lys Asp Ser Ser Gly Arg Gln Leu Ser Glu Val Phe<br>               1470                    1475                    1480 | 4526 |
| atc cag ctg ccc tcg cga aag gag ctg ccc gag tac tac gag ctc atc<br>Ile Gln Leu Pro Ser Arg Lys Glu Leu Pro Glu Tyr Tyr Glu Leu Ile<br>1485                       1490                    1495                    1500 | 4574 |
| cgc aag ccc gtg gac ttc aag aag ata aag gag cgc att cgc aac cac<br>Arg Lys Pro Val Asp Phe Lys Lys Ile Lys Glu Arg Ile Arg Asn His<br>               1505                    1510                    1515 | 4622 |
| aag tac cgc agc ctc aac gac cta gag aag gac gtc atg ctc ctg tgc<br>Lys Tyr Arg Ser Leu Asn Asp Leu Glu Lys Asp Val Met Leu Leu Cys<br>          1520                    1525                    1530 | 4670 |
| cag aac gca cag acc ttc aac ctg gag ggc tcc ctg atc tat gaa gac<br>Gln Asn Ala Gln Thr Phe Asn Leu Glu Gly Ser Leu Ile Tyr Glu Asp<br>1535                       1540                    1545 | 4718 |
| tcc atc gtc ttg cag tcg gtc ttc acc agc gtg cgg cag aaa atc gag<br>Ser Ile Val Leu Gln Ser Val Phe Thr Ser Val Arg Gln Lys Ile Glu<br>               1550                    1555                    1560 | 4766 |

```
aag gag gat gac agt gaa ggc gag gag agt gag gag gag gaa gag ggc    4814
Lys Glu Asp Asp Ser Glu Gly Glu Glu Ser Glu Glu Glu Glu Glu Gly
1565                1570                1575                1580 gag gag gaa ggc tcc gaa tcc gaa tct cgg tcc gtc aaa gtg aag atc    4862
Glu Glu Glu Gly Ser Glu Ser Glu Ser Arg Ser Val Lys Val Lys Ile
            1585                1590                1595 aag ctt ggc cgg aag gag aag gca cag gac cgg ctg aag ggc ggc cgg    4910
Lys Leu Gly Arg Lys Glu Lys Ala Gln Asp Arg Leu Lys Gly Gly Arg
        1600                1605                1610 cgg cgg ccg agc cga ggg tcc cga gcc aag ccg gtc gtg agt gac gat    4958
Arg Arg Pro Ser Arg Gly Ser Arg Ala Lys Pro Val Val Ser Asp Asp
    1615                1620                1625 gac agt gag gag gaa caa gag gag gac cgc tca gga agt ggc agc gaa    5006
Asp Ser Glu Glu Glu Gln Glu Glu Asp Arg Ser Gly Ser Gly Ser Glu
1630                1635                1640 gaa gac tgagcccga cattccagtc tcgaccccga gcccctcgtt ccagagctga      5062
Glu Asp
1645 gatggcatag gccttagcag taacgggtag cagcagatgt agtttcagac ttggagtaaa   5122 actgtataaa caaaagaatc ttccatattt atacagcaga gaagctgtag gactgtttgt   5182 gactggccct gtcctggcat cagtagcatc tgtaacagca ttaactgtct taaagagaga   5242 gagagagaat tccgaattgg ggaacacacg atacctgttt ttcttttccg ttgctggcag   5302 tactgttgcg ccgcagtttg gagtcactgt agttaagtgt ggatgcatgt gcgtcaccgt   5362 ccactcctcc tactgtattt tattggacag gtcagactcg ccgggggccc ggcgagggta   5422 tgtcagtgtc actggatgtc aaacagtaat aaattaaacc aacaac                 5468

<210> SEQ ID NO 67
<211> LENGTH: 1646
<212> TYPE: PRT
<213> ORGANISM: Homo sapiens

<400> SEQUENCE: 67

Met Ser Thr Pro Asp Pro Pro Leu Gly Gly Thr Pro Arg Pro Gly Pro
1               5                   10                  15

Ser Pro Gly Pro Gly Pro Ser Pro Gly Ala Met Leu Gly Pro Ser Pro
            20                  25                  30

Gly Pro Ser Pro Gly Ser Ala His Ser Met Met Gly Pro Ser Pro Gly
        35                  40                  45

Pro Pro Ser Ala Gly His Pro Ile Pro Thr Gln Gly Pro Gly Gly Tyr
    50                  55                  60

Pro Gln Asp Asn Met His Gln Met His Lys Pro Met Glu Ser Met His
65                  70                  75                  80

Glu Lys Gly Met Ser Asp Asp Pro Arg Tyr Asn Gln Met Lys Gly Met
                85                  90                  95

Gly Met Arg Ser Gly Gly His Ala Gly Met Gly Pro Pro Ser Pro
            100                 105                 110

Met Asp Gln His Ser Gln Gly Tyr Pro Ser Pro Leu Gly Gly Ser Glu
        115                 120                 125

His Ala Ser Ser Pro Val Pro Ala Ser Gly Pro Ser Gly Pro Gln
    130                 135                 140

Met Ser Ser Gly Pro Gly Gly Ala Pro Leu Asp Gly Ala Asp Pro Gln
145                 150                 155                 160

Ala Leu Gly Gln Gln Asn Arg Gly Pro Thr Pro Phe Asn Gln Asn Gln
                165                 170                 175
```

-continued

```
Leu His Gln Leu Arg Ala Gln Ile Met Ala Tyr Lys Met Leu Ala Arg
            180                 185                 190
Gly Gln Pro Leu Pro Asp His Leu Gln Met Ala Val Gln Gly Lys Arg
            195                 200                 205
Pro Met Pro Gly Met Gln Gln Met Pro Thr Leu Pro Pro Ser
210                 215                 220
Val Ser Ala Thr Gly Pro Gly Pro Gly Pro Gly Pro Gly Pro
225                 230                 235                 240
Gly Pro Gly Pro Ala Pro Pro Asn Tyr Ser Arg Pro His Gly Met Gly
            245                 250                 255
Gly Pro Asn Met Pro Pro Gly Pro Ser Gly Val Pro Pro Gly Met
            260                 265                 270
Pro Gly Gln Pro Pro Gly Gly Pro Pro Lys Pro Trp Pro Glu Gly Pro
            275                 280                 285
Met Ala Asn Ala Ala Ala Pro Thr Ser Thr Pro Gln Lys Leu Ile Pro
            290                 295                 300
Pro Gln Pro Thr Gly Arg Pro Ser Pro Ala Pro Pro Ala Val Pro Pro
305                 310                 315                 320
Ala Ala Ser Pro Val Met Pro Pro Gln Thr Gln Ser Pro Gly Gln Pro
            325                 330                 335
Ala Gln Pro Ala Pro Met Val Pro Leu His Gln Lys Gln Ser Arg Ile
            340                 345                 350
Thr Pro Ile Gln Lys Pro Arg Gly Leu Asp Pro Val Glu Ile Leu Gln
            355                 360                 365
Glu Arg Glu Tyr Arg Leu Gln Ala Arg Ile Ala His Arg Ile Gln Glu
            370                 375                 380
Leu Glu Asn Leu Pro Gly Ser Leu Ala Gly Asp Leu Arg Thr Lys Ala
385                 390                 395                 400
Thr Ile Glu Leu Lys Ala Leu Arg Leu Leu Asn Phe Gln Arg Gln Leu
            405                 410                 415
Arg Gln Glu Val Val Val Cys Met Arg Arg Asp Thr Ala Leu Glu Thr
            420                 425                 430
Ala Leu Asn Ala Lys Ala Tyr Lys Arg Ser Lys Arg Gln Ser Leu Arg
            435                 440                 445
Glu Ala Arg Ile Thr Glu Lys Leu Glu Lys Gln Gln Lys Ile Glu Gln
            450                 455                 460
Glu Arg Lys Arg Arg Gln Lys His Gln Glu Tyr Leu Asn Ser Ile Leu
465                 470                 475                 480
Gln His Ala Lys Asp Phe Lys Glu Tyr His Arg Ser Val Thr Gly Lys
            485                 490                 495
Ile Gln Lys Leu Thr Lys Ala Val Ala Thr Tyr His Ala Asn Thr Glu
            500                 505                 510
Arg Glu Gln Lys Lys Glu Asn Glu Arg Ile Glu Lys Glu Arg Met Arg
            515                 520                 525
Arg Leu Met Ala Glu Asp Glu Glu Gly Tyr Arg Lys Leu Ile Asp Gln
            530                 535                 540
Lys Lys Asp Lys Arg Leu Ala Tyr Leu Leu Gln Gln Thr Asp Glu Tyr
545                 550                 555                 560
Val Ala Asn Leu Thr Glu Leu Val Arg Gln His Lys Ala Ala Gln Val
            565                 570                 575
Ala Lys Glu Lys Lys Lys Lys Lys Lys Lys Ala Glu Asn Ala
            580                 585                 590
```

```
Glu Gly Gln Thr Pro Ala Ile Gly Pro Asp Gly Glu Pro Leu Asp Glu
        595                 600                 605

Thr Ser Gln Met Ser Asp Leu Pro Val Lys Val Ile His Val Glu Ser
610                 615                 620

Gly Lys Ile Leu Thr Gly Thr Asp Ala Pro Lys Ala Gly Gln Leu Glu
625                 630                 635                 640

Ala Trp Leu Glu Met Asn Pro Gly Tyr Glu Val Ala Pro Arg Ser Asp
                645                 650                 655

Ser Glu Glu Ser Gly Ser Glu Glu Glu Glu Glu Glu Glu Glu Glu Glu
                660                 665                 670

Gln Pro Gln Ala Ala Gln Pro Pro Thr Leu Pro Val Glu Glu Lys Lys
        675                 680                 685

Lys Ile Pro Asp Pro Asp Ser Asp Asp Val Ser Glu Val Asp Ala Arg
690                 695                 700

His Ile Ile Glu Asn Ala Lys Gln Asp Val Asp Asp Glu Tyr Gly Val
705                 710                 715                 720

Ser Gln Ala Leu Ala Arg Gly Leu Gln Ser Tyr Tyr Ala Val Ala His
                725                 730                 735

Ala Val Thr Glu Arg Val Asp Lys Gln Ser Ala Leu Met Val Asn Gly
                740                 745                 750

Val Leu Lys Gln Tyr Gln Ile Lys Gly Leu Glu Trp Leu Val Ser Leu
        755                 760                 765

Tyr Asn Asn Asn Leu Asn Gly Ile Leu Ala Asp Glu Met Gly Leu Gly
770                 775                 780

Lys Thr Ile Gln Thr Ile Ala Leu Ile Thr Tyr Leu Met Glu His Lys
785                 790                 795                 800

Arg Ile Asn Gly Pro Phe Leu Ile Ile Val Pro Leu Ser Thr Leu Ser
                805                 810                 815

Asn Trp Ala Tyr Glu Phe Asp Lys Trp Ala Pro Ser Val Val Lys Val
                820                 825                 830

Ser Tyr Lys Gly Ser Pro Ala Ala Arg Arg Ala Phe Val Pro Gln Leu
        835                 840                 845

Arg Ser Gly Lys Phe Asn Val Leu Leu Thr Thr Tyr Glu Tyr Ile Ile
850                 855                 860

Lys Asp Lys His Ile Leu Ala Lys Ile Arg Trp Lys Tyr Met Ile Val
865                 870                 875                 880

Asp Glu Gly His Arg Met Lys Asn His His Cys Lys Leu Thr Gln Val
                885                 890                 895

Leu Asn Thr His Tyr Val Ala Pro Arg Arg Leu Leu Leu Thr Gly Thr
                900                 905                 910

Pro Leu Gln Asn Lys Leu Pro Glu Leu Trp Ala Leu Leu Asn Phe Leu
        915                 920                 925

Leu Pro Thr Ile Phe Lys Ser Cys Ser Thr Phe Glu Gln Trp Phe Asn
930                 935                 940

Ala Pro Phe Ala Met Thr Gly Glu Lys Val Asp Leu Asn Glu Glu Glu
945                 950                 955                 960

Thr Ile Leu Ile Ile Arg Arg Leu His Lys Val Leu Arg Pro Phe Leu
                965                 970                 975

Leu Arg Arg Leu Lys Lys Glu Val Glu Ala Gln Leu Pro Glu Lys Val
                980                 985                 990

Glu Tyr Val Ile Lys Cys Asp Met Ser Ala Leu Gln Arg Val Leu Tyr
        995                 1000                1005

Arg His Met Gln Ala Lys Gly Val Leu Leu Thr Asp Gly Ser Glu Lys
```

-continued

```
            1010                1015                1020
Asp Lys Lys Gly Lys Gly Gly Thr Lys Thr Leu Met Asn Thr Ile Met
1025                1030                1035                1040

Gln Leu Arg Lys Ile Cys Asn His Pro Tyr Met Phe Gln His Ile Glu
                1045                1050                1055

Glu Ser Phe Ser Glu His Leu Gly Phe Thr Gly Gly Ile Val Gln Gly
                1060                1065                1070

Leu Asp Leu Tyr Arg Ala Ser Gly Lys Phe Glu Leu Leu Asp Arg Ile
            1075                1080                1085

Leu Pro Lys Leu Arg Ala Thr Asn His Lys Val Leu Leu Phe Cys Gln
1090                1095                1100

Met Thr Ser Leu Met Thr Ile Met Glu Asp Tyr Phe Ala Tyr Arg Gly
1105                1110                1115                1120

Phe Lys Tyr Leu Arg Leu Asp Gly Thr Thr Lys Ala Glu Asp Arg Gly
                1125                1130                1135

Met Leu Leu Lys Thr Phe Asn Glu Pro Gly Ser Glu Tyr Phe Ile Phe
            1140                1145                1150

Leu Leu Ser Thr Arg Ala Gly Gly Leu Gly Leu Asn Leu Gln Ser Ala
            1155                1160                1165

Asp Thr Val Ile Ile Phe Asp Ser Asp Trp Asn Pro His Gln Asp Leu
            1170                1175                1180

Gln Ala Gln Asp Arg Ala His Arg Ile Gly Gln Gln Asn Glu Val Arg
1185                1190                1195                1200

Val Leu Arg Leu Cys Thr Val Asn Ser Val Glu Glu Lys Ile Leu Ala
                1205                1210                1215

Ala Ala Lys Tyr Lys Leu Asn Val Asp Gln Lys Val Ile Gln Ala Gly
            1220                1225                1230

Met Phe Asp Gln Lys Ser Ser Ser His Glu Arg Arg Ala Phe Leu Gln
            1235                1240                1245

Ala Ile Leu Glu His Glu Glu Gln Asp Glu Ser Arg His Cys Ser Thr
1250                1255                1260

Gly Ser Gly Ser Ala Ser Phe Ala His Thr Ala Pro Pro Ala Gly
1265                1270                1275                1280

Val Asn Pro Asp Leu Glu Glu Pro Pro Leu Lys Glu Glu Asp Glu Val
            1285                1290                1295

Pro Asp Asp Glu Thr Val Asn Gln Met Ile Ala Arg His Glu Glu Glu
            1300                1305                1310

Phe Asp Leu Phe Met Arg Met Asp Leu Asp Arg Arg Arg Glu Glu Ala
            1315                1320                1325

Arg Asn Pro Lys Arg Lys Pro Arg Leu Met Glu Glu Asp Glu Leu Pro
1330                1335                1340

Ser Trp Ile Ile Lys Asp Asp Ala Glu Val Glu Arg Leu Thr Cys Glu
1345                1350                1355                1360

Glu Glu Glu Glu Lys Met Phe Gly Arg Gly Ser Arg His Arg Lys Glu
                1365                1370                1375

Val Asp Tyr Ser Asp Ser Leu Thr Glu Lys Gln Trp Leu Lys Ala Ile
            1380                1385                1390

Glu Glu Gly Thr Leu Glu Glu Ile Glu Glu Val Arg Gln Lys Lys
            1395                1400                1405

Ser Ser Arg Lys Arg Lys Arg Asp Ser Asp Ala Gly Ser Ser Thr Pro
1410                1415                1420

Thr Thr Ser Thr Arg Ser Arg Asp Lys Asp Asp Glu Ser Lys Lys Gln
1425                1430                1435                1440
```

```
Lys Lys Arg Gly Arg Pro Pro Ala Glu Lys Leu Ser Pro Asn Pro Pro
            1445                1450                1455

Asn Leu Thr Lys Lys Met Lys Lys Ile Val Asp Ala Val Ile Lys Tyr
        1460                1465                1470

Lys Asp Ser Ser Gly Arg Gln Leu Ser Glu Val Phe Ile Gln Leu Pro
    1475                1480                1485

Ser Arg Lys Glu Leu Pro Glu Tyr Tyr Glu Leu Ile Arg Lys Pro Val
1490                1495                1500

Asp Phe Lys Lys Ile Lys Glu Arg Ile Arg Asn His Lys Tyr Arg Ser
1505                1510                1515                1520

Leu Asn Asp Leu Glu Lys Asp Val Met Leu Leu Cys Gln Asn Ala Gln
            1525                1530                1535

Thr Phe Asn Leu Glu Gly Ser Leu Ile Tyr Glu Asp Ser Ile Val Leu
        1540                1545                1550

Gln Ser Val Phe Thr Ser Val Arg Gln Lys Ile Glu Lys Glu Asp Asp
    1555                1560                1565

Ser Glu Gly Glu Glu Ser Glu Glu Glu Glu Gly Glu Glu Glu Gly
1570                1575                1580

Ser Glu Ser Glu Ser Arg Ser Val Lys Val Lys Ile Lys Leu Gly Arg
1585                1590                1595                1600

Lys Glu Lys Ala Gln Asp Arg Leu Lys Gly Gly Arg Arg Pro Ser
            1605                1610                1615

Arg Gly Ser Arg Ala Lys Pro Val Val Ser Asp Asp Ser Glu Glu
        1620                1625                1630

Glu Gln Glu Glu Asp Arg Ser Gly Ser Gly Ser Glu Glu Asp
    1635                1640                1645

<210> SEQ ID NO 68
<211> LENGTH: 5564
<212> TYPE: DNA
<213> ORGANISM: Homo sapiens
<220> FEATURE:
<221> NAME/KEY: CDS
<222> LOCATION: (75)..(5108)
<220> FEATURE:
<221> NAME/KEY: conflict
<222> LOCATION: (1780)
<223> OTHER INFORMATION: GenBank Accession No. U29175 shows a C at this
      position (position 1784 in GenBank) rather than
      the G shown here.
<220> FEATURE:
<221> NAME/KEY: allele
<222> LOCATION: (26)
<223> OTHER INFORMATION: Polymorphism of either T or C in this noncoding
      region.
<220> FEATURE:
<221> NAME/KEY: allele
<222> LOCATION: (1583)
<223> OTHER INFORMATION: Polymorphism of A or G resulting in a silent
      mutation.
<220> FEATURE:
<221> NAME/KEY: allele
<222> LOCATION: (1598)
<223> OTHER INFORMATION: Polymorphism of T or C resulting in a silent
      mutation.
<220> FEATURE:
<221> NAME/KEY: allele
<222> LOCATION: (1892)
<223> OTHER INFORMATION: Polymorphism of A or G resulting in a silent
      mutation.
<220> FEATURE:
<221> NAME/KEY: misc_feature
<222> LOCATION: (4245)..(4340)
<223> OTHER INFORMATION: This is a 96 base insertion compared to SEQ ID
      NO:1.
```

<220> FEATURE:
<221> NAME/KEY: misc_feature
<222> LOCATION: (4594)..(4595)
<223> OTHER INFORMATION: A deletion of CAG occurs between these bases as compared to SEQ ID NO:1 (bases 4499-4501 of SEQ ID NO:1).

<400> SEQUENCE: 68

| | | |
|---|---|---|
| ggcgggggag gcgccgggaa gtcgatggcg ccggcggctc ctgcaggagg ccactgtctg | | 60 |

| | | |
|---|---|---|
| cagctcccgt gaag atg tcc act cca gac cca ccc ctg ggc gga act cct | | 110 |
| Met Ser Thr Pro Asp Pro Pro Leu Gly Gly Thr Pro | | |
| 1 5 10 | | |

| cgg cca ggt cct tcc ccg ggc cct ggc cct tcc cct gga gcc atg ctg | 158 |
|---|---|
| Arg Pro Gly Pro Ser Pro Gly Pro Gly Pro Ser Pro Gly Ala Met Leu | |
| 15 20 25 | |

| ggc cct agc ccg ggt ccc tcg ccg ggc tcc gcc cac agc atg atg ggg | 206 |
|---|---|
| Gly Pro Ser Pro Gly Pro Ser Pro Gly Ser Ala His Ser Met Met Gly | |
| 30 35 40 | |

| ccc agc cca ggg ccg ccc tca gca gga cac ccc atc ccc acc cag ggg | 254 |
|---|---|
| Pro Ser Pro Gly Pro Pro Ser Ala Gly His Pro Ile Pro Thr Gln Gly | |
| 45 50 55 60 | |

| cct gga ggg tac cct cag gac aac atg cac cag atg cac aag ccc atg | 302 |
|---|---|
| Pro Gly Gly Tyr Pro Gln Asp Asn Met His Gln Met His Lys Pro Met | |
| 65 70 75 | |

| gag tcc atg cat gag aag ggc atg tcg gac gac ccg cgc tac aac cag | 350 |
|---|---|
| Glu Ser Met His Glu Lys Gly Met Ser Asp Asp Pro Arg Tyr Asn Gln | |
| 80 85 90 | |

| atg aaa gga atg ggg atg cgg tca ggg ggc cat gct ggg atg ggg ccc | 398 |
|---|---|
| Met Lys Gly Met Gly Met Arg Ser Gly Gly His Ala Gly Met Gly Pro | |
| 95 100 105 | |

| ccg ccc agc ccc atg gac cag cac tcc caa ggt tac ccc tcg ccc ctg | 446 |
|---|---|
| Pro Pro Ser Pro Met Asp Gln His Ser Gln Gly Tyr Pro Ser Pro Leu | |
| 110 115 120 | |

| ggt ggc tct gag cat gcc tct agt cca gtt cca gcc agt ggc ccg tct | 494 |
|---|---|
| Gly Gly Ser Glu His Ala Ser Ser Pro Val Pro Ala Ser Gly Pro Ser | |
| 125 130 135 140 | |

| tcg ggg ccc cag atg tct tcc ggg cca gga ggt gcc ccg ctg gat ggt | 542 |
|---|---|
| Ser Gly Pro Gln Met Ser Ser Gly Pro Gly Gly Ala Pro Leu Asp Gly | |
| 145 150 155 | |

| gct gac ccc cag gcc ttg ggg cag cag aac cgg ggc cca acc cca ttt | 590 |
|---|---|
| Ala Asp Pro Gln Ala Leu Gly Gln Gln Asn Arg Gly Pro Thr Pro Phe | |
| 160 165 170 | |

| aac cag aac cag ctg cac cag ctc aga gct cag atc atg gcc tac aag | 638 |
|---|---|
| Asn Gln Asn Gln Leu His Gln Leu Arg Ala Gln Ile Met Ala Tyr Lys | |
| 175 180 185 | |

| atg ctg gcc agg ggg cag ccc ctc ccc gac cac ctg cag atg gcg gtg | 686 |
|---|---|
| Met Leu Ala Arg Gly Gln Pro Leu Pro Asp His Leu Gln Met Ala Val | |
| 190 195 200 | |

| cag ggc aag cgg ccg atg ccc ggg atg cag cag cag atg cca acg cta | 734 |
|---|---|
| Gln Gly Lys Arg Pro Met Pro Gly Met Gln Gln Gln Met Pro Thr Leu | |
| 205 210 215 220 | |

| cct cca ccc tcg gtg tcc gca aca gga ccc ggc cct ggc cct ggc cct | 782 |
|---|---|
| Pro Pro Pro Ser Val Ser Ala Thr Gly Pro Gly Pro Gly Pro Gly Pro | |
| 225 230 235 | |

| ggc ccc ggc ccg ggt ccc ggc ccg gca cct cca aat tac agc agg cct | 830 |
|---|---|
| Gly Pro Gly Pro Gly Pro Gly Pro Ala Pro Pro Asn Tyr Ser Arg Pro | |
| 240 245 250 | |

| cat ggt atg gga ggg ccc aac atg cct ccc cca gga ccc tcg ggc gtg | 878 |
|---|---|
| His Gly Met Gly Gly Pro Asn Met Pro Pro Pro Gly Pro Ser Gly Val | |
| 255 260 265 | |

-continued

| | |
|---|---|
| ccc ccc ggg atg cca ggc cag cct cct gga ggg cct ccc aag ccc tgg<br>Pro Pro Gly Met Pro Gly Gln Pro Pro Gly Gly Pro Pro Lys Pro Trp<br>270                            275                      280 | 926 |
| cct gaa gga ccc atg gcg aat gct gct gcc ccc acg agc acc cct cag<br>Pro Glu Gly Pro Met Ala Asn Ala Ala Ala Pro Thr Ser Thr Pro Gln<br>285                            290                      295                      300 | 974 |
| aag ctg att ccc ccg cag cca acg ggc cgc cct tcc ccc gcg ccc cct<br>Lys Leu Ile Pro Pro Gln Pro Thr Gly Arg Pro Ser Pro Ala Pro Pro<br>305                            310                      315 | 1022 |
| gcc gtc cca ccc gcc gcc tcg ccc gtg atg cca ccg cag acc cag tcc<br>Ala Val Pro Pro Ala Ala Ser Pro Val Met Pro Pro Gln Thr Gln Ser<br>320                          325                      330 | 1070 |
| ccc ggg cag ccg gcc cag ccc gcg ccc atg gtg cca ctg cac cag aag<br>Pro Gly Gln Pro Ala Gln Pro Ala Pro Met Val Pro Leu His Gln Lys<br>335                            340                      345 | 1118 |
| cag agc cgc atc acc ccc atc cag aag ccg cgg ggc ctc gac cct gtg<br>Gln Ser Arg Ile Thr Pro Ile Gln Lys Pro Arg Gly Leu Asp Pro Val<br>350                            355                      360 | 1166 |
| gag atc ctg cag gag cgc gag tac agg ctg cag gct cgc atc gca cac<br>Glu Ile Leu Gln Glu Arg Glu Tyr Arg Leu Gln Ala Arg Ile Ala His<br>365                            370                      375                      380 | 1214 |
| cga att cag gaa ctt gaa aac ctt ccc ggg tcc ctg gcc ggg gat ttg<br>Arg Ile Gln Glu Leu Glu Asn Leu Pro Gly Ser Leu Ala Gly Asp Leu<br>                        385                      390                      395 | 1262 |
| cga acc aaa gcg acc att gag ctc aag gcc ctc agg ctg ctg aac ttc<br>Arg Thr Lys Ala Thr Ile Glu Leu Lys Ala Leu Arg Leu Leu Asn Phe<br>            400                      405                      410 | 1310 |
| cag agg cag ctg cgc cag gag gtg gtg gtg tgc atg cgg agg gac aca<br>Gln Arg Gln Leu Arg Gln Glu Val Val Val Cys Met Arg Arg Asp Thr<br>            415                      420                      425 | 1358 |
| gcg ctg gag aca gcc ctc aat gct aag gcc tac aag cgc agc aag cgc<br>Ala Leu Glu Thr Ala Leu Asn Ala Lys Ala Tyr Lys Arg Ser Lys Arg<br>430                            435                      440 | 1406 |
| cag tcc ctg cgc gag gcc cgc atc act gag aag ctg gag aag cag cag<br>Gln Ser Leu Arg Glu Ala Arg Ile Thr Glu Lys Leu Glu Lys Gln Gln<br>445                            450                      455                      460 | 1454 |
| aag atc gag cag gag cgc aag cgc cgg cag aag cac cag gaa tac ctc<br>Lys Ile Glu Gln Glu Arg Lys Arg Arg Gln Lys His Gln Glu Tyr Leu<br>                      465                      470                      475 | 1502 |
| aat agc att ctc cag cat gcc aag gat ttc aag gaa tat cac aga tcc<br>Asn Ser Ile Leu Gln His Ala Lys Asp Phe Lys Glu Tyr His Arg Ser<br>                      480                      485                      490 | 1550 |
| gtc aca ggc aaa atc cag aag ctg acc aag gca gtg gcc acg tac cat<br>Val Thr Gly Lys Ile Gln Lys Leu Thr Lys Ala Val Ala Thr Tyr His<br>            495                      500                      505 | 1598 |
| gcc aac acg gag cgg gag cag aag aaa gag aac gag cgg atc gag aag<br>Ala Asn Thr Glu Arg Glu Gln Lys Lys Glu Asn Glu Arg Ile Glu Lys<br>510                            515                      520 | 1646 |
| gag cgc atg cgg agg ctc atg gct gaa gat gag gag ggg tac cgc aag<br>Glu Arg Met Arg Arg Leu Met Ala Glu Asp Glu Glu Gly Tyr Arg Lys<br>525                            530                      535                      540 | 1694 |
| ctc atc gac cag aag aag gac aag cgc ctg gcc tac ctc ttg cag cag<br>Leu Ile Asp Gln Lys Lys Asp Lys Arg Leu Ala Tyr Leu Leu Gln Gln<br>                      545                      550                      555 | 1742 |
| aca gac gag tac gtg gct aac ctc acg gag ctg gtg cgg cag cac aag<br>Thr Asp Glu Tyr Val Ala Asn Leu Thr Glu Leu Val Arg Gln His Lys<br>                      560                      565                      570 | 1790 |
| gct gcc cag gtc gcc aag gag aaa aag aag aaa aag aaa aag aag aag<br>Ala Ala Gln Val Ala Lys Glu Lys Lys Lys Lys Lys Lys Lys Lys Lys<br>575                            580                      585 | 1838 |

```
gca aat gca gaa gga cag acg cct gcc att ggg ccg gat ggc gag    1886
Ala Glu Asn Ala Glu Gly Gln Thr Pro Ala Ile Gly Pro Asp Gly Glu
    590             595                 600 cct cta gac gag acc agc cag atg agc gac ctc ccg gtg aag gtg atc   1934
Pro Leu Asp Glu Thr Ser Gln Met Ser Asp Leu Pro Val Lys Val Ile
605                 610                 615                 620 cac gtg gag agt ggg aag atc ctc aca ggc aca gat gcc ccc aaa gcc   1982
His Val Glu Ser Gly Lys Ile Leu Thr Gly Thr Asp Ala Pro Lys Ala
                625                 630                 635 ggg cag ctg gag gcc tgg ctc gag atg aac ccg ggg tat gaa gta gct   2030
Gly Gln Leu Glu Ala Trp Leu Glu Met Asn Pro Gly Tyr Glu Val Ala
            640                 645                 650 ccg agg tct gat agt gaa gaa agt ggc tca gaa gaa gag gaa gag gag   2078
Pro Arg Ser Asp Ser Glu Glu Ser Gly Ser Glu Glu Glu Glu Glu Glu
        655                 660                 665 gag gag gaa gag cag ccg cag gca gca cag cct ccc acc ctg ccc gtg   2126
Glu Glu Glu Glu Gln Pro Gln Ala Ala Gln Pro Pro Thr Leu Pro Val
    670                 675                 680 gag gag aag aag aag att cca gat cca gac agc gat gac gtc tct gag   2174
Glu Glu Lys Lys Lys Ile Pro Asp Pro Asp Ser Asp Asp Val Ser Glu
685                 690                 695                 700 gtg gac gcg cgg cac atc att gag aat gcc aag caa gat gtc gat gat   2222
Val Asp Ala Arg His Ile Ile Glu Asn Ala Lys Gln Asp Val Asp Asp
                705                 710                 715 gaa tat ggc gtg tcc cag gcc ctt gca cgt ggc ctg cag tcc tac tat   2270
Glu Tyr Gly Val Ser Gln Ala Leu Ala Arg Gly Leu Gln Ser Tyr Tyr
            720                 725                 730 gcc gtg gcc cat gct gtc act gag aga gtg gac aag cag tca gcg ctt   2318
Ala Val Ala His Ala Val Thr Glu Arg Val Asp Lys Gln Ser Ala Leu
        735                 740                 745 atg gtc aat ggt gtc ctc aaa cag tac cag atc aaa ggt ttg gag tgg   2366
Met Val Asn Gly Val Leu Lys Gln Tyr Gln Ile Lys Gly Leu Glu Trp
    750                 755                 760 ctg gtg tcc ctg tac aac aac aac ctg aac ggc atc ctg gcc gac gag   2414
Leu Val Ser Leu Tyr Asn Asn Asn Leu Asn Gly Ile Leu Ala Asp Glu
765                 770                 775                 780 atg ggc ctg ggg aag acc atc cag acc atc gcg ctc atc acg tac ctc   2462
Met Gly Leu Gly Lys Thr Ile Gln Thr Ile Ala Leu Ile Thr Tyr Leu
                785                 790                 795 atg gag cac aaa cgc atc aat ggg ccc ttc ctc atc atc gtg cct ctc   2510
Met Glu His Lys Arg Ile Asn Gly Pro Phe Leu Ile Ile Val Pro Leu
            800                 805                 810 tca acg ctg tcc aac tgg gcg tac gag ttt gac aag tgg gcc ccc tcc   2558
Ser Thr Leu Ser Asn Trp Ala Tyr Glu Phe Asp Lys Trp Ala Pro Ser
        815                 820                 825 gtg gtg aag gtg tct tac aag gga tcc cca gca gca aga cgg gcc ttt   2606
Val Val Lys Val Ser Tyr Lys Gly Ser Pro Ala Ala Arg Arg Ala Phe
    830                 835                 840 gtc ccc cag ctc cgg agt ggg aag ttc aac gtc ttg ctg acg acg tac   2654
Val Pro Gln Leu Arg Ser Gly Lys Phe Asn Val Leu Leu Thr Thr Tyr
845                 850                 855                 860 gag tac atc atc aaa gac aag cac atc ctc gcc aag atc cgt tgg aag   2702
Glu Tyr Ile Ile Lys Asp Lys His Ile Leu Ala Lys Ile Arg Trp Lys
                865                 870                 875 tac atg att gtg gac gaa ggt cac cgc atg aag aac cac cac tgc aag   2750
Tyr Met Ile Val Asp Glu Gly His Arg Met Lys Asn His His Cys Lys
            880                 885                 890 ctg acg cag gtg ctc aac acg cac tat gtg gca ccc cgc cgc ctg ctg   2798
Leu Thr Gln Val Leu Asn Thr His Tyr Val Ala Pro Arg Arg Leu Leu
```

```
                895                 900                 905
ctg acg ggc aca ccg ctg cag aac aag ctt ccc gag ctc tgg gcg ctg    2846
Leu Thr Gly Thr Pro Leu Gln Asn Lys Leu Pro Glu Leu Trp Ala Leu
    910                 915                 920 ctc aac ttc ctg ctg ccc acc atc ttc aag agc tgc agc acc ttc gag    2894
Leu Asn Phe Leu Leu Pro Thr Ile Phe Lys Ser Cys Ser Thr Phe Glu
925                 930                 935                 940 cag tgg ttt aac gca ccc ttt gcc atg acc ggg gaa aag gtg gac ctg    2942
Gln Trp Phe Asn Ala Pro Phe Ala Met Thr Gly Glu Lys Val Asp Leu
            945                 950                 955 aat gag gag gaa acc att ctc atc atc cgg cgt ctc cac aaa gtg ctg    2990
Asn Glu Glu Glu Thr Ile Leu Ile Ile Arg Arg Leu His Lys Val Leu
        960                 965                 970 cgg ccc ttc ttg ctc cga cga ctc aag aag gaa gtc gag gcc cag ttg    3038
Arg Pro Phe Leu Leu Arg Arg Leu Lys Lys Glu Val Glu Ala Gln Leu
    975                 980                 985 ccc gaa aag gtg gag tac gtc atc aag tgc gac atg tct gcg ctg cag    3086
Pro Glu Lys Val Glu Tyr Val Ile Lys Cys Asp Met Ser Ala Leu Gln
990                 995                 1000 cga gtg ctc tac cgc cac atg cag gcc aag ggc gtg ctg ctg act gat    3134
Arg Val Leu Tyr Arg His Met Gln Ala Lys Gly Val Leu Leu Thr Asp
1005                1010                1015                1020 ggc tcc gag aag gac aag aag ggc aaa ggc ggc acc aag acc ctg atg    3182
Gly Ser Glu Lys Asp Lys Lys Gly Lys Gly Gly Thr Lys Thr Leu Met
                1025                1030                1035 aac acc atc atg cag ctg cgg aag atc tgc aac cac ccc tac atg ttc    3230
Asn Thr Ile Met Gln Leu Arg Lys Ile Cys Asn His Pro Tyr Met Phe
            1040                1045                1050 cag cac atc gag gag tcc ttt tcc gag cac ttg ggg ttc act ggc ggc    3278
Gln His Ile Glu Glu Ser Phe Ser Glu His Leu Gly Phe Thr Gly Gly
        1055                1060                1065 att gtc caa ggg ctg gac ctg tac cga gcc tcg ggt aaa ttt gag ctt    3326
Ile Val Gln Gly Leu Asp Leu Tyr Arg Ala Ser Gly Lys Phe Glu Leu
    1070                1075                1080 ctt gat aga att ctt ccc aaa ctc cga gca acc aac cac aaa gtg ctg    3374
Leu Asp Arg Ile Leu Pro Lys Leu Arg Ala Thr Asn His Lys Val Leu
1085                1090                1095                1100 ctg ttc tgc caa atg acc tcc ctc atg acc atc atg gaa gat tac ttt    3422
Leu Phe Cys Gln Met Thr Ser Leu Met Thr Ile Met Glu Asp Tyr Phe
                1105                1110                1115 gcg tat cgc ggc ttt aaa tac ctc agg ctt gat gga acc acg aag gcg    3470
Ala Tyr Arg Gly Phe Lys Tyr Leu Arg Leu Asp Gly Thr Thr Lys Ala
            1120                1125                1130 gag gac cgg ggc atg ctg ctg aaa acc ttc aac gag ccc ggc tct gag    3518
Glu Asp Arg Gly Met Leu Leu Lys Thr Phe Asn Glu Pro Gly Ser Glu
        1135                1140                1145 tac ttc atc ttc ctg ctc agc acc cgg gct ggg ggg ctc ggc ctg aac    3566
Tyr Phe Ile Phe Leu Leu Ser Thr Arg Ala Gly Gly Leu Gly Leu Asn
    1150                1155                1160 ctc cag tcg gca gac act gtg atc att ttt gac agc gac tgg aat cct    3614
Leu Gln Ser Ala Asp Thr Val Ile Ile Phe Asp Ser Asp Trp Asn Pro
1165                1170                1175                1180 cac cag gac ctg caa gcg cag gac cga gcc cac cgc atc ggg cag cag    3662
His Gln Asp Leu Gln Ala Gln Asp Arg Ala His Arg Ile Gly Gln Gln
                1185                1190                1195 aac gag gtg cgt gtg ctc cgc ctc tgc acc gtc aac agc gtg gag gag    3710
Asn Glu Val Arg Val Leu Arg Leu Cys Thr Val Asn Ser Val Glu Glu
            1200                1205                1210 aag atc cta gct gca gcc aag tac aag ctc aac gtg gac cag aag gtg    3758
```

```
                                                      -continued

Lys Ile Leu Ala Ala Ala Lys Tyr Lys Leu Asn Val Asp Gln Lys Val
    1215                1220                1225 atc cag gcc ggc atg ttc gac cag aag tcc tcc agc cat gag cgg cgc        3806
Ile Gln Ala Gly Met Phe Asp Gln Lys Ser Ser Ser His Glu Arg Arg
    1230                1235                1240 gcc ttc ctg cag gcc atc ctg gag cac gag gag cag gat gag agc aga        3854
Ala Phe Leu Gln Ala Ile Leu Glu His Glu Glu Gln Asp Glu Ser Arg
1245                1250                1255                1260 cac tgc agc acg ggc agc ggc agt gcc agc ttc gcc cac act gcc cct        3902
His Cys Ser Thr Gly Ser Gly Ser Ala Ser Phe Ala His Thr Ala Pro
            1265                1270                1275 ccg cca gcg ggc gtc aac ccc gac ttg gag gag cca cct cta aag gag        3950
Pro Pro Ala Gly Val Asn Pro Asp Leu Glu Glu Pro Pro Leu Lys Glu
        1280                1285                1290 gaa gac gag gtg ccc gac gac gag acc gtc aac cag atg atc gcc cgg        3998
Glu Asp Glu Val Pro Asp Asp Glu Thr Val Asn Gln Met Ile Ala Arg
    1295                1300                1305 cac gag gag gag ttt gat ctg ttc atg cgc atg gac ctg gac cgc agg        4046
His Glu Glu Glu Phe Asp Leu Phe Met Arg Met Asp Leu Asp Arg Arg
    1310                1315                1320 cgc gag gag gcc cgc aac ccc aag cgg aag ccg cgc ctc atg gag gag        4094
Arg Glu Glu Ala Arg Asn Pro Lys Arg Lys Pro Arg Leu Met Glu Glu
1325                1330                1335                1340 gac gag ctc ccc tcg tgg atc atc aag gac gac gcg gag gtg gag cgg        4142
Asp Glu Leu Pro Ser Trp Ile Ile Lys Asp Asp Ala Glu Val Glu Arg
            1345                1350                1355 ctg acc tgt gag gag gag gag gag aag atg ttc ggc cgt ggc tcc cgc        4190
Leu Thr Cys Glu Glu Glu Glu Glu Lys Met Phe Gly Arg Gly Ser Arg
        1360                1365                1370 cac cgc aag gag gtg gac tac agc gac tca ctg acg gag aag cag tgg        4238
His Arg Lys Glu Val Asp Tyr Ser Asp Ser Leu Thr Glu Lys Gln Trp
    1375                1380                1385 ctc aag aaa att aca gga aaa gat atc cat gac aca gcc agc agt gtg        4286
Leu Lys Lys Ile Thr Gly Lys Asp Ile His Asp Thr Ala Ser Ser Val
    1390                1395                1400 gca cgt ggg cta caa ttc cag cgt ggc ctt cag ttc tgc aca cgt gcg        4334
Ala Arg Gly Leu Gln Phe Gln Arg Gly Leu Gln Phe Cys Thr Arg Ala
1405                1410                1415                1420 tca aag gcc atc gag gag ggc acg ctg gag gag atc gaa gag gag gtc        4382
Ser Lys Ala Ile Glu Glu Gly Thr Leu Glu Glu Ile Glu Glu Glu Val
            1425                1430                1435 cgg cag aag aaa tca tca cgg aag cgc aag cga gac agc gac gcc ggc        4430
Arg Gln Lys Lys Ser Ser Arg Lys Arg Lys Arg Asp Ser Asp Ala Gly
        1440                1445                1450 tcc tcc acc ccg acc acc agc acc cgc agc cgc gac aag gac gac gag        4478
Ser Ser Thr Pro Thr Thr Ser Thr Arg Ser Arg Asp Lys Asp Asp Glu
    1455                1460                1465 agc aag aag cag aag aag cgc ggg cgg ccg cct gcc gag aaa ctc tcc        4526
Ser Lys Lys Gln Lys Lys Arg Gly Arg Pro Pro Ala Glu Lys Leu Ser
    1470                1475                1480 cct aac cca ccc aac ctc acc aag aag atg aag aag att gtg gat gcc        4574
Pro Asn Pro Pro Asn Leu Thr Lys Lys Met Lys Lys Ile Val Asp Ala
1485                1490                1495                1500 gtg atc aag tac aag gac agc agt gga cgt cag ctc agc gag gtc ttc        4622
Val Ile Lys Tyr Lys Asp Ser Ser Gly Arg Gln Leu Ser Glu Val Phe
            1505                1510                1515 atc cag ctg ccc tcg cga aag gag ctg ccc gag tac tac gag ctc atc        4670
Ile Gln Leu Pro Ser Arg Lys Glu Leu Pro Glu Tyr Tyr Glu Leu Ile
        1520                1525                1530
```

-continued

| | |
|---|---|
| cgc aag ccc gtg gac ttc aag aag ata aag gag cgc att cgc aac cac<br>Arg Lys Pro Val Asp Phe Lys Lys Ile Lys Glu Arg Ile Arg Asn His<br>    1535                    1540                    1545 | 4718 |
| aag tac cgc agc ctc aac gac cta gag aag gac gtc atg ctc ctg tgc<br>Lys Tyr Arg Ser Leu Asn Asp Leu Glu Lys Asp Val Met Leu Leu Cys<br>1550                    1555                    1560 | 4766 |
| cag aac gca cag acc ttc aac ctg gag ggc tcc ctg atc tat gaa gac<br>Gln Asn Ala Gln Thr Phe Asn Leu Glu Gly Ser Leu Ile Tyr Glu Asp<br>1565                    1570                    1575                    1580 | 4814 |
| tcc atc gtc ttg cag tcg gtc ttc acc agc gtg cgg cag aaa atc gag<br>Ser Ile Val Leu Gln Ser Val Phe Thr Ser Val Arg Gln Lys Ile Glu<br>                  1585                    1590                    1595 | 4862 |
| aag gag gat gac agt gaa ggc gag gag agt gag gag gag gaa gag ggc<br>Lys Glu Asp Asp Ser Glu Gly Glu Glu Ser Glu Glu Glu Glu Gly<br>              1600                    1605                    1610 | 4910 |
| gag gag gaa ggc tcc gaa tcc gaa tct cgg tcc gtc aaa gtg aag atc<br>Glu Glu Glu Gly Ser Glu Ser Glu Ser Arg Ser Val Lys Val Lys Ile<br>              1615                    1620                    1625 | 4958 |
| aag ctt ggc cgg aag gag aag gca cag gac cgg ctg aag ggc ggc cgg<br>Lys Leu Gly Arg Lys Glu Lys Ala Gln Asp Arg Leu Lys Gly Gly Arg<br>1630                    1635                    1640 | 5006 |
| cgg cgg ccg agc cga ggg tcc cga gcc aag ccg gtc gtg agt gac gat<br>Arg Arg Pro Ser Arg Gly Ser Arg Ala Lys Pro Val Val Ser Asp Asp<br>1645                    1650                    1655                    1660 | 5054 |
| gac agt gag gag gaa caa gag gag gac cgc tca gga agt ggc agc gaa<br>Asp Ser Glu Glu Glu Gln Glu Glu Asp Arg Ser Gly Ser Gly Ser Glu<br>              1665                    1670                    1675 | 5102 |
| gaa gac tgagccccga cattccagtc tcgaccccga gcccctcgtt ccagagctga<br>Glu Asp | 5158 |
| gatggcatag gccttagcag taacgggtag cagcagatgt agtttcagac ttggagtaaa | 5218 |
| actgtataaa caaaagaatc ttccatattt atacagcaga gaagctgtag gactgtttgt | 5278 |
| gactggccct gtcctggcat cagtagcatc tgtaacagca ttaactgtct taaagagaga | 5338 |
| gagagagaat tccgaattgg ggaacacacg atacctgttt ttcttttccg ttgctggcag | 5398 |
| tactgttgcg ccgcagtttg gagtcactgt agttaagtgt ggatgcatgt gcgtcaccgt | 5458 |
| ccactcctcc tactgtattt tattggacag gtcagactcg ccgggggccc ggcgagggta | 5518 |
| tgtcagtgtc actggatgtc aaacagtaat aaattaaacc aacaac | 5564 |

<210> SEQ ID NO 69
<211> LENGTH: 1678
<212> TYPE: PRT
<213> ORGANISM: Homo sapiens

<400> SEQUENCE: 69

Met Ser Thr Pro Asp Pro Pro Leu Gly Gly Thr Pro Arg Pro Gly Pro
1                 5                        10                       15

Ser Pro Gly Pro Gly Pro Ser Pro Gly Ala Met Leu Gly Pro Ser Pro
                  20                       25                      30

Gly Pro Ser Pro Gly Ser Ala His Ser Met Met Gly Pro Ser Pro Gly
        35                       40                      45

Pro Pro Ser Ala Gly His Pro Ile Pro Thr Gln Gly Pro Gly Gly Tyr
50                      55                      60

Pro Gln Asp Asn Met His Gln Met His Lys Pro Met Glu Ser Met His
65                 70                       75                      80

Glu Lys Gly Met Ser Asp Asp Pro Arg Tyr Asn Gln Met Lys Gly Met
                  85                       90                      95

```
Gly Met Arg Ser Gly Gly His Ala Gly Met Pro Pro Ser Pro
            100                 105                 110
Met Asp Gln His Ser Gln Gly Tyr Pro Ser Pro Leu Gly Gly Ser Glu
            115                 120                 125
His Ala Ser Ser Pro Val Pro Ala Ser Gly Pro Ser Ser Gly Pro Gln
            130                 135                 140
Met Ser Ser Gly Pro Gly Gly Ala Pro Leu Asp Gly Ala Asp Pro Gln
145                 150                 155                 160
Ala Leu Gly Gln Gln Asn Arg Gly Pro Thr Pro Phe Asn Gln Asn Gln
                165                 170                 175
Leu His Gln Leu Arg Ala Gln Ile Met Ala Tyr Lys Met Leu Ala Arg
                180                 185                 190
Gly Gln Pro Leu Pro Asp His Leu Gln Met Ala Val Gln Gly Lys Arg
            195                 200                 205
Pro Met Pro Gly Met Gln Gln Gln Met Pro Thr Leu Pro Pro Pro Ser
210                 215                 220
Val Ser Ala Thr Gly Pro Gly Pro Gly Pro Gly Pro Gly Pro Gly Pro
225                 230                 235                 240
Gly Pro Gly Pro Ala Pro Pro Asn Tyr Ser Arg Pro His Gly Met Gly
                245                 250                 255
Gly Pro Asn Met Pro Pro Pro Gly Pro Ser Gly Val Pro Pro Gly Met
                260                 265                 270
Pro Gly Gln Pro Pro Gly Gly Pro Pro Lys Pro Trp Pro Glu Gly Pro
            275                 280                 285
Met Ala Asn Ala Ala Ala Pro Thr Ser Thr Pro Gln Lys Leu Ile Pro
            290                 295                 300
Pro Gln Pro Thr Gly Arg Pro Ser Pro Ala Pro Pro Ala Val Pro Pro
305                 310                 315                 320
Ala Ala Ser Pro Val Met Pro Pro Gln Thr Gln Ser Pro Gly Gln Pro
                325                 330                 335
Ala Gln Pro Ala Pro Met Val Pro Leu His Gln Lys Gln Ser Arg Ile
            340                 345                 350
Thr Pro Ile Gln Lys Pro Arg Gly Leu Asp Pro Val Glu Ile Leu Gln
            355                 360                 365
Glu Arg Glu Tyr Arg Leu Gln Ala Arg Ile Ala His Arg Ile Gln Glu
            370                 375                 380
Leu Glu Asn Leu Pro Gly Ser Leu Ala Gly Asp Leu Arg Thr Lys Ala
385                 390                 395                 400
Thr Ile Glu Leu Lys Ala Leu Arg Leu Leu Asn Phe Gln Arg Gln Leu
                405                 410                 415
Arg Gln Glu Val Val Val Cys Met Arg Arg Asp Thr Ala Leu Glu Thr
                420                 425                 430
Ala Leu Asn Ala Lys Ala Tyr Lys Arg Ser Lys Arg Gln Ser Leu Arg
            435                 440                 445
Glu Ala Arg Ile Thr Glu Lys Leu Glu Lys Gln Gln Lys Ile Glu Gln
            450                 455                 460
Glu Arg Lys Arg Arg Gln Lys His Gln Glu Tyr Leu Asn Ser Ile Leu
465                 470                 475                 480
Gln His Ala Lys Asp Phe Lys Glu Tyr His Arg Ser Val Thr Gly Lys
                485                 490                 495
Ile Gln Lys Leu Thr Lys Ala Val Ala Thr Tyr His Ala Asn Thr Glu
            500                 505                 510
```

-continued

```
Arg Glu Gln Lys Lys Glu Asn Glu Arg Ile Glu Lys Glu Arg Met Arg
            515                 520                 525

Arg Leu Met Ala Glu Asp Glu Glu Gly Tyr Arg Lys Leu Ile Asp Gln
        530                 535                 540

Lys Lys Asp Lys Arg Leu Ala Tyr Leu Leu Gln Gln Thr Asp Glu Tyr
545                 550                 555                 560

Val Ala Asn Leu Thr Glu Leu Val Arg Gln His Lys Ala Ala Gln Val
                565                 570                 575

Ala Lys Glu Lys Lys Lys Lys Lys Lys Lys Lys Ala Glu Asn Ala
            580                 585                 590

Glu Gly Gln Thr Pro Ala Ile Gly Pro Asp Gly Glu Pro Leu Asp Glu
            595                 600                 605

Thr Ser Gln Met Ser Asp Leu Pro Val Lys Val Ile His Val Glu Ser
        610                 615                 620

Gly Lys Ile Leu Thr Gly Thr Asp Ala Pro Lys Ala Gly Gln Leu Glu
625                 630                 635                 640

Ala Trp Leu Glu Met Asn Pro Gly Tyr Glu Val Ala Pro Arg Ser Asp
                645                 650                 655

Ser Glu Glu Ser Gly Ser Glu Glu Glu Glu Glu Glu Glu Glu Glu Glu
            660                 665                 670

Gln Pro Gln Ala Ala Gln Pro Pro Thr Leu Pro Val Glu Glu Lys Lys
            675                 680                 685

Lys Ile Pro Asp Pro Asp Ser Asp Asp Val Ser Glu Val Asp Ala Arg
690                 695                 700

His Ile Ile Glu Asn Ala Lys Gln Asp Val Asp Asp Glu Tyr Gly Val
705                 710                 715                 720

Ser Gln Ala Leu Ala Arg Gly Leu Gln Ser Tyr Tyr Ala Val Ala His
                725                 730                 735

Ala Val Thr Glu Arg Val Asp Lys Gln Ser Ala Leu Met Val Asn Gly
            740                 745                 750

Val Leu Lys Gln Tyr Gln Ile Lys Gly Leu Glu Trp Leu Val Ser Leu
        755                 760                 765

Tyr Asn Asn Asn Leu Asn Gly Ile Leu Ala Asp Glu Met Gly Leu Gly
770                 775                 780

Lys Thr Ile Gln Thr Ile Ala Leu Ile Thr Tyr Leu Met Glu His Lys
785                 790                 795                 800

Arg Ile Asn Gly Pro Phe Leu Ile Ile Val Pro Leu Ser Thr Leu Ser
                805                 810                 815

Asn Trp Ala Tyr Glu Phe Asp Lys Trp Ala Pro Ser Val Val Lys Val
            820                 825                 830

Ser Tyr Lys Gly Ser Pro Ala Ala Arg Arg Ala Phe Val Pro Gln Leu
        835                 840                 845

Arg Ser Gly Lys Phe Asn Val Leu Leu Thr Thr Tyr Glu Tyr Ile Ile
850                 855                 860

Lys Asp Lys His Ile Leu Ala Lys Ile Arg Trp Lys Tyr Met Ile Val
865                 870                 875                 880

Asp Glu Gly His Arg Met Lys Asn His His Cys Lys Leu Thr Gln Val
                885                 890                 895

Leu Asn Thr His Tyr Val Ala Pro Arg Arg Leu Leu Leu Thr Gly Thr
            900                 905                 910

Pro Leu Gln Asn Lys Leu Pro Glu Leu Trp Ala Leu Leu Asn Phe Leu
        915                 920                 925

Leu Pro Thr Ile Phe Lys Ser Cys Ser Thr Phe Glu Gln Trp Phe Asn
```

-continued

```
              930                935                940
Ala Pro Phe Ala Met Thr Gly Glu Lys Val Asp Leu Asn Glu Glu Glu
945                950                955                960

Thr Ile Leu Ile Ile Arg Arg Leu His Lys Val Leu Arg Pro Phe Leu
                965                970                975

Leu Arg Arg Leu Lys Lys Glu Val Glu Ala Gln Leu Pro Glu Lys Val
            980                985                990

Glu Tyr Val Ile Lys Cys Asp Met Ser Ala Leu Gln Arg Val Leu Tyr
        995                1000               1005

Arg His Met Gln Ala Lys Gly Val Leu Leu Thr Asp Gly Ser Glu Lys
    1010               1015               1020

Asp Lys Lys Gly Lys Gly Gly Thr Lys Thr Leu Met Asn Thr Ile Met
1025               1030               1035               1040

Gln Leu Arg Lys Ile Cys Asn His Pro Tyr Met Phe Gln His Ile Glu
                1045               1050               1055

Glu Ser Phe Ser Glu His Leu Gly Phe Thr Gly Gly Ile Val Gln Gly
            1060               1065               1070

Leu Asp Leu Tyr Arg Ala Ser Gly Lys Phe Glu Leu Leu Asp Arg Ile
        1075               1080               1085

Leu Pro Lys Leu Arg Ala Thr Asn His Lys Val Leu Leu Phe Cys Gln
    1090               1095               1100

Met Thr Ser Leu Met Thr Ile Met Glu Asp Tyr Phe Ala Tyr Arg Gly
1105               1110               1115               1120

Phe Lys Tyr Leu Arg Leu Asp Gly Thr Thr Lys Ala Glu Asp Arg Gly
                1125               1130               1135

Met Leu Leu Lys Thr Phe Asn Glu Pro Gly Ser Glu Tyr Phe Ile Phe
            1140               1145               1150

Leu Leu Ser Thr Arg Ala Gly Gly Leu Gly Leu Asn Leu Gln Ser Ala
        1155               1160               1165

Asp Thr Val Ile Ile Phe Asp Ser Asp Trp Asn Pro His Gln Asp Leu
    1170               1175               1180

Gln Ala Gln Asp Arg Ala His Arg Ile Gly Gln Gln Asn Glu Val Arg
1185               1190               1195               1200

Val Leu Arg Leu Cys Thr Val Asn Ser Val Glu Glu Lys Ile Leu Ala
                1205               1210               1215

Ala Ala Lys Tyr Lys Leu Asn Val Asp Gln Lys Val Ile Gln Ala Gly
            1220               1225               1230

Met Phe Asp Gln Lys Ser Ser Ser His Glu Arg Arg Ala Phe Leu Gln
        1235               1240               1245

Ala Ile Leu Glu His Glu Glu Gln Asp Glu Ser Arg His Cys Ser Thr
    1250               1255               1260

Gly Ser Gly Ser Ala Ser Phe Ala His Thr Ala Pro Pro Ala Gly
1265               1270               1275               1280

Val Asn Pro Asp Leu Glu Glu Pro Pro Leu Lys Glu Asp Glu Val
                1285               1290               1295

Pro Asp Asp Glu Thr Val Asn Gln Met Ile Ala Arg His Glu Glu Glu
            1300               1305               1310

Phe Asp Leu Phe Met Arg Met Asp Leu Asp Arg Arg Arg Glu Glu Ala
        1315               1320               1325

Arg Asn Pro Lys Arg Lys Pro Arg Leu Met Glu Glu Asp Glu Leu Pro
    1330               1335               1340

Ser Trp Ile Ile Lys Asp Asp Ala Glu Val Glu Arg Leu Thr Cys Glu
1345               1350               1355               1360
```

```
Glu Glu Glu Glu Lys Met Phe Gly Arg Gly Ser Arg His Arg Lys Glu
            1365                1370                1375
Val Asp Tyr Ser Asp Ser Leu Thr Glu Lys Gln Trp Leu Lys Lys Ile
        1380                1385                1390
Thr Gly Lys Asp Ile His Asp Thr Ala Ser Ser Val Ala Arg Gly Leu
        1395                1400                1405
Gln Phe Gln Arg Gly Leu Gln Phe Cys Thr Arg Ala Ser Lys Ala Ile
    1410                1415                1420
Glu Glu Gly Thr Leu Glu Glu Ile Glu Glu Val Arg Gln Lys Lys
1425                1430                1435                1440
Ser Ser Arg Lys Arg Lys Arg Asp Ser Asp Ala Gly Ser Ser Thr Pro
            1445                1450                1455
Thr Thr Ser Thr Arg Ser Arg Asp Lys Asp Asp Glu Ser Lys Lys Gln
        1460                1465                1470
Lys Lys Arg Gly Arg Pro Pro Ala Glu Lys Leu Ser Pro Asn Pro Pro
    1475                1480                1485
Asn Leu Thr Lys Lys Met Lys Lys Ile Val Asp Ala Val Ile Lys Tyr
        1490                1495                1500
Lys Asp Ser Ser Gly Arg Gln Leu Ser Glu Val Phe Ile Gln Leu Pro
1505                1510                1515                1520
Ser Arg Lys Glu Leu Pro Glu Tyr Tyr Glu Leu Ile Arg Lys Pro Val
            1525                1530                1535
Asp Phe Lys Lys Ile Lys Glu Arg Ile Arg Asn His Lys Tyr Arg Ser
            1540                1545                1550
Leu Asn Asp Leu Glu Lys Asp Val Met Leu Leu Cys Gln Asn Ala Gln
        1555                1560                1565
Thr Phe Asn Leu Glu Gly Ser Leu Ile Tyr Glu Asp Ser Ile Val Leu
        1570                1575                1580
Gln Ser Val Phe Thr Ser Val Arg Gln Lys Ile Glu Lys Glu Asp Asp
1585                1590                1595                1600
Ser Glu Gly Glu Glu Ser Glu Glu Glu Gly Glu Glu Glu Gly
            1605                1610                1615
Ser Glu Ser Glu Ser Arg Ser Val Lys Val Lys Ile Lys Leu Gly Arg
            1620                1625                1630
Lys Glu Lys Ala Gln Asp Arg Leu Lys Gly Gly Arg Arg Pro Ser
        1635                1640                1645
Arg Gly Ser Arg Ala Lys Pro Val Val Ser Asp Asp Asp Ser Glu Glu
    1650                1655                1660
Glu Gln Glu Glu Asp Arg Ser Gly Ser Gly Ser Glu Glu Asp
1665                1670                1675

<210> SEQ ID NO 70
<211> LENGTH: 5480
<212> TYPE: DNA
<213> ORGANISM: Homo sapiens
<220> FEATURE:
<221> NAME/KEY: CDS
<222> LOCATION: (75)..(5024)
<220> FEATURE:
<221> NAME/KEY: conflict
<222> LOCATION: (1780)
<223> OTHER INFORMATION: GenBank Accession No. U29175 shows a C at this
      position (position 1784 in GenBank) rather than
      the G shown here.
<220> FEATURE:
<221> NAME/KEY: allele
<222> LOCATION: (26)
<223> OTHER INFORMATION: Polymorphism of either T or C in this noncoding
```

```
       region.
<220> FEATURE:
<221> NAME/KEY: allele
<222> LOCATION: (1583)
<223> OTHER INFORMATION: Polymorphism of A or G resulting in a silent
      mutation.
<220> FEATURE:
<221> NAME/KEY: allele
<222> LOCATION: (1598)
<223> OTHER INFORMATION: Polymorphism of T or C resulting in a silent
      mutation.
<220> FEATURE:
<221> NAME/KEY: allele
<222> LOCATION: (1892)
<223> OTHER INFORMATION: Polymorphism of A or G resulting in a silent
      mutation.
<220> FEATURE:
<221> NAME/KEY: misc_feature
<222> LOCATION: (4245)..(4253)
<223> OTHER INFORMATION: Insertion of 9 basepairs as compared to SEQ ID
      NO:1.

<400> SEQUENCE: 70
ggcgggggag gcgccgggaa gtcgatggcg ccggcggctc ctgcaggagg ccactgtctg      60
cagctcccgt gaag atg tcc act cca gac cca ccc ctg ggc gga act cct      110
               Met Ser Thr Pro Asp Pro Pro Leu Gly Gly Thr Pro
                 1               5                  10 cgg cca ggt cct tcc ccg ggc cct ggc cct tcc cct gga gcc atg ctg      158
Arg Pro Gly Pro Ser Pro Gly Pro Gly Pro Ser Pro Gly Ala Met Leu
         15                  20                  25 ggc cct agc ccg ggt ccc tcg ccg ggc tcc gcc cac agc atg atg ggg      206
Gly Pro Ser Pro Gly Pro Ser Pro Gly Ser Ala His Ser Met Met Gly
 30                  35                  40 ccc agc cca ggg ccg ccc tca gca gga cac ccc atc ccc acc cag ggg      254
Pro Ser Pro Gly Pro Pro Ser Ala Gly His Pro Ile Pro Thr Gln Gly
 45                  50                  55                  60 cct gga ggg tac cct cag gac aac atg cac cag atg cac aag ccc atg      302
Pro Gly Gly Tyr Pro Gln Asp Asn Met His Gln Met His Lys Pro Met
                 65                  70                  75 gag tcc atg cat gag aag ggc atg tcg gac gac ccg cgc tac aac cag      350
Glu Ser Met His Glu Lys Gly Met Ser Asp Asp Pro Arg Tyr Asn Gln
             80                  85                  90 atg aaa gga atg ggg atg cgg tca ggg ggc cat gct ggg atg ggg ccc      398
Met Lys Gly Met Gly Met Arg Ser Gly Gly His Ala Gly Met Gly Pro
         95                 100                 105 ccg ccc agc ccc atg gac cag cac tcc caa ggt tac ccc tcg ccc ctg      446
Pro Pro Ser Pro Met Asp Gln His Ser Gln Gly Tyr Pro Ser Pro Leu
    110                 115                 120 ggt ggc tct gag cat gcc tct agt cca gtt cca gcc agt ggc ccg tct      494
Gly Gly Ser Glu His Ala Ser Ser Pro Val Pro Ala Ser Gly Pro Ser
125                 130                 135                 140 tcg ggg ccc cag atg tct tcc ggg cca gga ggt gcc ccg ctg gat ggt      542
Ser Gly Pro Gln Met Ser Ser Gly Pro Gly Gly Ala Pro Leu Asp Gly
                145                 150                 155 gct gac ccc cag gcc ttg ggg cag cag aac cgg ggc cca acc cca ttt      590
Ala Asp Pro Gln Ala Leu Gly Gln Gln Asn Arg Gly Pro Thr Pro Phe
            160                 165                 170 aac cag aac cag ctg cac cag ctc aga gct cag atc atg gcc tac aag      638
Asn Gln Asn Gln Leu His Gln Leu Arg Ala Gln Ile Met Ala Tyr Lys
        175                 180                 185 atg ctg gcc agg ggg cag ccc ctc ccc gac cac ctg cag atg gcg gtg      686
Met Leu Ala Arg Gly Gln Pro Leu Pro Asp His Leu Gln Met Ala Val
    190                 195                 200 cag ggc aag cgg ccg atg ccc ggg atg cag cag cag atg cca acg cta      734
```

```
Gln Gly Lys Arg Pro Met Pro Gly Met Gln Gln Met Pro Thr Leu
205                 210                 215                 220 cct cca ccc tcg gtg tcc gca aca gga ccc ggc cct ggc cct ggc cct    782
Pro Pro Pro Ser Val Ser Ala Thr Gly Pro Gly Pro Gly Pro Gly Pro
                    225                 230                 235 ggc ccc ggc ccg ggt ccc ggc ccg gca cct cca aat tac agc agg cct    830
Gly Pro Gly Pro Gly Pro Gly Pro Ala Pro Pro Asn Tyr Ser Arg Pro
                240                 245                 250 cat ggt atg gga ggg ccc aac atg cct ccc cca gga ccc tcg ggc gtg    878
His Gly Met Gly Gly Pro Asn Met Pro Pro Pro Gly Pro Ser Gly Val
                255                 260                 265 ccc ccc ggg atg cca ggc cag cct cct gga ggg cct ccc aag ccc tgg    926
Pro Pro Gly Met Pro Gly Gln Pro Pro Gly Gly Pro Pro Lys Pro Trp
            270                 275                 280 cct gaa gga ccc atg gcg aat gct gct gcc ccc acg agc acc cct cag    974
Pro Glu Gly Pro Met Ala Asn Ala Ala Ala Pro Thr Ser Thr Pro Gln
285                 290                 295                 300 aag ctg att ccc ccg cag cca acg ggc cgc cct tcc ccc gcg ccc cct   1022
Lys Leu Ile Pro Pro Gln Pro Thr Gly Arg Pro Ser Pro Ala Pro Pro
                    305                 310                 315 gcc gtc cca ccc gcc gcc tcg ccc gtg atg cca ccg cag acc cag tcc   1070
Ala Val Pro Pro Ala Ala Ser Pro Val Met Pro Pro Gln Thr Gln Ser
                320                 325                 330 ccc ggg cag ccg gcc cag ccc gcg ccc atg gtg cca ctg cac cag aag   1118
Pro Gly Gln Pro Ala Gln Pro Ala Pro Met Val Pro Leu His Gln Lys
            335                 340                 345 cag agc cgc atc acc ccc atc cag aag ccg cgg ggc ctc gac cct gtg   1166
Gln Ser Arg Ile Thr Pro Ile Gln Lys Pro Arg Gly Leu Asp Pro Val
350                 355                 360 gag atc ctg cag gag cgc gag tac agg ctg cag gct cgc atc gca cac   1214
Glu Ile Leu Gln Glu Arg Glu Tyr Arg Leu Gln Ala Arg Ile Ala His
365                 370                 375                 380 cga att cag gaa ctt gaa aac ctt ccc ggg tcc ctg gcc ggg gat ttg   1262
Arg Ile Gln Glu Leu Glu Asn Leu Pro Gly Ser Leu Ala Gly Asp Leu
                385                 390                 395 cga acc aaa gcg acc att gag ctc aag gcc ctc agg ctg ctg aac ttc   1310
Arg Thr Lys Ala Thr Ile Glu Leu Lys Ala Leu Arg Leu Leu Asn Phe
                400                 405                 410 cag agg cag ctg cgc cag gag gtg gtg gtg tgc atg cgg agg gac aca   1358
Gln Arg Gln Leu Arg Gln Glu Val Val Val Cys Met Arg Arg Asp Thr
            415                 420                 425 gcg ctg gag aca gcc ctc aat gct aag gcc tac aag cgc agc aag cgc   1406
Ala Leu Glu Thr Ala Leu Asn Ala Lys Ala Tyr Lys Arg Ser Lys Arg
430                 435                 440 cag tcc ctg cgc gag gcc cgc atc act gag aag ctg gag aag cag cag   1454
Gln Ser Leu Arg Glu Ala Arg Ile Thr Glu Lys Leu Glu Lys Gln Gln
445                 450                 455                 460 aag atc gag cag gag cgc aag cgc cgg cag aag cac cag gaa tac ctc   1502
Lys Ile Glu Gln Glu Arg Lys Arg Arg Gln Lys His Gln Glu Tyr Leu
                465                 470                 475 aat agc att ctc cag cat gcc aag gat ttc aag gaa tat cac aga tcc   1550
Asn Ser Ile Leu Gln His Ala Lys Asp Phe Lys Glu Tyr His Arg Ser
                480                 485                 490 gtc aca ggc aaa atc cag aag ctg acc aag gca gtg gcc acg tac cat   1598
Val Thr Gly Lys Ile Gln Lys Leu Thr Lys Ala Val Ala Thr Tyr His
            495                 500                 505 gcc aac acg gag cgg gag cag aag aaa gag aac gag cgg atc gag aag   1646
Ala Asn Thr Glu Arg Glu Gln Lys Lys Glu Asn Glu Arg Ile Glu Lys
510                 515                 520
```

```
gag cgc atg cgg agg ctc atg gct gaa gat gag gag ggg tac cgc aag     1694
Glu Arg Met Arg Arg Leu Met Ala Glu Asp Glu Glu Gly Tyr Arg Lys
525                 530                 535                 540 ctc atc gac cag aag aag gac aag cgc ctg gcc tac ctc ttg cag cag     1742
Leu Ile Asp Gln Lys Lys Asp Lys Arg Leu Ala Tyr Leu Leu Gln Gln
            545                 550                 555 aca gac gag tac gtg gct aac ctc acg gag ctg gtg cgg cag cac aag     1790
Thr Asp Glu Tyr Val Ala Asn Leu Thr Glu Leu Val Arg Gln His Lys
                560                 565                 570 gct gcc cag gtc gcc aag gag aaa aag aag aaa aag aaa aag aag aag     1838
Ala Ala Gln Val Ala Lys Glu Lys Lys Lys Lys Lys Lys Lys Lys
            575                 580                 585 gca gaa aat gca gaa gga cag acg cct gcc att ggg ccg gat ggc gag     1886
Ala Glu Asn Ala Glu Gly Gln Thr Pro Ala Ile Gly Pro Asp Gly Glu
590                 595                 600 cct cta gac gag acc agc cag atg agc gac ctc ccg gtg aag gtg atc     1934
Pro Leu Asp Glu Thr Ser Gln Met Ser Asp Leu Pro Val Lys Val Ile
605                 610                 615                 620 cac gtg gag agt ggg aag atc ctc aca ggc aca gat gcc ccc aaa gcc     1982
His Val Glu Ser Gly Lys Ile Leu Thr Gly Thr Asp Ala Pro Lys Ala
                625                 630                 635 ggg cag ctg gag gcc tgg ctc gag atg aac ccg ggg tat gaa gta gct     2030
Gly Gln Leu Glu Ala Trp Leu Glu Met Asn Pro Gly Tyr Glu Val Ala
            640                 645                 650 ccg agg tct gat agt gaa gaa agt ggc tca gaa gaa gag gaa gag gag     2078
Pro Arg Ser Asp Ser Glu Glu Ser Gly Ser Glu Glu Glu Glu Glu Glu
            655                 660                 665 gag gag gaa gag cag ccg cag gca gca cag cct ccc acc ctg ccc gtg     2126
Glu Glu Glu Glu Gln Pro Gln Ala Ala Gln Pro Pro Thr Leu Pro Val
670                 675                 680 gag gag aag aag aag att cca gat cca gac agc gat gac gtc tct gag     2174
Glu Glu Lys Lys Lys Ile Pro Asp Pro Asp Ser Asp Asp Val Ser Glu
685                 690                 695                 700 gtg gac gcg cgg cac atc att gag aat gcc aag caa gat gtc gat gat     2222
Val Asp Ala Arg His Ile Ile Glu Asn Ala Lys Gln Asp Val Asp Asp
                705                 710                 715 gaa tat ggc gtg tcc cag gcc ctt gca cgt ggc ctg cag tcc tac tat     2270
Glu Tyr Gly Val Ser Gln Ala Leu Ala Arg Gly Leu Gln Ser Tyr Tyr
            720                 725                 730 gcc gtg gcc cat gct gtc act gag aga gtg gac aag cag tca gcg ctt     2318
Ala Val Ala His Ala Val Thr Glu Arg Val Asp Lys Gln Ser Ala Leu
            735                 740                 745 atg gtc aat ggt gtc ctc aaa cag tac cag atc aaa ggt ttg gag tgg     2366
Met Val Asn Gly Val Leu Lys Gln Tyr Gln Ile Lys Gly Leu Glu Trp
    750                 755                 760 ctg gtg tcc ctg tac aac aac aac ctg aac ggc atc ctg gcc gac gag     2414
Leu Val Ser Leu Tyr Asn Asn Asn Leu Asn Gly Ile Leu Ala Asp Glu
765                 770                 775                 780 atg ggc ctg ggg aag acc atc cag acc atc gcg ctc atc acg tac ctc     2462
Met Gly Leu Gly Lys Thr Ile Gln Thr Ile Ala Leu Ile Thr Tyr Leu
                785                 790                 795 atg gag cac aaa cgc atc aat ggg ccc ttc ctc atc atc gtg cct ctc     2510
Met Glu His Lys Arg Ile Asn Gly Pro Phe Leu Ile Ile Val Pro Leu
            800                 805                 810 tca acg ctg tcc aac tgg gcg tac gag ttt gac aag tgg gcc ccc tcc     2558
Ser Thr Leu Ser Asn Trp Ala Tyr Glu Phe Asp Lys Trp Ala Pro Ser
            815                 820                 825 gtg gtg aag gtg tct tac aag gga tcc cca gca gca aga cgg gcc ttt     2606
Val Val Lys Val Ser Tyr Lys Gly Ser Pro Ala Ala Arg Arg Ala Phe
830                 835                 840
```

```
gtc ccc cag ctc cgg agt ggg aag ttc aac gtc ttg ctg acg acg tac    2654
Val Pro Gln Leu Arg Ser Gly Lys Phe Asn Val Leu Leu Thr Thr Tyr
845                 850                 855                 860 gag tac atc atc aaa gac aag cac atc ctc gcc aag atc cgt tgg aag    2702
Glu Tyr Ile Ile Lys Asp Lys His Ile Leu Ala Lys Ile Arg Trp Lys
                865                 870                 875 tac atg att gtg gac gaa ggt cac cgc atg aag aac cac cac tgc aag    2750
Tyr Met Ile Val Asp Glu Gly His Arg Met Lys Asn His His Cys Lys
            880                 885                 890 ctg acg cag gtg ctc aac acg cac tat gtg gca ccc cgc cgc ctg ctg    2798
Leu Thr Gln Val Leu Asn Thr His Tyr Val Ala Pro Arg Arg Leu Leu
        895                 900                 905 ctg acg ggc aca ccg ctg cag aac aag ctt ccc gag ctc tgg gcg ctg    2846
Leu Thr Gly Thr Pro Leu Gln Asn Lys Leu Pro Glu Leu Trp Ala Leu
    910                 915                 920 ctc aac ttc ctg ctg ccc acc atc ttc aag agc tgc agc acc ttc gag    2894
Leu Asn Phe Leu Leu Pro Thr Ile Phe Lys Ser Cys Ser Thr Phe Glu
925                 930                 935                 940 cag tgg ttt aac gca ccc ttt gcc atg acc ggg gaa aag gtg gac ctg    2942
Gln Trp Phe Asn Ala Pro Phe Ala Met Thr Gly Glu Lys Val Asp Leu
                945                 950                 955 aat gag gag gaa acc att ctc atc atc cgg cgt ctc cac aaa gtg ctg    2990
Asn Glu Glu Glu Thr Ile Leu Ile Ile Arg Arg Leu His Lys Val Leu
            960                 965                 970 cgg ccc ttc ttg ctc cga cga ctc aag aag gaa gtc gag gcc cag ttg    3038
Arg Pro Phe Leu Leu Arg Arg Leu Lys Lys Glu Val Glu Ala Gln Leu
        975                 980                 985 ccc gaa aag gtg gag tac gtc atc aag tgc gac atg tct gcg ctg cag    3086
Pro Glu Lys Val Glu Tyr Val Ile Lys Cys Asp Met Ser Ala Leu Gln
    990                 995                 1000 cga gtg ctc tac cgc cac atg cag gcc aag ggc gtg ctg ctg act gat    3134
Arg Val Leu Tyr Arg His Met Gln Ala Lys Gly Val Leu Leu Thr Asp
1005                1010                1015                1020 ggc tcc gag aag gac aag aag ggc aaa ggc ggc acc aag acc ctg atg    3182
Gly Ser Glu Lys Asp Lys Lys Gly Lys Gly Gly Thr Lys Thr Leu Met
                1025                1030                1035 aac acc atc atg cag ctg cgg aag atc tgc aac cac ccc tac atg ttc    3230
Asn Thr Ile Met Gln Leu Arg Lys Ile Cys Asn His Pro Tyr Met Phe
            1040                1045                1050 cag cac atc gag gag tcc ttt tcc gag cac ttg ggg ttc act ggc ggc    3278
Gln His Ile Glu Glu Ser Phe Ser Glu His Leu Gly Phe Thr Gly Gly
        1055                1060                1065 att gtc caa ggg ctg gac ctg tac cga gcc tcg ggt aaa ttt gag ctt    3326
Ile Val Gln Gly Leu Asp Leu Tyr Arg Ala Ser Gly Lys Phe Glu Leu
    1070                1075                1080 ctt gat aga att ctt ccc aaa ctc cga gca acc aac cac aaa gtg ctg    3374
Leu Asp Arg Ile Leu Pro Lys Leu Arg Ala Thr Asn His Lys Val Leu
1085                1090                1095                1100 ctg ttc tgc caa atg acc tcc ctc atg acc atc atg gaa gat tac ttt    3422
Leu Phe Cys Gln Met Thr Ser Leu Met Thr Ile Met Glu Asp Tyr Phe
                1105                1110                1115 gcg tat cgc ggc ttt aaa tac ctc agg ctt gat gga acc acg aag gcg    3470
Ala Tyr Arg Gly Phe Lys Tyr Leu Arg Leu Asp Gly Thr Thr Lys Ala
            1120                1125                1130 gag gac cgg ggc atg ctg ctg aaa acc ttc aac gag ccc ggc tct gag    3518
Glu Asp Arg Gly Met Leu Leu Lys Thr Phe Asn Glu Pro Gly Ser Glu
        1135                1140                1145 tac ttc atc ttc ctg ctc agc acc cgg gct ggg ggg ctc ggc ctg aac    3566
Tyr Phe Ile Phe Leu Leu Ser Thr Arg Ala Gly Gly Leu Gly Leu Asn
```

```
                                                                -continued
     1150                 1155                 1160
ctc cag tcg gca gac act gtg atc att ttt gac agc gac tgg aat cct          3614
Leu Gln Ser Ala Asp Thr Val Ile Ile Phe Asp Ser Asp Trp Asn Pro
1165                 1170                 1175                 1180 cac cag gac ctg caa gcg cag gac cga gcc cac cgc atc ggg cag cag          3662
His Gln Asp Leu Gln Ala Gln Asp Arg Ala His Arg Ile Gly Gln Gln
                 1185                 1190                 1195 aac gag gtg cgt gtg ctc cgc ctc tgc acc gtc aac agc gtg gag gag          3710
Asn Glu Val Arg Val Leu Arg Leu Cys Thr Val Asn Ser Val Glu Glu
         1200                 1205                 1210 aag atc cta gct gca gcc aag tac aag ctc aac gtg gac cag aag gtg          3758
Lys Ile Leu Ala Ala Ala Lys Tyr Lys Leu Asn Val Asp Gln Lys Val
     1215                 1220                 1225 atc cag gcc ggc atg ttc gac cag aag tcc tcc agc cat gag cgg cgc          3806
Ile Gln Ala Gly Met Phe Asp Gln Lys Ser Ser Ser His Glu Arg Arg
 1230                 1235                 1240 gcc ttc ctg cag gcc atc ctg gag cac gag gag cag gat gag agc aga          3854
Ala Phe Leu Gln Ala Ile Leu Glu His Glu Glu Gln Asp Glu Ser Arg
1245                 1250                 1255                 1260 cac tgc agc acg ggc agc ggc agt gcc agc ttc gcc cac act gcc cct          3902
His Cys Ser Thr Gly Ser Gly Ser Ala Ser Phe Ala His Thr Ala Pro
                 1265                 1270                 1275 ccg cca gcg ggc gtc aac ccc gac ttg gag gag cca cct cta aag gag          3950
Pro Pro Ala Gly Val Asn Pro Asp Leu Glu Glu Pro Pro Leu Lys Glu
         1280                 1285                 1290 gaa gac gag gtg ccc gac gac gag acc gtc aac cag atg atc gcc cgg          3998
Glu Asp Glu Val Pro Asp Asp Glu Thr Val Asn Gln Met Ile Ala Arg
     1295                 1300                 1305 cac gag gag gag ttt gat ctg ttc atg cgc atg gac ctg gac cgc agg          4046
His Glu Glu Glu Phe Asp Leu Phe Met Arg Met Asp Leu Asp Arg Arg
 1310                 1315                 1320 cgc gag gag gcc cgc aac ccc aag cgg aag ccg cgc ctc atg gag gag          4094
Arg Glu Glu Ala Arg Asn Pro Lys Arg Lys Pro Arg Leu Met Glu Glu
1325                 1330                 1335                 1340 gac gag ctc ccc tcg tgg atc atc aag gac gac gcg gag gtg gag cgg          4142
Asp Glu Leu Pro Ser Trp Ile Ile Lys Asp Asp Ala Glu Val Glu Arg
                 1345                 1350                 1355 ctg acc tgt gag gag gag gag gag aag atg ttc ggc cgt ggc tcc cgc          4190
Leu Thr Cys Glu Glu Glu Glu Glu Lys Met Phe Gly Arg Gly Ser Arg
         1360                 1365                 1370 cac cgc aag gag gtg gac tac agc gac tca ctg acg gag aag cag tgg          4238
His Arg Lys Glu Val Asp Tyr Ser Asp Ser Leu Thr Glu Lys Gln Trp
     1375                 1380                 1385 ctc aag acc ctg aag gcc atc gag gag ggc acg ctg gag gag atc gaa          4286
Leu Lys Thr Leu Lys Ala Ile Glu Glu Gly Thr Leu Glu Glu Ile Glu
 1390                 1395                 1400 gag gag gtc cgg cag aag aaa tca tca cgg aag cgc aag cga gac agc          4334
Glu Glu Val Arg Gln Lys Lys Ser Ser Arg Lys Arg Lys Arg Asp Ser
1405                 1410                 1415                 1420 gac gcc ggc tcc tcc acc ccg acc acc agc acc cgc agc cgc gac aag          4382
Asp Ala Gly Ser Ser Thr Pro Thr Thr Ser Thr Arg Ser Arg Asp Lys
                 1425                 1430                 1435 gac gac gag agc aag aag cag aag aag cgc ggg cgg ccg cct gcc gag          4430
Asp Asp Glu Ser Lys Lys Gln Lys Lys Arg Gly Arg Pro Pro Ala Glu
         1440                 1445                 1450 aaa ctc tcc cct aac cca ccc aac ctc acc aag aag atg aag aag att          4478
Lys Leu Ser Pro Asn Pro Pro Asn Leu Thr Lys Lys Met Lys Lys Ile
     1455                 1460                 1465 gtg gat gcc gtg atc aag tac aag gac agc agc agt gga cgt cag ctc          4526
```

```
                                                                       -continued Val Asp Ala Val Ile Lys Tyr Lys Asp Ser Ser Ser Gly Arg Gln Leu
   1470                1475                1480 agc gag gtc ttc atc cag ctg ccc tcg cga aag gag ctg ccc gag tac        4574
Ser Glu Val Phe Ile Gln Leu Pro Ser Arg Lys Glu Leu Pro Glu Tyr
1485                1490                1495                1500 tac gag ctc atc cgc aag ccc gtg gac ttc aag aag ata aag gag cgc        4622
Tyr Glu Leu Ile Arg Lys Pro Val Asp Phe Lys Lys Ile Lys Glu Arg
                1505                1510                1515 att cgc aac cac aag tac cgc agc ctc aac gac cta gag aag gac gtc        4670
Ile Arg Asn His Lys Tyr Arg Ser Leu Asn Asp Leu Glu Lys Asp Val
        1520                1525                1530 atg ctc ctg tgc cag aac gca cag acc ttc aac ctg gag ggc tcc ctg        4718
Met Leu Leu Cys Gln Asn Ala Gln Thr Phe Asn Leu Glu Gly Ser Leu
    1535                1540                1545 atc tat gaa gac tcc atc gtc ttg cag tcg gtc ttc acc agc gtg cgg        4766
Ile Tyr Glu Asp Ser Ile Val Leu Gln Ser Val Phe Thr Ser Val Arg
1550                1555                1560 cag aaa atc gag aag gag gat gac agt gaa ggc gag gag agt gag gag        4814
Gln Lys Ile Glu Lys Glu Asp Asp Ser Glu Gly Glu Glu Ser Glu Glu
1565                1570                1575                1580 gag gaa gag ggc gag gag gaa ggc tcc gaa tcc gaa tct cgg tcc gtc        4862
Glu Glu Glu Gly Glu Glu Glu Gly Ser Glu Ser Glu Ser Arg Ser Val
                1585                1590                1595 aaa gtg aag atc aag ctt ggc cgg aag gag aag gca cag gac cgg ctg        4910
Lys Val Lys Ile Lys Leu Gly Arg Lys Glu Lys Ala Gln Asp Arg Leu
        1600                1605                1610 aag ggc ggc cgg cgg cgg ccg agc cga ggg tcc cga gcc aag ccg gtc        4958
Lys Gly Gly Arg Arg Arg Pro Ser Arg Gly Ser Arg Ala Lys Pro Val
    1615                1620                1625 gtg agt gac gat gac agt gag gag gaa caa gag gag gac cgc tca gga        5006
Val Ser Asp Asp Asp Ser Glu Glu Glu Gln Glu Glu Asp Arg Ser Gly
   1630                1635                1640 agt ggc agc gaa gaa gac tgagccccga cattccagtc tcgaccccga               5054
Ser Gly Ser Glu Glu Asp
1645               1650 gcccctcgtt ccagagctga gatggcatag gccttagcag taacgggtag cagcagatgt      5114
agtttcagac ttggagtaaa actgtataaa caaaagaatc ttccatattt atacagcaga      5174
gaagctgtag gactgtttgt gactggccct gtcctggcat cagtagcatc tgtaacagca      5234
ttaactgtct taaagagaga gagagagaat tccgaattgg ggaacacacg atacctgttt      5294
ttcttttccg ttgctggcag tactgttgcg ccgcagtttg gagtcactgt agttaagtgt      5354
ggatgcatgt gcgtcaccgt ccactcctcc tactgtattt tattggacag gtcagactcg      5414 ccggggccc ggcgagggta tgtcagtgtc actggatgtc aaacagtaat aaattaaacc       5474
aacaac                                                                 5480

<210> SEQ ID NO 71
<211> LENGTH: 1650
<212> TYPE: PRT
<213> ORGANISM: Homo sapiens

<400> SEQUENCE: 71

Met Ser Thr Pro Asp Pro Pro Leu Gly Gly Thr Pro Arg Pro Gly Pro
1               5                   10                  15

Ser Pro Gly Pro Gly Pro Ser Pro Gly Ala Met Leu Gly Pro Ser Pro
            20                  25                  30

Gly Pro Ser Pro Gly Ser Ala His Ser Met Met Gly Pro Ser Pro Gly
        35                  40                  45
```

```
Pro Pro Ser Ala Gly His Pro Ile Pro Thr Gln Gly Pro Gly Tyr
    50                  55                  60

Pro Gln Asp Asn Met His Gln Met His Lys Pro Met Glu Ser Met His
65                  70                  75                  80

Glu Lys Gly Met Ser Asp Asp Pro Arg Tyr Asn Gln Met Lys Gly Met
                85                  90                  95

Gly Met Arg Ser Gly Gly His Ala Gly Met Gly Pro Pro Ser Pro
            100                 105                 110

Met Asp Gln His Ser Gln Gly Tyr Pro Ser Pro Leu Gly Ser Glu
            115                 120                 125

His Ala Ser Ser Pro Val Pro Ala Ser Gly Pro Ser Ser Gly Pro Gln
        130                 135                 140

Met Ser Ser Gly Pro Gly Gly Ala Pro Leu Asp Gly Ala Asp Pro Gln
145                 150                 155                 160

Ala Leu Gly Gln Gln Asn Arg Gly Pro Thr Pro Phe Asn Gln Asn Gln
                165                 170                 175

Leu His Gln Leu Arg Ala Gln Ile Met Ala Tyr Lys Met Leu Ala Arg
            180                 185                 190

Gly Gln Pro Leu Pro Asp His Leu Gln Met Ala Val Gln Gly Lys Arg
            195                 200                 205

Pro Met Pro Gly Met Gln Gln Gln Met Pro Thr Leu Pro Pro Pro Ser
    210                 215                 220

Val Ser Ala Thr Gly Pro Gly Pro Gly Pro Gly Pro Gly Pro Gly Pro
225                 230                 235                 240

Gly Pro Gly Pro Ala Pro Pro Asn Tyr Ser Arg Pro His Gly Met Gly
            245                 250                 255

Gly Pro Asn Met Pro Pro Pro Gly Pro Ser Gly Val Pro Pro Gly Met
            260                 265                 270

Pro Gly Gln Pro Pro Gly Gly Pro Lys Pro Trp Pro Glu Gly Pro
        275                 280                 285

Met Ala Asn Ala Ala Ala Pro Thr Ser Thr Pro Gln Lys Leu Ile Pro
    290                 295                 300

Pro Gln Pro Thr Gly Arg Pro Ser Pro Ala Pro Pro Ala Val Pro Pro
305                 310                 315                 320

Ala Ala Ser Pro Val Met Pro Pro Gln Thr Gln Ser Pro Gly Gln Pro
                325                 330                 335

Ala Gln Pro Ala Pro Met Val Pro Leu His Gln Lys Gln Ser Arg Ile
            340                 345                 350

Thr Pro Ile Gln Lys Pro Arg Gly Leu Asp Pro Val Glu Ile Leu Gln
        355                 360                 365

Glu Arg Glu Tyr Arg Leu Gln Ala Arg Ile Ala His Arg Ile Gln Glu
    370                 375                 380

Leu Glu Asn Leu Pro Gly Ser Leu Ala Gly Asp Leu Arg Thr Lys Ala
385                 390                 395                 400

Thr Ile Glu Leu Lys Ala Leu Arg Leu Leu Asn Phe Gln Arg Gln Leu
                405                 410                 415

Arg Gln Glu Val Val Val Cys Met Arg Arg Asp Thr Ala Leu Glu Thr
            420                 425                 430

Ala Leu Asn Ala Lys Ala Tyr Lys Arg Ser Lys Arg Gln Ser Leu Arg
            435                 440                 445

Glu Ala Arg Ile Thr Glu Lys Leu Glu Lys Gln Gln Lys Ile Glu Gln
    450                 455                 460
```

```
Glu Arg Lys Arg Arg Gln Lys His Gln Glu Tyr Leu Asn Ser Ile Leu
465                 470                 475                 480

Gln His Ala Lys Asp Phe Lys Glu Tyr His Arg Ser Val Thr Gly Lys
            485                 490                 495

Ile Gln Lys Leu Thr Lys Ala Val Ala Thr Tyr His Ala Asn Thr Glu
            500                 505                 510

Arg Glu Gln Lys Lys Glu Asn Glu Arg Ile Glu Lys Glu Arg Met Arg
            515                 520                 525

Arg Leu Met Ala Glu Asp Glu Glu Gly Tyr Arg Lys Leu Ile Asp Gln
530                 535                 540

Lys Lys Asp Lys Arg Leu Ala Tyr Leu Leu Gln Gln Thr Asp Glu Tyr
545                 550                 555                 560

Val Ala Asn Leu Thr Glu Leu Val Arg Gln His Lys Ala Ala Gln Val
                565                 570                 575

Ala Lys Glu Lys Lys Lys Lys Lys Lys Lys Lys Lys Ala Glu Asn Ala
            580                 585                 590

Glu Gly Gln Thr Pro Ala Ile Gly Pro Asp Gly Glu Pro Leu Asp Glu
            595                 600                 605

Thr Ser Gln Met Ser Asp Leu Pro Val Lys Val Ile His Val Glu Ser
610                 615                 620

Gly Lys Ile Leu Thr Gly Thr Asp Ala Pro Lys Ala Gly Gln Leu Glu
625                 630                 635                 640

Ala Trp Leu Glu Met Asn Pro Gly Tyr Glu Val Ala Pro Arg Ser Asp
                645                 650                 655

Ser Glu Glu Ser Gly Ser Glu Glu Glu Glu Glu Glu Glu Glu Glu Glu
            660                 665                 670

Gln Pro Gln Ala Ala Gln Pro Pro Thr Leu Pro Val Glu Glu Lys Lys
            675                 680                 685

Lys Ile Pro Asp Pro Asp Ser Asp Asp Val Ser Glu Val Asp Ala Arg
690                 695                 700

His Ile Ile Glu Asn Ala Lys Gln Asp Val Asp Asp Glu Tyr Gly Val
705                 710                 715                 720

Ser Gln Ala Leu Ala Arg Gly Leu Gln Ser Tyr Tyr Ala Val Ala His
            725                 730                 735

Ala Val Thr Glu Arg Val Asp Lys Gln Ser Ala Leu Met Val Asn Gly
            740                 745                 750

Val Leu Lys Gln Tyr Gln Ile Lys Gly Leu Glu Trp Leu Val Ser Leu
            755                 760                 765

Tyr Asn Asn Asn Leu Asn Gly Ile Leu Ala Asp Glu Met Gly Leu Gly
770                 775                 780

Lys Thr Ile Gln Thr Ile Ala Leu Ile Thr Tyr Leu Met Glu His Lys
785                 790                 795                 800

Arg Ile Asn Gly Pro Phe Leu Ile Ile Val Pro Leu Ser Thr Leu Ser
                805                 810                 815

Asn Trp Ala Tyr Glu Phe Asp Lys Trp Ala Pro Ser Val Val Lys Val
            820                 825                 830

Ser Tyr Lys Gly Ser Pro Ala Ala Arg Arg Ala Phe Val Pro Gln Leu
            835                 840                 845

Arg Ser Gly Lys Phe Asn Val Leu Leu Thr Thr Tyr Glu Tyr Ile Ile
        850                 855                 860

Lys Asp Lys His Ile Leu Ala Lys Ile Arg Trp Lys Tyr Met Ile Val
865                 870                 875                 880

Asp Glu Gly His Arg Met Lys Asn His His Cys Lys Leu Thr Gln Val
```

-continued

```
                885                 890                 895
Leu Asn Thr His Tyr Val Ala Pro Arg Arg Leu Leu Leu Thr Gly Thr
                900                 905                 910
Pro Leu Gln Asn Lys Leu Pro Glu Leu Trp Ala Leu Leu Asn Phe Leu
                915                 920                 925
Leu Pro Thr Ile Phe Lys Ser Cys Ser Thr Phe Glu Gln Trp Phe Asn
                930                 935                 940
Ala Pro Phe Ala Met Thr Gly Glu Lys Val Asp Leu Asn Glu Glu Glu
945                 950                 955                 960
Thr Ile Leu Ile Ile Arg Arg Leu His Lys Val Leu Arg Pro Phe Leu
                965                 970                 975
Leu Arg Arg Leu Lys Lys Glu Val Glu Ala Gln Leu Pro Glu Lys Val
                980                 985                 990
Glu Tyr Val Ile Lys Cys Asp Met Ser Ala Leu Gln Arg Val Leu Tyr
                995                 1000                1005
Arg His Met Gln Ala Lys Gly Val Leu Leu Thr Asp Gly Ser Glu Lys
                1010                1015                1020
Asp Lys Lys Gly Lys Gly Gly Thr Lys Thr Leu Met Asn Thr Ile Met
1025                1030                1035                1040
Gln Leu Arg Lys Ile Cys Asn His Pro Tyr Met Phe Gln His Ile Glu
                1045                1050                1055
Glu Ser Phe Ser Glu His Leu Gly Phe Thr Gly Gly Ile Val Gln Gly
                1060                1065                1070
Leu Asp Leu Tyr Arg Ala Ser Gly Lys Phe Glu Leu Leu Asp Arg Ile
                1075                1080                1085
Leu Pro Lys Leu Arg Ala Thr Asn His Lys Val Leu Leu Phe Cys Gln
                1090                1095                1100
Met Thr Ser Leu Met Thr Ile Met Glu Asp Tyr Phe Ala Tyr Arg Gly
1105                1110                1115                1120
Phe Lys Tyr Leu Arg Leu Asp Gly Thr Thr Lys Ala Glu Asp Arg Gly
                1125                1130                1135
Met Leu Leu Lys Thr Phe Asn Glu Pro Gly Ser Glu Tyr Phe Ile Phe
                1140                1145                1150
Leu Leu Ser Thr Arg Ala Gly Gly Leu Gly Leu Asn Leu Gln Ser Ala
                1155                1160                1165
Asp Thr Val Ile Ile Phe Asp Ser Asp Trp Asn Pro His Gln Asp Leu
                1170                1175                1180
Gln Ala Gln Asp Arg Ala His Arg Ile Gly Gln Gln Asn Glu Val Arg
1185                1190                1195                1200
Val Leu Arg Leu Cys Thr Val Asn Ser Val Glu Glu Lys Ile Leu Ala
                1205                1210                1215
Ala Ala Lys Tyr Lys Leu Asn Val Asp Gln Lys Val Ile Gln Ala Gly
                1220                1225                1230
Met Phe Asp Gln Lys Ser Ser Ser His Glu Arg Arg Ala Phe Leu Gln
                1235                1240                1245
Ala Ile Leu Glu His Glu Glu Gln Asp Glu Ser Arg His Cys Ser Thr
                1250                1255                1260
Gly Ser Gly Ser Ala Ser Phe Ala His Thr Ala Pro Pro Ala Gly
1265                1270                1275                1280
Val Asn Pro Asp Leu Glu Glu Pro Pro Leu Lys Glu Asp Glu Val
                1285                1290                1295
Pro Asp Asp Glu Thr Val Asn Gln Met Ile Ala Arg His Glu Glu Glu
                1300                1305                1310
```

```
Phe Asp Leu Phe Met Arg Met Asp Leu Asp Arg Arg Arg Glu Glu Ala
        1315                1320                1325
Arg Asn Pro Lys Arg Lys Pro Arg Leu Met Glu Glu Asp Glu Leu Pro
    1330                1335                1340
Ser Trp Ile Ile Lys Asp Asp Ala Glu Val Glu Arg Leu Thr Cys Glu
1345                1350                1355                1360
Glu Glu Glu Glu Lys Met Phe Gly Arg Gly Ser Arg His Arg Lys Glu
                1365                1370                1375
Val Asp Tyr Ser Asp Ser Leu Thr Glu Lys Gln Trp Leu Lys Thr Leu
        1380                1385                1390
Lys Ala Ile Glu Glu Gly Thr Leu Glu Glu Ile Glu Glu Val Arg
    1395                1400                1405
Gln Lys Lys Ser Ser Arg Lys Arg Lys Arg Asp Ser Asp Ala Gly Ser
    1410                1415                1420
Ser Thr Pro Thr Thr Ser Thr Arg Ser Arg Asp Lys Asp Asp Glu Ser
1425                1430                1435                1440
Lys Lys Gln Lys Lys Arg Gly Arg Pro Pro Ala Glu Lys Leu Ser Pro
                1445                1450                1455
Asn Pro Pro Asn Leu Thr Lys Lys Met Lys Lys Ile Val Asp Ala Val
        1460                1465                1470
Ile Lys Tyr Lys Asp Ser Ser Ser Gly Arg Gln Leu Ser Glu Val Phe
        1475                1480                1485
Ile Gln Leu Pro Ser Arg Lys Glu Leu Pro Glu Tyr Tyr Glu Leu Ile
        1490                1495                1500
Arg Lys Pro Val Asp Phe Lys Lys Ile Lys Glu Arg Ile Arg Asn His
1505                1510                1515                1520
Lys Tyr Arg Ser Leu Asn Asp Leu Glu Lys Asp Val Met Leu Leu Cys
                1525                1530                1535
Gln Asn Ala Gln Thr Phe Asn Leu Glu Gly Ser Leu Ile Tyr Glu Asp
            1540                1545                1550
Ser Ile Val Leu Gln Ser Val Phe Thr Ser Val Arg Gln Lys Ile Glu
        1555                1560                1565
Lys Glu Asp Asp Ser Glu Gly Glu Gly Ser Glu Glu Glu Glu Glu Gly
    1570                1575                1580
Glu Glu Glu Gly Ser Glu Ser Glu Ser Arg Ser Val Lys Val Lys Ile
1585                1590                1595                1600
Lys Leu Gly Arg Lys Glu Lys Ala Gln Asp Arg Leu Lys Gly Gly Arg
                1605                1610                1615
Arg Arg Pro Ser Arg Gly Ser Arg Ala Lys Pro Val Val Ser Asp Asp
        1620                1625                1630
Asp Ser Glu Glu Glu Gln Glu Glu Asp Arg Ser Gly Ser Gly Ser Glu
        1635                1640                1645
Glu Asp
    1650

<210> SEQ ID NO 72
<211> LENGTH: 5576
<212> TYPE: DNA
<213> ORGANISM: Homo sapiens
<220> FEATURE:
<221> NAME/KEY: CDS
<222> LOCATION: (75)..(5120)
<220> FEATURE:
<221> NAME/KEY: conflict
<222> LOCATION: (1780)
<223> OTHER INFORMATION: GenBank Accession No. U29175 shows a C at this
``` position (position 1784 in GenBank) rather than
the G shown here.
<220> FEATURE:
<221> NAME/KEY: allele
<222> LOCATION: (26)
<223> OTHER INFORMATION: Polymorphism of either T or C in this noncoding
region.
<220> FEATURE:
<221> NAME/KEY: allele
<222> LOCATION: (1583)
<223> OTHER INFORMATION: Polymorphism of A or G resulting in a silent
mutation.
<220> FEATURE:
<221> NAME/KEY: allele
<222> LOCATION: (1598)
<223> OTHER INFORMATION: Polymorphism of T or C resulting in a silent
mutation.
<220> FEATURE:
<221> NAME/KEY: allele
<222> LOCATION: (1892)
<223> OTHER INFORMATION: Polymorphism of A or G resulting in a silent
mutation.
<220> FEATURE:
<221> NAME/KEY: misc_feature
<222> LOCATION: (4245)..(4349)
<223> OTHER INFORMATION: This is a 105 basepair insertion as compared to
SEQ ID NO:1.

<400> SEQUENCE: 72

```
ggcgggggag gcgccgggaa gtcgatggcg ccggcggctc ctgcaggagg ccactgtctg      60
cagctcccgt gaag atg tcc act cca gac cca ccc ctg ggc gga act cct       110
              Met Ser Thr Pro Asp Pro Pro Leu Gly Gly Thr Pro
                1               5                  10 cgg cca ggt cct tcc ccg ggc cct ggc cct tcc cct gga gcc atg ctg       158
Arg Pro Gly Pro Ser Pro Gly Pro Gly Pro Ser Pro Gly Ala Met Leu
         15                  20                  25 ggc cct agc ccg ggt ccc tcg ccg ggc tcc gcc cac agc atg atg ggg       206
Gly Pro Ser Pro Gly Pro Ser Pro Gly Ser Ala His Ser Met Met Gly
     30                  35                  40 ccc agc cca ggg ccg ccc tca gca gga cac ccc atc ccc acc cag ggg       254
Pro Ser Pro Gly Pro Pro Ser Ala Gly His Pro Ile Pro Thr Gln Gly
 45                  50                  55                  60 cct gga ggg tac cct cag gac aac atg cac cag atg cac aag ccc atg       302
Pro Gly Gly Tyr Pro Gln Asp Asn Met His Gln Met His Lys Pro Met
                 65                  70                  75 gag tcc atg cat gag aag ggc atg tcg gac gac ccg cgc tac aac cag       350
Glu Ser Met His Glu Lys Gly Met Ser Asp Asp Pro Arg Tyr Asn Gln
             80                  85                  90 atg aaa gga atg ggg atg cgg tca ggg ggc cat gct ggg atg ggg ccc       398
Met Lys Gly Met Gly Met Arg Ser Gly Gly His Ala Gly Met Gly Pro
         95                 100                 105 ccg ccc agc ccc atg gac cag cac tcc caa ggt tac ccc tcg ccc ctg       446
Pro Pro Ser Pro Met Asp Gln His Ser Gln Gly Tyr Pro Ser Pro Leu
     110                 115                 120 ggt ggc tct gag cat gcc tct agt cca gtt cca gcc agt ggc ccg tct       494
Gly Gly Ser Glu His Ala Ser Ser Pro Val Pro Ala Ser Gly Pro Ser
125                 130                 135                 140 tcg ggg ccc cag atg tct tcc ggg cca gga ggt gcc ccg ctg gat ggt       542
Ser Gly Pro Gln Met Ser Ser Gly Pro Gly Gly Ala Pro Leu Asp Gly
                145                 150                 155 gct gac ccc cag gcc ttg ggg cag cag aac cgg ggc cca acc cca ttt       590
Ala Asp Pro Gln Ala Leu Gly Gln Gln Asn Arg Gly Pro Thr Pro Phe
            160                 165                 170 aac cag aac cag ctg cac cag ctc aga gct cag atc atg gcc tac aag       638
Asn Gln Asn Gln Leu His Gln Leu Arg Ala Gln Ile Met Ala Tyr Lys
        175                 180                 185
```

```
atg ctg gcc agg ggg cag ccc ctc ccc gac cac ctg cag atg gcg gtg    686
Met Leu Ala Arg Gly Gln Pro Leu Pro Asp His Leu Gln Met Ala Val
    190                 195                 200 cag ggc aag cgg ccg atg ccc ggg atg cag cag cag atg cca acg cta    734
Gln Gly Lys Arg Pro Met Pro Gly Met Gln Gln Gln Met Pro Thr Leu
205                 210                 215                 220 cct cca ccc tcg gtg tcc gca aca gga ccc ggc cct ggc cct ggc cct    782
Pro Pro Pro Ser Val Ser Ala Thr Gly Pro Gly Pro Gly Pro Gly Pro
                225                 230                 235 ggc ccc ggc ccg ggt ccc ggc ccg gca cct cca aat tac agc agg cct    830
Gly Pro Gly Pro Gly Pro Gly Pro Ala Pro Pro Asn Tyr Ser Arg Pro
            240                 245                 250 cat ggt atg gga ggg ccc aac atg cct ccc cca gga ccc tcg ggc gtg    878
His Gly Met Gly Gly Pro Asn Met Pro Pro Pro Gly Pro Ser Gly Val
        255                 260                 265 ccc ccc ggg atg cca ggc cag cct cct gga ggg cct ccc aag ccc tgg    926
Pro Pro Gly Met Pro Gly Gln Pro Pro Gly Gly Pro Pro Lys Pro Trp
    270                 275                 280 cct gaa gga ccc atg gcg aat gct gct gcc ccc acg agc acc cct cag    974
Pro Glu Gly Pro Met Ala Asn Ala Ala Ala Pro Thr Ser Thr Pro Gln
285                 290                 295                 300 aag ctg att ccc ccg cag cca acg ggc cgc cct tcc ccc gcg ccc cct   1022
Lys Leu Ile Pro Pro Gln Pro Thr Gly Arg Pro Ser Pro Ala Pro Pro
                305                 310                 315 gcc gtc cca ccc gcc gcc tcg ccc gtg atg cca ccg cag acc cag tcc   1070
Ala Val Pro Pro Ala Ala Ser Pro Val Met Pro Pro Gln Thr Gln Ser
            320                 325                 330 ccc ggg cag ccg gcc cag ccc gcg ccc atg gtg cca ctg cac cag aag   1118
Pro Gly Gln Pro Ala Gln Pro Ala Pro Met Val Pro Leu His Gln Lys
        335                 340                 345 cag agc cgc atc acc ccc atc cag aag ccg cgg ggc ctc gac cct gtg   1166
Gln Ser Arg Ile Thr Pro Ile Gln Lys Pro Arg Gly Leu Asp Pro Val
    350                 355                 360 gag atc ctg cag gag cgc gag tac agg ctg cag gct cgc atc gca cac   1214
Glu Ile Leu Gln Glu Arg Glu Tyr Arg Leu Gln Ala Arg Ile Ala His
365                 370                 375                 380 cga att cag gaa ctt gaa aac ctt ccc ggg tcc ctg gcc ggg gat ttg   1262
Arg Ile Gln Glu Leu Glu Asn Leu Pro Gly Ser Leu Ala Gly Asp Leu
                385                 390                 395 cga acc aaa gcg acc att gag ctc aag gcc ctc agg ctg ctg aac ttc   1310
Arg Thr Lys Ala Thr Ile Glu Leu Lys Ala Leu Arg Leu Leu Asn Phe
            400                 405                 410 cag agg cag ctg cgc cag gag gtg gtg gtg tgc atg cgg agg gac aca   1358
Gln Arg Gln Leu Arg Gln Glu Val Val Val Cys Met Arg Arg Asp Thr
        415                 420                 425 gcg ctg gag aca gcc ctc aat gct aag gcc tac aag cgc agc aag cgc   1406
Ala Leu Glu Thr Ala Leu Asn Ala Lys Ala Tyr Lys Arg Ser Lys Arg
    430                 435                 440 cag tcc ctg cgc gag gcc cgc atc act gag aag ctg gag aag cag cag   1454
Gln Ser Leu Arg Glu Ala Arg Ile Thr Glu Lys Leu Glu Lys Gln Gln
445                 450                 455                 460 aag atc gag cag gag cgc aag cgc cgg cag aag cac cag gaa tac ctc   1502
Lys Ile Glu Gln Glu Arg Lys Arg Arg Gln Lys His Gln Glu Tyr Leu
                465                 470                 475 aat agc att ctc cag cat gcc aag gat ttc aag gaa tat cac aga tcc   1550
Asn Ser Ile Leu Gln His Ala Lys Asp Phe Lys Glu Tyr His Arg Ser
            480                 485                 490 gtc aca ggc aaa atc cag aag ctg acc aag gca gtg gcc acg tac cat   1598
Val Thr Gly Lys Ile Gln Lys Leu Thr Lys Ala Val Ala Thr Tyr His
```

-continued

```
              495                 500                 505
gcc aac acg gag cgg gag cag aag aaa gag aac gag cgg atc gag aag      1646
Ala Asn Thr Glu Arg Glu Gln Lys Lys Glu Asn Glu Arg Ile Glu Lys
    510                 515                 520 gag cgc atg cgg agg ctc atg gct gaa gat gag gag ggg tac cgc aag      1694
Glu Arg Met Arg Arg Leu Met Ala Glu Asp Glu Glu Gly Tyr Arg Lys
525                 530                 535                 540 ctc atc gac cag aag aag gac aag cgc ctg gcc tac ctc ttg cag cag      1742
Leu Ile Asp Gln Lys Lys Asp Lys Arg Leu Ala Tyr Leu Leu Gln Gln
            545                 550                 555 aca gac gag tac gtg gct aac ctc acg gag ctg gtg cgg cag cac aag      1790
Thr Asp Glu Tyr Val Ala Asn Leu Thr Glu Leu Val Arg Gln His Lys
                560                 565                 570 gct gcc cag gtc gcc aag gag aaa aag aag aaa aag aaa aag aag aag      1838
Ala Ala Gln Val Ala Lys Glu Lys Lys Lys Lys Lys Lys Lys Lys Lys
            575                 580                 585 gca gaa aat gca gaa gga cag acg cct gcc att ggg ccg gat ggc gag      1886
Ala Glu Asn Ala Glu Gly Gln Thr Pro Ala Ile Gly Pro Asp Gly Glu
        590                 595                 600 cct cta gac gag acc agc cag atg agc gac ctc ccg gtg aag gtg atc      1934
Pro Leu Asp Glu Thr Ser Gln Met Ser Asp Leu Pro Val Lys Val Ile
605                 610                 615                 620 cac gtg gag agt ggg aag atc ctc aca ggc aca gat gcc ccc aaa gcc      1982
His Val Glu Ser Gly Lys Ile Leu Thr Gly Thr Asp Ala Pro Lys Ala
                625                 630                 635 ggg cag ctg gag gcc tgg ctc gag atg aac ccg ggg tat gaa gta gct      2030
Gly Gln Leu Glu Ala Trp Leu Glu Met Asn Pro Gly Tyr Glu Val Ala
            640                 645                 650 ccg agg tct gat agt gaa gaa agt ggc tca gaa gaa gag gaa gag gag      2078
Pro Arg Ser Asp Ser Glu Glu Ser Gly Ser Glu Glu Glu Glu Glu Glu
        655                 660                 665 gag gag gaa gag cag ccg cag gca gca cag cct ccc acc ctg ccc gtg      2126
Glu Glu Glu Glu Gln Pro Gln Ala Ala Gln Pro Pro Thr Leu Pro Val
    670                 675                 680 gag gag aag aag aag att cca gat cca gac agc gat gac gtc tct gag      2174
Glu Glu Lys Lys Lys Ile Pro Asp Pro Asp Ser Asp Asp Val Ser Glu
685                 690                 695                 700 gtg gac gcg cgg cac atc att gag aat gcc aag caa gat gtc gat gat      2222
Val Asp Ala Arg His Ile Ile Glu Asn Ala Lys Gln Asp Val Asp Asp
                705                 710                 715 gaa tat ggc gtg tcc cag gcc ctt gca cgt ggc ctg cag tcc tac tat      2270
Glu Tyr Gly Val Ser Gln Ala Leu Ala Arg Gly Leu Gln Ser Tyr Tyr
            720                 725                 730 gcc gtg gcc cat gct gtc act gag aga gtg gac aag cag tca gcg ctt      2318
Ala Val Ala His Ala Val Thr Glu Arg Val Asp Lys Gln Ser Ala Leu
        735                 740                 745 atg gtc aat ggt gtc ctc aaa cag tac cag atc aaa ggt ttg gag tgg      2366
Met Val Asn Gly Val Leu Lys Gln Tyr Gln Ile Lys Gly Leu Glu Trp
    750                 755                 760 ctg gtg tcc ctg tac aac aac aac ctg aac ggc atc ctg gcc gac gag      2414
Leu Val Ser Leu Tyr Asn Asn Asn Leu Asn Gly Ile Leu Ala Asp Glu
765                 770                 775                 780 atg ggc ctg ggg aag acc atc cag acc atc gcg ctc atc acg tac ctc      2462
Met Gly Leu Gly Lys Thr Ile Gln Thr Ile Ala Leu Ile Thr Tyr Leu
                785                 790                 795 atg gag cac aaa cgc atc aat ggg ccc ttc ctc atc atc gtg cct ctc      2510
Met Glu His Lys Arg Ile Asn Gly Pro Phe Leu Ile Ile Val Pro Leu
            800                 805                 810 tca acg ctg tcc aac tgg gcg tac gag ttt gac aag tgg gcc ccc tcc      2558
```

-continued

| | | |
|---|---|---|
| Ser Thr Leu Ser Asn Trp Ala Tyr Glu Phe Asp Lys Trp Ala Pro Ser<br>815 820 825 | | |
| gtg gtg aag gtg tct tac aag gga tcc cca gca gca aga cgg gcc ttt<br>Val Val Lys Val Ser Tyr Lys Gly Ser Pro Ala Ala Arg Arg Ala Phe<br>830 835 840 | 2606 | |
| gtc ccc cag ctc cgg agt ggg aag ttc aac gtc ttg ctg acg acg tac<br>Val Pro Gln Leu Arg Ser Gly Lys Phe Asn Val Leu Leu Thr Thr Tyr<br>845 850 855 860 | 2654 | |
| gag tac atc atc aaa gac aag cac atc ctc gcc aag atc cgt tgg aag<br>Glu Tyr Ile Ile Lys Asp Lys His Ile Leu Ala Lys Ile Arg Trp Lys<br>865 870 875 | 2702 | |
| tac atg att gtg gac gaa ggt cac cgc atg aag aac cac cac tgc aag<br>Tyr Met Ile Val Asp Glu Gly His Arg Met Lys Asn His His Cys Lys<br>880 885 890 | 2750 | |
| ctg acg cag gtg ctc aac acg cac tat gtg gca ccc cgc cgc ctg ctg<br>Leu Thr Gln Val Leu Asn Thr His Tyr Val Ala Pro Arg Arg Leu Leu<br>895 900 905 | 2798 | |
| ctg acg ggc aca ccg ctg cag aac aag ctt ccc gag ctc tgg gcg ctg<br>Leu Thr Gly Thr Pro Leu Gln Asn Lys Leu Pro Glu Leu Trp Ala Leu<br>910 915 920 | 2846 | |
| ctc aac ttc ctg ctg ccc acc atc ttc aag agc tgc agc acc ttc gag<br>Leu Asn Phe Leu Leu Pro Thr Ile Phe Lys Ser Cys Ser Thr Phe Glu<br>925 930 935 940 | 2894 | |
| cag tgg ttt aac gca ccc ttt gcc atg acc ggg gaa aag gtg gac ctg<br>Gln Trp Phe Asn Ala Pro Phe Ala Met Thr Gly Glu Lys Val Asp Leu<br>945 950 955 | 2942 | |
| aat gag gag gaa acc att ctc atc atc cgg cgt ctc cac aaa gtg ctg<br>Asn Glu Glu Glu Thr Ile Leu Ile Ile Arg Arg Leu His Lys Val Leu<br>960 965 970 | 2990 | |
| cgg ccc ttc ttg ctc cga cga ctc aag aag gaa gtc gag gcc cag ttg<br>Arg Pro Phe Leu Leu Arg Arg Leu Lys Lys Glu Val Glu Ala Gln Leu<br>975 980 985 | 3038 | |
| ccc gaa aag gtg gag tac gtc atc aag tgc gac atg tct gcg ctg cag<br>Pro Glu Lys Val Glu Tyr Val Ile Lys Cys Asp Met Ser Ala Leu Gln<br>990 995 1000 | 3086 | |
| cga gtg ctc tac cgc cac atg cag gcc aag ggc gtg ctg ctg act gat<br>Arg Val Leu Tyr Arg His Met Gln Ala Lys Gly Val Leu Leu Thr Asp<br>1005 1010 1015 1020 | 3134 | |
| ggc tcc gag aag gac aag aag ggc aaa ggc ggc acc aag acc ctg atg<br>Gly Ser Glu Lys Asp Lys Lys Gly Lys Gly Gly Thr Lys Thr Leu Met<br>1025 1030 1035 | 3182 | |
| aac acc atc atg cag ctg cgg aag atc tgc aac cac ccc tac atg ttc<br>Asn Thr Ile Met Gln Leu Arg Lys Ile Cys Asn His Pro Tyr Met Phe<br>1040 1045 1050 | 3230 | |
| cag cac atc gag gag tcc ttt tcc gag cac ttg ggg ttc act ggc ggc<br>Gln His Ile Glu Glu Ser Phe Ser Glu His Leu Gly Phe Thr Gly Gly<br>1055 1060 1065 | 3278 | |
| att gtc caa ggg ctg gac ctg tac cga gcc tcg ggt aaa ttt gag ctt<br>Ile Val Gln Gly Leu Asp Leu Tyr Arg Ala Ser Gly Lys Phe Glu Leu<br>1070 1075 1080 | 3326 | |
| ctt gat aga att ctt ccc aaa ctc cga gca acc aac cac aaa gtg ctg<br>Leu Asp Arg Ile Leu Pro Lys Leu Arg Ala Thr Asn His Lys Val Leu<br>1085 1090 1095 1100 | 3374 | |
| ctg ttc tgc caa atg acc tcc ctc atg acc atc atg gaa gat tac ttt<br>Leu Phe Cys Gln Met Thr Ser Leu Met Thr Ile Met Glu Asp Tyr Phe<br>1105 1110 1115 | 3422 | |
| gcg tat cgc ggc ttt aaa tac ctc agg ctt gat gga acc acg aag gcg<br>Ala Tyr Arg Gly Phe Lys Tyr Leu Arg Leu Asp Gly Thr Thr Lys Ala<br>1120 1125 1130 | 3470 | |

```
gag gac cgg ggc atg ctg ctg aaa acc ttc aac gag ccc ggc tct gag    3518
Glu Asp Arg Gly Met Leu Leu Lys Thr Phe Asn Glu Pro Gly Ser Glu
        1135                1140                1145 tac ttc atc ttc ctg ctc agc acc cgg gct ggg ggg ctc ggc ctg aac    3566
Tyr Phe Ile Phe Leu Leu Ser Thr Arg Ala Gly Gly Leu Gly Leu Asn
    1150                1155                1160 ctc cag tcg gca gac act gtg atc att ttt gac agc gac tgg aat cct    3614
Leu Gln Ser Ala Asp Thr Val Ile Ile Phe Asp Ser Asp Trp Asn Pro
1165                1170                1175                1180 cac cag gac ctg caa gcg cag gac cga gcc cac cgc atc ggg cag cag    3662
His Gln Asp Leu Gln Ala Gln Asp Arg Ala His Arg Ile Gly Gln Gln
            1185                1190                1195 aac gag gtg cgt gtg ctc cgc ctc tgc acc gtc aac agc gtg gag gag    3710
Asn Glu Val Arg Val Leu Arg Leu Cys Thr Val Asn Ser Val Glu Glu
        1200                1205                1210 aag atc cta gct gca gcc aag tac aag ctc aac gtg gac cag aag gtg    3758
Lys Ile Leu Ala Ala Ala Lys Tyr Lys Leu Asn Val Asp Gln Lys Val
    1215                1220                1225 atc cag gcc ggc atg ttc gac cag aag tcc tcc agc cat gag cgg cgc    3806
Ile Gln Ala Gly Met Phe Asp Gln Lys Ser Ser Ser His Glu Arg Arg
1230                1235                1240 gcc ttc ctg cag gcc atc ctg gag cac gag gag cag gat gag agc aga    3854
Ala Phe Leu Gln Ala Ile Leu Glu His Glu Glu Gln Asp Glu Ser Arg
1245                1250                1255                1260 cac tgc agc acg ggc agc ggc agt gcc agc ttc gcc cac act gcc cct    3902
His Cys Ser Thr Gly Ser Gly Ser Ala Ser Phe Ala His Thr Ala Pro
            1265                1270                1275 ccg cca gcg ggc gtc aac ccc gac ttg gag gag cca cct cta aag gag    3950
Pro Pro Ala Gly Val Asn Pro Asp Leu Glu Glu Pro Pro Leu Lys Glu
        1280                1285                1290 gaa gac gag gtg ccc gac gac gag acc gtc aac cag atg atc gcc cgg    3998
Glu Asp Glu Val Pro Asp Asp Glu Thr Val Asn Gln Met Ile Ala Arg
    1295                1300                1305 cac gag gag gag ttt gat ctg ttc atg cgc atg gac ctg gac cgc agg    4046
His Glu Glu Glu Phe Asp Leu Phe Met Arg Met Asp Leu Asp Arg Arg
1310                1315                1320 cgc gag gag gcc cgc aac ccc aag cgg aag ccg cgc ctc atg gag gag    4094
Arg Glu Glu Ala Arg Asn Pro Lys Arg Lys Pro Arg Leu Met Glu Glu
1325                1330                1335                1340 gac gag ctc ccc tcg tgg atc atc aag gac gac gcg gag gtg gag cgg    4142
Asp Glu Leu Pro Ser Trp Ile Ile Lys Asp Asp Ala Glu Val Glu Arg
            1345                1350                1355 ctg acc tgt gag gag gag gag gag aag atg ttc ggc cgt ggc tcc cgc    4190
Leu Thr Cys Glu Glu Glu Glu Glu Lys Met Phe Gly Arg Gly Ser Arg
        1360                1365                1370 cac cgc aag gag gtg gac tac agc gac tca ctg acg gag aag cag tgg    4238
His Arg Lys Glu Val Asp Tyr Ser Asp Ser Leu Thr Glu Lys Gln Trp
    1375                1380                1385 ctc aag aaa att aca gga aaa gat atc cat gac aca gcc agc agt gtg    4286
Leu Lys Lys Ile Thr Gly Lys Asp Ile His Asp Thr Ala Ser Ser Val
1390                1395                1400 gca cgt ggg cta caa ttc cag cgt ggc ctt cag ttc tgc aca cgt gcg    4334
Ala Arg Gly Leu Gln Phe Gln Arg Gly Leu Gln Phe Cys Thr Arg Ala
1405                1410                1415                1420 tca aag acc ctg aag gcc atc gag gag ggc acg ctg gag gag atc gaa    4382
Ser Lys Thr Leu Lys Ala Ile Glu Glu Gly Thr Leu Glu Glu Ile Glu
            1425                1430                1435 gag gag gtc cgg cag aag aaa tca tca cgg aag cgc aag cga gac agc    4430
Glu Glu Val Arg Gln Lys Lys Ser Ser Arg Lys Arg Lys Arg Asp Ser
        1440                1445                1450
```

```
gac gcc ggc tcc tcc acc ccg acc acc agc acc cgc agc cgc gac aag    4478
Asp Ala Gly Ser Ser Thr Pro Thr Thr Ser Thr Arg Ser Arg Asp Lys
        1455                1460                1465 gac gac gag agc aag aag cag aag aag cgc ggg cgg ccg cct gcc gag    4526
Asp Asp Glu Ser Lys Lys Gln Lys Lys Arg Gly Arg Pro Pro Ala Glu
1470                1475                1480 aaa ctc tcc cct aac cca ccc aac ctc acc aag aag atg aag aag att    4574
Lys Leu Ser Pro Asn Pro Pro Asn Leu Thr Lys Lys Met Lys Lys Ile
1485                1490                1495                1500 gtg gat gcc gtg atc aag tac aag gac agc agc agt gga cgt cag ctc    4622
Val Asp Ala Val Ile Lys Tyr Lys Asp Ser Ser Ser Gly Arg Gln Leu
        1505                1510                1515 agc gag gtc ttc atc cag ctg ccc tcg cga aag gag ctg ccc gag tac    4670
Ser Glu Val Phe Ile Gln Leu Pro Ser Arg Lys Glu Leu Pro Glu Tyr
            1520                1525                1530 tac gag ctc atc cgc aag ccc gtg gac ttc aag aag ata aag gag cgc    4718
Tyr Glu Leu Ile Arg Lys Pro Val Asp Phe Lys Lys Ile Lys Glu Arg
        1535                1540                1545 att cgc aac cac aag tac cgc agc ctc aac gac cta gag aag gac gtc    4766
Ile Arg Asn His Lys Tyr Arg Ser Leu Asn Asp Leu Glu Lys Asp Val
    1550                1555                1560 atg ctc ctg tgc cag aac gca cag acc ttc aac ctg gag ggc tcc ctg    4814
Met Leu Leu Cys Gln Asn Ala Gln Thr Phe Asn Leu Glu Gly Ser Leu
1565                1570                1575                1580 atc tat gaa gac tcc atc gtc ttg cag tcg gtc ttc acc agc gtg cgg    4862
Ile Tyr Glu Asp Ser Ile Val Leu Gln Ser Val Phe Thr Ser Val Arg
            1585                1590                1595 cag aaa atc gag aag gag gat gac agt gaa ggc gag gag agt gag gag    4910
Gln Lys Ile Glu Lys Glu Asp Asp Ser Glu Gly Glu Glu Ser Glu Glu
        1600                1605                1610 gag gaa gag ggc gag gag gaa ggc tcc gaa tcc gaa tct cgg tcc gtc    4958
Glu Glu Glu Gly Glu Glu Glu Gly Ser Glu Ser Glu Ser Arg Ser Val
    1615                1620                1625 aaa gtg aag atc aag ctt ggc cgg aag gag aag gca cag gac cgg ctg    5006
Lys Val Lys Ile Lys Leu Gly Arg Lys Glu Lys Ala Gln Asp Arg Leu
1630                1635                1640 aag ggc ggc cgg cgg cgg ccg agc cga ggg tcc cga gcc aag ccg gtc    5054
Lys Gly Gly Arg Arg Arg Pro Ser Arg Gly Ser Arg Ala Lys Pro Val
1645                1650                1655                1660 gtg agt gac gat gac agt gag gag gaa caa gag gag gac cgc tca gga    5102
Val Ser Asp Asp Asp Ser Glu Glu Glu Gln Glu Glu Asp Arg Ser Gly
            1665                1670                1675 agt ggc agc gaa gaa gac tgagccccga cattccagtc tcgaccccga           5150
Ser Gly Ser Glu Glu Asp
            1680 gcccctcgtt ccagagctga gatggcatag gccttagcag taacgggtag cagcagatgt    5210 agtttcagac ttggagtaaa actgtataaa caaaagaatc ttccatattt atacagcaga    5270 gaagctgtag gactgtttgt gactggccct gtcctggcat cagtagcatc tgtaacagca    5330 ttaactgtct taaagagaga gagagagaat tccgaattgg ggaacacacg atacctgttt    5390 ttcttttccg ttgctggcag tactgttgcg ccgcagtttg gagtcactgt agttaagtgt    5450 ggatgcatgt gcgtcaccgt ccactcctcc tactgtattt tattggacag gtcagactcg    5510 ccgggggccc ggcgagggta tgtcagtgtc actggatgtc aaacagtaat aaattaaacc    5570 aacaac                                                                5576

<210> SEQ ID NO 73
```

-continued

```
<211> LENGTH: 1682
<212> TYPE: PRT
<213> ORGANISM: Homo sapiens

<400> SEQUENCE: 73

Met Ser Thr Pro Asp Pro Pro Leu Gly Gly Thr Pro Arg Pro Gly Pro
 1               5                  10                  15

Ser Pro Gly Pro Gly Pro Ser Pro Gly Ala Met Leu Gly Pro Ser Pro
            20                  25                  30

Gly Pro Ser Pro Gly Ser Ala His Ser Met Met Gly Pro Ser Pro Gly
        35                  40                  45

Pro Pro Ser Ala Gly His Pro Ile Pro Thr Gln Gly Pro Gly Gly Tyr
    50                  55                  60

Pro Gln Asp Asn Met His Gln Met His Lys Pro Met Glu Ser Met His
65                  70                  75                  80

Glu Lys Gly Met Ser Asp Asp Pro Arg Tyr Asn Gln Met Lys Gly Met
                85                  90                  95

Gly Met Arg Ser Gly Gly His Ala Gly Met Gly Pro Pro Ser Pro
            100                 105                 110

Met Asp Gln His Ser Gln Gly Tyr Pro Ser Pro Leu Gly Gly Ser Glu
            115                 120                 125

His Ala Ser Ser Pro Val Pro Ala Ser Gly Pro Ser Ser Gly Pro Gln
        130                 135                 140

Met Ser Ser Gly Pro Gly Gly Ala Pro Leu Asp Gly Ala Asp Pro Gln
145                 150                 155                 160

Ala Leu Gly Gln Gln Asn Arg Gly Pro Thr Pro Phe Asn Gln Asn Gln
                165                 170                 175

Leu His Gln Leu Arg Ala Gln Ile Met Ala Tyr Lys Met Leu Ala Arg
            180                 185                 190

Gly Gln Pro Leu Pro Asp His Leu Gln Met Ala Val Gln Gly Lys Arg
        195                 200                 205

Pro Met Pro Gly Met Gln Gln Gln Met Pro Thr Leu Pro Pro Pro Ser
    210                 215                 220

Val Ser Ala Thr Gly Pro Gly Pro Gly Pro Gly Pro Gly Pro Gly Pro
225                 230                 235                 240

Gly Pro Gly Pro Ala Pro Pro Asn Tyr Ser Arg Pro His Gly Met Gly
                245                 250                 255

Gly Pro Asn Met Pro Pro Pro Gly Pro Ser Gly Val Pro Pro Gly Met
            260                 265                 270

Pro Gly Gln Pro Pro Gly Gly Pro Pro Lys Pro Trp Pro Glu Gly Pro
        275                 280                 285

Met Ala Asn Ala Ala Ala Pro Thr Ser Thr Pro Gln Lys Leu Ile Pro
    290                 295                 300

Pro Gln Pro Thr Gly Arg Pro Ser Pro Ala Pro Pro Ala Val Pro Pro
305                 310                 315                 320

Ala Ala Ser Pro Val Met Pro Pro Gln Thr Gln Ser Pro Gly Gln Pro
                325                 330                 335

Ala Gln Pro Ala Pro Met Val Pro Leu His Gln Lys Gln Ser Arg Ile
            340                 345                 350

Thr Pro Ile Gln Lys Pro Arg Gly Leu Asp Pro Val Glu Ile Leu Gln
        355                 360                 365

Glu Arg Glu Tyr Arg Leu Gln Ala Arg Ile Ala His Arg Ile Gln Glu
    370                 375                 380

Leu Glu Asn Leu Pro Gly Ser Leu Ala Gly Asp Leu Arg Thr Lys Ala
```

```
385                 390                 395                 400
Thr Ile Glu Leu Lys Ala Leu Arg Leu Leu Asn Phe Gln Arg Gln Leu
                405                 410                 415
Arg Gln Glu Val Val Cys Met Arg Arg Asp Thr Ala Leu Glu Thr
                420                 425                 430
Ala Leu Asn Ala Lys Ala Tyr Lys Arg Ser Lys Arg Gln Ser Leu Arg
                435                 440                 445
Glu Ala Arg Ile Thr Glu Lys Leu Glu Lys Gln Gln Lys Ile Glu Gln
            450                 455                 460
Glu Arg Lys Arg Arg Gln Lys His Gln Glu Tyr Leu Asn Ser Ile Leu
465                 470                 475                 480
Gln His Ala Lys Asp Phe Lys Glu Tyr His Arg Ser Val Thr Gly Lys
                485                 490                 495
Ile Gln Lys Leu Thr Lys Ala Val Ala Thr Tyr His Ala Asn Thr Glu
                500                 505                 510
Arg Glu Gln Lys Lys Glu Asn Glu Arg Ile Glu Lys Glu Arg Met Arg
                515                 520                 525
Arg Leu Met Ala Glu Asp Glu Gly Tyr Arg Lys Leu Ile Asp Gln
                530                 535                 540
Lys Lys Asp Lys Arg Leu Ala Tyr Leu Leu Gln Gln Thr Asp Glu Tyr
545                 550                 555                 560
Val Ala Asn Leu Thr Glu Leu Val Arg Gln His Lys Ala Ala Gln Val
                565                 570                 575
Ala Lys Glu Lys Lys Lys Lys Lys Lys Lys Ala Glu Asn Ala
                580                 585                 590
Glu Gly Gln Thr Pro Ala Ile Gly Pro Asp Gly Glu Pro Leu Asp Glu
                595                 600                 605
Thr Ser Gln Met Ser Asp Leu Pro Val Lys Val Ile His Val Glu Ser
                610                 615                 620
Gly Lys Ile Leu Thr Gly Thr Asp Ala Pro Lys Ala Gly Gln Leu Glu
625                 630                 635                 640
Ala Trp Leu Glu Met Asn Pro Gly Tyr Glu Val Ala Pro Arg Ser Asp
                645                 650                 655
Ser Glu Glu Ser Gly Ser Glu Glu Glu Glu Glu Glu Glu Glu
                660                 665                 670
Gln Pro Gln Ala Ala Gln Pro Pro Thr Leu Pro Val Glu Glu Lys Lys
                675                 680                 685
Lys Ile Pro Asp Pro Asp Ser Asp Asp Val Ser Glu Val Asp Ala Arg
                690                 695                 700
His Ile Ile Glu Asn Ala Lys Gln Asp Val Asp Asp Glu Tyr Gly Val
705                 710                 715                 720
Ser Gln Ala Leu Ala Arg Gly Leu Gln Ser Tyr Tyr Ala Val Ala His
                725                 730                 735
Ala Val Thr Glu Arg Val Asp Lys Gln Ser Ala Leu Met Val Asn Gly
                740                 745                 750
Val Leu Lys Gln Tyr Gln Ile Lys Gly Leu Glu Trp Leu Val Ser Leu
                755                 760                 765
Tyr Asn Asn Asn Leu Asn Gly Ile Leu Ala Asp Glu Met Gly Leu Gly
                770                 775                 780
Lys Thr Ile Gln Thr Ile Ala Leu Ile Thr Tyr Leu Met Glu His Lys
785                 790                 795                 800
Arg Ile Asn Gly Pro Phe Leu Ile Ile Val Pro Leu Ser Thr Leu Ser
                805                 810                 815
```

-continued

```
Asn Trp Ala Tyr Glu Phe Asp Lys Trp Ala Pro Ser Val Val Lys Val
            820                 825                 830

Ser Tyr Lys Gly Ser Pro Ala Ala Arg Arg Ala Phe Val Pro Gln Leu
            835                 840                 845

Arg Ser Gly Lys Phe Asn Val Leu Leu Thr Thr Tyr Glu Tyr Ile Ile
            850                 855                 860

Lys Asp Lys His Ile Leu Ala Lys Ile Arg Trp Lys Tyr Met Ile Val
865                 870                 875                 880

Asp Glu Gly His Arg Met Lys Asn His His Cys Lys Leu Thr Gln Val
                885                 890                 895

Leu Asn Thr His Tyr Val Ala Pro Arg Arg Leu Leu Leu Thr Gly Thr
            900                 905                 910

Pro Leu Gln Asn Lys Leu Pro Glu Leu Trp Ala Leu Leu Asn Phe Leu
            915                 920                 925

Leu Pro Thr Ile Phe Lys Ser Cys Ser Thr Phe Glu Gln Trp Phe Asn
            930                 935                 940

Ala Pro Phe Ala Met Thr Gly Glu Lys Val Asp Leu Asn Glu Glu Glu
945                 950                 955                 960

Thr Ile Leu Ile Ile Arg Arg Leu His Lys Val Leu Arg Pro Phe Leu
            965                 970                 975

Leu Arg Arg Leu Lys Lys Glu Val Glu Ala Gln Leu Pro Glu Lys Val
            980                 985                 990

Glu Tyr Val Ile Lys Cys Asp Met Ser Ala Leu Gln Arg Val Leu Tyr
            995                 1000                1005

Arg His Met Gln Ala Lys Gly Val Leu Leu Thr Asp Gly Ser Glu Lys
            1010                1015                1020

Asp Lys Lys Gly Lys Gly Gly Thr Lys Thr Leu Met Asn Thr Ile Met
1025                1030                1035                1040

Gln Leu Arg Lys Ile Cys Asn His Pro Tyr Met Phe Gln His Ile Glu
            1045                1050                1055

Glu Ser Phe Ser Glu His Leu Gly Phe Thr Gly Gly Ile Val Gln Gly
            1060                1065                1070

Leu Asp Leu Tyr Arg Ala Ser Gly Lys Phe Glu Leu Leu Asp Arg Ile
            1075                1080                1085

Leu Pro Lys Leu Arg Ala Thr Asn His Lys Val Leu Leu Phe Cys Gln
            1090                1095                1100

Met Thr Ser Leu Met Thr Ile Met Glu Asp Tyr Phe Ala Tyr Arg Gly
1105                1110                1115                1120

Phe Lys Tyr Leu Arg Leu Asp Gly Thr Thr Lys Ala Glu Asp Arg Gly
            1125                1130                1135

Met Leu Leu Lys Thr Phe Asn Glu Pro Gly Ser Glu Tyr Phe Ile Phe
            1140                1145                1150

Leu Leu Ser Thr Arg Ala Gly Gly Leu Gly Leu Asn Leu Gln Ser Ala
            1155                1160                1165

Asp Thr Val Ile Ile Phe Asp Ser Asp Trp Asn Pro His Gln Asp Leu
            1170                1175                1180

Gln Ala Gln Asp Arg Ala His Arg Ile Gly Gln Gln Asn Glu Val Arg
1185                1190                1195                1200

Val Leu Arg Leu Cys Thr Val Asn Ser Val Glu Glu Lys Ile Leu Ala
            1205                1210                1215

Ala Ala Lys Tyr Lys Leu Asn Val Asp Gln Lys Val Ile Gln Ala Gly
            1220                1225                1230
```

```
Met Phe Asp Gln Lys Ser Ser Ser His Glu Arg Arg Ala Phe Leu Gln
    1235                1240                1245

Ala Ile Leu Glu His Glu Glu Gln Asp Glu Ser Arg His Cys Ser Thr
    1250                1255                1260

Gly Ser Gly Ser Ala Ser Phe Ala His Thr Ala Pro Pro Pro Ala Gly
1265                1270                1275                1280

Val Asn Pro Asp Leu Glu Glu Pro Pro Leu Lys Glu Glu Asp Glu Val
            1285                1290                1295

Pro Asp Asp Glu Thr Val Asn Gln Met Ile Ala Arg His Glu Glu Glu
                1300                1305                1310

Phe Asp Leu Phe Met Arg Met Asp Leu Asp Arg Arg Arg Glu Glu Ala
    1315                1320                1325

Arg Asn Pro Lys Arg Lys Pro Arg Leu Met Glu Glu Asp Glu Leu Pro
    1330                1335                1340

Ser Trp Ile Ile Lys Asp Asp Ala Glu Val Glu Arg Leu Thr Cys Glu
1345                1350                1355                1360

Glu Glu Glu Lys Met Phe Gly Arg Gly Ser Arg His Arg Lys Glu
            1365                1370                1375

Val Asp Tyr Ser Asp Ser Leu Thr Glu Lys Gln Trp Leu Lys Lys Ile
            1380                1385                1390

Thr Gly Lys Asp Ile His Asp Thr Ala Ser Ser Val Ala Arg Gly Leu
    1395                1400                1405

Gln Phe Gln Arg Gly Leu Gln Phe Cys Thr Arg Ala Ser Lys Thr Leu
    1410                1415                1420

Lys Ala Ile Glu Glu Gly Thr Leu Glu Glu Ile Glu Glu Val Arg
1425                1430                1435                1440

Gln Lys Lys Ser Ser Arg Lys Arg Lys Arg Asp Ser Asp Ala Gly Ser
                1445                1450                1455

Ser Thr Pro Thr Thr Ser Thr Arg Ser Arg Asp Lys Asp Asp Glu Ser
            1460                1465                1470

Lys Lys Gln Lys Lys Arg Gly Arg Pro Pro Ala Glu Lys Leu Ser Pro
    1475                1480                1485

Asn Pro Pro Asn Leu Thr Lys Lys Met Lys Lys Ile Val Asp Ala Val
    1490                1495                1500

Ile Lys Tyr Lys Asp Ser Ser Ser Gly Arg Gln Leu Ser Glu Val Phe
1505                1510                1515                1520

Ile Gln Leu Pro Ser Arg Lys Glu Leu Pro Glu Tyr Tyr Glu Leu Ile
            1525                1530                1535

Arg Lys Pro Val Asp Phe Lys Lys Ile Lys Glu Arg Ile Arg Asn His
            1540                1545                1550

Lys Tyr Arg Ser Leu Asn Asp Leu Glu Lys Asp Val Met Leu Leu Cys
    1555                1560                1565

Gln Asn Ala Gln Thr Phe Asn Leu Glu Gly Ser Leu Ile Tyr Glu Asp
    1570                1575                1580

Ser Ile Val Leu Gln Ser Val Phe Thr Ser Val Arg Gln Lys Ile Glu
1585                1590                1595                1600

Lys Glu Asp Asp Ser Glu Gly Glu Glu Ser Glu Glu Glu Glu Glu Gly
            1605                1610                1615

Glu Glu Glu Gly Ser Glu Ser Glu Ser Arg Ser Val Lys Val Lys Ile
            1620                1625                1630

Lys Leu Gly Arg Lys Glu Lys Ala Gln Asp Arg Leu Lys Gly Gly Arg
    1635                1640                1645

Arg Arg Pro Ser Arg Gly Ser Arg Ala Lys Pro Val Val Ser Asp Asp
```

```
                1650                1655                1660
Asp Ser Glu Glu Glu Gln Glu Glu Asp Arg Ser Gly Ser Gly Ser Glu
1665                1670                1675                1680

Glu Asp

<210> SEQ ID NO 74
<211> LENGTH: 5477
<212> TYPE: DNA
<213> ORGANISM: Homo sapiens
<220> FEATURE:
<221> NAME/KEY: CDS
<222> LOCATION: (75)..(5021)
<220> FEATURE:
<221> NAME/KEY: conflict
<222> LOCATION: (1780)
<223> OTHER INFORMATION: GenBank Accession No. U29175 shows a C at this
      position (position 1784 in GenBank) rather than
      the G shown here.
<220> FEATURE:
<221> NAME/KEY: allele
<222> LOCATION: (26)
<223> OTHER INFORMATION: Polymorphism of either T or C in this noncoding
      region.
<220> FEATURE:
<221> NAME/KEY: allele
<222> LOCATION: (1583)
<223> OTHER INFORMATION: Polymorphism of A or G resulting in a silent
      mutation.
<220> FEATURE:
<221> NAME/KEY: allele
<222> LOCATION: (1598)
<223> OTHER INFORMATION: Polymorphism of T or C resulting in a silent
      mutation.
<220> FEATURE:
<221> NAME/KEY: allele
<222> LOCATION: (1892)
<223> OTHER INFORMATION: Polymorphism of A or G resulting in a silent
      mutation.
<220> FEATURE:
<221> NAME/KEY: misc_feature
<222> LOCATION: (1445)..(1453)
<223> OTHER INFORMATION: Insertion of 9 basepairs as compared to SEQ ID
      NO:1.
<220> FEATURE:
<221> NAME/KEY: misc_feature
<222> LOCATION: (4507)..(4508)
<223> OTHER INFORMATION: Deletion of CAG between these basepairs as
      compared to SEQ ID NO:1 (basepairs 4499-4501 of
      SEQ ID NO:1).

<400> SEQUENCE: 74
ggcgggggag gcgccgggaa gtcgatggcg ccggcggctc ctgcaggagg ccactgtctg      60
cagctcccgt gaag atg tcc act cca gac cca ccc ctg ggc gga act cct      110
              Met Ser Thr Pro Asp Pro Pro Leu Gly Gly Thr Pro
                1               5                   10 cgg cca ggt cct tcc ccg ggc cct ggc cct tcc cct gga gcc atg ctg      158
Arg Pro Gly Pro Ser Pro Gly Pro Gly Pro Ser Pro Gly Ala Met Leu
        15                  20                  25 ggc cct agc ccg ggt ccc tcg ccg ggc tcc gcc cac agc atg atg ggg      206
Gly Pro Ser Pro Gly Pro Ser Pro Gly Ser Ala His Ser Met Met Gly
    30                  35                  40 ccc agc cca ggg ccg ccc tca gca gga cac ccc atc ccc acc cag ggg      254
Pro Ser Pro Gly Pro Pro Ser Ala Gly His Pro Ile Pro Thr Gln Gly
45                  50                  55                  60 cct gga ggg tac cct cag gac aac atg cac cag atg cac aag ccc atg      302
Pro Gly Gly Tyr Pro Gln Asp Asn Met His Gln Met His Lys Pro Met
                65                  70                  75 gag tcc atg cat gag aag ggc atg tcg gac gac ccg cgc tac aac cag      350
Glu Ser Met His Glu Lys Gly Met Ser Asp Asp Pro Arg Tyr Asn Gln
```

```
                    80                  85                  90
atg aaa gga atg ggg atg cgg tca ggg ggc cat gct ggg atg ggg ccc        398
Met Lys Gly Met Gly Met Arg Ser Gly Gly His Ala Gly Met Gly Pro
        95                 100                 105 ccg ccc agc ccc atg gac cag cac tcc caa ggt tac ccc tcg ccc ctg        446
Pro Pro Ser Pro Met Asp Gln His Ser Gln Gly Tyr Pro Ser Pro Leu
    110                 115                 120 ggt ggc tct gag cat gcc tct agt cca gtt cca gcc agt ggc ccg tct        494
Gly Gly Ser Glu His Ala Ser Ser Pro Val Pro Ala Ser Gly Pro Ser
125                 130                 135                 140 tcg ggg ccc cag atg tct tcc ggg cca gga ggt gcc ccg ctg gat ggt        542
Ser Gly Pro Gln Met Ser Ser Gly Pro Gly Gly Ala Pro Leu Asp Gly
                145                 150                 155 gct gac ccc cag gcc ttg ggg cag cag aac cgg ggc cca acc cca ttt        590
Ala Asp Pro Gln Ala Leu Gly Gln Gln Asn Arg Gly Pro Thr Pro Phe
            160                 165                 170 aac cag aac cag ctg cac cag ctc aga gct cag atc atg gcc tac aag        638
Asn Gln Asn Gln Leu His Gln Leu Arg Ala Gln Ile Met Ala Tyr Lys
        175                 180                 185 atg ctg gcc agg ggg cag ccc ctc ccc gac cac ctg cag atg gcg gtg        686
Met Leu Ala Arg Gly Gln Pro Leu Pro Asp His Leu Gln Met Ala Val
    190                 195                 200 cag ggc aag cgg ccg atg ccc ggg atg cag cag cag atg cca acg cta        734
Gln Gly Lys Arg Pro Met Pro Gly Met Gln Gln Gln Met Pro Thr Leu
205                 210                 215                 220 cct cca ccc tcg gtg tcc gca aca gga ccc ggc cct ggc cct ggc cct        782
Pro Pro Pro Ser Val Ser Ala Thr Gly Pro Gly Pro Gly Pro Gly Pro
                225                 230                 235 ggc ccc ggc ccg ggt ccc ggc ccg gca cct cca aat tac agc agg cct        830
Gly Pro Gly Pro Gly Pro Gly Pro Ala Pro Pro Asn Tyr Ser Arg Pro
            240                 245                 250 cat ggt atg gga ggg ccc aac atg cct ccc cca gga ccc tcg ggc gtg        878
His Gly Met Gly Gly Pro Asn Met Pro Pro Pro Gly Pro Ser Gly Val
        255                 260                 265 ccc ccc ggg atg cca ggc cag cct cct gga ggg cct ccc aag ccc tgg        926
Pro Pro Gly Met Pro Gly Gln Pro Pro Gly Gly Pro Pro Lys Pro Trp
    270                 275                 280 cct gaa gga ccc atg gcg aat gct gct gcc ccc acg agc acc cct cag        974
Pro Glu Gly Pro Met Ala Asn Ala Ala Ala Pro Thr Ser Thr Pro Gln
285                 290                 295                 300 aag ctg att ccc ccg cag cca acg ggc cgc cct tcc ccc gcg ccc cct       1022
Lys Leu Ile Pro Pro Gln Pro Thr Gly Arg Pro Ser Pro Ala Pro Pro
                305                 310                 315 gcc gtc cca ccc gcc gcc tcg ccc gtg atg cca ccg cag acc cag tcc       1070
Ala Val Pro Pro Ala Ala Ser Pro Val Met Pro Pro Gln Thr Gln Ser
            320                 325                 330 ccc ggg cag ccg gcc cag ccc gcg ccc atg gtg cca ctg cac cag aag       1118
Pro Gly Gln Pro Ala Gln Pro Ala Pro Met Val Pro Leu His Gln Lys
        335                 340                 345 cag agc cgc atc acc ccc atc cag aag ccg cgg ggc ctc gac cct gtg       1166
Gln Ser Arg Ile Thr Pro Ile Gln Lys Pro Arg Gly Leu Asp Pro Val
    350                 355                 360 gag atc ctg cag gag cgc gag tac agg ctg cag gct cgc atc gca cac       1214
Glu Ile Leu Gln Glu Arg Glu Tyr Arg Leu Gln Ala Arg Ile Ala His
365                 370                 375                 380 cga att cag gaa ctt gaa aac ctt ccc ggg tcc ctg gcc ggg gat ttg       1262
Arg Ile Gln Glu Leu Glu Asn Leu Pro Gly Ser Leu Ala Gly Asp Leu
                385                 390                 395 cga acc aaa gcg acc att gag ctc aag gcc ctc agg ctg ctg aac ttc       1310
```

-continued

```
Arg Thr Lys Ala Thr Ile Glu Leu Lys Ala Leu Arg Leu Leu Asn Phe
        400                 405                 410
cag agg cag ctg cgc cag gag gtg gtg gtg tgc atg cgg agg gac aca      1358
Gln Arg Gln Leu Arg Gln Glu Val Val Val Cys Met Arg Arg Asp Thr
        415                 420                 425
gcg ctg gag aca gcc ctc aat gct aag gcc tac aag cgc agc aag cgc      1406
Ala Leu Glu Thr Ala Leu Asn Ala Lys Ala Tyr Lys Arg Ser Lys Arg
    430                 435                 440
cag tcc ctg cgc gag gcc cgc atc act gag aag ctg gag aag cag cag      1454
Gln Ser Leu Arg Glu Ala Arg Ile Thr Glu Lys Leu Glu Lys Gln Gln
445                 450                 455                 460
aag atc gag cag gag cgc aag cgc cgg cag aag cac cag gaa tac ctc      1502
Lys Ile Glu Gln Glu Arg Lys Arg Arg Gln Lys His Gln Glu Tyr Leu
                465                 470                 475
aat agc att ctc cag cat gcc aag gat ttc aag gaa tat cac aga tcc      1550
Asn Ser Ile Leu Gln His Ala Lys Asp Phe Lys Glu Tyr His Arg Ser
            480                 485                 490
gtc aca ggc aaa atc cag aag ctg acc aag gca gtg gcc acg tac cat      1598
Val Thr Gly Lys Ile Gln Lys Leu Thr Lys Ala Val Ala Thr Tyr His
        495                 500                 505
gcc aac acg gag cgg gag cag aag aaa gag aac gag cgg atc gag aag      1646
Ala Asn Thr Glu Arg Glu Gln Lys Lys Glu Asn Glu Arg Ile Glu Lys
    510                 515                 520
gag cgc atg cgg agg ctc atg gct gaa gat gag gag ggg tac cgc aag      1694
Glu Arg Met Arg Arg Leu Met Ala Glu Asp Glu Glu Gly Tyr Arg Lys
525                 530                 535                 540
ctc atc gac cag aag aag gac aag cgc ctg gcc tac ctc ttg cag cag      1742
Leu Ile Asp Gln Lys Lys Asp Lys Arg Leu Ala Tyr Leu Leu Gln Gln
                545                 550                 555
aca gac gag tac gtg gct aac ctc acg gag ctg gtg cgg cag cac aag      1790
Thr Asp Glu Tyr Val Ala Asn Leu Thr Glu Leu Val Arg Gln His Lys
            560                 565                 570
gct gcc cag gtc gcc aag gag aaa aag aag aaa aag aaa aag aag aag      1838
Ala Ala Gln Val Ala Lys Glu Lys Lys Lys Lys Lys Lys Lys Lys Lys
        575                 580                 585
gca gaa aat gca gaa gga cag acg cct gcc att ggg ccg gat ggc gag      1886
Ala Glu Asn Ala Glu Gly Gln Thr Pro Ala Ile Gly Pro Asp Gly Glu
    590                 595                 600
cct cta gac gag acc agc cag atg agc gac ctc ccg gtg aag gtg atc      1934
Pro Leu Asp Glu Thr Ser Gln Met Ser Asp Leu Pro Val Lys Val Ile
605                 610                 615                 620
cac gtg gag agt ggg aag atc ctc aca ggc aca gat gcc ccc aaa gcc      1982
His Val Glu Ser Gly Lys Ile Leu Thr Gly Thr Asp Ala Pro Lys Ala
                625                 630                 635
ggg cag ctg gag gcc tgg ctc gag atg aac ccg ggg tat gaa gta gct      2030
Gly Gln Leu Glu Ala Trp Leu Glu Met Asn Pro Gly Tyr Glu Val Ala
            640                 645                 650
ccg agg tct gat agt gaa gaa agt ggc tca gaa gaa gag gaa gag gag      2078
Pro Arg Ser Asp Ser Glu Glu Ser Gly Ser Glu Glu Glu Glu Glu Glu
        655                 660                 665
gag gag gaa gag cag ccg cag gca gca cag cct ccc acc ctg ccc gtg      2126
Glu Glu Glu Glu Gln Pro Gln Ala Ala Gln Pro Pro Thr Leu Pro Val
    670                 675                 680
gag gag aag aag aag att cca gat cca gac agc gat gac gtc tct gag      2174
Glu Glu Lys Lys Lys Ile Pro Asp Pro Asp Ser Asp Asp Val Ser Glu
685                 690                 695                 700
gtg gac gcg cgg cac atc att gag aat gcc aag caa gat gtc gat gat      2222
Val Asp Ala Arg His Ile Ile Glu Asn Ala Lys Gln Asp Val Asp Asp
                705                 710                 715
```

-continued

| | |
|---|---|
| gaa tat ggc gtg tcc cag gcc ctt gca cgt ggc ctg cag tcc tac tat<br>Glu Tyr Gly Val Ser Gln Ala Leu Ala Arg Gly Leu Gln Ser Tyr Tyr<br>720                        725                     730 | 2270 |
| gcc gtg gcc cat gct gtc act gag aga gtg gac aag cag tca gcg ctt<br>Ala Val Ala His Ala Val Thr Glu Arg Val Asp Lys Gln Ser Ala Leu<br>        735                     740                     745 | 2318 |
| atg gtc aat ggt gtc ctc aaa cag tac cag atc aaa ggt ttg gag tgg<br>Met Val Asn Gly Val Leu Lys Gln Tyr Gln Ile Lys Gly Leu Glu Trp<br>750                        755                     760 | 2366 |
| ctg gtg tcc ctg tac aac aac aac ctg aac ggc atc ctg gcc gac gag<br>Leu Val Ser Leu Tyr Asn Asn Asn Leu Asn Gly Ile Leu Ala Asp Glu<br>765                        770                     775                     780 | 2414 |
| atg ggc ctg ggg aag acc atc cag acc atc gcg ctc atc acg tac ctc<br>Met Gly Leu Gly Lys Thr Ile Gln Thr Ile Ala Leu Ile Thr Tyr Leu<br>        785                     790                     795 | 2462 |
| atg gag cac aaa cgc atc aat ggg ccc ttc ctc atc atc gtg cct ctc<br>Met Glu His Lys Arg Ile Asn Gly Pro Phe Leu Ile Ile Val Pro Leu<br>            800                     805                     810 | 2510 |
| tca acg ctg tcc aac tgg gcg tac gag ttt gac aag tgg gcc ccc tcc<br>Ser Thr Leu Ser Asn Trp Ala Tyr Glu Phe Asp Lys Trp Ala Pro Ser<br>815                        820                     825 | 2558 |
| gtg gtg aag gtg tct tac aag gga tcc cca gca gca aga cgg gcc ttt<br>Val Val Lys Val Ser Tyr Lys Gly Ser Pro Ala Ala Arg Arg Ala Phe<br>830                        835                     840 | 2606 |
| gtc ccc cag ctc cgg agt ggg aag ttc aac gtc ttg ctg acg acg tac<br>Val Pro Gln Leu Arg Ser Gly Lys Phe Asn Val Leu Leu Thr Thr Tyr<br>845                        850                     855                     860 | 2654 |
| gag tac atc atc aaa gac aag cac atc ctc gcc aag atc cgt tgg aag<br>Glu Tyr Ile Ile Lys Asp Lys His Ile Leu Ala Lys Ile Arg Trp Lys<br>                    865                     870                     875 | 2702 |
| tac atg att gtg gac gaa ggt cac cgc atg aag aac cac cac tgc aag<br>Tyr Met Ile Val Asp Glu Gly His Arg Met Lys Asn His His Cys Lys<br>880                        885                     890 | 2750 |
| ctg acg cag gtg ctc aac acg cac tat gtg gca ccc cgc cgc ctg ctg<br>Leu Thr Gln Val Leu Asn Thr His Tyr Val Ala Pro Arg Arg Leu Leu<br>        895                     900                     905 | 2798 |
| ctg acg ggc aca ccg ctg cag aac aag ctt ccc gag ctc tgg gcg ctg<br>Leu Thr Gly Thr Pro Leu Gln Asn Lys Leu Pro Glu Leu Trp Ala Leu<br>910                        915                     920 | 2846 |
| ctc aac ttc ctg ctg ccc acc atc ttc aag agc tgc agc acc ttc gag<br>Leu Asn Phe Leu Leu Pro Thr Ile Phe Lys Ser Cys Ser Thr Phe Glu<br>925                        930                     935                     940 | 2894 |
| cag tgg ttt aac gca ccc ttt gcc atg acc ggg gaa aag gtg gac ctg<br>Gln Trp Phe Asn Ala Pro Phe Ala Met Thr Gly Glu Lys Val Asp Leu<br>                    945                     950                     955 | 2942 |
| aat gag gag gaa acc att ctc atc atc cgg cgt ctc cac aaa gtg ctg<br>Asn Glu Glu Glu Thr Ile Leu Ile Ile Arg Arg Leu His Lys Val Leu<br>960                        965                     970 | 2990 |
| cgg ccc ttc ttg ctc cga cga ctc aag aag gaa gtc gag gcc cag ttg<br>Arg Pro Phe Leu Leu Arg Arg Leu Lys Lys Glu Val Glu Ala Gln Leu<br>        975                     980                     985 | 3038 |
| ccc gaa aag gtg gag tac gtc atc aag tgc gac atg tct gcg ctg cag<br>Pro Glu Lys Val Glu Tyr Val Ile Lys Cys Asp Met Ser Ala Leu Gln<br>990                        995                    1000 | 3086 |
| cga gtg ctc tac cgc cac atg cag gcc aag ggc gtg ctg ctg act gat<br>Arg Val Leu Tyr Arg His Met Gln Ala Lys Gly Val Leu Leu Thr Asp<br>1005                  1010                  1015                  1020 | 3134 |
| ggc tcc gag aag gac aag aag ggc aaa ggc ggc acc aag acc ctg atg<br>Gly Ser Glu Lys Asp Lys Lys Gly Lys Gly Gly Thr Lys Thr Leu Met<br>                1025                  1030                  1035 | 3182 |

-continued

| | |
|---|---|
| aac acc atc atg cag ctg cgg aag atc tgc aac cac ccc tac atg ttc<br>Asn Thr Ile Met Gln Leu Arg Lys Ile Cys Asn His Pro Tyr Met Phe<br>          1040                  1045              1050 | 3230 |
| cag cac atc gag gag tcc ttt tcc gag cac ttg ggg ttc act ggc ggc<br>Gln His Ile Glu Glu Ser Phe Ser Glu His Leu Gly Phe Thr Gly Gly<br>    1055                  1060              1065 | 3278 |
| att gtc caa ggg ctg gac ctg tac cga gcc tcg ggt aaa ttt gag ctt<br>Ile Val Gln Gly Leu Asp Leu Tyr Arg Ala Ser Gly Lys Phe Glu Leu<br>1070                  1075              1080 | 3326 |
| ctt gat aga att ctt ccc aaa ctc cga gca acc aac cac aaa gtg ctg<br>Leu Asp Arg Ile Leu Pro Lys Leu Arg Ala Thr Asn His Lys Val Leu<br>1085                  1090              1095              1100 | 3374 |
| ctg ttc tgc caa atg acc tcc ctc atg acc atc atg gaa gat tac ttt<br>Leu Phe Cys Gln Met Thr Ser Leu Met Thr Ile Met Glu Asp Tyr Phe<br>          1105                  1110              1115 | 3422 |
| gcg tat cgc ggc ttt aaa tac ctc agg ctt gat gga acc acg aag gcg<br>Ala Tyr Arg Gly Phe Lys Tyr Leu Arg Leu Asp Gly Thr Thr Lys Ala<br>             1120                  1125              1130 | 3470 |
| gag gac cgg ggc atg ctg ctg aaa acc ttc aac gag ccc ggc tct gag<br>Glu Asp Arg Gly Met Leu Leu Lys Thr Phe Asn Glu Pro Gly Ser Glu<br>          1135                  1140              1145 | 3518 |
| tac ttc atc ttc ctg ctc agc acc cgg gct ggg ggg ctc ggc ctg aac<br>Tyr Phe Ile Phe Leu Leu Ser Thr Arg Ala Gly Gly Leu Gly Leu Asn<br>    1150                  1155              1160 | 3566 |
| ctc cag tcg gca gac act gtg atc att ttt gac agc gac tgg aat cct<br>Leu Gln Ser Ala Asp Thr Val Ile Ile Phe Asp Ser Asp Trp Asn Pro<br>1165                  1170              1175              1180 | 3614 |
| cac cag gac ctg caa gcg cag gac cga gcc cac cgc atc ggg cag cag<br>His Gln Asp Leu Gln Ala Gln Asp Arg Ala His Arg Ile Gly Gln Gln<br>             1185                  1190              1195 | 3662 |
| aac gag gtg cgt gtg ctc cgc ctc tgc acc gtc aac agc gtg gag gag<br>Asn Glu Val Arg Val Leu Arg Leu Cys Thr Val Asn Ser Val Glu Glu<br>          1200                  1205              1210 | 3710 |
| aag atc cta gct gca gcc aag tac aag ctc aac gtg gac cag aag gtg<br>Lys Ile Leu Ala Ala Ala Lys Tyr Lys Leu Asn Val Asp Gln Lys Val<br>       1215                  1220              1225 | 3758 |
| atc cag gcc ggc atg ttc gac cag aag tcc tcc agc cat gag cgg cgc<br>Ile Gln Ala Gly Met Phe Asp Gln Lys Ser Ser Ser His Glu Arg Arg<br>          1230                  1235              1240 | 3806 |
| gcc ttc ctg cag gcc atc ctg gag cac gag gag cag gat gag agc aga<br>Ala Phe Leu Gln Ala Ile Leu Glu His Glu Glu Gln Asp Glu Ser Arg<br>1245                  1250              1255              1260 | 3854 |
| cac tgc agc acg ggc agc ggc agt gcc agc ttc gcc cac act gcc cct<br>His Cys Ser Thr Gly Ser Gly Ser Ala Ser Phe Ala His Thr Ala Pro<br>             1265                  1270              1275 | 3902 |
| ccg cca gcg ggc gtc aac ccc gac ttg gag gag cca cct cta aag gag<br>Pro Pro Ala Gly Val Asn Pro Asp Leu Glu Glu Pro Pro Leu Lys Glu<br>          1280                  1285              1290 | 3950 |
| gaa gac gag gtg ccc gac gac gag acc gtc aac cag atg atc gcc cgg<br>Glu Asp Glu Val Pro Asp Asp Glu Thr Val Asn Gln Met Ile Ala Arg<br>       1295                  1300              1305 | 3998 |
| cac gag gag gag ttt gat ctg ttc atg cgc atg gac ctg gac cgc agg<br>His Glu Glu Glu Phe Asp Leu Phe Met Arg Met Asp Leu Asp Arg Arg<br>          1310                  1315              1320 | 4046 |
| cgc gag gag gcc cgc aac ccc aag cgg aag ccg cgc ctc atg gag gag<br>Arg Glu Glu Ala Arg Asn Pro Lys Arg Lys Pro Arg Leu Met Glu Glu<br>1325                  1330              1335              1340 | 4094 |
| gac gag ctc ccc tcg tgg atc atc aag gac gac gcg gag gtg gag cgg<br>Asp Glu Leu Pro Ser Trp Ile Ile Lys Asp Asp Ala Glu Val Glu Arg | 4142 |

```
              1345                 1350                 1355
ctg acc tgt gag gag gag gag gag aag atg ttc ggc cgt ggc tcc cgc     4190
Leu Thr Cys Glu Glu Glu Glu Glu Lys Met Phe Gly Arg Gly Ser Arg
            1360                 1365                 1370 cac cgc aag gag gtg gac tac agc gac tca ctg acg gag aag cag tgg     4238
His Arg Lys Glu Val Asp Tyr Ser Asp Ser Leu Thr Glu Lys Gln Trp
        1375                 1380                 1385 ctc aag acc ctg aag gcc atc gag gag ggc acg ctg gag gag atc gaa     4286
Leu Lys Thr Leu Lys Ala Ile Glu Glu Gly Thr Leu Glu Glu Ile Glu
    1390                 1395                 1400 gag gag gtc cgg cag aag aaa tca tca cgg aag cgc aag cga gac agc     4334
Glu Glu Val Arg Gln Lys Lys Ser Ser Arg Lys Arg Lys Arg Asp Ser
1405                 1410                 1415                 1420 gac gcc ggc tcc tcc acc ccg acc acc agc acc cgc agc cgc gac aag     4382
Asp Ala Gly Ser Ser Thr Pro Thr Thr Ser Thr Arg Ser Arg Asp Lys
                1425                 1430                 1435 gac gac gag agc aag aag cag aag aag cgc ggg cgg ccg cct gcc gag     4430
Asp Asp Glu Ser Lys Lys Gln Lys Lys Arg Gly Arg Pro Pro Ala Glu
            1440                 1445                 1450 aaa ctc tcc cct aac cca ccc aac ctc acc aag aag atg aag aag att     4478
Lys Leu Ser Pro Asn Pro Pro Asn Leu Thr Lys Lys Met Lys Lys Ile
        1455                 1460                 1465 gtg gat gcc gtg atc aag tac aag gac agc agt gga cgt cag ctc agc     4526
Val Asp Ala Val Ile Lys Tyr Lys Asp Ser Ser Gly Arg Gln Leu Ser
    1470                 1475                 1480 gag gtc ttc atc cag ctg ccc tcg cga aag gag ctg ccc gag tac tac     4574
Glu Val Phe Ile Gln Leu Pro Ser Arg Lys Glu Leu Pro Glu Tyr Tyr
1485                 1490                 1495                 1500 gag ctc atc cgc aag ccc gtg gac ttc aag aag ata aag gag cgc att     4622
Glu Leu Ile Arg Lys Pro Val Asp Phe Lys Lys Ile Lys Glu Arg Ile
                1505                 1510                 1515 cgc aac cac aag tac cgc agc ctc aac gac cta gag aag gac gtc atg     4670
Arg Asn His Lys Tyr Arg Ser Leu Asn Asp Leu Glu Lys Asp Val Met
            1520                 1525                 1530 ctc ctg tgc cag aac gca cag acc ttc aac ctg gag ggc tcc ctg atc     4718
Leu Leu Cys Gln Asn Ala Gln Thr Phe Asn Leu Glu Gly Ser Leu Ile
        1535                 1540                 1545 tat gaa gac tcc atc gtc ttg cag tcg gtc ttc acc agc gtg cgg cag     4766
Tyr Glu Asp Ser Ile Val Leu Gln Ser Val Phe Thr Ser Val Arg Gln
    1550                 1555                 1560 aaa atc gag aag gag gat gac agt gaa ggc gag gag agt gag gag gag     4814
Lys Ile Glu Lys Glu Asp Asp Ser Glu Gly Glu Glu Ser Glu Glu Glu
1565                 1570                 1575                 1580 gaa gag ggc gag gag gaa ggc tcc gaa tcc gaa tct cgg tcc gtc aaa     4862
Glu Glu Gly Glu Glu Gly Ser Glu Ser Glu Ser Arg Ser Val Lys
                1585                 1590                 1595 gtg aag atc aag ctt ggc cgg aag gag aag gca cag gac cgg ctg aag     4910
Val Lys Ile Lys Leu Gly Arg Lys Glu Lys Ala Gln Asp Arg Leu Lys
            1600                 1605                 1610 ggc ggc cgg cgg cgg ccg agc cga ggg tcc cga gcc aag ccg gtc gtg     4958
Gly Gly Arg Arg Arg Pro Ser Arg Gly Ser Arg Ala Lys Pro Val Val
        1615                 1620                 1625 agt gac gat gac agt gag gag gaa caa gag gag gac cgc tca gga agt     5006
Ser Asp Asp Asp Ser Glu Glu Glu Gln Glu Glu Asp Arg Ser Gly Ser
    1630                 1635                 1640 ggc agc gaa gaa gac tgagcccga cattccagtc tcgaccccga gccctcgtt       5061
Gly Ser Glu Glu Asp
1645 ccagagctga gatggcatag gccttagcag taacgggtag cagcagatgt agtttcagac    5121
```

-continued

```
ttggagtaaa actgtataaa caaaagaatc ttccatattt atacagcaga gaagctgtag      5181
gactgtttgt gactggccct gtcctggcat cagtagcatc tgtaacagca ttaactgtct      5241
taaagagaga gagagagaat tccgaattgg ggaacacacg atacctgttt ttcttttccg      5301
ttgctggcag tactgttgcg ccgcagtttg gagtcactgt agttaagtgt ggatgcatgt      5361
gcgtcaccgt ccactcctcc tactgtattt tattggacag gtcagactcg ccgggggccc      5421
ggcgagggta tgtcagtgtc actggatgtc aaacagtaat aaattaaacc aacaac         5477
```

<210> SEQ ID NO 75
<211> LENGTH: 1649
<212> TYPE: PRT
<213> ORGANISM: Homo sapiens

<400> SEQUENCE: 75

```
Met Ser Thr Pro Asp Pro Pro Leu Gly Gly Thr Pro Arg Pro Gly Pro
 1               5                  10                  15

Ser Pro Gly Pro Gly Pro Ser Pro Gly Ala Met Leu Gly Pro Ser Pro
             20                  25                  30

Gly Pro Ser Pro Gly Ser Ala His Ser Met Met Gly Pro Ser Pro Gly
         35                  40                  45

Pro Pro Ser Ala Gly His Pro Ile Pro Thr Gln Gly Pro Gly Gly Tyr
     50                  55                  60

Pro Gln Asp Asn Met His Gln Met His Lys Pro Met Glu Ser Met His
 65                  70                  75                  80

Glu Lys Gly Met Ser Asp Asp Pro Arg Tyr Asn Gln Met Lys Gly Met
                 85                  90                  95

Gly Met Arg Ser Gly Gly His Ala Gly Met Gly Pro Pro Ser Pro
             100                 105                 110

Met Asp Gln His Ser Gln Gly Tyr Pro Ser Pro Leu Gly Gly Ser Glu
         115                 120                 125

His Ala Ser Ser Pro Val Pro Ala Ser Gly Pro Ser Ser Gly Pro Gln
    130                 135                 140

Met Ser Ser Gly Pro Gly Gly Ala Pro Leu Asp Gly Ala Asp Pro Gln
145                 150                 155                 160

Ala Leu Gly Gln Gln Asn Arg Gly Pro Thr Pro Phe Asn Gln Asn Gln
                165                 170                 175

Leu His Gln Leu Arg Ala Gln Ile Met Ala Tyr Lys Met Leu Ala Arg
            180                 185                 190

Gly Gln Pro Leu Pro Asp His Leu Gln Met Ala Val Gln Gly Lys Arg
        195                 200                 205

Pro Met Pro Gly Met Gln Gln Gln Met Pro Thr Leu Pro Pro Pro Ser
    210                 215                 220

Val Ser Ala Thr Gly Pro Gly Pro Gly Pro Gly Pro Gly Pro Gly Pro
225                 230                 235                 240

Gly Pro Gly Pro Ala Pro Pro Asn Tyr Ser Arg Pro His Gly Met Gly
                245                 250                 255

Gly Pro Asn Met Pro Pro Pro Gly Pro Ser Gly Val Pro Pro Gly Met
            260                 265                 270

Pro Gly Gln Pro Pro Gly Gly Pro Pro Lys Pro Trp Pro Glu Gly Pro
        275                 280                 285

Met Ala Asn Ala Ala Ala Pro Thr Ser Thr Pro Gln Lys Leu Ile Pro
    290                 295                 300

Pro Gln Pro Thr Gly Arg Pro Ser Pro Ala Pro Pro Ala Val Pro Pro
```

-continued

```
305                 310                 315                 320
Ala Ala Ser Pro Val Met Pro Pro Gln Thr Gln Ser Pro Gly Gln Pro
                325                 330                 335
Ala Gln Pro Ala Pro Met Val Pro Leu His Gln Lys Gln Ser Arg Ile
                340                 345                 350
Thr Pro Ile Gln Lys Pro Arg Gly Leu Asp Pro Val Glu Ile Leu Gln
                355                 360                 365
Glu Arg Glu Tyr Arg Leu Gln Ala Arg Ile Ala His Arg Ile Gln Glu
                370                 375                 380
Leu Glu Asn Leu Pro Gly Ser Leu Ala Gly Asp Leu Arg Thr Lys Ala
385                 390                 395                 400
Thr Ile Glu Leu Lys Ala Leu Arg Leu Leu Asn Phe Gln Arg Gln Leu
                405                 410                 415
Arg Gln Glu Val Val Val Cys Met Arg Arg Asp Thr Ala Leu Glu Thr
                420                 425                 430
Ala Leu Asn Ala Lys Ala Tyr Lys Arg Ser Lys Arg Gln Ser Leu Arg
                435                 440                 445
Glu Ala Arg Ile Thr Glu Lys Leu Glu Lys Gln Gln Lys Ile Glu Gln
                450                 455                 460
Glu Arg Lys Arg Arg Gln Lys His Gln Glu Tyr Leu Asn Ser Ile Leu
465                 470                 475                 480
Gln His Ala Lys Asp Phe Lys Glu Tyr His Arg Ser Val Thr Gly Lys
                485                 490                 495
Ile Gln Lys Leu Thr Lys Ala Val Ala Thr Tyr His Ala Asn Thr Glu
                500                 505                 510
Arg Glu Gln Lys Lys Glu Asn Glu Arg Ile Glu Lys Glu Arg Met Arg
                515                 520                 525
Arg Leu Met Ala Glu Asp Glu Glu Gly Tyr Arg Lys Leu Ile Asp Gln
                530                 535                 540
Lys Lys Asp Lys Arg Leu Ala Tyr Leu Leu Gln Gln Thr Asp Glu Tyr
545                 550                 555                 560
Val Ala Asn Leu Thr Glu Leu Val Arg Gln His Lys Ala Ala Gln Val
                565                 570                 575
Ala Lys Glu Lys Lys Lys Lys Lys Lys Lys Lys Ala Glu Asn Ala
                580                 585                 590
Glu Gly Gln Thr Pro Ala Ile Gly Pro Asp Gly Glu Pro Leu Asp Glu
                595                 600                 605
Thr Ser Gln Met Ser Asp Leu Pro Val Lys Val Ile His Val Glu Ser
                610                 615                 620
Gly Lys Ile Leu Thr Gly Thr Asp Ala Pro Lys Ala Gly Gln Leu Glu
625                 630                 635                 640
Ala Trp Leu Glu Met Asn Pro Gly Tyr Glu Val Ala Pro Arg Ser Asp
                645                 650                 655
Ser Glu Glu Ser Gly Ser Glu Glu Glu Glu Glu Glu Glu Glu
                660                 665                 670
Gln Pro Gln Ala Ala Gln Pro Pro Thr Leu Pro Val Glu Lys Lys
                675                 680                 685
Lys Ile Pro Asp Pro Asp Ser Asp Asp Val Ser Glu Val Asp Ala Arg
                690                 695                 700
His Ile Ile Glu Asn Ala Lys Gln Asp Val Asp Asp Glu Tyr Gly Val
705                 710                 715                 720
Ser Gln Ala Leu Ala Arg Gly Leu Gln Ser Tyr Tyr Ala Val Ala His
                725                 730                 735
```

-continued

Ala Val Thr Glu Arg Val Asp Lys Gln Ser Ala Leu Met Val Asn Gly
        740                 745                 750

Val Leu Lys Gln Tyr Gln Ile Lys Gly Leu Glu Trp Leu Val Ser Leu
        755                 760                 765

Tyr Asn Asn Asn Leu Asn Gly Ile Leu Ala Asp Glu Met Gly Leu Gly
        770                 775                 780

Lys Thr Ile Gln Thr Ile Ala Leu Ile Thr Tyr Leu Met Glu His Lys
785                 790                 795                 800

Arg Ile Asn Gly Pro Phe Leu Ile Ile Val Pro Leu Ser Thr Leu Ser
                805                 810                 815

Asn Trp Ala Tyr Glu Phe Asp Lys Trp Ala Pro Ser Val Val Lys Val
                820                 825                 830

Ser Tyr Lys Gly Ser Pro Ala Ala Arg Arg Ala Phe Val Pro Gln Leu
        835                 840                 845

Arg Ser Gly Lys Phe Asn Val Leu Leu Thr Thr Tyr Glu Tyr Ile Ile
        850                 855                 860

Lys Asp Lys His Ile Leu Ala Lys Ile Arg Trp Lys Tyr Met Ile Val
865                 870                 875                 880

Asp Glu Gly His Arg Met Lys Asn His His Cys Lys Leu Thr Gln Val
                885                 890                 895

Leu Asn Thr His Tyr Val Ala Pro Arg Arg Leu Leu Leu Thr Gly Thr
                900                 905                 910

Pro Leu Gln Asn Lys Leu Pro Glu Leu Trp Ala Leu Leu Asn Phe Leu
        915                 920                 925

Leu Pro Thr Ile Phe Lys Ser Cys Ser Thr Phe Glu Gln Trp Phe Asn
        930                 935                 940

Ala Pro Phe Ala Met Thr Gly Glu Lys Val Asp Leu Asn Glu Glu Glu
945                 950                 955                 960

Thr Ile Leu Ile Ile Arg Arg Leu His Lys Val Leu Arg Pro Phe Leu
                965                 970                 975

Leu Arg Arg Leu Lys Lys Glu Val Glu Ala Gln Leu Pro Glu Lys Val
                980                 985                 990

Glu Tyr Val Ile Lys Cys Asp Met Ser Ala Leu Gln Arg Val Leu Tyr
        995                 1000                1005

Arg His Met Gln Ala Lys Gly Val Leu Leu Thr Asp Gly Ser Glu Lys
    1010                1015                1020

Asp Lys Lys Gly Lys Gly Gly Thr Lys Thr Leu Met Asn Thr Ile Met
1025                1030                1035                1040

Gln Leu Arg Lys Ile Cys Asn His Pro Tyr Met Phe Gln His Ile Glu
                1045                1050                1055

Glu Ser Phe Ser Glu His Leu Gly Phe Thr Gly Gly Ile Val Gln Gly
            1060                1065                1070

Leu Asp Leu Tyr Arg Ala Ser Gly Lys Phe Glu Leu Leu Asp Arg Ile
        1075                1080                1085

Leu Pro Lys Leu Arg Ala Thr Asn His Lys Val Leu Leu Phe Cys Gln
    1090                1095                1100

Met Thr Ser Leu Met Thr Ile Met Glu Asp Tyr Phe Ala Tyr Arg Gly
1105                1110                1115                1120

Phe Lys Tyr Leu Arg Leu Asp Gly Thr Thr Lys Ala Glu Asp Arg Gly
                1125                1130                1135

Met Leu Leu Lys Thr Phe Asn Glu Pro Gly Ser Glu Tyr Phe Ile Phe
                1140                1145                1150

-continued

```
Leu Leu Ser Thr Arg Ala Gly Gly Leu Gly Leu Asn Leu Gln Ser Ala
    1155                1160                1165

Asp Thr Val Ile Ile Phe Asp Ser Asp Trp Asn Pro His Gln Asp Leu
    1170                1175                1180

Gln Ala Gln Asp Arg Ala His Arg Ile Gly Gln Gln Asn Glu Val Arg
1185                1190                1195                1200

Val Leu Arg Leu Cys Thr Val Asn Ser Val Glu Glu Lys Ile Leu Ala
            1205                1210                1215

Ala Ala Lys Tyr Lys Leu Asn Val Asp Gln Lys Val Ile Gln Ala Gly
            1220                1225                1230

Met Phe Asp Gln Lys Ser Ser Ser His Glu Arg Arg Ala Phe Leu Gln
            1235                1240                1245

Ala Ile Leu Glu His Glu Glu Gln Asp Glu Ser Arg His Cys Ser Thr
            1250                1255                1260

Gly Ser Gly Ser Ala Ser Phe Ala His Thr Ala Pro Pro Ala Gly
1265                1270                1275                1280

Val Asn Pro Asp Leu Glu Glu Pro Pro Leu Lys Glu Glu Asp Glu Val
            1285                1290                1295

Pro Asp Asp Glu Thr Val Asn Gln Met Ile Ala Arg His Glu Glu Glu
            1300                1305                1310

Phe Asp Leu Phe Met Arg Met Asp Leu Asp Arg Arg Arg Glu Glu Ala
    1315                1320                1325

Arg Asn Pro Lys Arg Lys Pro Arg Leu Met Glu Glu Asp Glu Leu Pro
    1330                1335                1340

Ser Trp Ile Ile Lys Asp Asp Ala Glu Val Glu Arg Leu Thr Cys Glu
1345                1350                1355                1360

Glu Glu Glu Glu Lys Met Phe Gly Arg Gly Ser Arg His Arg Lys Glu
            1365                1370                1375

Val Asp Tyr Ser Asp Ser Leu Thr Glu Lys Gln Trp Leu Lys Thr Leu
            1380                1385                1390

Lys Ala Ile Glu Glu Gly Thr Leu Glu Glu Ile Glu Glu Glu Val Arg
            1395                1400                1405

Gln Lys Lys Ser Ser Arg Lys Arg Lys Arg Asp Ser Asp Ala Gly Ser
    1410                1415                1420

Ser Thr Pro Thr Thr Ser Thr Arg Ser Arg Asp Lys Asp Asp Glu Ser
1425                1430                1435                1440

Lys Lys Gln Lys Lys Arg Gly Arg Pro Pro Ala Glu Lys Leu Ser Pro
            1445                1450                1455

Asn Pro Pro Asn Leu Thr Lys Lys Met Lys Lys Ile Val Asp Ala Val
            1460                1465                1470

Ile Lys Tyr Lys Asp Ser Ser Gly Arg Gln Leu Ser Glu Val Phe Ile
            1475                1480                1485

Gln Leu Pro Ser Arg Lys Glu Leu Pro Glu Tyr Tyr Glu Leu Ile Arg
    1490                1495                1500

Lys Pro Val Asp Phe Lys Lys Ile Lys Glu Arg Ile Arg Asn His Lys
1505                1510                1515                1520

Tyr Arg Ser Leu Asn Asp Leu Glu Lys Asp Val Met Leu Leu Cys Gln
            1525                1530                1535

Asn Ala Gln Thr Phe Asn Leu Glu Gly Ser Leu Ile Tyr Glu Asp Ser
            1540                1545                1550

Ile Val Leu Gln Ser Val Phe Thr Ser Val Arg Gln Lys Ile Glu Lys
            1555                1560                1565

Glu Asp Asp Ser Glu Gly Glu Glu Ser Glu Glu Glu Glu Glu Gly Glu
```

```
              1570                1575                1580
     Glu Glu Gly Ser Glu Ser Glu Ser Arg Ser Val Lys Val Lys Ile Lys
     1585                1590                1595                1600

Leu Gly Arg Lys Glu Lys Ala Gln Asp Arg Leu Lys Gly Gly Arg Arg
                     1605                1610                1615

Arg Pro Ser Arg Gly Ser Arg Ala Lys Pro Val Val Ser Asp Asp Asp
                     1620                1625                1630

Ser Glu Glu Glu Gln Glu Glu Asp Arg Ser Gly Ser Gly Ser Glu Glu
             1635                1640                1645

Asp

<210> SEQ ID NO 76
<211> LENGTH: 5573
<212> TYPE: DNA
<213> ORGANISM: Homo sapiens
<220> FEATURE:
<221> NAME/KEY: CDS
<222> LOCATION: (75)..(5117)
<220> FEATURE:
<221> NAME/KEY: conflict
<222> LOCATION: (1780)
<223> OTHER INFORMATION: GenBank Accession No. U29175 shows a C at this
      position (position 1784 in GenBank) rather than
      the G shown here.
<220> FEATURE:
<221> NAME/KEY: allele
<222> LOCATION: (26)
<223> OTHER INFORMATION: Polymorphism of either T or C in this noncoding
      region.
<220> FEATURE:
<221> NAME/KEY: allele
<222> LOCATION: (1583)
<223> OTHER INFORMATION: Polymorphism of A or G resulting in a silent
      mutation.
<220> FEATURE:
<221> NAME/KEY: allele
<222> LOCATION: (1598)
<223> OTHER INFORMATION: Polymorphism of T or C resulting in a silent
      mutation.
<220> FEATURE:
<221> NAME/KEY: allele
<222> LOCATION: (1892)
<223> OTHER INFORMATION: Polymorphism of A or G resulting in a silent
      mutation.
<220> FEATURE:
<221> NAME/KEY: misc_feature
<222> LOCATION: (4245)..(4349)
<223> OTHER INFORMATION: Addition of 105 basepairs compared to SEQ ID
      NO:1.
<220> FEATURE:
<221> NAME/KEY: misc_feature
<222> LOCATION: (4603)..(4604)
<223> OTHER INFORMATION: Deletion of CAG between these two basepairs as
      compared to SEQ ID NO:1 (deletion of basepairs
      4499-4501 of SEQ ID NO:1).

<400> SEQUENCE: 76
ggcgggggag gcgccgggaa gtcgatggcg ccggcggctc ctgcaggagg ccactgtctg     60
cagctcccgt gaag atg tcc act cca gac cca ccc ctg ggc gga act cct     110
              Met Ser Thr Pro Asp Pro Pro Leu Gly Gly Thr Pro
                1               5                   10 cgg cca ggt cct tcc ccg ggc cct ggc cct tcc cct gga gcc atg ctg     158
Arg Pro Gly Pro Ser Pro Gly Pro Gly Pro Ser Pro Gly Ala Met Leu
         15                  20                  25 ggc cct agc ccg ggt ccc tcg ccg ggc tcc gcc cac agc atg atg ggg     206
Gly Pro Ser Pro Gly Pro Ser Pro Gly Ser Ala His Ser Met Met Gly
     30                  35                  40 ccc agc cca ggg ccg ccc tca gca gga cac ccc atc ccc acc cag ggg     254
```

```
                                                                        -continued Pro Ser Pro Gly Pro Ser Ala Gly His Pro Ile Pro Thr Gln Gly
 45                  50                  55                  60 cct gga ggg tac cct cag gac aac atg cac cag atg cac aag ccc atg        302
Pro Gly Gly Tyr Pro Gln Asp Asn Met His Gln Met His Lys Pro Met
                     65                  70                  75 gag tcc atg cat gag aag ggc atg tcg gac gac ccg cgc tac aac cag        350
Glu Ser Met His Glu Lys Gly Met Ser Asp Asp Pro Arg Tyr Asn Gln
             80                  85                  90 atg aaa gga atg ggg atg cgg tca ggg ggc cat gct ggg atg ggg ccc        398
Met Lys Gly Met Gly Met Arg Ser Gly Gly His Ala Gly Met Gly Pro
         95                 100                 105 ccg ccc agc ccc atg gac cag cac tcc caa ggt tac ccc tcg ccc ctg        446
Pro Pro Ser Pro Met Asp Gln His Ser Gln Gly Tyr Pro Ser Pro Leu
    110                 115                 120 ggt ggc tct gag cat gcc tct agt cca gtt cca gcc agt ggc ccg tct        494
Gly Gly Ser Glu His Ala Ser Ser Pro Val Pro Ala Ser Gly Pro Ser
125                 130                 135                 140 tcg ggg ccc cag atg tct tcc ggg cca gga ggt gcc ccg ctg gat ggt        542
Ser Gly Pro Gln Met Ser Ser Gly Pro Gly Gly Ala Pro Leu Asp Gly
                145                 150                 155 gct gac ccc cag gcc ttg ggg cag cag aac cgg ggc cca acc cca ttt        590
Ala Asp Pro Gln Ala Leu Gly Gln Gln Asn Arg Gly Pro Thr Pro Phe
            160                 165                 170 aac cag aac cag ctg cac cag ctc aga gct cag atc atg gcc tac aag        638
Asn Gln Asn Gln Leu His Gln Leu Arg Ala Gln Ile Met Ala Tyr Lys
        175                 180                 185 atg ctg gcc agg ggg cag ccc ctc ccc gac cac ctg cag atg gcg gtg        686
Met Leu Ala Arg Gly Gln Pro Leu Pro Asp His Leu Gln Met Ala Val
    190                 195                 200 cag ggc aag cgg ccg atg ccc ggg atg cag cag cag atg cca acg cta        734
Gln Gly Lys Arg Pro Met Pro Gly Met Gln Gln Gln Met Pro Thr Leu
205                 210                 215                 220 cct cca ccc tcg gtg tcc gca aca gga ccc ggc cct ggc cct ggc cct        782
Pro Pro Pro Ser Val Ser Ala Thr Gly Pro Gly Pro Gly Pro Gly Pro
                225                 230                 235 ggc ccc ggc ccg ggt ccc ggc ccg gca cct cca aat tac agc agg cct        830
Gly Pro Gly Pro Gly Pro Gly Pro Ala Pro Pro Asn Tyr Ser Arg Pro
            240                 245                 250 cat ggt atg gga ggg ccc aac atg cct ccc cca gga ccc tcg ggc gtg        878
His Gly Met Gly Gly Pro Asn Met Pro Pro Pro Gly Pro Ser Gly Val
        255                 260                 265 ccc ccc ggg atg cca ggc cag cct cct gga ggg cct ccc aag ccc tgg        926
Pro Pro Gly Met Pro Gly Gln Pro Pro Gly Gly Pro Pro Lys Pro Trp
    270                 275                 280 cct gaa gga ccc atg gcg aat gct gct gcc ccc acg agc acc cct cag        974
Pro Glu Gly Pro Met Ala Asn Ala Ala Ala Pro Thr Ser Thr Pro Gln
285                 290                 295                 300 aag ctg att ccc ccg cag cca acg ggc cgc cct tcc ccc gcg ccc cct       1022
Lys Leu Ile Pro Pro Gln Pro Thr Gly Arg Pro Ser Pro Ala Pro Pro
                305                 310                 315 gcc gtc cca ccc gcc gcc tcg ccc gtg atg cca ccg cag acc cag tcc       1070
Ala Val Pro Pro Ala Ala Ser Pro Val Met Pro Pro Gln Thr Gln Ser
            320                 325                 330 ccc ggg cag ccg gcc cag ccc gcg ccc atg gtg cca ctg cac cag aag       1118
Pro Gly Gln Pro Ala Gln Pro Ala Pro Met Val Pro Leu His Gln Lys
        335                 340                 345 cag agc cgc atc acc ccc atc cag aag ccg cgg ggc ctc gac cct gtg       1166
Gln Ser Arg Ile Thr Pro Ile Gln Lys Pro Arg Gly Leu Asp Pro Val
    350                 355                 360
```

```
gag atc ctg cag gag cgc gag tac agg ctg cag gct cgc atc gca cac    1214
Glu Ile Leu Gln Glu Arg Glu Tyr Arg Leu Gln Ala Arg Ile Ala His
365                 370                 375                 380 cga att cag gaa ctt gaa aac ctt ccc ggg tcc ctg gcc ggg gat ttg    1262
Arg Ile Gln Glu Leu Glu Asn Leu Pro Gly Ser Leu Ala Gly Asp Leu
                385                 390                 395 cga acc aaa gcg acc att gag ctc aag gcc ctc agg ctg ctg aac ttc    1310
Arg Thr Lys Ala Thr Ile Glu Leu Lys Ala Leu Arg Leu Leu Asn Phe
400                 405                 410 cag agg cag ctg cgc cag gag gtg gtg gtg tgc atg cgg agg gac aca    1358
Gln Arg Gln Leu Arg Gln Glu Val Val Val Cys Met Arg Arg Asp Thr
            415                 420                 425 gcg ctg gag aca gcc ctc aat gct aag gcc tac aag cgc agc aag cgc    1406
Ala Leu Glu Thr Ala Leu Asn Ala Lys Ala Tyr Lys Arg Ser Lys Arg
430                 435                 440 cag tcc ctg cgc gag gcc cgc atc act gag aag ctg gag aag cag cag    1454
Gln Ser Leu Arg Glu Ala Arg Ile Thr Glu Lys Leu Glu Lys Gln Gln
445                 450                 455                 460 aag atc gag cag gag cgc aag cgc cgg cag aag cac cag gaa tac ctc    1502
Lys Ile Glu Gln Glu Arg Lys Arg Arg Gln Lys His Gln Glu Tyr Leu
                465                 470                 475 aat agc att ctc cag cat gcc aag gat ttc aag gaa tat cac aga tcc    1550
Asn Ser Ile Leu Gln His Ala Lys Asp Phe Lys Glu Tyr His Arg Ser
            480                 485                 490 gtc aca ggc aaa atc cag aag ctg acc aag gca gtg gcc acg tac cat    1598
Val Thr Gly Lys Ile Gln Lys Leu Thr Lys Ala Val Ala Thr Tyr His
495                 500                 505 gcc aac acg gag cgg gag cag aag aaa gag aac gag cgg atc gag aag    1646
Ala Asn Thr Glu Arg Glu Gln Lys Lys Glu Asn Glu Arg Ile Glu Lys
510                 515                 520 gag cgc atg cgg agg ctc atg gct gaa gat gag gag ggg tac cgc aag    1694
Glu Arg Met Arg Arg Leu Met Ala Glu Asp Glu Glu Gly Tyr Arg Lys
525                 530                 535                 540 ctc atc gac cag aag aag gac aag cgc ctg gcc tac ctc ttg cag cag    1742
Leu Ile Asp Gln Lys Lys Asp Lys Arg Leu Ala Tyr Leu Leu Gln Gln
                545                 550                 555 aca gac gag tac gtg gct aac ctc acg gag ctg gtg cgg cag cac aag    1790
Thr Asp Glu Tyr Val Ala Asn Leu Thr Glu Leu Val Arg Gln His Lys
            560                 565                 570 gct gcc cag gtc gcc aag gag aaa aag aag aaa aag aaa aag aag aag    1838
Ala Ala Gln Val Ala Lys Glu Lys Lys Lys Lys Lys Lys Lys Lys Lys
575                 580                 585 gca gaa aat gca gaa gga cag acg cct gcc att ggg ccg gat ggc gag    1886
Ala Glu Asn Ala Glu Gly Gln Thr Pro Ala Ile Gly Pro Asp Gly Glu
590                 595                 600 cct cta gac gag acc agc cag atg agc gac ctc ccg gtg aag gtg atc    1934
Pro Leu Asp Glu Thr Ser Gln Met Ser Asp Leu Pro Val Lys Val Ile
605                 610                 615                 620 cac gtg gag agt ggg aag atc ctc aca ggc aca gat gcc ccc aaa gcc    1982
His Val Glu Ser Gly Lys Ile Leu Thr Gly Thr Asp Ala Pro Lys Ala
                625                 630                 635 ggg cag ctg gag gcc tgg ctc gag atg aac ccg ggt tat gaa gta gct    2030
Gly Gln Leu Glu Ala Trp Leu Glu Met Asn Pro Gly Tyr Glu Val Ala
            640                 645                 650 ccg agg tct gat agt gaa gaa agt ggc tca gaa gaa gag gaa gag gag    2078
Pro Arg Ser Asp Ser Glu Glu Ser Gly Ser Glu Glu Glu Glu Glu Glu
655                 660                 665 gag gag gaa gag cag ccg cag gca gca cag cct ccc acc ctg ccc gtg    2126
Glu Glu Glu Glu Gln Pro Gln Ala Ala Gln Pro Pro Thr Leu Pro Val
670                 675                 680
```

```
gag gag aag aag aag att cca gat cca gac agc gat gac gtc tct gag      2174
Glu Glu Lys Lys Lys Ile Pro Asp Pro Asp Ser Asp Asp Val Ser Glu
685             690                 695                 700 gtg gac gcg cgg cac atc att gag aat gcc aag caa gat gtc gat gat      2222
Val Asp Ala Arg His Ile Ile Glu Asn Ala Lys Gln Asp Val Asp Asp
        705                 710                 715 gaa tat ggc gtg tcc cag gcc ctt gca cgt ggc ctg cag tcc tac tat      2270
Glu Tyr Gly Val Ser Gln Ala Leu Ala Arg Gly Leu Gln Ser Tyr Tyr
            720                 725                 730 gcc gtg gcc cat gct gtc act gag aga gtg gac aag cag tca gcg ctt      2318
Ala Val Ala His Ala Val Thr Glu Arg Val Asp Lys Gln Ser Ala Leu
                735                 740                 745 atg gtc aat ggt gtc ctc aaa cag tac cag atc aaa ggt ttg gag tgg      2366
Met Val Asn Gly Val Leu Lys Gln Tyr Gln Ile Lys Gly Leu Glu Trp
750                 755                 760 ctg gtg tcc ctg tac aac aac aac ctg aac ggc atc ctg gcc gac gag      2414
Leu Val Ser Leu Tyr Asn Asn Asn Leu Asn Gly Ile Leu Ala Asp Glu
765                 770                 775                 780 atg ggc ctg ggg aag acc atc cag acc atc gcg ctc atc acg tac ctc      2462
Met Gly Leu Gly Lys Thr Ile Gln Thr Ile Ala Leu Ile Thr Tyr Leu
                785                 790                 795 atg gag cac aaa cgc atc aat ggg ccc ttc ctc atc gtg cct ctc          2510
Met Glu His Lys Arg Ile Asn Gly Pro Phe Leu Ile Ile Val Pro Leu
            800                 805                 810 tca acg ctg tcc aac tgg gcg tac gag ttt gac aag tgg gcc ccc tcc      2558
Ser Thr Leu Ser Asn Trp Ala Tyr Glu Phe Asp Lys Trp Ala Pro Ser
                815                 820                 825 gtg gtg aag gtg tct tac aag gga tcc cca gca gca aga cgg gcc ttt      2606
Val Val Lys Val Ser Tyr Lys Gly Ser Pro Ala Ala Arg Arg Ala Phe
830                 835                 840 gtc ccc cag ctc cgg agt ggg aag ttc aac gtc ttg ctg acg acg tac      2654
Val Pro Gln Leu Arg Ser Gly Lys Phe Asn Val Leu Leu Thr Thr Tyr
845                 850                 855                 860 gag tac atc atc aaa gac aag cac atc ctc gcc aag atc cgt tgg aag      2702
Glu Tyr Ile Ile Lys Asp Lys His Ile Leu Ala Lys Ile Arg Trp Lys
                865                 870                 875 tac atg att gtg gac gaa ggt cac cgc atg aag aac cac cac tgc aag      2750
Tyr Met Ile Val Asp Glu Gly His Arg Met Lys Asn His His Cys Lys
            880                 885                 890 ctg acg cag gtg ctc aac acg cac tat gtg gca ccc cgc cgc ctg ctg      2798
Leu Thr Gln Val Leu Asn Thr His Tyr Val Ala Pro Arg Arg Leu Leu
                895                 900                 905 ctg acg ggc aca ccg ctg cag aac aag ctt ccc gag ctc tgg gcg ctg      2846
Leu Thr Gly Thr Pro Leu Gln Asn Lys Leu Pro Glu Leu Trp Ala Leu
910                 915                 920 ctc aac ttc ctg ctg ccc acc atc ttc aag agc tgc agc acc ttc gag      2894
Leu Asn Phe Leu Leu Pro Thr Ile Phe Lys Ser Cys Ser Thr Phe Glu
925                 930                 935                 940 cag tgg ttt aac gca ccc ttt gcc atg acc ggg gaa aag gtg gac ctg      2942
Gln Trp Phe Asn Ala Pro Phe Ala Met Thr Gly Glu Lys Val Asp Leu
                945                 950                 955 aat gag gag gaa acc att ctc atc atc cgg cgt ctc cac aaa gtg ctg      2990
Asn Glu Glu Glu Thr Ile Leu Ile Ile Arg Arg Leu His Lys Val Leu
            960                 965                 970 cgg ccc ttc ttg ctc cga cga ctc aag aag gaa gtc gag gcc cag ttg      3038
Arg Pro Phe Leu Leu Arg Arg Leu Lys Lys Glu Val Glu Ala Gln Leu
                975                 980                 985 ccc gaa aag gtg gag tac gtc atc aag tgc gac atg tct gcg ctg cag      3086
Pro Glu Lys Val Glu Tyr Val Ile Lys Cys Asp Met Ser Ala Leu Gln
```

```
            990                 995                1000
cga gtg ctc tac cgc cac atg cag gcc aag ggc gtg ctg ctg act gat    3134
Arg Val Leu Tyr Arg His Met Gln Ala Lys Gly Val Leu Leu Thr Asp
1005                1010                1015                1020 ggc tcc gag aag gac aag aag ggc aaa ggc ggc acc aag acc ctg atg    3182
Gly Ser Glu Lys Asp Lys Lys Gly Lys Gly Gly Thr Lys Thr Leu Met
                1025                1030                1035 aac acc atc atg cag ctg cgg aag atc tgc aac cac ccc tac atg ttc    3230
Asn Thr Ile Met Gln Leu Arg Lys Ile Cys Asn His Pro Tyr Met Phe
            1040                1045                1050 cag cac atc gag gag tcc ttt tcc gag cac ttg ggg ttc act ggc ggc    3278
Gln His Ile Glu Glu Ser Phe Ser Glu His Leu Gly Phe Thr Gly Gly
        1055                1060                1065 att gtc caa ggg ctg gac ctg tac cga gcc tcg ggt aaa ttt gag ctt    3326
Ile Val Gln Gly Leu Asp Leu Tyr Arg Ala Ser Gly Lys Phe Glu Leu
    1070                1075                1080 ctt gat aga att ctt ccc aaa ctc cga gca acc aac cac aaa gtg ctg    3374
Leu Asp Arg Ile Leu Pro Lys Leu Arg Ala Thr Asn His Lys Val Leu
1085                1090                1095                1100 ctg ttc tgc caa atg acc tcc ctc atg acc atc atg gaa gat tac ttt    3422
Leu Phe Cys Gln Met Thr Ser Leu Met Thr Ile Met Glu Asp Tyr Phe
                1105                1110                1115 gcg tat cgc ggc ttt aaa tac ctc agg ctt gat gga acc acg aag gcg    3470
Ala Tyr Arg Gly Phe Lys Tyr Leu Arg Leu Asp Gly Thr Thr Lys Ala
            1120                1125                1130 gag gac cgg ggc atg ctg ctg aaa acc ttc aac gag ccc ggc tct gag    3518
Glu Asp Arg Gly Met Leu Leu Lys Thr Phe Asn Glu Pro Gly Ser Glu
        1135                1140                1145 tac ttc atc ttc ctg ctc agc acc cgg gct ggg ggg ctc ggc ctg aac    3566
Tyr Phe Ile Phe Leu Leu Ser Thr Arg Ala Gly Gly Leu Gly Leu Asn
    1150                1155                1160 ctc cag tcg gca gac act gtg atc att ttt gac agc gac tgg aat cct    3614
Leu Gln Ser Ala Asp Thr Val Ile Ile Phe Asp Ser Asp Trp Asn Pro
1165                1170                1175                1180 cac cag gac ctg caa gcg cag gac cga gcc cac cgc atc ggg cag cag    3662
His Gln Asp Leu Gln Ala Gln Asp Arg Ala His Arg Ile Gly Gln Gln
                1185                1190                1195 aac gag gtg cgt gtg ctc cgc ctc tgc acc gtc aac agc gtg gag gag    3710
Asn Glu Val Arg Val Leu Arg Leu Cys Thr Val Asn Ser Val Glu Glu
            1200                1205                1210 aag atc cta gct gca gcc aag tac aag ctc aac gtg gac cag aag gtg    3758
Lys Ile Leu Ala Ala Ala Lys Tyr Lys Leu Asn Val Asp Gln Lys Val
        1215                1220                1225 atc cag gcc ggc atg ttc gac cag aag tcc tcc agc cat gag cgg cgc    3806
Ile Gln Ala Gly Met Phe Asp Gln Lys Ser Ser Ser His Glu Arg Arg
    1230                1235                1240 gcc ttc ctg cag gcc atc ctg gag cac gag gag cag gat gag agc aga    3854
Ala Phe Leu Gln Ala Ile Leu Glu His Glu Glu Gln Asp Glu Ser Arg
1245                1250                1255                1260 cac tgc agc acg ggc agc ggc agt gcc agc ttc gcc cac act gcc cct    3902
His Cys Ser Thr Gly Ser Gly Ser Ala Ser Phe Ala His Thr Ala Pro
                1265                1270                1275 ccg cca gcg ggc gtc aac ccc gac ttg gag gag cca cct cta aag gag    3950
Pro Pro Ala Gly Val Asn Pro Asp Leu Glu Glu Pro Pro Leu Lys Glu
            1280                1285                1290 gaa gac gag gtg ccc gac gac gag acc gtc aac cag atg atc gcc cgg    3998
Glu Asp Glu Val Pro Asp Asp Glu Thr Val Asn Gln Met Ile Ala Arg
        1295                1300                1305 cac gag gag gag ttt gat ctg ttc atg cgc atg gac ctg gac cgc agg    4046
```

```
                His Glu Glu Phe Asp Leu Phe Met Arg Met Asp Leu Asp Arg Arg
                    1310                1315                1320 cgc gag gag gcc cgc aac ccc aag cgg aag ccg cgc ctc atg gag gag        4094
Arg Glu Glu Ala Arg Asn Pro Lys Arg Lys Pro Arg Leu Met Glu Glu
1325                1330                1335                1340 gac gag ctc ccc tcg tgg atc atc aag gac gac gcg gag gtg gag cgg        4142
Asp Glu Leu Pro Ser Trp Ile Ile Lys Asp Asp Ala Glu Val Glu Arg
                1345                1350                1355 ctg acc tgt gag gag gag gag gag aag atg ttc ggc cgt ggc tcc cgc        4190
Leu Thr Cys Glu Glu Glu Glu Glu Lys Met Phe Gly Arg Gly Ser Arg
            1360                1365                1370 cac cgc aag gag gtg gac tac agc gac tca ctg acg gag aag cag tgg        4238
His Arg Lys Glu Val Asp Tyr Ser Asp Ser Leu Thr Glu Lys Gln Trp
        1375                1380                1385 ctc aag aaa att aca gga aaa gat atc cat gac aca gcc agc agt gtg        4286
Leu Lys Lys Ile Thr Gly Lys Asp Ile His Asp Thr Ala Ser Ser Val
    1390                1395                1400 gca cgt ggg cta caa ttc cag cgt ggc ctt cag ttc tgc aca cgt gcg        4334
Ala Arg Gly Leu Gln Phe Gln Arg Gly Leu Gln Phe Cys Thr Arg Ala
1405                1410                1415                1420 tca aag acc ctg aag gcc atc gag gag ggc acg ctg gag gag atc gaa        4382
Ser Lys Thr Leu Lys Ala Ile Glu Glu Gly Thr Leu Glu Glu Ile Glu
                1425                1430                1435 gag gag gtc cgg cag aag aaa tca tca cgg aag cgc aag cga gac agc        4430
Glu Glu Val Arg Gln Lys Lys Ser Ser Arg Lys Arg Lys Arg Asp Ser
            1440                1445                1450 gac gcc ggc tcc tcc acc ccg acc acc agc acc cgc agc cgc gac aag        4478
Asp Ala Gly Ser Ser Thr Pro Thr Thr Ser Thr Arg Ser Arg Asp Lys
        1455                1460                1465 gac gac gag agc aag aag cag aag aag cgc ggg cgg ccg cct gcc gag        4526
Asp Asp Glu Ser Lys Lys Gln Lys Lys Arg Gly Arg Pro Pro Ala Glu
    1470                1475                1480 aaa ctc tcc cct aac cca ccc aac ctc acc aag aag atg aag aag att        4574
Lys Leu Ser Pro Asn Pro Pro Asn Leu Thr Lys Lys Met Lys Lys Ile
1485                1490                1495                1500 gtg gat gcc gtg atc aag tac aag gac agc agt gga cgt cag ctc agc        4622
Val Asp Ala Val Ile Lys Tyr Lys Asp Ser Ser Gly Arg Gln Leu Ser
                1505                1510                1515 gag gtc ttc atc cag ctg ccc tcg cga aag gag ctg ccc gag tac tac        4670
Glu Val Phe Ile Gln Leu Pro Ser Arg Lys Glu Leu Pro Glu Tyr Tyr
            1520                1525                1530 gag ctc atc cgc aag ccc gtg gac ttc aag aag ata aag gag cgc att        4718
Glu Leu Ile Arg Lys Pro Val Asp Phe Lys Lys Ile Lys Glu Arg Ile
        1535                1540                1545 cgc aac cac aag tac cgc agc ctc aac gac cta gag aag gac gtc atg        4766
Arg Asn His Lys Tyr Arg Ser Leu Asn Asp Leu Glu Lys Asp Val Met
    1550                1555                1560 ctc ctg tgc cag aac gca cag acc ttc aac ctg gag ggc tcc ctg atc        4814
Leu Leu Cys Gln Asn Ala Gln Thr Phe Asn Leu Glu Gly Ser Leu Ile
1565                1570                1575                1580 tat gaa gac tcc atc gtc ttg cag tcg gtc ttc acc agc gtg cgg cag        4862
Tyr Glu Asp Ser Ile Val Leu Gln Ser Val Phe Thr Ser Val Arg Gln
                1585                1590                1595 aaa atc gag aag gag gat gac agt gaa ggc gag gag agt gag gag gag        4910
Lys Ile Glu Lys Glu Asp Asp Ser Glu Gly Glu Glu Ser Glu Glu Glu
            1600                1605                1610 gaa gag ggc gag gag gaa ggc tcc gaa tcc gaa tct cgg tcc gtc aaa        4958
Glu Glu Gly Glu Glu Gly Ser Glu Ser Glu Ser Arg Ser Val Lys
        1615                1620                1625
```

-continued

```
gtg aag atc aag ctt ggc cgg aag gag aag gca cag gac cgg ctg aag      5006
Val Lys Ile Lys Leu Gly Arg Lys Glu Lys Ala Gln Asp Arg Leu Lys
        1630                1635                1640 ggc ggc cgg cgg cgg ccg agc cga ggg tcc cga gcc aag ccg gtc gtg      5054
Gly Gly Arg Arg Arg Pro Ser Arg Gly Ser Arg Ala Lys Pro Val Val
1645                1650                1655                1660 agt gac gat gac agt gag gag gaa caa gag gag gac cgc tca gga agt      5102
Ser Asp Asp Asp Ser Glu Glu Glu Gln Glu Glu Asp Arg Ser Gly Ser
                1665                1670                1675 ggc agc gaa gaa gac tgagccccga cattccagtc tcgaccccga gcccctcgtt      5157
Gly Ser Glu Glu Asp
            1680 ccagagctga gatggcatag gccttagcag taacgggtag cagcagatgt agtttcagac    5217 ttggagtaaa actgtataaa caaaagaatc ttccatattt atacagcaga gaagctgtag    5277 gactgtttgt gactggccct gtcctggcat cagtagcatc tgtaacagca ttaactgtct    5337 taaagagaga gagagagaat tccgaattgg ggaacacacg atacctgttt ttcttttccg    5397 ttgctggcag tactgttgcg ccgcagtttg gagtcactgt agttaagtgt ggatgcatgt    5457 gcgtcaccgt ccactcctcc tactgtattt tattggacag gtcagactcg ccgggggccc    5517 ggcgagggta tgtcagtgtc actggatgtc aaacagtaat aaattaaacc aacaac        5573
```

<210> SEQ ID NO 77
<211> LENGTH: 1681
<212> TYPE: PRT
<213> ORGANISM: Homo sapiens

<400> SEQUENCE: 77

```
Met Ser Thr Pro Asp Pro Pro Leu Gly Gly Thr Pro Arg Pro Gly Pro
1               5                   10                  15

Ser Pro Gly Pro Gly Pro Ser Pro Gly Ala Met Leu Gly Pro Ser Pro
            20                  25                  30

Gly Pro Ser Pro Gly Ser Ala His Ser Met Met Gly Pro Ser Pro Gly
        35                  40                  45

Pro Pro Ser Ala Gly His Pro Ile Pro Thr Gln Gly Pro Gly Gly Tyr
    50                  55                  60

Pro Gln Asp Asn Met His Gln Met His Lys Pro Met Glu Ser Met His
65                  70                  75                  80

Glu Lys Gly Met Ser Asp Asp Pro Arg Tyr Asn Gln Met Lys Gly Met
                85                  90                  95

Gly Met Arg Ser Gly Gly His Ala Gly Met Gly Pro Pro Ser Pro
            100                 105                 110

Met Asp Gln His Ser Gln Gly Tyr Pro Ser Pro Leu Gly Gly Ser Glu
        115                 120                 125

His Ala Ser Ser Pro Val Pro Ala Ser Gly Pro Ser Ser Gly Pro Gln
    130                 135                 140

Met Ser Ser Gly Pro Gly Gly Ala Pro Leu Asp Gly Ala Asp Pro Gln
145                 150                 155                 160

Ala Leu Gly Gln Gln Asn Arg Gly Pro Thr Pro Phe Asn Gln Asn Gln
                165                 170                 175

Leu His Gln Leu Arg Ala Gln Ile Met Ala Tyr Lys Met Leu Ala Arg
            180                 185                 190

Gly Gln Pro Leu Pro Asp His Leu Gln Met Ala Val Gln Gly Lys Arg
        195                 200                 205

Pro Met Pro Gly Met Gln Gln Met Pro Thr Leu Pro Pro Pro Ser
    210                 215                 220
```

-continued

Val Ser Ala Thr Gly Pro Gly Pro Gly Pro Gly Pro Gly Pro
225                 230                 235                 240

Gly Pro Gly Pro Ala Pro Pro Asn Tyr Ser Arg Pro His Gly Met Gly
            245                 250                 255

Gly Pro Asn Met Pro Pro Gly Pro Ser Gly Val Pro Pro Gly Met
        260                 265                 270

Pro Gly Gln Pro Pro Gly Gly Pro Pro Lys Pro Trp Pro Glu Gly Pro
        275                 280                 285

Met Ala Asn Ala Ala Ala Pro Thr Ser Thr Pro Gln Lys Leu Ile Pro
290                 295                 300

Pro Gln Pro Thr Gly Arg Pro Ser Pro Ala Pro Pro Ala Val Pro Pro
305                 310                 315                 320

Ala Ala Ser Pro Val Met Pro Pro Gln Thr Gln Ser Pro Gly Gln Pro
            325                 330                 335

Ala Gln Pro Ala Pro Met Val Pro Leu His Gln Lys Gln Ser Arg Ile
            340                 345                 350

Thr Pro Ile Gln Lys Pro Arg Gly Leu Asp Pro Val Glu Ile Leu Gln
        355                 360                 365

Glu Arg Glu Tyr Arg Leu Gln Ala Arg Ile Ala His Arg Ile Gln Glu
370                 375                 380

Leu Glu Asn Leu Pro Gly Ser Leu Ala Gly Asp Leu Arg Thr Lys Ala
385                 390                 395                 400

Thr Ile Glu Leu Lys Ala Leu Arg Leu Leu Asn Phe Gln Arg Gln Leu
            405                 410                 415

Arg Gln Glu Val Val Val Cys Met Arg Arg Asp Thr Ala Leu Glu Thr
            420                 425                 430

Ala Leu Asn Ala Lys Ala Tyr Lys Arg Ser Lys Arg Gln Ser Leu Arg
            435                 440                 445

Glu Ala Arg Ile Thr Glu Lys Leu Glu Lys Gln Gln Lys Ile Glu Gln
450                 455                 460

Glu Arg Lys Arg Arg Gln Lys His Gln Glu Tyr Leu Asn Ser Ile Leu
465                 470                 475                 480

Gln His Ala Lys Asp Phe Lys Glu Tyr His Arg Ser Val Thr Gly Lys
            485                 490                 495

Ile Gln Lys Leu Thr Lys Ala Val Ala Thr Tyr His Ala Asn Thr Glu
        500                 505                 510

Arg Glu Gln Lys Lys Glu Asn Glu Arg Ile Glu Lys Glu Arg Met Arg
        515                 520                 525

Arg Leu Met Ala Glu Asp Glu Glu Gly Tyr Arg Lys Leu Ile Asp Gln
530                 535                 540

Lys Lys Asp Lys Arg Leu Ala Tyr Leu Leu Gln Gln Thr Asp Glu Tyr
545                 550                 555                 560

Val Ala Asn Leu Thr Glu Leu Val Arg Gln His Lys Ala Ala Gln Val
            565                 570                 575

Ala Lys Glu Lys Lys Lys Lys Lys Lys Lys Lys Ala Glu Asn Ala
            580                 585                 590

Glu Gly Gln Thr Pro Ala Ile Gly Pro Asp Gly Glu Pro Leu Asp Glu
        595                 600                 605

Thr Ser Gln Met Ser Asp Leu Pro Val Lys Val Ile His Val Glu Ser
610                 615                 620

Gly Lys Ile Leu Thr Gly Thr Asp Ala Pro Lys Ala Gly Gln Leu Glu
625                 630                 635                 640

```
Ala Trp Leu Glu Met Asn Pro Gly Tyr Glu Val Ala Pro Arg Ser Asp
                645                 650                 655

Ser Glu Glu Ser Gly Ser Glu Glu Glu Glu Glu Glu Glu Glu Glu Glu
            660                 665                 670

Gln Pro Gln Ala Ala Gln Pro Thr Leu Pro Val Glu Glu Lys Lys
        675                 680                 685

Lys Ile Pro Asp Pro Asp Ser Asp Val Ser Glu Val Asp Ala Arg
690                 695                 700

His Ile Ile Glu Asn Ala Lys Gln Asp Val Asp Asp Glu Tyr Gly Val
705                 710                 715                 720

Ser Gln Ala Leu Ala Arg Gly Leu Gln Ser Tyr Tyr Ala Val Ala His
                725                 730                 735

Ala Val Thr Glu Arg Val Asp Lys Gln Ser Ala Leu Met Val Asn Gly
                740                 745                 750

Val Leu Lys Gln Tyr Gln Ile Lys Gly Leu Glu Trp Leu Val Ser Leu
            755                 760                 765

Tyr Asn Asn Asn Leu Asn Gly Ile Leu Ala Asp Glu Met Gly Leu Gly
    770                 775                 780

Lys Thr Ile Gln Thr Ile Ala Leu Ile Thr Tyr Leu Met Glu His Lys
785                 790                 795                 800

Arg Ile Asn Gly Pro Phe Leu Ile Ile Val Pro Leu Ser Thr Leu Ser
                805                 810                 815

Asn Trp Ala Tyr Glu Phe Asp Lys Trp Ala Pro Ser Val Val Lys Val
                820                 825                 830

Ser Tyr Lys Gly Ser Pro Ala Ala Arg Arg Ala Phe Val Pro Gln Leu
                835                 840                 845

Arg Ser Gly Lys Phe Asn Val Leu Leu Thr Thr Tyr Glu Tyr Ile Ile
    850                 855                 860

Lys Asp Lys His Ile Leu Ala Lys Ile Arg Trp Lys Tyr Met Ile Val
865                 870                 875                 880

Asp Glu Gly His Arg Met Lys Asn His Cys Lys Leu Thr Gln Val
                885                 890                 895

Leu Asn Thr His Tyr Val Ala Pro Arg Arg Leu Leu Leu Thr Gly Thr
                900                 905                 910

Pro Leu Gln Asn Lys Leu Pro Glu Leu Trp Ala Leu Leu Asn Phe Leu
    915                 920                 925

Leu Pro Thr Ile Phe Lys Ser Cys Ser Thr Phe Glu Gln Trp Phe Asn
    930                 935                 940

Ala Pro Phe Ala Met Thr Gly Glu Lys Val Asp Leu Asn Glu Glu Glu
945                 950                 955                 960

Thr Ile Leu Ile Ile Arg Arg Leu His Lys Val Leu Arg Pro Phe Leu
                965                 970                 975

Leu Arg Arg Leu Lys Lys Glu Val Glu Ala Gln Leu Pro Glu Lys Val
            980                 985                 990

Glu Tyr Val Ile Lys Cys Asp Met Ser Ala Leu Gln Arg Val Leu Tyr
        995                 1000                1005

Arg His Met Gln Ala Lys Gly Val Leu Leu Thr Asp Gly Ser Glu Lys
    1010                1015                1020

Asp Lys Lys Gly Lys Gly Gly Thr Lys Thr Leu Met Asn Thr Ile Met
1025                1030                1035                1040

Gln Leu Arg Lys Ile Cys Asn His Pro Tyr Met Phe Gln His Ile Glu
                1045                1050                1055

Glu Ser Phe Ser Glu His Leu Gly Phe Thr Gly Gly Ile Val Gln Gly
```

1060                1065                1070
Leu Asp Leu Tyr Arg Ala Ser Gly Lys Phe Glu Leu Leu Asp Arg Ile
                1075                1080                1085
Leu Pro Lys Leu Arg Ala Thr Asn His Lys Val Leu Leu Phe Cys Gln
            1090                1095                1100
Met Thr Ser Leu Met Thr Ile Met Glu Asp Tyr Phe Ala Tyr Arg Gly
1105                1110                1115                1120
Phe Lys Tyr Leu Arg Leu Asp Gly Thr Thr Lys Ala Glu Asp Arg Gly
                1125                1130                1135
Met Leu Leu Lys Thr Phe Asn Glu Pro Gly Ser Glu Tyr Phe Ile Phe
            1140                1145                1150
Leu Leu Ser Thr Arg Ala Gly Gly Leu Gly Leu Asn Leu Gln Ser Ala
                1155                1160                1165
Asp Thr Val Ile Ile Phe Asp Ser Asp Trp Asn Pro His Gln Asp Leu
            1170                1175                1180
Gln Ala Gln Asp Arg Ala His Arg Ile Gly Gln Gln Asn Glu Val Arg
1185                1190                1195                1200
Val Leu Arg Leu Cys Thr Val Asn Ser Val Glu Glu Lys Ile Leu Ala
                1205                1210                1215
Ala Ala Lys Tyr Lys Leu Asn Val Asp Gln Lys Val Ile Gln Ala Gly
            1220                1225                1230
Met Phe Asp Gln Lys Ser Ser Ser His Glu Arg Arg Ala Phe Leu Gln
            1235                1240                1245
Ala Ile Leu Glu His Glu Glu Gln Asp Glu Ser Arg His Cys Ser Thr
        1250                1255                1260
Gly Ser Gly Ser Ala Ser Phe Ala His Thr Ala Pro Pro Ala Gly
1265                1270                1275                1280
Val Asn Pro Asp Leu Glu Glu Pro Pro Leu Lys Glu Glu Asp Glu Val
                1285                1290                1295
Pro Asp Asp Glu Thr Val Asn Gln Met Ile Ala Arg His Glu Glu Glu
            1300                1305                1310
Phe Asp Leu Phe Met Arg Met Asp Leu Asp Arg Arg Arg Glu Glu Ala
            1315                1320                1325
Arg Asn Pro Lys Arg Lys Pro Arg Leu Met Glu Glu Asp Glu Leu Pro
        1330                1335                1340
Ser Trp Ile Ile Lys Asp Asp Ala Glu Val Glu Arg Leu Thr Cys Glu
1345                1350                1355                1360
Glu Glu Glu Glu Lys Met Phe Gly Arg Gly Ser Arg His Arg Lys Glu
                1365                1370                1375
Val Asp Tyr Ser Asp Ser Leu Thr Glu Lys Gln Trp Leu Lys Lys Ile
            1380                1385                1390
Thr Gly Lys Asp Ile His Asp Thr Ala Ser Ser Val Ala Arg Gly Leu
        1395                1400                1405
Gln Phe Gln Arg Gly Leu Gln Phe Cys Thr Arg Ala Ser Lys Thr Leu
    1410                1415                1420
Lys Ala Ile Glu Glu Gly Thr Leu Glu Glu Ile Glu Glu Val Arg
1425                1430                1435                1440
Gln Lys Lys Ser Ser Arg Lys Arg Lys Arg Asp Ser Asp Ala Gly Ser
                1445                1450                1455
Ser Thr Pro Thr Thr Ser Thr Arg Ser Arg Asp Lys Asp Asp Glu Ser
            1460                1465                1470
Lys Lys Gln Lys Lys Arg Gly Arg Pro Pro Ala Glu Lys Leu Ser Pro
        1475                1480                1485

```
Asn Pro Pro Asn Leu Thr Lys Lys Met Lys Lys Ile Val Asp Ala Val
    1490                1495                1500
Ile Lys Tyr Lys Asp Ser Ser Gly Arg Gln Leu Ser Glu Val Phe Ile
1505                1510                1515                1520
Gln Leu Pro Ser Arg Lys Glu Leu Pro Glu Tyr Tyr Glu Leu Ile Arg
                1525                1530                1535
Lys Pro Val Asp Phe Lys Lys Ile Lys Glu Arg Ile Arg Asn His Lys
                1540                1545                1550
Tyr Arg Ser Leu Asn Asp Leu Glu Lys Asp Val Met Leu Leu Cys Gln
            1555                1560                1565
Asn Ala Gln Thr Phe Asn Leu Glu Gly Ser Leu Ile Tyr Glu Asp Ser
    1570                1575                1580
Ile Val Leu Gln Ser Val Phe Thr Ser Val Arg Gln Lys Ile Glu Lys
1585                1590                1595                1600
Glu Asp Asp Ser Glu Gly Glu Glu Ser Glu Glu Glu Glu Glu Gly Glu
                1605                1610                1615
Glu Glu Gly Ser Glu Ser Glu Ser Arg Ser Val Lys Val Lys Ile Lys
            1620                1625                1630
Leu Gly Arg Lys Glu Lys Ala Gln Asp Arg Leu Lys Gly Gly Arg Arg
            1635                1640                1645
Arg Pro Ser Arg Gly Ser Arg Ala Lys Pro Val Val Ser Asp Asp Asp
    1650                1655                1660
Ser Glu Glu Glu Gln Glu Glu Asp Arg Ser Gly Ser Gly Ser Glu Glu
1665                1670                1675                1680
Asp
```

BRG1 IS A TUMOR SUPPRESSOR THAT IS MUTATED IN PROSTATE AND OTHER CANCER TYPES

CROSS-REFERENCE TO RELATED APPLICATIONS

This application is related to Ser. No. 60/125,806 which was filed Mar. 23, 1999 and which is incorporated herein by reference.

BACKGROUND OF THE INVENTION

The present invention relates to deletion of the BRG1 gene or a portion of this gene in a human cancer. This gene has been previously reported in the literature, being originally cloned by Khavari et al. (1993). It was shown to be a human homolog of Drosophila brahma. Brahma is an activator of multiple homeotic genes and an important regulator of development. Using the yeast two hybrid assay it was also found that BRG1 binds specifically to the retinoblastoma tumor suppressor protein, RB (Dunaief et al., 1994).

The publications and other materials used herein to illuminate the background of the invention or provide additional details respecting the practice, are incorporated herein by reference, and for convenience are referenced in the following text and respectively grouped in the appended List of References.

The genetics of cancer is complicated, involving multiple dominant, positive regulators of the transformed state (oncogenes) as well as multiple recessive, negative regulators (tumor suppressor genes). Over one hundred oncogenes have been characterized. Fewer than a dozen tumor suppressor genes have been identified, but the number is expected to increase beyond fifty (Knudson, 1993).

The involvement of so many genes underscores the complexity of the growth control mechanisms that operate in cells to maintain the integrity of normal tissue. This complexity is manifested in another way. So far, no single gene has been shown to participate in the development of all, or even the majority of human cancers. The most common oncogenic mutations are in the H-ras gene, found in 10–15% of all solid tumors (Anderson et al., 1992). The most frequently mutated tumor suppressor gene is the p53 gene, mutated in roughly 50% of all tumors. Without a target that is common to all transformed cells, the dream of a "magic bullet" that can destroy or revert cancer cells while leaving normal tissue unharmed is improbable. The hope for a new generation of specifically targeted antitumor drugs may rest on the ability to identify tumor suppressor genes or oncogenes that play general roles in control of cell division.

The tumor suppressor genes, which have been cloned and characterized, influence susceptibility to: 1) retinoblastoma (RB1); 2) Wilms' tumor (WT1); 3) Li-Fraumeni (TP53); 4) Familial adenomatous polyposis (APC); 5) Neurofibromatosis type 1 (NF1); 6) Neurofibromatosis type 2 (NF2); 7) von Hippel-Lindau syndrome (VHL); and 8) Multiple endocrine neoplasia type 2A (MEN2A).

Tumor suppressor loci that have been mapped genetically but not yet isolated include genes for: Multiple endocrine neoplasia type 1 (MEN 1); Lynch cancer family syndrome 2 (LCFS2); Neuroblastoma (NB); Basal cell nevus syndrome (BCNS); Beckwith-Wiedemann syndrome (BWS); Renal cell carcinoma (RCC); Tuberous sclerosis 1 (TSC 1); and Tuberous sclerosis 2 (TSC2). The tumor suppressor genes that have been characterized to date encode products with similarities to a variety of protein types, including DNA binding proteins (WT1), ancillary transcription regulators (RB1), GTPase activating proteins or GAPs (NF1), cytoskeletal components (NF2), membrane bound receptor kinases (MEN2A), and others with no obvious similarity to known proteins (APC and VHL).

In many cases, the tumor suppressor gene originally identified through genetic studies has been shown in some sporadic tumors to be lost or mutated. This result suggests that regions of chromosomal aberration may signify the position of important tumor suppressor genes involved both in genetic predisposition to cancer and in sporadic cancer.

One of the hallmarks of several tumor suppressor genes characterized to date is that they are deleted at high frequency in certain tumor types. The deletions often involve loss of a single allele, a so-called loss of heterozygosity (LOH), but may also involve homozygous deletion of both alleles. For LOH, the remaining allele is presumed to be nonfunctional, either because of a preexisting inherited mutation, or because of a secondary sporadic mutation. Whereas LOH events commonly involve chromosomal deletions spanning many megabases of DNA, homozygous deletions are relatively small in size, probably due to the presence of essential genes in their proximity. Indeed, the identification of tumor suppressor genes has been facilitated by the discovery of homozygous deletions present within the genomes of cancer cell lines and xenografts; examples include p16 (Kamb et al., 1994), DPC4 (Hahn et al., 1996), BRCA2 (Wooster et al., 1995; Tavtigian et al., 1996) and MMAC1PTEN (Steck et al., 1997; Li et al., 1997).

Cells in tissues have only three serious options in life—they can grow and divide, not grow but stay alive, or die by apoptosis. Tumors may arise either by inappropriate growth and division or by cells failing to die when they should. One of the mechanisms for controlling tumor growth might involve direct regulation of the cell cycle. For example, genes that control the decision to initiate DNA replication are attractive candidates for oncogenes or tumor suppressor genes, depending on whether they have a stimulatory or inhibitory role in the process. Progression of eukaryotic cells through the cell cycle ($G_1$, S, $G_2$ and M phases) is governed by the sequential formation, activation and subsequent inactivation of a series of cyclin/cyclin-dependent kinase (Cdk) complexes. Cyclin D's/Cdk2,4,5, Cyclin E/Cdk2, Cyclin A/Cdk2 and Cyclin B/A/Cdk2 have been shown to be involved in this process. Cyclin D's and Cdk2, Cdk4 and Cdk5 have been implicated in the transition from $G_1$ to S; that is, when cells grow and decide whether to begin DNA replication. Additional cell cycle control elements have recently been discovered. These elements are inhibitors of Cdks (Cdk inhibitors, CKI), and include Far1, p21, p40, p20 and p16 (Marx, 1994; Nasmyth & Hunt, 1993).

Recently, several oncogenes and tumor suppressor genes have been found to participate directly in the cell cycle. For example, one of the cyclins (proteins that promote DNA replication) has been implicated as an oncogene (Motokura et al., 1991; Lammie et al., 1991; Withers et al., 1991; Rosenberg et al., 1991), and tumor suppressor Rb interacts with the primary cyclin-binding partners, the Cdks (Ewen et al., 1993). Identification of a melanoma susceptibility locus would open the way for genetic screening of individuals to assess, for example, the increased risk of cancer due to sunlight exposure. A family of multiple tumor suppressor (MTS) genes has also been found and studied (Kamb et al., 1994; Liu et al., 1995b; Jiang et al., 1995; Stone et al., 1995a; Stone et al., 1995b; Gruis et al., 1995; Liu et al., 1995a; Hannon and Beach, 1994; Serrano et al., 1993). The MTS may also predispose to a large number of other cancer sites, including but not limited to, leukemia, astrocytoma, glioblastoma, lymphoma, glioma, Hodgkin's lymphoma, multiple myeloma, sarcoma, myosarcoma, cholangiocarcinoma, squamous cell carcinoma, CLL, and cancers of the pancreas, breast, brain, prostate, bladder, thyroid, ovary, uterus, testis, kidney, stomach, colon and rectum. In addition, since MTS influences progression of several different tumor types, it should be useful for determining prognosis in cancer patients. Thus, MTS may serve as the basis for development of very important diagnostic tests, one capable of predicting the predisposition to cancer, such as melanoma, ocular melanoma, leukemia, astrocytoma, glioblastoma, lymphoma, glioma, Hodgkin's lymphoma, multiple myeloma, sarcoma, myosarcoma, cholangiocarcinoma, squamous cell carcinoma, CLL, and cancers of the pancreas, breast, brain, prostate, bladder, thyroid, ovary, uterus, testis, kidney, stomach, colon and rectum, and one capable of predicting the prognosis of cancer. Furthermore, since MTS is involved in the progression of multiple tumor types, MTS may provide the means, either directly or indirectly, for a general anti-cancer therapy by virtue of its ability to suppress tumor growth. For example, restoration of the normal MTS function to a tumor cell may transmute the cell into non-malignancy.

Just as the MTS genes appear to be involved in suppressing several types of tumors, the BRG1 gene of the present invention also is involved in suppressing tumors. Although the BRG1 gene was previously known (Khavari et al., 1993), the association between BRG1 and tumor forrnation was unknown prior to the present work. Specifically, there has been no previous report showing that the BRG1 gene is targeted for mutations. It was recognized that BRG1 binds specifically to the retinoblastoma tumor suppressor protein, RB (Dunaief et al. 1994).

SUMMARY OF THE INVENTION

The present invention relates to somatic mutations in the BRG1 gene in human cancers and their use in the diagnosis and prognosis of human cancer. The invention further relates to germline mutations in the BRG1 gene and their use in the diagnosis of predisposition to prostate cancer. The invention also relates to the therapy of human cancers which result from having a mutation in the BRG1 gene, including gene therapy, protein replacement therapy and protein mimetics. Finally, the invention relates to the screening of drugs for cancer therapy.

SUMMARY OF SEQUENCE LISTING

SEQ ID NO:1 is the cDNA for BRG1.

SEQ ID NO:2 is the amino acid sequence of BRG1.

SEQ ID NOs:3–4 are hypothetical DNAs used to illustrate percent homology.

SEQ ID NOs:5–16 are primers used for homozygous deletion analysis of BRG1 in the cell line TSU-pr1.

SEQ ID NO:17 is exon 10 plus flanking intron sequence of genomic BRG1.

SEQ ID NOs:18–25 are primers used for amplification of cDNA for mutation screening of a region of the BRG1 coding sequence.

SEQ ID NOs:26–29 are primers used for an analysis of BRG1 genomic DNA.

SEQ ID NOs:30–58 are genomic DNA sequences for all exons plus some flanking intron of BRG1.

Table 6 sets out the correspondence between exon number, SEQ ID NO and base numbers of each SEQ ID NO corresponding to exon.

SEQ ID NO:59 is exon 29B.

SEQ ID NO:60 is the BRG1 mRNA produced in each of cell lines DU145 and NCI-H1299.

SEQ ID NO:61 is the BRG1 protein produced in each of cell lines DU145 and NCI-H1299.

SEQ ID NOs:62–63 are the cDNA and protein for BRG1 containing a mutation at base 1704.

SEQ ID NOs:64–77 are splice variants of SEQ ID NO:1 and the encoded proteins.

DETAILED DESCRIPTION OF THE INVENTION

The present invention relates to somatic mutations in the BRG1 gene in human cancers, especially prostate cancer, and their use in the diagnosis and prognosis of human cancer. The invention further relates to germline mutations in the BRG1 gene and their use in the diagnosis of predisposition to various cancers, especially prostate cancer. The invention also relates to the therapy of human cancers which have a mutation in the BRG1 gene, including gene therapy, protein replacement therapy and protein mimetics. Finally, the invention relates to the screening of drugs for cancer therapy.

The present invention provides an isolated polynucleotide comprising all, or a portion of the BRG1 locus or of a mutated BRG1 locus, preferably at least eight bases and not more than about 100 kb in length. Such polynucleotides may be antisense polynucleotides. The present invention also provides a recombinant construct comprising such an isolated polynucleotide, for example, a recombinant construct suitable for expression in a transformed host cell.

Also provided by the present invention are methods of detecting a polynucleotide comprising a portion of the BRG1 locus or its expression product in an analyte. Such methods may further comprise the step of amplifying the portion of the BRG1 locus, and may further include a step of providing a set of polynucleotides which are primers for amplification of said portion of the BRG1 locus. The method is useful for either diagnosis of the predisposition to cancer or the diagnosis or prognosis of cancer.

The present invention also provides isolated antibodies, preferably monoclonal antibodies, which specifically bind to an isolated polypeptide comprised of at least five amino acid residues encoded by the BRG1 locus.

The present invention also provides kits for detecting in an analyte a polynucleotide comprising a portion of the BRG1 locus, the kits comprising a polynucleotide complementary to the portion of the BRG1 locus packaged in a suitable container, and instructions for their use.

The present invention further provides methods of preparing a polynucleotide comprising polymerizing nucleotides to yield a sequence comprised of at least eight consecutive nucleotides of the BRG1 locus; and methods of preparing a polypeptide comprising polymerizing amino acids to yield a sequence comprising at least five amino acids encoded within the BRG1 locus.

In addition, the present invention provides methods of screening drugs for cancer therapy to identify suitable drugs for restoring BRG1 gene product function.

Finally, the present invention provides the means necessary for production of gene-based therapies directed at cancer cells. These therapeutic agents may take the form of polynucleotides comprising all or a portion of the BRG1 locus placed in appropriate vectors or delivered to target cells in more direct ways such that the function of the BRG1 protein is reconstituted. Therapeutic agents may also take the form of polypeptides based on either a portion of, or the entire protein sequence of BRG1. These may functionally replace the activity of BRG1 in vivo.

It is a discovery of the present invention that the BRG1 locus predisposes individuals to prostate cancer. By using microcell fusion-mediated chromosomal transfer to introduce human chromosome 19 into highly metastatic rat and human prostate cancer cells, suppression of tumorigenicity in vivo in athymic nude mice was demonstrated by Gao et al. (1999). Specifically, it is a region at human chromosome 19p13.1 that is responsible for tumor suppression. It was therefore predicted that a candidate tumor suppressor gene would reside within this region. We localized a gene called BRG1 by radiation hybrid mapping to chromosome band 19p13.1. BRG1 was originally cloned by Khavari et al. (1993). It was shown to be a human homolog of Drosophila brahma. Brahma is an activator of multiple homeotic genes and an important regulator of development. Using the yeast two hybrid assay, it was also found that BRG1 binds specifically to the retinoblastoma tumor suppressor protein, RB (Dunaief et al., 1994). Together these data suggested that BRG1 may be an excellent tumor suppressor candidate and could be targeted for mutations.

The BRG1 locus was first recognized as containing a tumor suppressor gene when we noted it to be part of a homozygous deletion in a prostate tumor cell line called TSU-pr1. A homozygous deletion scan by PCR of a panel of 192 tumor cell line genomic DNAs showed that the 3' portion, including coding sequences of the BRG1 gene, is deleted in the prostate cell line TSU-pr1. Further investigation for additional mutations in other tumor cell lines led to the identification of a deletion of bases 1677–1761 of the open reading frame of BRG1 in prostate tumor cell line DU145 and in lung cancer cell line NCIH1299. This deletion causes a frameshift. The wild-type sequence of BRG1 was not detected in these cell lines indicating that a normal BRG1 product would not be found. This is consistent with the notion that BRG1 is a tumor suppressor gene.

According to the diagnostic and prognostic method of the present invention, alteration of the wild-type BRG1 locus is detected. In addition, the method can be performed by detecting the wild-type BRG1 locus and confirming the lack of a predisposition or neoplasia. "Alteration of a wild-type gene" encompasses all forms of mutations including deletions, insertions and point mutations in the coding and noncoding regions. Deletions may be of the entire gene or only a portion of the gene. Point mutations may result in stop codons, frameshift mutations or amino acid substitutions. Somatic mutations are those which occur only in certain tissues, e.g., in the tumor tissue, and are not inherited in the germline. Germline mutations can be found in any of a body's tissues and are inherited. If only a single allele is somatically mutated, an early neoplastic state is indicated. However, if both alleles are mutated, then a late neoplastic state is indicated. A BRG1 allele which is not deleted (e.g., that found on the sister chromosome to a chromosome carrying a BRG1 deletion) can be screened for other mutations, such as insertions, small deletions, and point mutations. It is believed that many mutations found in tumor tissues will be those leading to decreased expression of the BRG1 gene product. However, mutations leading to non-functional gene products would also lead to a cancerous state. Point mutational events may occur in regulatory regions, such as in the promoter of the gene, leading to loss or diminution of expression of the mRNA. Point mutations may also abolish proper RNA processing, leading to loss of expression of the BRG1 gene product, or a decrease in mRNA stability or translation efficiency.

Useful diagnostic techniques include, but are not limited to fluorescent in situ hybridization (FISH), direct DNA sequencing, PFGE analysis, Southern blot analysis, single stranded conformation analysis (SSCA), RNase protection assay, allele-specific oligonucleotide (ASO), dot blot analysis, hybridization using nucleic acid modified with gold nanoparticles and PCR-SSCP, as discussed in detail further below. Also useful is the recently developed technique of DNA microchip technology.

Predisposition to cancers, such as prostate and the other cancers identified herein, can be ascertained by testing any tissue of a human for mutations of the BRG1 gene. For example, a person who has inherited a germline BRG1 mutation would be prone to develop cancers. This can be determined by testing DNA from any tissue of the person's body. Most simply, blood can be drawn and DNA extracted from the cells of the blood. In addition, prenatal diagnosis can be accomplished by testing fetal cells, placental cells or amniotic fluid for mutations of the BRG1 gene. Alteration of a wild-type BRG1 allele, whether, for example, by point mutation or by deletion, can be detected by any of the means discussed herein.

There are several methods that can be used to detect DNA sequence variation. Direct DNA sequencing, either manual sequencing or automated fluorescent sequencing can detect sequence variation. Another approach is the single-stranded conformation polymorphism assay (SSCP) (Orita et al., 1989). This method does not detect all sequence changes, especially if the DNA fragment size is greater than 200 bp, but can be optimized to detect most DNA sequence variation. The reduced detection sensitivity is a disadvantage, but the increased throughput possible with SSCP makes it an attractive, viable alternative to direct sequencing for mutation detection on a research basis. The fragments which have shifted mobility on SSCP gels are then sequenced to determine the exact nature of the DNA sequence variation. Other approaches based on the detection of mismatches between the two complementary DNA strands include clamped denaturing gel electrophoresis (CDGE) (Sheffield et al., 1991), heteroduplex analysis (HA) (White et al., 1992) and chemical mismatch cleavage (CMC) (Grompe et al., 1989). None of the methods described above will detect large deletions, duplications or insertions, nor will they detect a regulatory mutation which affects transcription or translation of the protein. Other methods which might detect these classes of mutations such as a protein truncation assay or the asymmetric assay, detect only specific types of mutations and would not detect missense mutations. A review of currently available methods of detecting DNA sequence variation can be found in a recent review by Grompe (1993). Once a mutation is known, an allele specific detection approach such as allele specific oligonucleotide (ASO) hybridization can be utilized to rapidly screen large numbers of other samples for that same mutation. Such a technique can utilize probes which are labeled with gold nanoparticles to yield a visual color result (Elghanian et al., 1997).

In order to detect the alteration of the wild-type BRG1 gene in a tissue, it is helpful to isolate the tissue free from surrounding normal tissues. Means for enriching a tissue preparation for tumor cells are known in the art. For example, the tissue may be isolated from paraffin or cryostat sections. Cancer cells may also be separated from normal cells by flow cytometry. These techniques, as well as other techniques for separating tumor cells from normal cells, are well known in the art. If the tumor tissue is highly contaminated with normal cells, detection of mutations is more difficult.

A rapid preliminary analysis to detect polymorphisms in DNA sequences can be performed by looking at a series of Southern blots of DNA cut with one or more restriction enzymes, preferably a large number of restriction enzymes. Each blot contains a series of normal individuals and a series of cancer cases, tumors, or both. Southern blots displaying hybridizing fragments (differing in length from control DNA when probed with sequences near or including the BRG1 locus) indicate a possible mutation. If restriction enzymes which produce very large restriction fragments are used, then pulsed field gel electrophoresis ("PFGE") is employed.

Detection of point mutations may be accomplished by molecular cloning of the BRG1 allele and sequencing that allele using techniques well known in the art. Alternatively, the gene sequences can be amplified, using known techniques, directly from a genomic DNA preparation from the tumor tissue. The DNA sequence of the amplified sequences can then be determined.

There are six well known methods for a more complete, yet still indirect, test for confirming the presence of a susceptibility allele: 1) single stranded conformation analysis ("SSCA") (Orita et al., 1989); 2) denaturing gradient gel electrophoresis ("DGGE") (Wartell et al., 1990; Sheffield et al., 1989); 3) RNase protection assays (Finkelstein et al., 1990; Kinszler et al., 1991); 4) allele-specific oligonucleotides ("ASOs") (Conner et al., 1983); 5) the use of proteins which recognize nucleotide mismatches, such as the *E. coli* mutS protein (Modrich, 1991); and 6) allele-specific PCR (Ruano and Kidd, 1989). For allele-specific PCR, primers are used which hybridize at their 3' ends to a particular BRG1 mutation. If the particular BRG1 mutation is not present, an amplification product is not observed. Amplification Refractory Mutation System (ARMS) can also be used, as disclosed in European Patent Application Publication No. 0332435 and in Newton et al., 1989. Insertions and deletions of genes can also be detected by cloning, sequencing and amplification. In addition, restriction fragment length polymorphism (RFLP) probes for the gene or surrounding marker genes can be used to score alteration of an allele or an insertion in a polymorphic fragment. Such a method is particularly useful for screening relatives of an affected individual for the presence of the BRG1 mutation found in that individual. Other techniques for detecting insertions and deletions as known in the art can be used.

In the first three methods (i.e., SSCA, DGGE and RNase protection assay), a new electrophoretic band appears. SSCA detects a band which migrates differentially because the sequence change causes a difference in single-strand, intramolecular base pairing. RNase protection involves cleavage of the mutant polynucleotide into two or more smaller fragments. DGGE detects differences in migration rates of mutant sequences compared to wild-type sequences, using a denaturing gradient gel. In an allele-specific oligonucleotide assay, an oligonucleotide is designed which detects a specific sequence, and the assay is performed by detecting the presence or absence of a hybridization signal. In the mutS assay, the protein binds only to sequences that contain a nucleotide mismatch in a heteroduplex between mutant and wild-type sequences.

Mismatches, according to the present invention, are hybridized nucleic acid duplexes in which the two strands are not 100% complementary. Lack of total homology may be due to deletions, insertions, inversions or substitutions. Mismatch detection can be used to detect point mutations in the gene or its mRNA product. While these techniques are less sensitive than sequencing, they are simpler to perform on a large number of tumor samples. An example of a mismatch cleavage technique is the RNase protection method. In the practice of the present invention, the method involves the use of a labeled riboprobe which is complementary to the human wild-type BRG1 gene coding sequence. The riboprobe and either mRNA or DNA isolated from the tumor tissue are annealed (hybridized) together and subsequently digested with the enzyme RNase A which is able to detect some mismatches in a duplex RNA structure. If a mismatch is detected by RNase A, it cleaves at the site of the mismatch. Thus, when the annealed RNA preparation is separated on an electrophoretic gel matrix, if a mismatch has been detected and cleaved by RNase A, an RNA product will be seen which is smaller than the full length duplex RNA for the riboprobe and the mRNA or DNA. The riboprobe need not be the full length of the BRG1 mRNA or gene but can be a segment of either. If the riboprobe comprises only a segment of the BRG1 mRNA or gene, it will be desirable to use a number of these probes to screen the whole mRNA sequence for mismatches.

In similar fashion, DNA probes can be used to detect mismatches, through enzymatic or chemical cleavage. See, e.g., Cotton et al., 1988; Shenk et al., 1975; Novack et al., 1986. Alternatively, mismatches can be detected by shifts in the electrophoretic mobility of mismatched duplexes relative to matched duplexes. See, e.g., Cariello, 1988. With either riboprobes or DNA probes, the cellular mRNA or DNA which might contain a mutation can be amplified using PCR (see below) before hybridization. Changes in DNA of the BRG1 gene can also be detected using Southern hybridization, especially if the changes are gross rearrangements, such as deletions and insertions.

DNA sequences of the BRG1 gene which have been amplified by use of PCR may also be screened using allele-specific probes. These probes are nucleic acid oligomers, each of which contains a region of the BRG1 gene sequence harboring a known mutation. For example, one oligomer may be about 30 nucleotides in length, corresponding to a portion of the BRG1 gene sequence. By use of a battery of such allele-specific probes, PCR amplification products can be screened to identify the presence of a previously identified mutation in the BRG1 gene. Hybridization of allele-specific probes with amplified BRG1 sequences can be performed, for example, on a nylon filter. Hybridization to a particular probe under high stringency hybridization conditions indicates the presence of the same mutation in the tumor tissue as in the allele-specific probe. High stringency hybridization conditions are defined as those conditions which allow an 8 basepair stretch of a first nucleic acid (a probe) to bind to a 100% perfectly complementary 8 basepair stretch of nucleic acid while simultaneously preventing binding of said first nucleic acid to a nucleic acid which is not 100% complementary, i.e., binding will not occur if there is a mismatch.

The newly developed technique of nucleic acid analysis via microchip technology is also applicable to the present invention. In this technique, literally thousands of distinct oligonucleotide probes are built up in an array on a silicon chip. Nucleic acid to be analyzed is fluorescently labeled and hybridized to the probes on the chip. It is also possible to study nucleic acid-protein interactions using these nucleic acid microchips. Using this technique one can determine the presence of mutations or even sequence the nucleic acid being analyzed or one can measure expression levels of a gene of interest. The method is one of parallel processing of many, even thousands, of probes at once and can tremendously increase the rate of analysis. Several papers have been published which use this technique. Some of these are Hacia et al., 1996; Shoemaker et al., 1996; Chee et al., 1996; Lockhart et al., 1996; DeRisi et al., 1996; Lipshutz et al., 1995. This method has already been used to screen people for mutations in the breast cancer gene BRCA1 (Hacia et al., 1996). This new technology has been reviewed in a news article in Chemical and Engineering News (Borman, 1996) and been the subject of an editorial (Nature Genetics, 1996). Also see Fodor (1997).

The most definitive test for mutations in a candidate locus is to directly compare genomic BRG1 sequences from cancer patients with those from a control population. Alternatively, one could sequence messenger RNA after amplification, e.g., by PCR, thereby eliminating the necessity of determining the exon structure of the candidate gene.

Mutations from cancer patients falling outside the coding region of BRG1 can be detected by examining the non-coding regions, such as introns and regulatory sequences near or within the BRG1 gene. An early indication that mutations in noncoding regions are important may come from Northern blot experiments that reveal messenger RNA molecules of abnormal size or abundance in cancer patients as compared to control individuals.

Alteration of BRG1 mRNA expression can be detected by any techniques known in the art. These include Northern blot analysis, PCR amplification, RNase protection and the microchip method discussed above. Diminished mRNA expression indicates an alteration of the wild-type BRG1 gene. Alteration of wild-type BRG1 genes can also be detected by screening for alteration of wild-type BRG1 protein. For example, monoclonal antibodies immunoreactive with BRG1 can be used to screen a tissue. Lack of cognate antigen would indicate a BRG1 mutation. Antibodies specific for products of mutant alleles could also be used to detect mutant BRG1 gene product. Such immunological assays can be done in any convenient formats known in the art. These include Western blots, immunohistochemical assays and ELISA assays. Any means for detecting an altered BRG1 protein can be used to detect alteration of wild-type BRG1 genes. Functional assays can be used. For example, it is known that BRG1 protein binds specifically to the retinoblastoma tumor suppressor protein RB (Dunaief et al., 1994). Thus, an assay for this binding ability can be employed. Finding a mutant BRG1 gene product indicates alteration of a wild-type BRG1 gene.

Mutant BRG1 genes or gene products can also be detected in other human body samples, such as serum, stool, urine and sputum. The same techniques discussed above for detection of mutant BRG1 genes or gene products in tissues can be applied to other body samples. Cancer cells are sloughed off from tumors and appear in such body samples. In addition, the BRG1 gene product itself may be secreted into the extracellular space and found in these body samples even in the absence of cancer cells. By screening such body samples, a simple early diagnosis can be achieved for many types of cancers. In addition, the progress of chemotherapy or radiotherapy can be monitored more easily by testing such body samples for mutant BRG1 genes or gene products.

The methods of diagnosis of the present invention are applicable to any tumor in which BRG1 has a role in tumorigenesis. The diagnostic method of the present invention is useful for clinicians, so they can decide upon an appropriate course of treatment.

The primer pairs of the present invention are useful for determination of the nucleotide sequence of a particular BRG1 allele using the PCR. The pairs of single-stranded DNA primers can be annealed to sequences within or surrounding the BRG1 gene in order to prime amplifying DNA synthesis of the BRG1 gene itself. A complete set of these primers allows synthesis of all of the nucleotides of the BRG1 gene coding sequences, i.e., the exons. The set of primers preferably allows synthesis of both intron and exon sequences. Allele-specific primers can also be used. Such primers anneal only to particular BRG1 mutant alleles, and thus will only amplify a product in the presence of the mutant allele as a template.

In order to facilitate subsequent cloning of amplified sequences, primers may have restriction enzyme site sequences appended to their 5' ends. Thus, all nucleotides of the primers are derived from BRG1 sequences or sequences adjacent to BRG1, except for the few nucleotides necessary to form a restriction enzyme site. Such enzymes and sites are well known in the art. The primers themselves can be synthesized using techniques which are well known in the art. Generally, the primers can be made using oligonucleotide synthesizing machines which are commercially available. Given the sequence of BRG1 shown in SEQ ID NO:1 design of particular primers is well within the skill of the art.

The nucleic acid probes provided by the present invention are useful for a number of purposes. They can be used in Southern hybridization to genomic DNA and in the RNase protection method for detecting point mutations. The probes can be used to detect PCR amplification products. They may also be used to detect mismatches with the BRG1 gene or mRNA using other techniques.

Definitions

The present invention employs the following definitions:

"Amplification of Polynucleotides" utilizes methods such as the polymerase chain reaction (PCR), ligation amplification (or ligase chain reaction, LCR) and amplification methods based on the use of Q-beta replicase. Also useful are strand displacement amplification (SDA), thermophilic SDA, and nucleic acid sequence based amplification (3SR or NASBA). These methods are well known and widely practiced in the art. See, e.g., U.S. Pat. Nos. 4,683,195 and 4,683,202 and Innis et al., 1990 (for PCR); and Wu and Wallace, 1989 (for LCR); U.S. Pat. Nos. 5,270,184 and 5,455,166 and Walker et al., 1992 (for SDA); Spargo et al., 1996 (for thermophilic SDA) and U.S. Pat. No. 5,409,818, Fahy et al., 1991 and Compton, 1991 for 3SR and NASBA. Reagents and hardware for conducting PCR are commercially available. Primers useful to amplify sequences from the BRG1 region are preferably complementary to, and hybridize specifically to, sequences in the BRG1 region or in regions that flank a target region therein. BRG1 sequences generated by amplification may be sequenced directly. Alternatively, but less desirably, the amplified sequence(s) may be cloned prior to sequence analysis. A method for the direct cloning and sequence analysis of enzymatically amplified genomic segments has been described by Scharf, 1986.

"Analyte polynucleotide" and "analyte strand" refer to a single- or double-stranded polynucleotide which is suspected of containing a target sequence, and which may be present in a variety of types of samples, including biological samples.

"Antibodies." The present invention also provides polyclonal and/or monoclonal antibodies and fragments thereof, and immunologic binding equivalents thereof, which are capable of specifically binding to the BRG1 polypeptides and fragments thereof or to polynucleotide sequences from the BRG1 region, particularly from the BRG1 locus or a portion thereof The term "antibody" is used both to refer to a homogeneous molecular entity, or a mixture such as a serum product made up of a plurality of different molecular entities. Polypeptides may be prepared synthetically in a peptide synthesizer and coupled to a carrier molecule (e.g., keyhole limpet hemocyanin) and injected over several months into rabbits. Rabbit sera is tested for immunoreactivity to the BRG1 polypeptide or fragment. Monoclonal antibodies may be made by injecting mice with the protein polypeptides, fusion proteins or fragments thereof. Monoclonal antibodies will be screened by ELISA and tested for specific immunoreactivity with BRG1 polypeptide or fragments thereof. See, Harlow & Lane, 1988. These antibodies will be useful in assays as well as pharmaceuticals.

Once a sufficient quantity of desired polypeptide has been obtained, it may be used for various purposes. A typical use is the production of antibodies specific for binding. These antibodies may be either polyclonal or monoclonal, and may be produced by in vitro or in vivo techniques well known in the art.

For production of polyclonal antibodies, an appropriate target immune system, typically mouse or rabbit, is selected. Substantially purified antigen is presented to the immune system in a fashion determined by methods appropriate for the animal and by other parameters well known to immunologists. Typical sites for injection are in footpads, intramuscularly, intraperitoneally, or intradermally. Of course, other species may be substituted for mouse or rabbit. Polyclonal antibodies are then purified using techniques known in the art, adjusted for the desired specificity.

An immunological response is usually assayed with an immunoassay. Normally, such immunoassays involve some purification of a source of antigen, for example, that produced by the same cells and in the same fashion as the antigen. A variety of immunoassay methods are well known in the art. See, e.g., Harlow and Lane, 1988, or Goding, 1986.

Monoclonal antibodies with affinities of $10^{-8}$ $M^{-1}$ or preferably $10^{-9}$ to $10^{-10}$ $M^{-1}$ or stronger will typically be made by standard procedures as described, e.g., in Harlow and Lane, 1988 or Goding, 1986. Briefly, appropriate animals will be selected and the desired immunization protocol followed. After the appropriate period of time, the spleens of such animals are excised and individual spleen cells fused, typically, to immortalized myeloma cells under appropriate selection conditions. Thereafter, the cells are clonally separated and the supernatants of each clone tested for their production of an appropriate antibody specific for the desired region of the antigen.

Other suitable techniques involve in vitro exposure of lymphocytes to the antigenic polypeptides, or alternatively, to selection of libraries of antibodies in phage or similar vectors. See Huse et al., 1989. The polypeptides and antibodies of the present invention may be used with or without modification. Frequently, polypeptides and antibodies will be labeled by joining, either covalently or non-covalently, a substance which provides for a detectable signal. A wide variety of labels and conjugation techniques are known and are reported extensively in both the scientific and patent literature. Suitable labels include radionuclides, enzymes, substrates, cofactors, inhibitors, fluorescent agents, chemiluminescent agents, magnetic particles and the like. Patents teaching the use of such labels include U.S. Pat. Nos. 3,817,837; 3,850,752; 3,939,350; 3,996,345; 4,277,437; 4,275,149; and 4,366,241. Also, recombinant immunoglobulins may be produced (see U.S. Pat. No. 4,816,567).

"Binding partner" refers to a molecule capable of binding a ligand molecule with high specificity, as for example, an antigen and an antigen-specific antibody or an enzyme and its inhibitor. In general, the specific binding partners must bind with sufficient affinity to immobilize the analyte copy/complementary strand duplex (in the case of polynucleotide hybridization) under the isolation conditions. Specific binding partners are known in the art and include, for example, biotin and avidin or streptavidin, IgG and protein A, the numerous, known receptor-ligand couples, and complementary polynucleotide strands. In the case of complementary polynucleotide binding partners, the partners are normally at least about 15 bases in length, and may be at least 40 bases in length. It is well recognized by those of skill in the art that lengths shorter than 15 (e.g., 8 bases), between 15 and 40, and greater than 40 bases may also be used. The polynucleotides may be composed of DNA, RNA, or synthetic nucleotide analogs. Further binding partners can be identified using, e.g., the two-hybrid yeast screening assay as described herein.

A "biological sample" refers to a sample of tissue or fluid suspected of containing an analyte polynucleotide or polypeptide from an individual including, but not limited to, e.g., plasma, serum, spinal fluid, lymph fluid, the external sections of the skin, respiratory, intestinal, and genitourinary tracts, tears, saliva, blood cells, tumors, organs, tissue and samples of in vitro cell culture constituents.

As used herein, the terms "diagnosing" or "prognosing," as used in the context of neoplasia, are used to indicate 1) the classification of lesions as neoplasia, 2) the determination of the severity of the neoplasia, or 3) the monitoring of the disease progression, prior to, during and after treatment.

"Encode". A polynucleotide is said to "encode" a polypeptide if, in its native state or when manipulated by methods well known to those skilled in the art, it can be transcribed and/or translated to produce the mRNA for and/or the polypeptide or a fragment thereof. The anti-sense strand is the complement of such a nucleic acid, and the encoding sequence can be deduced therefrom.

"Isolated" or "substantially pure". An "isolated" or "substantially pure" nucleic acid (e.g., an RNA, DNA or a mixed polymer) is one which is substantially separated from other cellular components which naturally accompany a native human sequence or protein, e.g., ribosomes, polymerases, many other human genome sequences and proteins. The term embraces a nucleic acid sequence or protein which has been removed from its naturally occurring environment, and includes recombinant or cloned DNA isolates and chemically synthesized analogs or analogs biologically synthesized by heterologous systems.

"BRG1 Allele" refers to normal alleles of the BRG1 locus as well as alleles carrying variations that predispose individuals to develop cancer. Such predisposing alleles are also called "BRG1 susceptibility alleles".

"BRG1 Locus," "BRG1 gene," "BRG1 Nucleic Acids" or "BRG1 Polynucleotide" refers to polynucleotides, all of which are in the BRG1 region, that are likely to be expressed in normal tissue, certain alleles of which predispose an individual to develop prostate cancer. Mutations at the BRG1 locus may be involved in the initiation and/or progression of other types of tumors. The locus is indicated in part by mutations that predispose individuals to develop cancer. These mutations fall within the BRG1 region described infra. The BRG1 locus is intended to include coding sequences, intervening sequences and regulatory elements controlling transcription and/or translation. The BRG1 locus is intended to include all allelic variations of the DNA sequence.

These terms, when applied to a nucleic acid, refer to a nucleic acid which encodes a BRG1 polypeptide, fragment, homolog or variant, including, e.g., protein fusions or deletions. The nucleic acids of the present invention will possess a sequence which is either derived from, or substantially similar to, a natural BRG1-encoding gene or one having substantial homology with a natural BRG1-encoding gene or a portion thereof. The cDNA for BRG1 is shown in SEQ ID NO:1 and the encoded polypeptide sequence is given as SEQ ID NO:2.

The BRG1 gene or nucleic acid includes normal alleles of the BRG1 gene including silent alleles having no effect on the amino acid sequence of BRG1 as well as alleles leading to amino acid sequence variants of BRG1 that do not substantially affect its function. These terms also include alleles having one or more mutations which adversely affect the function of BRG1. A mutation may be a change in the BRG1 nucleic acid sequence which produces a deleterious change in the amino acid sequence of BRG1, resulting in partial or complete loss of BRG1 function, or may be a change in the nucleic acid sequence which results in the loss of effective BRG1 expression or the production of aberrant forms of BRG1.

The BRG1 nucleic acid may be that shown in SEQ ID NO:1 or it may be an allele as described above or a variant or derivative differing from that shown by a change which is one or more of addition, insertion, deletion and substitution of one or more nucleotides of the sequence shown. Changes to the nucleotide sequence may result in an amino acid change at the protein level, or not, as determined by the genetic code.

Thus, nucleic acid according to the present invention may include a sequence different from the sequence shown in SEQ ID NO:1 yet encode a polypeptide with the same amino acid sequence as shown in SEQ ID NO:2. That is, nucleic acids of the present invention include sequences which are degenerate as a result of the genetic code. On the other hand, the encoded polypeptide may comprise an amino acid sequence which differs by one or more amino acid residues from the amino acid sequence shown in SEQ ID NO:2. Nucleic acid encoding a polypeptide which is an amino acid sequence variant, derivative or allele of the amino acid sequence shown in SEQ ID NO:2 is also provided by the present invention.

The BRG1 gene also refers to (a) any DNA sequence that (i) hybridizes to the complement of the DNA sequences that encode the amino acid sequence set forth in SEQ ID NO:1 under highly stringent conditions (Ausubel et al., 1992) and (ii) encodes a gene product functionally equivalent to BRG1, or (b) any DNA sequence that (i) hybridizes to the complement of the DNA sequences that encode the amino acid sequence set forth in SEQ ID NO:2 under less stringent conditions, such as moderately stringent conditions (Ausubel et al., 1992) and (ii) encodes a gene product functionally equivalent to BRG1. The invention also includes nucleic acid molecules that are the complements of the sequences described herein.

The polynucleotide compositions of this invention include RNA, cDNA, genomic DNA, synthetic forms, and mixed polymers, both sense and antisense strands, and may be chemically or biochemically modified or may contain non-natural or derivatized nucleotide bases, as will be readily appreciated by those skilled in the art. Such modifications include, for example, labels, methylation, substitution of one or more of the naturally occurring nucleotides with an analog, internucleotide modifications such as uncharged linkages (e.g., methyl phosphonates, phosphotriesters, phosphoamidates, carbamates, etc.), charged linkages (e.g., phosphorothioates, phosphorodithioates, etc.), pendent moieties (e.g., polypeptides), intercalators (e.g., acridine, psoralen, etc.). chelators, alkylators, and modified linkages (e.g., alpha anomeric nucleic acids, etc.). Also included are synthetic molecules that mimic polynucleotides in their ability to bind to a designated sequence via hydrogen bonding and other chemical interactions. Such molecules are known in the art and include, for example, those in which peptide linkages substitute for phosphate linkages in the backbone of the molecule.

The present invention provides recombinant nucleic acids comprising all or part of the BRG1 region. The recombinant construct may be capable of replicating autonomously in a host cell. Alternatively, the recombinant construct may become integrated into the chromosomal DNA of the host cell. Such a recombinant polynucleotide comprises a polynucleotide of genomic, cDNA, semi-synthetic, or synthetic origin which, by virtue of its origin or manipulation 1) is not associated with all or a portion of a polynucleotide with which it is associated in nature; 2) is linked to a polynucleotide other than that to which it is linked in nature; or 3) does not occur in nature. Where nucleic acid according to the invention includes RNA, reference to the sequence shown should be construed as reference to the RNA equivalent, with U substituted for T.

Therefore, recombinant nucleic acids comprising sequences otherwise not naturally occurring are provided by this invention. Although the wild-type sequence may be employed, it will often be altered, e.g., by deletion, substitution or insertion.

cDNA or genomic libraries of various types may be screened as natural sources of the nucleic acids of the present invention, or such nucleic acids may be provided by amplification of sequences resident in genomic DNA or other natural sources, e.g., by PCR. The choice of cDNA libraries normally corresponds to a tissue source which is abundant in mRNA for the desired proteins. Phage libraries are normally preferred, but other types of libraries may be used. Clones of a library are spread onto plates, transferred to a substrate for screening, denatured and probed for the presence of desired sequences.

The DNA sequences used in this invention will usually comprise at least about five codons (15 nucleotides), more usually at least about 7–15 codons, and most preferably, at least about 35 codons. One or more introns may also be present. This number of nucleotides is usually about the minimal length required for a successful probe that would hybridize specifically with a BRG1-encoding sequence. In this context, oligomers of as low as 8 nucleotides, more generally 8–17 nucleotides, can be used for probes, especially in connection with chip technology.

Techniques for nucleic acid manipulation are described generally, for example, in Sambrook et al., 1989 or Ausubel et al., 1992. Reagents useful in applying such techniques, such as restriction enzymes and the like, are widely known in the art and commercially available from such vendors as New England BioLabs, Boehringer Mannheim, Amersham, Promega Biotech, U. S. Biochemicals, New England Nuclear, and a number of other sources. The recombinant nucleic acid sequences used to produce fusion proteins of the present invention may be derived from natural or synthetic sequences. Many natural gene sequences are obtainable from various cDNA or from genomic libraries using appropriate probes. See, GenBank, National Institutes of Health.

As used herein, the terms "BRG1 locus," "BRG1 allele" and "BRG1 region" all refer to the double-stranded DNA comprising the locus, allele, or region, as well as either of the single-stranded DNAs comprising the locus, allele or region.

As used herein, a "portion" of the BRG1 locus or region or allele is defined as having a minimal size of at least about eight nucleotides, or preferably about 15 nucleotides, or more preferably at least about 25 nucleotides, and may have a minimal size of at least about 40 nucleotides. This definition includes all sizes in the range of 8–40 nucleotides as well as greater than 40 nucleotides. Thus, this definition includes nucleic acids of 8, 12, 15, 20, 25, 40, 60, 80, 100, 200, 300, 400, 500 nucleotides or nucleic acids having any number of nucleotides within these ranges of values (e.g., 9, 10, 11, 16, 23, 30, 38, 50, 72, 121, etc., nucleotides), or nucleic acids having more than 500 nucleotides.

"BRG1 protein" or "BRG1 polypeptide" refers to a protein or polypeptide encoded by the BRG1 locus, variants or fragments thereof. The term "polypeptide" refers to a polymer of amino acids and its equivalent and does not refer to a specific length of the product; thus, peptides, oligopeptides and proteins are included within the definition of a polypeptide. This term also does not refer to, or exclude modifications of the polypeptide, for example, glycosylations, acetylations, phosphorylations, and the like. Included within the definition are, for example, polypeptides containing one or more analogs of an amino acid (including, for example, unnatural amino acids, etc.), polypeptides with substituted linkages as well as other modifications known in the art, both naturally and non-naturally occurring. Ordinarily, such polypeptides will be at least about 50% homologous to the native BRG1 sequence, preferably in excess of about 90%, and more preferably at least about 95% homologous. Also included are proteins encoded by DNA which hybridize under high or low stringency conditions, to BRG1-encoding nucleic acids and closely related polypeptides or proteins retrieved by antisera to the BRG1 protein.

The BRG1 polypeptide may be that shown in SEQ ID NO:2 which may be in isolated and/or purified form, free or substantially free of material with which it is naturally associated. The polypeptide may, if produced by expression in a prokaryotic cell or produced synthetically, lack native post-translational processing, such as glycosylation. Alternatively, the present invention is also directed to polypeptides which are sequence variants, alleles or derivatives of the BRG1 polypeptide. Such polypeptides may have an amino acid sequence which differs from that set forth in SEQ ID NO:2 by one or more of addition, substitution, deletion or insertion of one or more amino acids. Preferred such polypeptides have BRG1 function.

Substitutional variants typically contain the exchange of one amino acid for another at one or more sites within the protein, and may be designed to modulate one or more properties of the polypeptide, such as stability against proteolytic cleavage, without the loss of other functions or properties. Amino acid substitutions may be made on the basis of similarity in polarity, charge, solubility, hydrophobicity, hydrophilicity, and/or the amphipathic nature of the residues involved. Preferred substitutions are ones which are conservative, that is, one amino acid is replaced with one of similar shape and charge. Conservative substitutions are well known in the art and typically include substitutions within the following groups: glycine, alanine; valine, isoleucine, leucine; aspartic acid, glutamic acid; asparagine, glutamine; serine, threonine; lysine, arginine; and tyrosine, phenylalanine.

Certain amino acids may be substituted for other amino acids in a protein structure without appreciable loss of interactive binding capacity with structures such as, for example, antigen-binding regions of antibodies or binding sites on substrate molecules or binding sites on proteins interacting with the BRG1 polypeptide. Since it is the interactive capacity and nature of a protein which defines that protein's biological functional activity, certain amino acid substitutions can be made in a protein sequence, and its underlying DNA coding sequence, and nevertheless obtain a protein with like properties. In making such changes, the hydropathic index of amino acids may be considered. The importance of the hydrophobic amino acid index in conferring interactive biological function on a protein is generally understood in the art (Kyte and Doolittle, 1982). Alternatively, the substitution of like amino acids can be made effectively on the basis of hydrophilicity. The importance of hydrophilicity in conferring interactive biological function of a protein is generally understood in the art (U.S. Pat. No. 4,554,101). The use of the hydrophobic index or hydrophilicity in designing polypeptides is further discussed in U.S. Pat. No . 5,691,198.

The length of polypeptide sequences compared for homology will generally be at least about 16 amino acids, usually at least about 20 residues, more usually at least about 24 residues, typically at least about 28 residues, and preferably more than about 35 residues.

"Operably linked" refers to a juxtaposition wherein the components so described are in a relationship permitting them to function in their intended manner. For instance, a promoter is operably linked to a coding sequence if the promoter affects its transcription or expression.

The term peptide mimetic or mimetic is intended to refer to a substance which has the essential biological activity of the BRG1 polypeptide. A peptide mimetic may be a peptide-containing molecule that mimics elements of protein secondary structure (Johnson et al., 1993). The underlying rationale behind the use of peptide mimetics is that the peptide backbone of proteins exists chiefly to orient amino acid side chains in such a way as to facilitate molecular interactions, such as those of antibody and antigen, enzyme and substrate or scaffolding proteins. A peptide mimetic is designed to permit molecular interactions similar to the natural molecule. A mimetic may not be a peptide at all, but it will retain the essential biological activity of natural BRG1 polypeptide.

"Probes". Polynucleotide polymorphisms associated with BRG1 alleles which predispose to certain cancers or are associated with most cancers are detected by hybridization with a polynucleotide probe which forms a stable hybrid with that of the target sequence, under highly stringent to moderately stringent hybridization and wash conditions. If it is expected that the probes will be perfectly complementary to the target sequence, high stringency conditions will be used. Hybridization stringency may be lessened if some mismatching is expected, for example, if variants are expected with the result that the probe will not be completely complementary. Conditions are chosen which rule out nonspecific/adventitious bindings, that is, which minimize noise. (It should be noted that throughout this disclosure, if it is simply stated that "stringent" conditions are used that is meant to be read as "high stringency" conditions are used.) Since such indications identify neutral DNA polymorphisms as well as mutations, these indications need further analysis to demonstrate detection of a BRG1 susceptibility allele.

Probes for BRG1 alleles may be derived from the sequences of the BRG1 region, its cDNA, functionally equivalent sequences, or the complements thereof. The probes may be of any suitable length, which span all or a portion of the BRG1 region, and which allow specific hybridization to the BRG1 region. If the target sequence contains a sequence identical to that of the probe, the probes may be short, e.g., in the range of about 8–30 base pairs, since the hybrid will be relatively stable under even highly stringent conditions. If some degree of mismatch is expected with the probe, i.e., if it is suspected that the probe will hybridize to a variant region, a longer probe may be employed which hybridizes to the target sequence with the requisite specificity.

The probes will include an isolated polynucleotide attached to a label or reporter molecule and may be used to isolate other polynucleotide sequences, having sequence similarity by standard methods. For techniques for preparing and labeling probes see, e.g., Sambrook et al. (1989) or Ausubel et al. (1992). Other similar polynucleotides may be selected by using homologous polynucleotides. Alternatively, polynucleotides encoding these or similar polypeptides may be synthesized or selected by use of the redundancy in the genetic code. Various codon substitutions may be introduced, e.g., by silent changes (thereby producing various restriction sites) or to optimize expression for a particular system. Mutations may be introduced to modify the properties of the polypeptide, perhaps to change ligand-binding affinities, interchain affinities, or the polypeptide degradation or turnover rate.

Probes comprising synthetic oligonucleotides or other polynucleotides of the present invention may be derived from naturally occurring or recombinant single- or double-stranded polynucleotides, or be chemically synthesized. Probes may also be labeled by nick translation, Klenow fill-in reaction, or other methods known in the art.

Portions of the polynucleotide sequence having at least about eight nucleotides, usually at least about 15 nucleotides, and fewer than about 9 Kb, usually fewer than about 1.0 Kb, from a polynucleotide sequence encoding BRG1 are preferred as probes. This definition therefore includes probes of sizes 8 nucleotides through 9000 nucleotides. Thus, this definition includes probes of 8, 12, 15, 20, 25, 40, 60, 80, 100, 200, 300, 400 or 500 nucleotides or probes having any number of nucleotides within these ranges of values (e.g., 9, 10, 11, 16, 23, 30, 38, 50, 72, 121, etc. nucleotides) or probes having more than 500 nucleotides. The probes may also be used to determine whether mRNA encoding BRG1 is present in a cell or tissue.

Similar considerations and nucleotide lengths are also applicable to primers which may be used for the amplification of all or part of the BRG1 gene. Thus, a definition for primers includes primers of 8, 12, 15, 20, 25, 40, 60, 80, 100, 200, 300, 400, 500 nucleotides, or primers having any number of nucleotides within these ranges of values (e.g., 9, 10, 11, 16, 23, 30, 38, 50, 72, 121, etc. nucleotides), or primers having more than 500 nucleotides, or any number of nucleotides between 500 and 9000. The primers may also be used to determine whether mRNA encoding BRG1 is present in a cell or tissue. The present invention includes all novel primers having at least 8 nucleotides derived from the BRG1 locus for amplifying the BRG1 gene, its complement or functionally equivalent nucleic acid sequences. The present invention does not include primers which exist in the prior art. That is, the present invention includes all primers having at least 8 nucleotides with the proviso that it does not include primers existing in the prior art.

"Protein modifications or fragments" are provided by the present invention for BRG1 polypeptides or fragments thereof which are substantially homologous to primary structural sequence but which include, e.g., in vivo or in vitro chemical and biochemical modifications or which incorporate unusual amino acids. Such modifications include, for example, acetylation, carboxylation, phosphorylation, glycosylation, ubiquitination, labeling, e.g., with radionuclides, and various enzymatic modifications, as will be readily appreciated by those well skilled in the art. A variety of methods for labeling polypeptides and of substituents or labels useful for such purposes are well known in the art, and include radioactive isotopes such as $^{32}P$, ligands, which bind to labeled antiligands (e.g., antibodies), fluorophores, chemiluminescent agents, enzymes, and antiligands which can serve as specific binding pair members for a labeled ligand. The choice of label depends on the sensitivity required, ease of conjugation with the primer, stability requirements, and available instrumentation. Methods of labeling polypeptides are well known in the art. See, e.g., Sambrook et al. (1989) or Ausubel et al. (1992).

Besides substantially full-length polypeptides, the present invention provides for biologically active fragments of the polypeptides. Significant biological activities include RB binding activity, immunological activity and other biological activities characteristic of BRG1 polypeptides. Immunological activities include both immunogenic function in a target immune system, as well as sharing of immunological epitopes for binding, serving as either a competitor or substitute antigen for an epitope of the BRG1 protein. As used herein, "epitope" refers to an antigenic determinant of a polypeptide. An epitope could comprise three amino acids in a spatial conformation which is unique to the epitope. Generally, an epitope consists of at least five such amino acids, and more usually consists of at least 8–10 such amino acids. Methods of determining the spatial conformation of such amino acids are known in the art.

For immunological purposes, tandem-repeat polypeptide segments may be used as immunogens, thereby producing highly antigenic proteins. Alternatively, such polypeptides will serve as highly efficient competitors for specific binding. Production of antibodies specific for BRG1 polypeptides or fragments thereof is described below.

The present invention also provides for fusion polypeptides, comprising BRG1 polypeptides and fragments. Homologous polypeptides may be fusions between two or more BRG1 polypeptide sequences or between the sequences of BRG1 and a related protein. Likewise, heterologous fusions may be constructed which would exhibit a combination of properties or activities of the derivative proteins. For example, ligand-binding or other domains may be "swapped" between different new fusion polypeptides or fragments. Such homologous or heterologous fusion polypeptides may display, for example, altered strength or specificity of binding. Fusion partners include immunoglobulins, bacterial β-galactosidase, trpE, protein A, β-lactamase, alpha amylase, alcohol dehydrogenase and yeast alpha mating factor. See, e.g., Godowski et al. (1988).

Fusion proteins will typically be made by either recombinant nucleic acid methods, as described below, or may be chemically synthesized. Techniques for the synthesis of polypeptides are described, for example, in Merrifield (1963).

"Protein purification" refers to various methods for the isolation of the BRG1 polypeptides from other biological material, such as from cells transformed with recombinant nucleic acids encoding BRG1, and are well known in the art. For example, such polypeptides may be purified by immunoaffinity chromatography employing, e.g., the antibodies provided by the present invention. Various methods of protein purification are well known in the art, and include those described in Deutscher (1990) and Scopes (1982).

The terms "isolated", "substantially pure", and "substantially homogeneous" are used interchangeably to describe a protein or polypeptide which has been separated from components which accompany it in its natural state. A monomeric protein is substantially pure when at least about 60 to 75% of a sample exhibits a single polypeptide sequence. A substantially pure protein will typically comprise about 60 to 90% W/W of a protein sample, more usually about 95%, and preferably will be over about 99% pure. Protein purity or homogeneity may be indicated by a number of means well known in the art, such as polyacrylamide gel electrophoresis or a protein sample, followed by visualizing a single polypeptide band upon staining the gel. For certain purposes, higher resolution may be provided by using HPLC or other means well known in the art which are utilized for purification.

A BRG1 protein is substantially free of naturally associated components when it is separated from the native contaminants which accompany it in its natural state. Thus, a polypeptide which is chemically synthesized or synthesized in a cellular system different from the cell from which it naturally originates will be substantially free from its naturally associated components. A protein may also be rendered substantially free of naturally associated components by isolation, using protein purification techniques well known in the art.

A polypeptide produced as an expression product of an isolated and manipulated genetic sequence is an "isolated polypeptide," as used herein, even if expressed in a homologous cell type. Synthetically made forms or molecules expressed by heterologous cells are inherently isolated molecules.

"Recombinant nucleic acid" is a nucleic acid which is not naturally occurring, or which is made by the artificial combination of two otherwise separated segments of sequence. This artificial combination is often accomplished by either chemical synthesis means, or by the artificial manipulation of isolated segments of nucleic acids, e.g., by genetic engineering techniques. Such is usually done to replace a codon with a redundant codon encoding the same or a conservative amino acid, while typically introducing or removing a sequence recognition site. Alternatively, it is performed to join together nucleic acid segments of desired functions to generate a desired combination of functions.

"Regulatory sequences" refers to those sequences normally within 100 Kb of the coding region of a locus, but they may also be more distant from the coding region, which affect the expression of the gene (including transcription of the gene, and translation, splicing, stability or the like of the messenger RNA).

"Substantial homology or similarity". A nucleic acid or fragment thereof is "substantially homologous" ("or substantially similar") to another if, when optimally aligned (with appropriate nucleotide insertions or deletions) with the other nucleic acid (or its complementary strand), there is nucleotide sequence identity in at least about 60% of the nucleotide bases, usually at least about 70%, more usually at least about 80%, preferably at least about 90%, and more preferably at least about 95–98% of the nucleotide bases.

To determine homology between two different nucleic acids, the percent homology is to be determined using the BLASTN program "BLAST 2 sequences". This program is available for public use from the National Center for Biotechnology Information (NCBI) over the Internet (http://www.ncbi.nlm.nih.gov/gorf/bl2.html) (Altschul et al., 1997). The parameters to be used are whatever combination of the following yields the highest calculated percent homology (as calculated below) with the default parameters shown in parentheses:

Program—blastn
Matrix—0 BLOSUM62
Reward for a match—0 or 1 (1)
Penalty for a mismatch—0, −1, −2 or −3 (−2)
Open gap penalty—0, 1, 2, 3, 4 or 5 (5)
Extension gap penalty—0 or 1 (1)
Gap x_dropoff—0 or 50 (50)
Expect—10

Along with a variety of other results, this program shows a percent identity across the complete strands or across regions of the two nucleic acids being matched. The program shows as part of the results an alignment and identity of the two strands being compared. If the strands are of equal length then the identity will be calculated across the complete length of the nucleic acids. If the strands are of unequal lengths, then the length of the shorter nucleic acid is to be used. If the nucleic acids are quite similar across a portion of their sequences but different across the rest of their sequences, the blastn program "BLAST 2 Sequences" will show an identity across only the similar portions, and these portions are reported individually. For purposes of determining homology herein, the percent homology refers to the shorter of the two sequences being compared. If any one region is shown in different alignments with differing percent identities, the alignments which yield the greatest homology are to be used. The averaging is to be performed as in this example of SEQ ID NOs:3 and 4.

5'-ACCGTAGCTACGTACGTATATAGAAAGGGCGC-GTCGTCGTCGCGTATGACGAC TTAGCATGC-3' (SEQ ID NO:3)

5'-ACCGGTAGCTACGTACGTTATTTAGAAAGGGG-TGTGTGTGTGTGTGTAAACCGGG GTTTTCGG-GATCGTCCGTCGCGTATGACGACTTAGC-CATGCACGGTATATCGTATTA GGACTAGCGATTGACTAG-3' (SEQ ID NO:4)

The program "BLAST 2 Sequences" shows differing alignments of these two nucleic acids depending upon the parameters which are selected. As examples, four sets of parameters were selected for comparing SEQ ID NOs:3 and 4 (gap x_dropoff was 50 for all cases), with the results shown in Table 1. It is to be noted that none of the sets of parameters selected as shown in Table 1 is necessarily the best set of parameters for comparing these sequences. The percent homology is calculated by multiplying for each region showing identity the fraction of bases of the shorter strand within a region times the percent identity for that region and adding all of these together. For example, using the first set of parameters shown in Table 1, SEQ ID NO:3 is the short sequence (63 bases), and two regions of identity are shown, the first encompassing bases 4–29 (26 bases) of SEQ ID NO:3 with 92% identity to SEQ ID NO:4 and the second encompassing bases 39–59 (21 bases) of SEQ ID NO:3 with 100% identity to SEQ ID NO:4. Bases 1–3, 30–38 and 60–63 (16 bases) are not shown as having any identity with SEQ ID NO:4. Percent homology is calculated as: $(26/63)(92)+(21/63)(100)+(16/63)(0)=71.3\%$ homology. The percents of homology calculate using each of the four sets of parameters shown are listed in Table 1. Several other combinations of parameters are possible, but they are not listed for the sake of brevity. It is seen that each set of parameters resulted in a different calculated percent homology. Because the result yielding the highest percent homology is to be used, based solely on these four sets of parameters one would state that SEQ ID NOs:3 and 4 have 87.1% homology. Again it is to be noted that use of other parameters may show an even higher homology for SEQ ID NOs:3 and 4, but for brevity not all the possible results are shown.

TABLE 1

| | | | Parameter Values | | | |
|---|---|---|---|---|---|---|
| Match | Mis-match | Open Gap | Extension Gap | Regions of identiy (%) | | Homology |
| 1 | −2 | 5 | 1 | 4–29 of 3 and 5–31 of 4 (92%) | 39–59 of 3 and 71–91 of 4 (100%) | 71.3 |
| 1 | −2 | 2 | 1 | 4–29 of 3 and 5–31 of 4 (92%) | 33–63 of 3 and 64–96 of 4 (93%) | 83.7 |
| 1 | −1 | 5 | 1 | — | 30–59 of 3 and 61–91 of 4 (93%) | 44.3 |
| 1 | −1 | 2 | 1 | 4–29 of 3 and 5–31 of 4 (92%) | 30–63 of 3 and 61–96 of 4 (91%) | 87.1 |

Alternatively, substantial homology or (similarity) exists when a nucleic acid or fragment thereof will hybridize to another nucleic acid (or a complementary strand thereof) under selective hybridization conditions, to a strand, or to its complement. Selectivity of hybridization exists when hybridization which is substantially more selective than total lack of specificity occurs. Typically, selective hybridization will occur when there is at least about 55% homology over a stretch of at least about 14 nucleotides, preferably at least about 65%, more preferably at least about 75%, and most preferably at least about 90%. See, Kanehisa, 1984. The length of homology comparison, as described, may be over longer stretches, and in certain embodiments will often be over a stretch of at least about eight nucleotides, usually at least about 20 nucleotides, more usually at least about 24 nucleotides, typically at least about 28 nucleotides, more typically at least about 32 nucleotides, and preferably at least about 36 or more nucleotides.

Nucleic acid hybridization will be affected by such conditions as salt concentration, temperature, or organic solvents, in addition to the base composition, length of the complementary strands, and the number of nucleotide base mismatches between the hybridizing nucleic acids, as will be readily appreciated by those skilled in the art. Stringent temperature conditions will generally include temperatures in excess of 30° C., typically in excess of 37° C., and preferably in excess of 45° C. Stringent salt conditions will ordinarily be less than 1000 mM, typically less than 500 mM, and preferably less than 200 mM. However, the combination of parameters is much more important than the measure of any single parameter. The stringency conditions are dependent on the length of the nucleic acid and the base composition of the nucleic acid and can be determined by techniques well known in the art. See, e.g., Wetmur & Davidson, 1968.

Probe sequences may also hybridize specifically to duplex DNA under certain conditions to form triplex or other higher order DNA complexes. The preparation of such probes and suitable hybridization conditions are well known in the art.

The terms "substantial homology" or "substantial identity", when referring to polypeptides, indicate that the polypeptide or protein in question exhibits at least about 30% identity with an entire naturally-occurring protein or a portion thereof, usually at least about 70% identity, more usually at least about 80% identity, preferably at least about 90% identity, and more preferably at least about 95% identity.

Homology, for polypeptides, is typically measured using sequence analysis software. See, e.g., the Sequence Analysis Software Package of the Genetics Computer Group, University of Wisconsin Biotechnology Center, 910 University Avenue, Madison, Wis. 53705. Protein analysis software matches similar sequences using measures of homology assigned to various substitutions, deletions and other modifications. Conservative substitutions typically include substitutions within the following groups: glycine, alanine; valine, isoleucine, leucine; aspartic acid, glutamic acid; asparagine, glutamine; serine, threonine; lysine, arginine; and phenylalanine, tyrosine.

"Substantially similar function" refers to the function of a modified nucleic acid or a modified protein, with reference to the wild-type BRG1 nucleic acid or wild-type BRG1 polypeptide. The modified polypeptide will be substantially homologous to the wild-type BRG1 polypeptide and will have substantially the same function. The modified polypeptide may have an altered amino acid sequence and/or may contain modified amino acids. In addition to the function of binding to RB, the modified polypeptide may have other useful properties, such as a longer half-life. The RB binding activity of the modified polypeptide may be substantially the same as the activity of the wild-type BRG1 polypeptide. Alternatively, the RB binding activity of the modified polypeptide may be higher or lower than the activity of the wild-type BRG1 polypeptide. The modified polypeptide is synthesized using conventional techniques, or is encoded by a modified nucleic acid and produced using conventional techniques. The modified nucleic acid is prepared by conventional techniques. A nucleic acid with a function substantially similar to the wild-type BRG1 gene function produces the modified protein described above.

A polypeptide "fragment," "portion" or "segment" is a stretch of amino acid residues of at least about five to seven contiguous amino acids, often at least about seven to nine contiguous amino acids, typically at least about nine to 13 contiguous amino acids and, most preferably, at least about 20 to 30 or more contiguous amino acids.

The polypeptides of the present invention, if soluble, may be coupled to a solid-phase support, e.g., nitrocellulose, nylon, column packing materials (e.g., Sepharose beads), magnetic beads, glass wool, plastic, metal, polymer gels, cells, or other substrates. Such supports may take the form, for example, of beads, wells, dipsticks, or membranes.

"Target region" refers to a region of the nucleic acid which is amplified and/or detected. The term "target sequence" refers to a sequence with which a probe or primer will form a stable hybrid under desired conditions.

The practice of the present invention employs, unless otherwise indicated, conventional techniques of chemistry, molecular biology, microbiology, recombinant DNA, genetics, and immunology. See, e.g., Maniatis et al. (1982); Sambrook et al. (1989); Ausubel et al. (1992); Glover (1985); Anand (1992); Guthrie and Fink (1991). A general discussion of techniques and materials for human gene mapping is provided, e.g., in White and Lalouel (1988).

Preparation of Recombinant or Chemically Synthesized Nucleic Acids, Vectors Transformation, Host Cells Large amounts of the polynucleotides of the present invention may be produced by replication in a suitable host cell. Natural or synthetic polynucleotide fragments coding for a desired fragment will be incorporated into recombinant polynucleotide constructs, usually DNA constructs, capable of introduction into and replication in a prokaryotic or eukaryotic cell. Usually the polynucleotide constructs will be suitable for replication in a unicellular host, such as yeast or bacteria, but may also be intended for introduction to (with and without integration within the genome) cultured mammalian or plant or other eukaryotic cell lines. The purification of nucleic acids produced by the methods of the present invention are described, e.g., in Sambrook et al. (1989) or Ausubel et al. (1992).

The polynucleotides of the present invention may also be produced by chemical synthesis, e.g., by the phosphoramidite method described by Beaucage & Caruthers (1981) or the triester method according to Matteucci and Caruthers (1981), and may be performed on commercial, automated oligonucleotide synthesizers. A double-stranded fragment may be obtained from the single-stranded product of chemical synthesis either by synthesizing the complementary strand and annealing the strands together under appropriate conditions or by adding the complementary strand using DNA polymerase with an appropriate primer sequence.

Polynucleotide constructs prepared for introduction into a prokaryotic or eukaryotic host may comprise a replication system recognized by the host, including the intended polynucleotide fragment encoding the desired polypeptide, and will preferably also include transcription and translational initiation regulatory sequences operably linked to the polypeptide encoding segment. Expression vectors may include, for example, an origin of replication or autonomously replicating sequence (ARS) and expression control sequences, a promoter, an enhancer and necessary processing information sites, such as ribosome-binding sites, RNA splice sites, polyadenylation sites, transcriptional terminator sequences, and mRNA stabilizing sequences. Secretion signals may also be included where appropriate which allow the protein to cross and/or lodge in cell membranes or be secreted from the cell. Such vectors may be prepared by means of standard recombinant techniques well known in the art and discussed, for example, in Sambrook et al. (1989) or Ausubel et al. (1992).

An appropriate promoter and other necessary vector sequences will be selected so as to be functional in the host, and may include, when appropriate, those naturally associated with BRG1 genes. Examples of workable combinations of cell lines and expression vectors are described in Sambrook et al. (1989) or Ausubel et al. (1992); see also, e.g., Metzger et al. (1988). Many useful vectors are known in the art and may be obtained from such vendors as Stratagene, New England Biolabs, Promega Biotech, and others. Promoters such as the trp, lac and phage promoters, tRNA promoters and glycolytic enzyme promoters may be used in prokaryotic hosts. Useful yeast promoters include promoter regions for metallothionein, 3-phosphoglycerate kinase or other glycolytic enzymes such as enolase or glyceraldehyde-3-phosphate dehydrogenase, enzymes responsible for maltose and galactose utilization, and others. Vectors and promoters suitable for use in yeast expression are further described in Hitzeman et al., EP 73,675A. Appropriate non-native mammalian promoters might include the early and late promoters from SV40 (Fiers et al., 1978) or promoters derived from murine molony leukemia virus, mouse tumor virus, avian sarcoma viruses, adenovirus II, bovine papilloma virus or polyoma. Insect promoters may be derived from baculovirus. In addition, the construct may be joined to an amplifiable gene (e.g., DHFR) so that multiple copies of the gene may be made. For appropriate enhancer and other expression control sequences, see also *Enhancers and Eukaryotic Gene Expression*, Cold Spring Harbor Press, Cold Spring Harbor, N.Y. (1983). See also, e.g., U.S. Pat. Nos. 5,691,198; 5,753,500; 5,747,469 and 5,436,146.

While such expression vectors may replicate autonomously, they may also replicate by being inserted into the genome of the host cell, by methods well known in the art.

Expression and cloning vectors will likely contain a selectable marker, a gene encoding a protein necessary for survival or growth of a host cell transformed with the vector. The presence of this gene ensures growth of only those host cells which express the inserts. Typical selection genes encode proteins that a) confer resistance to antibiotics or other toxic substances, e.g. ampicillin, neomycin, methotrexate, etc., b) complement auxotrophic deficiencies, or c) supply critical nutrients not available from complex media, e.g., the gene encoding D-alanine racemase for Bacilli. The choice of the proper selectable marker will depend on the host cell, and appropriate markers for different hosts are well known in the art.

The vectors containing the nucleic acids of interest can be transcribed in vitro, and the resulting RNA introduced into the host cell by well-known methods, e.g., by injection (see, T. Kubo et al. (1988)), or the vectors can be introduced directly into host cells by methods well known in the art, which vary depending on the type of cellular host, including electroporation; transfection employing calcium chloride, rubidium chloride, calcium phosphate, DEAE-dextran, or other substances; microprojectile bombardment; lipofection; infection (where the vector isran infectious agent, such as a retroviral genome); and other methods. See generally, Sambrook et al. (1989) and Ausubel et al. (1992). The introduction of the polynucleotides into the host cell by any method known in the art, including, inter alia, those described above, will be referred to herein as "transformation." The cells into which have been introduced nucleic acids described above are meant to also include the progeny of such cells.

Large quantities of the nucleic acids and polypeptides of the present invention may be prepared by expressing the BRG1 nucleic acids or portions thereof in vectors or other expression vehicles in compatible prokaryotic or eukaryotic host cells. The most commonly used prokaryotic hosts are strains of *Escherichia coli*, although other prokaryotes, such as *Bacillus subtilis* or Pseudomonas may also be used.

Mammalian or other eukaryotic host cells, such as those of yeast, filamentous fungi, plant, insect, or amphibian or avian species, may also be useful for production of the proteins of the present invention. Propagation of mammalian cells in culture is per se well known. See, Jakoby and Pastan (eds.) (1979). Examples of commonly used mammalian host cell lines are VERO and HeLa cells, Chinese hamster ovary (CHO) cells, and WI38, BHK, and COS cell lines, although it will be appreciated by the skilled practitioner that other cell lines may be appropriate, e.g., to provide higher expression, desirable glycosylation patterns, or other features. An example of a commonly used insect cell line is SF9.

Clones are selected by using markers depending on the mode of the vector construction. The marker may be on the same or a different DNA molecule, preferably the same DNA molecule. In prokaryotic hosts, the transformant may be selected, e.g., by resistance to ampicillin, tetracycline or other antibiotics. Production of a particular product based on temperature sensitivity may also serve as an appropriate marker.

Prokaryotic or eukaryotic cells transformed with the polynucleotides of the present invention will be useful not only for the production of the nucleic acids and polypeptides of the present invention, but also, for example, in studying the characteristics of BRG1 polypeptides.

Antisense polynucleotide sequences are useful in preventing or diminishing the expression of the BRG1 locus, as will be appreciated by those skilled in the art. For example, polynucleotide vectors containing all or a portion of the BRG1 locus or other sequences from the BRG1 region (particularly those flanking the BRG1 locus) may be placed under the control of a promoter in an antisense orientation and introduced into a cell. Expression of such an antisense construct within a cell will interfere with BRG1 transcription and/or translation and/or replication.

Methods of Use: Nucleic Acid Diagnosis and Diagnostic Kits

In order to detect the presence of a BRG1 allele predisposing an individual to cancer, a biological sample such as blood is prepared and analyzed for the presence or absence of susceptibility alleles of BRG1. In order to detect the presence of neoplasia, the progression toward malignancy of a precursor lesion, or as a prognostic indicator., a biological sample of the lesion is prepared and analyzed for the presence or absence of neoplastic alleles of BRG1. Results of these tests and interpretive information are returned to the health care provider for communication to the tested individual. Such diagnoses may be performed by diagnostic laboratories, or, alternatively, diagnostic kits are manufactured and sold to health care providers or to private individuals for self-diagnosis.

Initially, the screening method involves amplification of the relevant BRG1 sequences, e.g., by PCR, followed by DNA sequence analysis. In another preferred embodiment of the invention, the screening method involves a non-PCR based strategy. Such screening methods include two-step label amplification methodologies that are well known in the art. Both PCR and non-PCR based screening strategies can detect target sequences with a high level of sensitivity.

The most popular method used today is target amplification. Here, the target nucleic acid sequence is amplified with polymerases. One particularly preferred method using polymerase-driven amplification is the polymerase chain reaction (PCR). The polymerase chain reaction and other polymerase-driven amplification assays can achieve over a million-fold increase in copy number through the use of polymerase-driven amplification cycles. Once amplified, the resulting nucleic acid can be sequenced or used as a substrate for DNA probes.

When the probes are used to detect the presence of the target sequences (for example, in screening for cancer susceptibility), the biological sample to be analyzed, such as blood or serum, may be treated, if desired, to extract the nucleic acids. The sample nucleic acid may be prepared in various ways to facilitate detection of the target sequence; e.g. denaturation, restriction digestion, electrophoresis or dot blotting. The targeted region of the analyte nucleic acid usually must be at least partially single-stranded to form hybrids with the targeting sequence of the probe. If the sequence is naturally single-stranded, denaturation will not be required. However, if the sequence is double-stranded, the sequence will probably need to be denatured. Denaturation can be carried out by various techniques known in the art.

Analyte nucleic acid and probe are incubated under conditions which promote stable hybrid formation of the target sequence in the probe with the putative targeted sequence in the analyte. The region of the probes which is used to bind to the analyte can be made completely complementary to the targeted region. Therefore, high stringency conditions are desirable in order to prevent false positives. However, conditions of high stringency are used only if the probes are complementary to regions of the chromosome which are unique in the genome. The stringency of hybridization is determined by a number of factors during hybridization and during the washing procedure, including temperature, ionic strength, base composition, probe length, and concentration of formamide. These factors are outlined in, for example, Maniatis et al. (1982) and Sambrook et al. (1989). Under certain circumstances, the formation of higher order hybrids, such as triplexes, quadraplexes, etc., may be desired to provide the means of detecting target sequences.

Detection, if any, of the resulting hybrid is usually accomplished by the use of labeled probes. Alternatively, the probe may be unlabeled, but may be detectable by specific binding with a ligand which is labeled, either directly or indirectly. Suitable labels, and methods for labeling probes and ligands are known in the art, and include, for example, radioactive labels which may be incorporated by known methods (e.g., nick translation, random priming or kinasing), biotin, fluorescent groups, chemiluminescent groups (e.g., dioxetanes, particularly triggered dioxetanes), enzymes, antibodies, gold nanoparticles and the like. Variations of this basic scheme are known in the art, and include those variations that facilitate separation of the hybrids to be detected from extraneous materials and/or that amplify the signal from the labeled moiety. A number of these variations are reviewed in, e.g., Matthews and Kricka (1988); Landegren et al. (1988); Mifflin (1989); U.S. Pat. No. 4,868,105; and in EPO Publication No. 225,807.

Non-PCR based screening assays are also contemplated in this invention. This procedure hybridizes a nucleic acid probe (or an analog such as a methyl phosphonate backbone replacing the normal phosphodiester), to the low level DNA target. This probe may have an enzyme covalently linked to the probe, such that the covalent linkage does not interfere with the specificity of the hybridization. This enzyme-probe-conjugate-target nucleic acid complex can then be isolated away from the free probe enzyme conjugate and a substrate is added for enzyme detection. Enzymatic activity is observed as a change in color development or luminescent output resulting in a $10^3$–$10^6$ increase in sensitivity. For an example relating to the preparation of oligodeoxynucleotide-alkaline phosphatase conjugates and their use as hybridization probes see Jablonski et al. (1986).

Two-step label amplification methodologies are known in the art. These assays work on the principle that a small ligand (such as digoxigenin, biotin, or the like) is attached to a nucleic acid probe capable of specifically binding BRG1. Allele specific probes are also contemplated within the scope of this example and exemplary allele specific probes include probes encompassing the predisposing mutations of this disclosure.

In one example, the small ligand attached to the nucleic acid probe is specifically recognized by an antibody-enzyme conjugate. In one embodiment of this example, digoxigenin is attached to the nucleic acid probe. Hybridization is detected by an antibody-alkaline phosphatase conjugate which turns over a chemiluminescent substrate. For methods for labeling nucleic acid probes according to this embodiment see Martin et al. (1990). In a second example, the small ligand is recognized by a second ligand-enzyme conjugate that is capable of specifically complexing to the first ligand. A well known embodiment of this example is the biotin-avidin type of interactions. For methods for labeling nucleic acid probes and their use in biotin-avidin based assays see Rigby et al. (1977) and Nguyen et al. (1992).

It is also contemplated within the scope of this invention that the nucleic acid probe assays will employ a cocktail of nucleic acid probes capable of detecting BRG1 genes. Thus, in one example to detect the presence of BRG1 in a cell sample, more than one probe complementary to BRG1 is employed and in particular the number of different probes is alternatively 2, 3, or 5 different nucleic acid probe sequences. In another example, to detect the presence of mutations in the BRG1 gene sequence in a patient, more than one probe complementary to BRG1 is employed where the cocktail includes probes capable of binding to the allele-specific mutations identified in populations of patients with alterations in BRG1. In this embodiment, any number of probes can be used, and will preferably include probes corresponding to the major gene mutations identified as predisposing an individual to prostate or other cancer.

It is further contemplated within the scope of this invention that the nucleic acid probe assays of this invention will employ the recently developed nucleic acid microchip technology which utilizes an array of many thousands of probes bound to a chip to analyze a sample. This method thus analyzes the sample simultaneously using all of the probes which are bound to the microchip. For published examples of this technology see Hacia et al. (1996); Shoemaker et al. (1996); Chee et al. (1996); Lockhart et al. (1996); DeRisi et al. (1996); Lipshutz et al. (1995).

Methods of Use: Peptide Diagnosis and Diagnostic Kits

The neoplastic condition of lesions can also be detected on the basis of the alteration of wild-type BRG1 polypeptide. Such alterations can be determined by sequence analysis in accordance with conventional techniques. More preferably, antibodies (polyclonal or monoclonal) are used to detect differences in or the absence of BRG1 peptides. In a preferred embodiment of the invention, antibodies will immunoprecipitate BRG1 proteins from solution as well as react with BRG1 protein on Western or inimmunoblots of polyacrylamide gels. In another preferred embodiment, antibodies will detect BRG1 proteins in paraffin or frozen tissue sections, using immunocytochemical techniques. Techniques for raising and purifying antibodies are well known in the art, and any such techniques may be chosen to achieve the preparation of the invention.

Preferred embodiments relating to methods for detecting BRG1 or its mutations include enzyme linked immunosorbent assays (ELISA), radioimmunoassays (RIA), immunoradiometric assays (IRMA) and immunoenzymatic assays (IEMA), including sandwich assays using monoclonal and/or polyclonal antibodies. Exemplary sandwich assays are described by David et al. (U.S. Pat. Nos. 4,376,110 and 4,486,530, hereby incorporated by reference) and exemplified in Example 10.

Methods of Use: Drug Screening

The present invention is particularly useful for screening compounds by using the BRG1 polypeptide or fragments thereof in any of a variety of drug screening techniques. The BRG1 polypeptide or fragment employed in such a test may either be free in solution, affixed to a solid support, or borne on a cell surface. One method of drug screening measures the binding of RB by BRG1. One may measure, for example, to what extent the binding activity of BRG1 is enhanced, or possibly inhibited, by the agent being tested.

One method of drug screening utilizes eucaryotic or procaryotic host cells which are stably transformed with recombinant polynucleotides expressing the polypeptide or fragment, preferably in competitive binding assays. Such cells, either in viable or fixed form, can be used for standard binding assays. One may measure, for example, for the formation of complexes between a BRG1 polypeptide or fragment and the agent being tested, or examine the degree to which the formation of a complex between a BRG1 polypeptide or fragment and a known ligand is interfered with by the agent being tested.

Thus, the present invention provides methods of screening for drugs comprising contacting such an agent with a BRG1 polypeptide or fragment thereof and assaying (i) for the presence of a complex between the agent and the BRG1 polypeptide or fragment, or (ii) for the presence of a complex between the BRG1 polypeptide or fragment and a ligand, by methods well known in the art. In such competitive binding assays the BRG1 polypeptide or fragment is typically labeled. Free BRG1 polypeptide or fragment is separated from that present in a protein:protein complex, and the amount of free (i.e., uncomplexed) label is a measure of the binding of the agent being tested to BRG1 or its interference with BRG1:ligand binding. One may also measure the amount of bound, rather than free. BRG1. It is also possible to label the ligand rather than the BRG1 and to measure the amount of ligand binding to BRG1 in the presence and in the absence of the drug being tested.

Another technique for drug screening provides high throughput screening for compounds having suitable binding affinity to the BRG1 polypeptide and is described in detail in Geysen (published PCT published application WO 84/03564). Briefly stated, large numbers of different small peptide test compounds are synthesized on a solid substrate, such as plastic pins or some other surface. The peptide test compounds are reacted with BRG1 polypeptide and washed. Bound BRG1 polypeptide is then detected by methods well known in the art.

Purified BRG1 can be coated directly onto plates for use in the aforementioned drug screening techniques. However, non-neutralizing antibodies to the polypeptide can be used to capture antibodies to immobilize the BRG1 polypeptide on the solid phase.

This invention also contemplates the use of competitive drug screening assays in which neutralizing antibodies capable of specifically binding the BRG1 polypeptide compete with a test compound for binding to the BRG1 polypeptide or fragments thereof. In this manner, the antibodies can be used to detect the presence of any peptide which shares one or more antigenic determinants of the BRG1 polypeptide.

The invention is particularly useful for screening compounds by using BRG1 protein in transformed cells, transfected oocytes or transgenic animals. The drug is added to the cells in culture or administered to a transgenic animal containing mutant BRG1 and the effect on cell growth is compared to the cell growth of cells or in animals containing the wild-type BRG1. Drug candidates which result in cell growth at a more normal level are useful for treating or preventing prostate or other cancer.

The above screening methods are not limited to assays employing only BRG1 but are also applicable to studying BRG1-protein complexes. Such assays can be performed in vitro. BRG1 interacts with RB to regulate a set of transcription factors known as E2Fs. This set of transcription factors controls a set of genes regulating G1 to S transition in the cell cycle. If this transition is blocked, the cell cycle will not progress and growth arrest occurs. Drugs that can replace a defective BRG1 in the interaction with or stimulation of RB will continue to maintain the control of E2Fs and can provide a therapeutic avenue. Drugs can be screened for their binding to wild-type RB, especially those that bind at the same site at which BRG1 interacts with RB. Such assays can be performed, e.g., by performing competitive binding assays of BRG1 and putative drug to RB. Drugs obtained from such a screen can then be used in in vivo assays.

The polypeptide of the invention may also be used for screening compounds developed as a result of combinatorial library technology. Combinatorial library technology provides an efficient way of testing a potential vast number of different substances for ability to modulate activity of a polypeptide. Such libraries and their use are known in the art. The use of peptide libraries is preferred. See, for example, WO 97/02048.

Briefly, a method of screening for a substance which modulates activity of a polypeptide may include contacting one or more test substances with the polypeptide in a suitable reaction medium, testing the activity of the treated polypeptide and comparing that activity with the activity of the polypeptide in comparable reaction medium untreated with the test substance or substances. A difference in activity between the treated and untreated polypeptides is indicative of a modulating effect of the relevant test substance or substances.

Prior to or as well as being screened for modulation of activity, test substances may be screened for ability to interact with the polypeptide, e.g., in a yeast two-hybrid system (e.g., Bartel et al., 1993; Fields and Song, 1989; Chevray and Nathans, 1992, Lee et al., 1995). This system may be used as a coarse screen prior to testing a substance for actual ability to modulate activity of the polypeptide. Alternatively, the screen could be used to screen test substances for binding to a BRG1 specific binding partner, or to find mimetics of the BRG1 polypeptide.

Following identification of a substance which modulates or affects polypeptide activity, the substance may be investigated further. Furthermore, it may be manufactured and/or used in preparation, i.e., manufacture or formulation, or a composition such as a medicament, pharmaceutical composition or drug. These may be administered to individuals.

Thus, the present invention extends in various aspects not only to a substance identified using a nucleic acid molecule as a modulator of polypeptide activity, in accordance with what is disclosed herein, but also a pharmaceutical composition, medicament, drug or other composition comprising such a substance, a method comprising administration of such a composition comprising such a substance, a method comprising administration of such a composition to a patient, e.g., for treatment (which may include preventative treatment) of cancer, use of such a substance in the manufacture of a composition for administration, e.g., for treatment of cancer, and a method of making a pharmaceutical composition comprising admixing such a substance with a pharmaceutically acceptable excipient, vehicle or carrier, and optionally other ingredients.

A substance identified as a modulator of polypeptide function may be peptide or non-peptide in nature. Non-peptide small molecules are often preferred for many in vivo pharmaceutical uses. Accordingly, a mimetic or mimic of the substance (particularly if a peptide) may be designed for pharmaceutical use.

The designing of mimetics to a known pharmaceutically active compound is a known approach to the development of pharmaceuticals based on a lead compound. This might be desirable where the active compound is difficult or expensive to synthesize or where it is unsuitable for a particular method of administration, e.g., peptides are unsuitable active agents for oral compositions as they tend to be quickly degraded by proteases in the alimentary canal. Mimetic design, synthesis and testing is generally used to avoid randomly screening large numbers of molecules for a target property.

There are several steps commonly taken in the design of a mimetic from a compound having a given target property. First, the particular parts of the compound that are critical and/or important in determining the target property are determined. In the case of a peptide, this can be done by systematically varying the amino acid residues in the peptide, e.g., by substituting each residue in turn. Alanine scans of peptide are commonly used to refine such peptide motifs. These parts or residues constituting the active region of the compound are known as its pharmacophore.

Once the pharmacophore has been found, its structure is modeled according to its physical properties, e.g., stereochemistry, bonding, size and/or charge, using data from a range of sources, e.g., spectroscopic techniques, x-ray diffraction data and NMR. Computational analysis, similarity mapping (which models the charge and/or volume of a pharmacophore, rather than the bonding between atoms) and other techniques can be used in this modeling process.

In a variant of this approach, the three-dimensional structure of the ligand and its binding partner are modeled. This can be especially useful where the ligand and/or binding partner change conformation on binding, allowing the model to take account of this in the design of the mimetic.

A template molecule is then selected onto which chemical groups which mimic the pharmacophore can be grafted. The template molecule and the chemical groups grafted onto it can conveniently be selected so that the mimetic is easy to synthesize, is likely to be pharmacologically acceptable, and does not degrade in vivo, while retaining the biological activity of the lead compound. Alternatively, where the mimetic is peptide-based, further stability can be achieved by cyclizing the peptide, increasing its rigidity. The mimetic or mimetics found by this approach can then be screened to see whether they have the target property, or to what extent they exhibit it. Further optimization or modification can then be carried out to arrive at one or more final mimetics for in vivo or clinical testing.

Methods of Use: Rational Drug Design

The goal of rational drug design is to produce structural analogs of biologically active polypeptides of interest or of small molecules with which they interact (e.g., agonists, antagonists, inhibitors or enhancers) in order to fashion drugs which are, for example, more active or stable forms of the polypeptide, or which, e.g., enhance or interfere with the function of a polypeptide in vivo. See, e.g., Hodgson (1991). In one approach, one first determines the three-dimensional structure of a protein of interest (e.g., BRG1) or, for example, of BRG1-RB complex, by x-ray crystallography, by computer modeling or most typically, by a combination of approaches. Less often, useful information regarding the structure of a polypeptide may be gained by modeling based on the structure of homologous proteins. An example of rational drug design is the development of HIV protease inhibitors (Erickson et al., 1990). In addition, peptides (e.g., BRG1) are analyzed by an alanine scan (Wells, 1991). In this technique, an amino acid residue is replaced by Ala, and its effect on the peptide's activity is determined. Each of the amino acid residues of the peptide is analyzed in this manner to determine the important regions of the peptide.

It is also possible to isolate a target-specific antibody, selected by a functional assay, and then to solve its crystal structure. In principle, this approach yields a pharmacore upon which subsequent drug design can be based. It is possible to bypass protein crystallography altogether by generating anti-idiotypic antibodies (anti-ids) to a functional, pharmacologically active antibody. As a mirror image of a mirror image, the binding site of the anti-ids would be expected to be an analog of the original receptor. The anti-id could then be used to identify and isolate peptides from banks of chemically or biologically produced banks of peptides. Selected peptides would then act as the pharmacore.

Thus, one may design drugs which have, e.g., improved BRG1 activity or stability or which act as enhancers, inhibitors, agonists, antagonists, etc. of BRG1 activity. By virtue of the availability of cloned BRG1 sequences, sufficient amounts of the BRG1 polypeptide may be made available to perform such analytical studies as x-ray crystallography. In addition, the knowledge of the BRG1 protein sequence will guide those employing computer modeling techniques in place of, or in addition to, x-ray crystallography.

Methods of Use: Gene Therapy

According to the present invention, a method is also provided of supplying wild-type BRG1 function to a cell which carries mutant BRG1 alleles. Supplying such a function should suppress neoplastic growth of the recipient cells. The wild-type BRG1 gene or a part of the gene may be introduced into the cell in a vector such that the gene remains extrachromosomal. In such a situation, the gene will be expressed by the cell from the extrachromosomal location. If a gene portion is introduced and expressed in a cell carrying a mutant BRG1 allele, the gene portion should encode a part of the BRG1 protein which is required for non-neoplastic growth of the cell. More preferred is the situation where the wild-type BRG1 gene or a part thereof is introduced into the mutant cell in such a way that it recombines with the endogenous mutant BRG1 gene present in the cell. Such recombination requires a double recombination event which results in the correction of the BRG1 gene mutation. Vectors for introduction of genes both for recombination and for extrachromosomal maintenance are known in the art, and any suitable vector may be used. Methods for introducing DNA into cells such as electroporation, calcium phosphate co-precipitation and viral transduction are known in the art, and the choice of method is within the competence of the practitioner. Cells transformed with the wild-type BRG1 gene can be used as model systems to study cancer remission and drug treatments which promote such remission.

As generally discussed above, the BRG1 gene or fragment, where applicable, may be employed in gene therapy methods in order to increase the amount of the expression products of such genes in cancer cells. Such gene therapy is particularly appropriate for use in both cancerous and pre-cancerous cells, in which the level of BRG1 polypeptide is absent or diminished compared to normal cells. It may also be useful to increase the level of expression of a given BRG1 gene even in those tumor cells in which the mutant gene is expressed at a "normal" level, but the gene product is not fully functional.

Gene therapy would be carried out according to generally accepted methods, for example, as described by Friedman (1991) or Culver (1996). Cells from a patient's tumor would be first analyzed by the diagnostic methods described above, to ascertain the production of BRG1 polypeptide in the tumor cells. A virus or plasmid vector, containing a copy of the BRG1 gene linked to expression control elements and capable of replicating inside the tumor cells, is prepared. Suitable vectors are known, such as disclosed in U.S. Pat. No. 5,252,479 and PCT published application WO 93/07282 and U.S. Pat. Nos. 5,691,198; 5,747,469; 5,436,146 and 5,753,500. The vector is then injected into the patient, either locally at the site of the tumor or systemically (in order to reach any tumor cells that may have metastasized to other sites). If the transfected gene is not permanently incorporated into the genome of each of the targeted tumor cells, the treatment may have to be repeated periodically.

Gene transfer systems known in the art may be useful in the practice of the gene therapy methods of the present invention. These include viral and nonviral transfer methods. A number of viruses have been used as gene transfer vectors or as the basis for repairing gene transfer vectors, including papovaviruses (e.g., SV40, Madzak et al., 1992), adenovirus (Berkner, 1992; Berkner et al., 1988; Gorziglia and Kapikian, 1992; Quantin et al., 1992; Rosenfeld et al., 1992; Wilkinson and Akrigg, 1992; Stratford-Perricaudet et al., 1990; Schneider et al., 1998), vaccinia virus (Moss, 1992; Moss, 1996), adeno-associated virus (Muzyczka, 1992; Ohi et al., 1990; Russell and Hirata, 1998), herpesviruses including HSV and EBV (Margolskee, 1992; Johnson et al., 1992; Fink et al., 1992; Breakefield and Geller, 1987; Freese et al., 1990; Fink et al., 1996), lentiviruses (Naldini et al., 1996), Sindbis and Semliki Forest virus (Berglund et al., 1993), and retroviruses of avian (Bandyopadhyay and Temin, 1984; Petropoulos et al., 1992), murine (Miller, 1992; Miller et al., 1985; Sorge et al., 1984; Mann and Baltimore, 1985; Miller et al., 1988), and human origin (Shimada et al., 1991; Helseth et al., 1990; Page et al., 1990; Buchschacher and Panganiban, 1992). Most human gene therapy protocols have been based on disabled murine retroviruses, although adenovirus and adeno-associated virus are also being used.

Nonviral gene transfer methods known in the art include chemical techniques such as calcium phosphate coprecipitation (Graham and van der Eb, 1973; Pellicer et al., 1980); mechanical techniques, for example microinjection (Anderson et al., 1980; Gordon et al., 1980; Brinster et al., 1981; Costantini and Lacy, 1981); membrane fusion-mediated transfer via liposomes (Felgner et al., 1987; Wang and Huang, 1989; Kaneda et al, 1989; Stewart et al., 1992; Nabel et al., 1990; Lim et al., 1991); and direct DNA uptake and receptor-mediated DNA transfer (Wolff et al., 1990; Wu et al., 1991; Zenke et al., 1990; Wu et al., 1989; Wolff et al., 1991; Wagner et al., 1990; Wagner et al., 1991; Cotten et al., 1990; Curiel et al., 1992; Curiel et al., 1991). Viral-mediated gene transfer can be combined with direct in vivo gene transfer using liposome delivery, allowing one to direct the viral vectors to the tumor cells and not into the surrounding nondividing cells. Alternatively, the retroviral vector producer cell line can be injected into tumors (Culver et al., 1992). Injection of producer cells would then provide a continuous source of vector particles. This technique has been approved for use in humans with inoperable brain tumors.

In an approach which combines biological and physical gene transfer methods, plasmid DNA of any size is combined with a polylysine-conjugated antibody specific to the adenovirus hexon protein, and the resulting complex is bound to an adenovirus vector. The trimolecular complex is then used to infect cells. The adenovirus vector permits efficient binding, internalization, and degradation of the endosome before the coupled DNA is damaged. For other techniques for the delivery of adenovirus based vectors see Schneider et al. (1998) and U.S. Pat. Nos. 5,691,198; 5,747,469; 5,436,146 and 5,753,500.

Liposome/DNA complexes have been shown to be capable of mediating direct in vivo gene transfer. While in standard liposome preparations the gene transfer process is nonspecific, localized in vivo uptake and expression have been reported in tumor deposits, for example, following direct in situ administration (Nabel, 1992).

Expression vectors in the context of gene therapy are meant to include those constructs containing sequences sufficient to express a polynucleotide that has been cloned therein. In viral expression vectors, the construct contains viral sequences sufficient to support packaging of the construct. If the polynucleotide comprises BRG1, expression will produce BRG1. If the polynucleotide encodes an antisense polynucleotide or a ribozyme, expression will produce the antisense polynucleotide or ribozyme. Thus in this context, expression does not require that a protein product be synthesized. In addition to the polynucleotide cloned into the expression vector, the vector also contains a promoter functional in eukaryotic cells. The cloned polynucleotide sequence is under control of this promoter. Suitable eukaryotic promoters include those described above. The expression vector may also include sequences, such as selectable markers and other sequences described herein.

Gene transfer techniques which target DNA directly to prostate is preferred. Receptor-mediated gene transfer, for example, is accomplished by the conjugation of DNA (usually in the form of covalently closed supercoiled plasmid) to a protein ligand via polylysine. Ligands are chosen on the basis of the presence of the corresponding ligand receptors on the cell surface of the target cell/tissue type. These ligand-DNA conjugates can be injected directly into the blood if desired and are directed to the target tissue where receptor binding and internalization of the DNA-protein complex occurs. To overcome the problem of intracellular destruction of DNA, coinfection with adenovirus can be included to disrupt endosome function.

The therapy is as follows: patients who carry a BRG1 susceptibility allele are treated with a gene delivery vehicle such that some or all of their prostate precursor cells receive at least one additional copy of a functional normal BRG1 allele. In this step, the treated individuals have reduced risk of prostate or other cancer to the extent that the effect of the susceptible allele has been countered by the presence of the normal allele.

Methods of Use: Peptide Therapy

Peptides which have BRG1 activity can be supplied to cells which carry mutant or missing BRG1 alleles. The sequence of the BRG1 protein is disclosed (SEQ ID NO:2). Protein can be produced by expression of the cDNA sequence in bacteria, for example, using known expression vectors. Alternatively, BRG1 polypeptide can be extracted from BRG1-producing mammalian cells. In addition, the techniques of synthetic chemistry can be employed to synthesize BRG1 protein. Any of such techniques can provide the preparation of the present invention which comprises the BRG1 protein. The preparation is substantially free of other human proteins. This is most readily accomplished by synthesis in a microorganism or in vitro.

Active BRG1 molecules can be introduced into cells by microinjection or by use of liposomes, for example. Alternatively, some active molecules may be taken up by cells, actively or by diffusion. Extracellular application of the BRG1 gene product may be sufficient to affect tumor growth. Supply of molecules with BRG1 activity should lead to partial reversal of the neoplastic state. Other molecules with BRG1 activity (for example, peptides, drugs or organic compounds) may also be used to effect such a reversal. Modified polypeptides having substantially similar function are also used for peptide therapy.

Methods of Use: Transformed Hosts

Similarly, cells and animals which carry a mutant BRG1 allele can be used as model systems to study and test for substances which have potential as therapeutic agents. The cells are typically cultured epithelial cells. These may be isolated from individuals with BRG1 mutations, either somatic or germline. Alternatively, the cell line can be engineered to carry the mutation in the BRG1 allele, as described above. After a test substance is applied to the cells, the neoplastically transformed phenotype of the cell is determined. Any trait of neoplastically transformed cells can be assessed, including anchorage-independent growth, tumorigenicity in nude mice, invasiveness of cells, and growth factor dependence. Assays for each of these traits are known in the art.

Animals for testing therapeutic agents can be selected after mutagenesis of whole animals or after treatment of germline cells or zygotes. Such treatments include insertion of mutant BRG1 alleles, usually from a second animal species, as well as insertion of disrupted homologous genes. Alternatively, the endogenous BRG1 gene of the animals may be disrupted by insertion or deletion mutation or other genetic alterations using conventional techniques (Capecchi, 1989; Valancius and Smithies. 1991; Hasty et al., 1991; Shinkai et al., 1992; Mombaerts et al., 1992; Philpott et al., 1992; Snouwaert et al., 1992; Donehower et al., 1992). After test substances have been administered to the animals, the growth of tumors must be assessed. If the test substance prevents or suppresses the growth of tumors, then the test substance is a candidate therapeutic agent for the treatment of the cancers identified herein. These animal models provide an extremely important testing vehicle for potential therapeutic products.

The identification of the association between the BRG1 gene mutations and prostate and other cancers permits the early presymptomatic screening of individuals to identify those at risk for developing such cancers. To identify such individuals, BRG1 alleles are screened for mutations either directly or after cloning the alleles. The alleles are tested for the presence of nucleic acid sequence differences from the normal allele using any suitable technique, including but not limited to, one of the following methods: fluorescent in situ hybridization (FISH), direct DNA sequencing, PFGE analysis, Southern blot analysis, single stranded conformation analysis (SSCP), linkage analysis, RNase protection assay, allele specific oligonucleotide (ASO), dot blot analysis and PCR-SSCP analysis. Also useful is the recently developed technique of DNA microchip technology. For example, either (1) the nucleotide sequence of both the cloned alleles and normal BRG1 gene or appropriate fragment (coding sequence or genomic sequence) are determined and then compared, or (2) the RNA transcripts of the BRG1 gene or gene fragment are hybridized to single stranded whole genomic DNA from an individual to be tested, and the resulting heteroduplex is treated with Ribonuclease A (RNase A) and run on a denaturing gel to detect the location of any mismatches. Two of these methods can be carried out according to the following procedures.

The alleles of the BRG1 gene in an individual to be tested are cloned using conventional techniques. For example, a blood sample is obtained from the individual. The genomic DNA isolated from the cells in this sample is partially digested to an average fragment size of approximately 20 kb. Fragments in the range from 18–21 kb are isolated. The resulting fragments are ligated into an appropriate vector. The sequences of the clones are then determined and compared to the normal BRG1 gene.

Alternatively, polymerase chain reactions (PCRs) are performed with primer pairs for the 5' region or the exons of the BRG1 gene. PCRs can also be performed with primer pairs based on any sequence of the normal BRG1 gene. For example, primer pairs for one of the introns can be prepared and utilized. Finally, RT-PCR can also be performed on the mRNA. The amplified products are then analyzed by single stranded conformation polymorphisms (SSCP) using conventional techniques to identify any differences and these are then sequenced and compared to the normal gene sequence.

Individuals can be quickly screened for common BRG1 gene variants by amplifying the individual's DNA using suitable primer pairs and analyzing the amplified product, e.g. by dot-blot hybridization using allele-specific oligonucleotide probes.

The second method employs RNase A to assist in the detection of differences between the normal BRG1 gene and defective genes. This comparison is performed in steps using small (500 bp) restriction fragments of the BRG1 gene as the probe. First, the BRG1 gene is digested with a restriction enzyme(s) that cuts the gene sequence into fragments of approximately 500 bp. These fragments are separated on an electrophoresis gel, purified from the gel and cloned individually, in both orientations, into an SP6 vector (e.g., pSP64 or pSP65). The SP6-based plasmids containing inserts of the BRG1 gene fragments are transcribed in vitro using the SP6 transcription system, well known in the art, in the presence of $[\alpha-^{32}P]GTP$, generating radiolabeled RNA transcripts of both strands of the gene.

Individually, these RNA transcripts are used to form heteroduplexes with the allelic DNA using conventional techniques. Mismatches that occur in the RNA:DNA heteroduplex, owing to sequence differences between the BRG1 fragment and the BRG1 allele subclone from the individual, result in cleavage in the RNA strand when treated with RNase A. Such mismatches can be the result of point mutations or small deletions in the individual's allele. Cleavage of the RNA strand yields two or more small RNA fragments, which run faster on the denaturing gel than the RNA probe itself.

Any differences which are found, will identify an individual as having a molecular variant of the BRG1 gene and the consequent presence of or predisposition toward prostate cancer. These variants can take a number of forms. The most severe forms would be frame shift mutations or large deletions which would cause the gene to code for an abnormal protein or one which would significantly alter protein expression. Less severe disruptive mutations would include small in-frame deletions and nonconservative base pair substitutions which would have a significant effect on the protein produced, such as changes to or from a cysteine residue, from a basic to an acidic amino acid or vice versa, from a hydrophobic to hydrophilic amino acid or vice versa, or other mutations which would affect secondary or tertiary protein structure. Silent mutations or those resulting in conservative amino acid substitutions would not generally be expected to disrupt protein function.

Genetic testing will enable practitioners to identify individuals at risk for prostate cancer at, or even before, birth. Presymptomatic diagnosis will enable prevention of the cancer. Finally, this invention changes our understanding of the cause and treatment of prostate cancer.

Methods of Use: Transgenic/Knockout Animals

In one embodiment of the invention, transgenic animals are produced which contain a functional transgene encoding a functional BRG1 polypeptide or variants thereof. Transgenic animals expressing BRG1 transgenes, recombinant cell lines derived from such animals and transgenic embryos may be useful in methods for screening for and identifying agents that induce or repress function of BRG1. Transgenic animals of the present invention also can be used as models for studying indications such as cancers.

In one embodiment of the invention, a BRG1 transgene is introduced into a non-human host to produce a transgenic animal expressing a human or murine BRG1 gene. The transgenic animal is produced by the integration of the transgene into the genome in a manner that permits the expression of the transgene. Methods for producing transgenic animals are generally described in U.S. Pat. No. 4,873,191; Brinster et al. (1985); and "Manipulating the Mouse Embryo; A Laboratory Manual" 2nd edition (eds., Hogan, Beddington, Costantini and Long, Cold Spring Harbor Laboratory Press (1994); which is incorporated herein by reference in its entirety).

It may be desirable to replace the endogenous BRG1 by homologous recombination between the transgene and the endogenous gene; or the endogenous gene may be eliminated by deletion as in the preparation of "knock-out" animals. Typically, a BRG1 gene flanked by genomic sequences is transferred by microinjection into a fertilized egg. The microinjected eggs are implanted into a host female, and the progeny are screened for the expression of the transgene. Transgenic animals may be produced from the fertilized eggs from a number of animals including, but not limited to reptiles, amphibians, birds, mammals, and fish. Within a particularly preferred embodiment, transgenic mice are generated which overexpress BRG1 or express a mutant form of the polypeptide. Alternatively, the absence of a BRG1 in "knock-out" mice permits the study of the effects that loss of BRG1 protein has on a cell in vivo. Knock-out mice also provide a model for the development of BRG1-related cancers.

Methods for producing knockout animals are generally described by Shastry (1995), Shastry (1998) and Osterrieder and Wolf (1998). The production of conditional knockout animals, in which the gene is active until knocked out at the desired time is generally described by Feil et al. (1996), Gagneten et al. (1997) and Lobe and Nagy (1998). Each of these references is incorporated herein by reference.

As noted above, transgenic animals and cell lines derived from such animals may find use in certain testing experiments. In this regard, transgenic animals and cell lines capable of expressing wild-type or mutant BRG1 may be exposed to test substances. These test substances can be screened for the ability to enhance wild-type BRG1 expression and or function or impair the expression or function of mutant BRG1.

Pharmaceutical Compositions and Routes of Administration

The BRG1 polypeptides, antibodies, peptides and nucleic acids of the present invention can be formulated in pharmaceutical compositions, which are prepared according to conventional pharmaceutical compounding techniques. See, for example, *Remington's Pharmaceutical Sciences*, 18th Ed. (1990, Mack Publishing Co., Easton, Pa.). The composition may contain the active agent or pharmaceutically acceptable salts of the active agent. These compositions may comprise, in addition to one of the active substances, a pharmaceutically acceptable excipient, carrier, buffer, stabilizer or other materials well known in the art. Such materials should be non-toxic and should not interfere with the efficacy of the active ingredient. The carrier may take a wide variety of forms depending on the form of preparation desired for administration, e.g., intravenous, oral, intrathecal, epineural or parenteral.

For oral administration, the compounds can be formulated into solid or liquid preparations such as capsules, pills, tablets, lozenges, melts, powders, suspensions or emulsions.

In preparing the compositions in oral dosage form, any of the usual pharmaceutical media may be employed, such as, for example, water, glycols, oils, alcohols, flavoring agents, preservatives, coloring agents, suspending agents, and the like in the case of oral liquid preparations (such as, for example, suspensions, elixirs and solutions); or carriers such as starches, sugars, diluents, granulating agents, lubricants, binders, disintegrating agents and the like in the case of oral solid preparations (such as, for example, powders, capsules and tablets). Because of their ease in administration, tablets and capsules represent the most advantageous oral dosage unit form, in which case solid pharmaceutical carriers are obviously employed. If desired, tablets may be sugar-coated or enteric-coated by standard techniques. The active agent can be encapsulated to make it stable to passage through the gastrointestinal tract while at the same time allowing for passage across the blood brain barrier. See for example, WO 96/11698.

For parenteral administration, the compound may be dissolved in a pharmaceutical carrier and administered as either a solution or a suspension. Illustrative of suitable carriers are water, saline, dextrose solutions, fructose solutions, ethanol, or oils of animal, vegetative or synthetic origin. The carrier may also contain other ingredients, for example, preservatives, suspending agents, solubilizing agents, buffers and the like. When the compounds are being administered intrathecally, they may also be dissolved in cerebrospinal fluid.

The active agent is preferably administered in a therapeutically effective amount. The actual amount administered, and the rate and time-course of administration, will depend on the nature and severity of the condition being treated. Prescription of treatment, e.g. decisions on dosage, timing, etc., is within the responsibility of general practitioners or specialists, and typically takes account of the disorder to be treated, the condition of the individual patient, the site of delivery, the method of administration and other factors known to practitioners. Examples of techniques and protocols can be found in *Remington's Pharmaceutical Sciences*.

Alternatively, targeting therapies may be used to deliver the active agent more specifically to certain types of cell, by the use of targeting systems such as antibodies or cell specific ligands. Targeting may be desirable for a variety of reasons, e.g. if the agent is unacceptably toxic, or if it would otherwise require too high a dosage, or if it would not otherwise be able to enter the target cells.

Instead of administering these agents directly, they could be produced in the target cell, e.g. in a viral vector such as described above or in a cell based delivery system such as described in U.S. Pat. No. 5,550,050 and published PCT application Nos. WO 92/19195, WO 94/25503, WO 95/01203, WO 95/05452, WO 96/02286, WO 96/02646, WO 96/40871, WO 96/40959 and WO 97/12635, designed for implantation in a patient. The vector could be targeted to the specific cells to be treated, or it could contain regulatory elements which are more tissue specific to the target cells. The cell based delivery system is designed to be implanted in a patient's body at the desired target site and contains a coding sequence for the active agent. Alternatively, the agent could be administered in a precursor form for conversion to the active form by an activating agent produced in, or targeted to, the cells to be treated. See for example, EP 425,731 A and WO 90/07936.

The present invention is described by reference to the following Examples, which are offered by way of illustration and are not intended to limit the invention in any manner. Standard techniques well known in the art or the techniques specifically described below were utilized.

EXAMPLE 1

Radiation Hybrid Mapping of BRG1 to Chromosome Band 19p13.1

To map the chromosomal location of BRG1, a primer pair of BRG.F1 and BRG.F1 (the sequences for these are shown below in Table 2) was designed to specifically amplify a product from human but not hamster genomic DNA. This STS was used to screen a somatic human-hamster hybrid cell line panel (Genebridge panel 4 from Human Genome Project, Sanger Center). The Whitehead Institute radiation hybrid map (http://carbon.wi.mit.edu:8000/cgi-bin/contig/rhmapper.p1) and the Genetic Location Database (http://cedar.genetics.soton.ac.uk/public html/gmap.html) were used to assign the relative chromosomal location of the gene. BRG1 was placed 4.19 cR from the genetic map marker WI-4669. This corresponds to a region on chromosome band 19p13.1.

EXAMPLE 2

Identification of a Homozygous Deletion in a Prostate Tumor Cell Line

A homozygous deletion scan by PCR of a panel of 192 tumor cell line genomic DNAs was performed. The screening was performed with a number of sequence tagged site (STS) probes for homozygous deletions (see Green and Olson (1990) for the use of STSs in genome mapping and see Vollrath et al. (1992) for a method of deletion mapping using STSs). Homozygous deletion searches were performed as follows: Total genomic DNA was purified from cancer cell lines using the Easy-DNA kit (Invitrogen). Using the cell line DNAs as templates, 20 μL PCR amplifications were performed with either TaqPlus (Stratagene) or AmpliTaq Gold (Perkin Elmer) and subsequently fractionated on 2–3% Nu Sieve (FMC Bioproducts) agarose gels. In general, the PCR conditions used were an initial denaturation step at 95° C. for 1 minute (TaqPlus) or 10 minutes (AmpliTaq Gold), followed by 35 cycles of denaturation at 96° C. for 12 seconds, annealing at 55° C. for 15 seconds and extension at 72° C. for 45 seconds. The homozygous deletion in TSU-pr1 was detected using the STS primer pairs shown in Table 2. The absence of detection of a PCR product is interpreted as a homozygous deletion at that region. The screen showed a deletion of a 3' portion of BRG1 in prostate tumor cell line TSU-pr1.

TABLE 2

Primers Used for Homozygous Deletion Analysis of BRG1 in the Cell Line TSU-pr1

| Primer Name | Sequence (SEQ ID NO) | Transcript Position* | Region Deleted |
|---|---|---|---|
| BRG.F3 | ACTGTCTGCAGCTCCCGTGAA (5) | 53–158 | No |
| BRG.R3 | CAGCATGGCTCCAGGGGAAGG (6) | | |
| BRG.F5 | AGATCCGTTGGAAGTACATGAT (7) | 2689–2785 | No |
| BRG.R5 | GGTGCCACATAGTGCGTGTTGA (8) | | |
| BRG.F12 | GCAGTGCCAGCTTCGCCCAC (9) | 3874–3990 | No |
| BRG.R12 | TCATCTGGTTGACGGTCTCG (10) | | |

TABLE 2-continued

Primers Used for Homozygous Deletion Analysis of BRG1 in the Cell Line TSU-pr1

| Primer Name | Sequence (SEQ ID NO) | Transcript Position* | Region Deleted |
|---|---|---|---|
| BRG.F9 | CGAGAAGGAGGATGACAGTG (11) | 4766–4867 | Yes |
| BG.R9 | TTGATCTTCACTTTGACGGACC (12) | | |
| BRG.F8 | CGGAAGGAGAAGGCACAGGA (13) | 4875–4973 | Yes |
| BRG.R8 | CTCCTCACTGTCATCGTCAC (14) | | |
| BRG.F1 | CCCGACATTCCAGTCTCGAC (15) | 5021–5218 | Yes |
| BRG.R1 | ACAGATGCTACTGATGCCAG (16) | | |

*The numbering is based upon SEQ ID NO:1.

EXAMPLE 3

Mutation Analysis of Tumor Cell Lines

Screening of tumor cell lines was performed to find mutations in BRG1 other than homozygous deletions. Primers were developed to generate amplicons from cDNA to mutation screen the coding region of the BRG1 gene at the nucleotide level. These primers are shown in Table 3. BRG.2A and BRG.3P were used to generate a primary amplicon followed by a nested PCR with secondary primers BRG.2D and BRG.2S. Sequencing of the BRG.2D and BRG.2S product with M13 forward and reverse primers revealed a deletion in the sequence. A confirmation experiment was performed but with a different set of primary (BRG.2A2 and BRG.2P2) and secondary (BRG.2D2 and BRG.2S2) amplicons.

TABLE 3

Primers Used for Amplification of cDNA for Mutation Screening of a Region of the BRG1 Coding Sequence

| Primer Name | Sequence (SEQ ID NO) |
|---|---|
| BRG.2A | CAGAAGCTGATTCCCCCGCAG (18) |
| BRG.3P | AGCAGCACTTTGTGGTTGGTTG (19) |
| BRG.2D | GTTTTCCCAGTCACGACGGCCACGTACCATGCCAACAC (20) |
| BRG.2S | AGGAAACAGCTATGACCATGCTGGTCTCGTCTAGAGGCT (21) |
| BRG.2A2 | AGCCCTGGCCTGAAGGACCC (22) |
| BRG.2P2 | CGCTGACTGCTTGTCCACTC (23) |
| BRG.2D2 | GTTTTCCCAGTCACGACGTCTCCAGCATGCCAAGGATT (24) |
| BRG.2S2 | AGGAAACAGCTATGACCATGGCGTCTGTCCTTCTGCATT (25) |

These experiments identified mutations in three cell lines other than TSU-pr1. The cell line ALAB from mammary gland has a C→T mutation at position 1630 of the ORF (position 1704 of SEQ ID NO:1 or position 1708 of GenBank Accession No. U29175) in exon 10 changing Gln544 to a stop codon. The mutated gene is SEQ ID NO:62 and the encoded protein is SEQ ID NO:63. The wild-type allele is seen neither in the genomic DNA nor cDNA of this cell line. A second prostate tumor cell line called DU145 was found to have a G to T mutation at a splice donor site at position 1761 of the ORF (position 1835 of the cDNA sequence shown as SEQ ID NO:1 or position 1839 of GenBank Accession No. U29175). This mutation in DU145 is at the final base of exon 10. A lung tumor cell line called NCI-H1299 was found to have a 69 base pair deletion of the genomic DNA that abrogates the same splice donor site as in DU145. This deletion covers bases 239–307 of SEQ ID NO:17 which shows the exon 10 sequence plus its bordering intron sequence for BRG1 (see Example 4 below). Bases 100–267 of SEQ ID NO:17 are exon 10 and correspond to bases 1668–1835 of SEQ ID NO:1 or 1672–1839 of GenBank Accession No. U29175. The 69 base pair deletion includes 29 base pairs of exon (corresponding to bases 1733–1761 of the ORF or 1807–1835 of SEQ ID NO: 1) and 40 base pairs of intron following exon 10. In the case of DU145 and NCI-H1299, the mutation at the normal donor splice site or region results in the utilization of a cryptic donor splice site in the exon. The use of this cryptic site causes the frameshift deletion (1677–1761 of the ORF or 1751–1835 of SEQ ID NO:1 or 1755–1839 of GenBank Accession No. U29175) that was observed in the mRNA. For both DU145 and NCI-H1299, the resulting mRNA formed is that shown in SEQ ID NO:60 and the encoded protein is shown as SEQ ID NO:61.

Further screening resulted in the identification of several more mutations. Table 4 lists the mutations in BRG1 which have been identified.

TABLE 4

BRG1 Variants in Tumor Cell Lines

| Tumor Cell Line | Tissue | Alteration[d] | Exon | Genotype[b] | Predicted Effect |
|---|---|---|---|---|---|
| TSU-Pr1[a] | Prostate | Homozygous deletion | Multiple | H | Truncated product |
| A-427 | Lung | Homozygous deletion | Multiple | H | Truncated product |
| Su86.86 | Pancreas | A553G | 4 | HET | Gln → Arg |
| Hs578T | Breast | C663T | 4 | H | Pro → Ser |
| Hs700T | Pancreas | 803C deletion | 4 | H | Frameshift |
| NIH-OVCAR3 | Ovary | A1282G | 7 | HET | Glu → Gly |
| ALAB | Breast | C1704T | 10 | H | Gln → Stop |
| DU145[a] | Prostate | G1835T; splice site | 10 | H | Frameshift |
| NCI-H1299[a] | Lung | 69 base deletion | 10 | H | Frameshift |
| HCT-15 | Colon | C2727T | 19 | HET | Arg → Cys |
| HCT-116 | Colon | T3562C | 25 | H | Leu → Pro |
| SNU-C2B | Cecum | C3631T | 26 | HET | Ala → Val |
|  |  | G4081A[c] | 29 |  | Arg → His |
| WiDr | Colon | G3924A | 27 | HET | Asp → Asn |
| Hs683 | Brain | T4900C | 34 | HET | Leu → Pro |
| C33A | Cervical tumor | Insert ACC between 2391 and 2392[c] | 16 | HET | Insertion of a His |
| C33A | Cervical tumor | A3817G[e] | 26 | HET | Gln → Arg |

Total of 92 tumor cell lines screened: 1 bladder, 22 breast, 1 cecum, 16 colon, 7 gliomas, 14 lung, 6 melanoma, 7 ovary, 11 pancreas, 4 prostate and 3 testis.
[a]These BRG1 mutations were found in the genomic DNAs of these cell lines. All other alterations reported in this table were observed in BRG1 cDNA of the corresponding cell lines.
[b]H: hemizygous, homozygous or expression of one allele; HET: heterozygous.
[c]The two missense alterations were determined to occur on the same allele of BRG1 in SNU-C2B; the other allele of the gene was therefore wild type.
[d]Base numbering is based on SEQ ID NO:1.
[e]It is not known whether the two mutations in C33A are on the same or on different chromosomes.

EXAMPLE 4

Analysis of BRG1 Genomic DNA

Genomic sequences at the region of the deletion seen in cell lines DU145 and NCI-H1299 were analyzed by PCR. The following primer sets were used for amplification:

Primary PCR primer pairs: BRGDF1 and BRGDR1
Secondary PCR primer pairs: BRGDF2 and BRGDR2
Sequencing primers: BRGDF2 and BRGDR2
BRGDF1 is 5'-GGTGGCACGGCACCCGCGTGA-3' SEQ ID NO:26
BRGDF2 is 5'-TACGCGTGCCCTCAGTGCGCTT-3' SEQ ID NO:27
BRGDR1 is 5'-TCTGCATTTTCTGCCTTCTGGAA-3' SEQ ID NO:28
BRGDR2 is 5'-TAGAGAGAGACACGGTCAGGC-3' SEQ ID NO:29

The genomic sequence from BRGDF2-BRGDR2, as determined from seven different genomic DNA sources is:

5'-tacgcgtgccctcagtgcgcttctggattgactggccatgggtgctcacaga-catgcacattgtgccaccacattgcagtaacoccccatg cttttgtag-GCTGAAGATGAGGAGGGGTACCG-CAAGCTCATCGACCAGAAGAAGGACAA GCGCCTGGCCTACCTCTTGCAGCAGACA-GACGAGTACGTGGCTAACCTCACGGAGCT GGTGCGGCAGCACAAGGCTGCCCAG-GTCGCCA AGGAGAAAAAGAAGAAAAAGAAAAAGA AGgtgtgctgggcctggcatoagtgcccgccgcgggtgggatgggagc-agccgtcttcacgtgtgtggcctcagccttgtgggtcagggc ctgaccgtgtctctctcta-3' (SEQ ID NO:17).

The upper case letters represent exon 10 and the lower case letters represent flanking intron. The exon corresponds to bases 1594–1761 of the ORF or 1668–1835 of SEQ ID NO:1 or 1672–1839 of GenBank Accession No. U29175. Cell line NCI-H1299 has a 69 base pair deletion corresponding to the underlined region of SEQ ID NO:17 shown above (this includes the final 29 bases of exon 10 plus 40 bases of following intron). The loss of the splice site at the end of exon 10 (both in DU145 and NCI-H1299) leads to use of a cryptic splice site within exon 10 resulting in an mRNA lacking the 85 bases shown in italics (the final 85 bases of exon 10) thereby causing a frameshift mutation.

The sequence analysis also showed a discrepancy at position 1706 of the ORF (position 1780 of SEQ ID NO:1 or 1784 of GenBank Accession No. 29175). GenBank shows this to be a C whereas our results indicate that this base is a G. This changes the encoded amino acid at position 569 of the protein from a proline to an arginine.

EXAMPLE 5

Intron-Exon Junctions of BRG1

The genomic BRG1 structure has been analyzed to locate the boundaries of each exon. BRG1 comprises 35 exons. The positions of the exons based upon the cDNA sequence shown in SEQ ID NO:1 are shown in Table 5.

For Table 5, numbering is based upon SEQ ID NO:1. The ATG start codon is at position 75. Position 26 is polymorphic for T and C and is part of the 5' untranslated region.

Position 1583 shows an A to G polymorphism (silent change of Ala to Ala). Position 1598 shows a T to C polymorphism (silent change of His to His). Position 1892 is polymorphic for A and G (silent change of Leu to Leu). Position 1780 is a G rather than a C as shown in GenBank Accession No. U29175 (position 1784 in GenBank) resulting in an arginine at amino acid 569 rather than a proline as shown in the GenBank sequence.

The exons plus their flanking intron sequences are each shown in the Sequence Listing. Table 6 indicates which SEQ ID NO corresponds to which exon and indicates the regions of exon and intron. Note that in some instances a complete intron between two exons has been sequenced and therefore the two exons plus flanking introns are shown as a single SEQ ID NO.

An alternative splice form of BRG1 was also found. This includes additional exon sequence between exons 29 and 30 as shown above. We refer to this additional sequence as exon 29B. Exon 29B is 96 base pairs long, is in-frame with the rest of the open reading frame, and does not include a stop codon. The sequence for exon 29B is:

5'-AAAATTACAGGAAAAGATATCCATGACACAGC-CAGCAGrGTGGCACGTGGGCTAC AATTCCAGCGTGGCCTTCAGTTCTGCACACGT-GCGTCAAAG-3' (SEQ ID NO:59).

Two alternative transcript lengths have been seen. The longer transcript contains the full sequence shown as SEQ ID NO:1 and has a poly A tail added. A shorter transcript has also been observed which ends at base 5260 of SEQ ID NO:1 and has a poly A tail added after this last base.

TABLE 5

Position of Exons in the Open Reading Frame of BRG1

| Exon | Position | Comment |
|---|---|---|
| 1 | 1–43 | Non-coding 5' untranslated region |
| 2 | 44–296 | Contains 5' untranslated region and ATG |
| 3 | 297–429 | |
| 4 | 430–834 | |
| 5 | 835–933 | |
| 6 | 934–1192 | |
| 7 | 1193–1319 | |
| 8 | 1320–1493 | |
| 9 | 1494–1667 | |
| 10 | 1668–1835 | |
| 11 | 1836–1886 | Affected exon; base discrepancy at 1706; is a G |
| 12 | 1887–2017 | |
| 13 | 2018–2075 | |
| 14 | 2076–2197 | |
| 15 | 2198–2348 | |
| 16 | 2349–2512 | |
| 17 | 2513–2579 | |
| 18 | 2580–2690 | |
| 19 | 2691–2933 | |
| 20 | 2934–3047 | |
| 21 | 3048–3155 | |
| 22 | 3156–3242 | |
| 23 | 3243–3289 | |
| 24 | 3290–3456 | |
| 25 | 3457–3620 | |
| 26 | 3621–3848 | |
| 27 | 3849–3947 | |
| 28 | 3948–4025 | |
| 29 | 4026–4244 | |
| 30 | 4245–4498 | |
| 31 | 4499–4607 | |
| 32 | 4608–4709 | |
| 33 | 4710–4842 | |
| 34 | 4843–4985 | |
| 35 | 4986–5475 | Contains TGA and 3' untranslated region |

TABLE 6

Intron/Exon Sequence

| Exon | SEQ ID NO | Base Numbers of Exon |
|---|---|---|
| 1 | 30 | 303–345 |
| 2 | 31 | 302–554 |
| 3 | 32 | 302–434 |
| 4 | 33 | 302–706 |
| 5 | 33 | 1018–1116 |
| 6 | 34 | 302–560 |
| 7 | 35 | 302–428 |
| 8 | 36 | 302–475 |
| 9 | 37 | 302–475 |
| 10 | 38 | 302–469 |
| 11 | 38 | 583–633 |
| 12 | 39 | 302–432 |
| 13 | 39 | 613–670 |
| 14 | 40 | 302–423 |
| 15 | 41 | 302–452 |
| 16 | 42 | 302–465 |
| 17 | 43 | 302–368 |
| 18 | 44 | 302–412 |
| 19 | 45 | 302–544 |
| 20 | 46 | 302–415 |
| 21 | 47 | 302–409 |
| 22 | 48 | 302–388 |
| 23 | 49 | 302–348 |
| 24 | 50 | 302–468 |
| 25 | 51 | 302–465 |
| 26 | 52 | 302–529 |
| 27 | 52 | 779–877 |
| 28 | 52 | 1135–1212 |
| 29 | 53 | 302–520 |
| 29B | 54 | 36–131 |
| 30 | 55 | 302–555 |
| 31 | 56 | 302–410 |
| 32 | 56 | 835–936 |
| 33 | 57 | 302–434 |
| 34 | 57 | 594–736 |
| 35 | 58 | 302–791 (end of transcript) |

EXAMPLE 6

BRG1 ISOFORMS

Alternative splicing of BRG1 has been seen at three positions within the gene. The various possible combinations of these three alternative splices leads to eight possible isoforms of the gene, not including variations in sites of poly A addition. The most prevalent isoform is that given by the cDNA shown in SEQ ID NO:1. One of the three splice variants has already been discussed, that being the presence or absence of exon 29B. A second splice variant is a deletion of CAG at the beginning of exon 31. The third splice variant is a 9 basepair insertion (5'-ACCCTGAAG-3') at the beginning of exon 30. Table 7 shows the possible isoforms which can result from combinations of these three alternative splices. The cDNAs and encoded proteins of each isoformn are listed in Table 7 by SEQ ID NO and the sequences of each isoform are set forth in the Sequence Listing.

TABLE 7

BRG1 Isoforms

| Isoform | Alternative Splices | SEQ ID NOs |
|---|---|---|
| 1 | None | 1 and 2 |
| 2 | Inclusion of exon 29B | 64 and 65 |
| 3 | Includes a CAG deletion at the beginning of exon 31 | 66 and 67 |

TABLE 7-continued

BRG1 Isoforms

| Isoform | Alternative Splices | SEQ ID NOs |
|---|---|---|
| 4 | Includes exon 29B and a CAG deletion at the beginning of exon 31 | 68 and 69 |
| 5 | Includes an insertion of ACCCTGAAG at the beginning of exon 30 | 70 and 71 |
| 6 | Includes exon 29B and an insertion of ACCCTGAAG at the beginning of exon 30 | 72 and 73 |
| 7 | Includes an insertion of ACCCTGAAG at the beginning of exon 30 and a CAG deletion at the beginning of exon 31 | 74 and 75 |
| 8 | Includes exon 29B, an insertion of ACCCTGAAG at the beginning of exon 30 and a CAG deletion at the beginning of exon 31 | 76 and 77 |

EXAMPLE 7

Two Step Assay to Detect the Presence of BRG1 in a Sample

Patient sample is processed according to the method disclosed by Antonarakis et al. (1985), separated through a 1% agarose gel and transferred to nylon membrane for Southern blot analysis. Membranes are UV cross linked at 150 mJ using a GS Gene Linker (Bio-Rad). A BRG1 probe is subcloned into pTZ18U. The phagemids are transformed into E. coli MV1190 infected with M13KO7 helper phage (Bio-Rad, Richmond, Calif.). Single stranded DNA is isolated according to standard procedures (see Sambrook et al., 1989).

Blots are prehybridized for 15–30 min at 65° C. in 7% sodium dodecyl sulfate (SDS) in 0.5 M NaPO$_4$. The methods follow those described by Nguyen, et al., 1992. The blots are hybridized overnight at 65° C. in 7% SDS, 0.5 M NaPO$_4$ with 25–50 ng/ml single stranded probe DNA. Post-hybridization washes consist of two 30 min washes in 5% SDS, 40 mM NaPO$_4$ at 65° C., followed by two 30-min washes in 1% SDS, 40 mM NaPO$_4$ at 65° C.

Next the blots are rinsed with phosphate buffered saline (pH 6.8) for 5 min at room temperature and incubated with 0.2% casein in PBS for 30–60 min. at room temperature and rinsed in PBS for 5 min. The blots are then preincubated for 5–10 minutes in a shaking water bath at 45° C. with hybridization buffer consisting of 6 M urea, 0.3 M NaCl, and 5×Denhardt's solution (see Sambrook, et al., 1989). The buffer is removed and replaced with 50–75 μl/cm$^2$ fresh hybridization buffer plus 2.5 nM of the covalently crosslinked oligonucleotide-alkaline phosphatase conjugate with the nucleotide sequence complementary to the universal primer site (UP-AP, Bio-Rad). The blots are hybridized for 20–30 min at 45° C. and post hybridization washes are incubated at 45° C. as two 10 min washes in 6 M urea, 1×standard saline citrate (SSC), 0.1% SDS and one 10 min wash in 1×SSC, 0.1% Triton®X-100. The blots are rinsed for 10 min at room temp. with 1×SSC.

Blots are incubated for 10 min at room temperature with shaking in the substrate buffer consisting of 0.1 M diethanolamine, 1 mM MgCl$_2$, 0.02% sodium azide, pH 10.0. Individual blots are placed in heat sealable bags with substrate buffer and 0.2 mM AMPPD (3-(2'-spiroadamantane)-4-methoxy-4-(3'-phosphoryloxy)phenyl-1,2-dioxetane, disodium salt, Bio-Rad). After a 20 min incubation at room temperature with shaking, the excess AMPPD solution is removed. The blot is exposed to X-ray film overnight. Positive bands indicate the presence of BRG1.

EXAMPLE 8

Generation of Polyclonal Antibody against BRG1

Segments of BRG1 coding sequence are expressed as fusion protein in E. coli. The overexpressed protein is purified by gel elution and used to immunize rabbits and mice using a procedure similar to the one described by Harlow and Lane (1988). This procedure has been shown to generate Abs against various other proteins (for example, see Kraemer et al., 1993).

Briefly, a stretch of BRG1 coding sequence is cloned as a fusion protein in plasmid PET5A (Novagen, Inc., Madison, Wis.). After induction with IPTG, the overexpression of a fusion protein with the expected molecular weight is verified by SDS/PAGE. Fusion protein is purified from the gel by electroelution. The identification of the protein as the BRG1 fusion product is verified by protein sequencing at the N-terminus. Next, the purified protein is used as immunogen in rabbits. Rabbits are immunized with 100 μg of the protein in complete Freund's adjuvant and boosted twice in 3 week intervals, first with 100 μg of immunogen in incomplete Freund's adjuvant followed by 100 μg of immunogen in PBS. Antibody containing serum is collected two weeks thereafter.

This procedure is repeated to generate antibodies against the mutant forms of the BRG1 gene. These antibodies, in conjunction with antibodies to wild type BRG1, are used to detect the presence and the relative level of the mutant forms in various tissues and biological fluids.

EXAMPLE 9

Generation of Monoclonal Antibodies Specific for BRG1

Monoclonal antibodies are generated according to the following protocol. Mice are immunized with immunogen comprising intact BRG1 or BRG1 peptides (wild type or mutant) conjugated to keyhole limpet hemocyanin using glutaraldehyde or EDC as is well known.

The immunogen is mixed with an adjuvant. Each mouse receives four injections of 10 to 100 μg of immunogen and after the fourth injection blood samples are taken from the mice to determine if the serum contains antibody to the immunogen. Serum titer is determined by ELISA or RIA. Mice with sera indicating the presence of antibody to the immunogen are selected for hybridoma production.

Spleens are removed from immune mice and a single cell suspension is prepared (see Harlow and Lane, 1988). Cell fusions are performed essentially as described by Kohler and Milstein (1975). Briefly, P3.65.3 myeloma cells (American Type Culture Collection, Rockville, Md.) are fused with immune spleen cells using polyethylene glycol as described by Harlow and Lane (1988). Cells are plated at a density of 2×10$^5$ cells/well in 96 well tissue culture plates. Individual wells are examined for growth and the supernatants of wells with growth are tested for the presence of BRG1 specific antibodies by ELISA or RIA using wild type or mutant BRG1 target protein. Cells in positive wells are expanded and subcloned to establish and confirm monoclonality.

Clones with the desired specificities are expanded and grown as ascites in mice or in a hollow fiber system to produce sufficient quantities of antibody for characterization and assay development.

EXAMPLE 10

Sandwich Assay for BRG1

Monoclonal antibody is attached to a solid surface such as a plate, tube, bead, or particle. Preferably, the antibody is attached to the well surface of a 96-well ELISA plate. 100 μl sample (e.g., serum, urine, tissue cytosol) containing the BRG1 peptide/protein (wild-type or mutants) is added to the solid phase antibody. The sample is incubated for 2 hrs at room temperature. Next the sample fluid is decanted, and the solid phase is washed with buffer to remove unbound material. 100 μl of a second monoclonal antibody (to a different determinant on the BRG1 peptide/protein) is added to the solid phase. This antibody is labeled with a detector molecule (e.g., $^{125}$I, enzyme, fluorophore, or a chromophore) and the solid phase with the second antibody is incubated for two hrs at room temperature. The second antibody is decanted and the solid phase is washed with buffer to remove unbound material.

The amount of bound label, which is proportional to the amount of BRG1 peptide/protein present in the sample, is quantified. Separate assays are performed using monoclonal antibodies which are specific for the wild-type BRG1 as well as monoclonal antibodies specific for each of the mutations identified in BRG1.

It will be appreciated that the methods and compositions of the instant invention can be incorporated in the form of a variety of embodiments, only a few of which are disclosed herein. It will be apparent to the artisan that other embodiments exist and do not depart from the spirit of the invention. Thus, the described embodiments are illustrative and should not be construed as restrictive.

LIST OF REFERENCES

Altschul S F, et al. (1997). *Nucl. Acids Res.* 25:3389–3402.

Anand, R (1992). *Techniques for the Analysis of Complex Genomes*, (Academic Press).

Anderson W F, et al. (1980). *Proc. Natl. Acad. Sci. USA* 77:5399–5403.

Anderson J A, et al. (1992). *J. Otolaryngology* 21:321–326.

Antonarakis S E, et al. (1985). *New Engl. J. Med.* 313:842–848.

Ausubel F M, et al. (1992). *Current Protocols in Molecular Biology*, (John Wiley and Sons, New York, N.Y.).

Bandyopadhyay P K and Temin H M (1984). *Mol. Cell. Biol.* 4:749–754.

Bartel P L, et al. (1993). In *Cellular Interactions in Development: A Practical Approach*, Oxford University Press, pp. 153–179.

Beaucage S L and Caruthers M H (1981). *Tetra. Letts.* 22:1859–1862.

Berglund P, et al. (1993). *Biotechnology* 11:916–920.

Berkner K L (1992). *Curr. Top. Microbiol. Immunol.* 158:39–66.

Berkner K L, et al. (1988). *BioTechniques* 6:616–629.

Borman S (1996). *Chemical & Engineering News*, December 9 issue, pp. 42–43.

Breakefield X O and Geller A I (1987). *Mol. Neurobiol.* 1:337–371.

Brinster R L, et al. (1981). *Cell* 27:223–231.

Brinster R L, et al. (1985). *Proc. Natl. Acad. Sci. USA* 82:4438–4442.

Buchschacher G L and Panganiban A T (1992). *J. Virol.* 66:2731–2739.

Capecchi M R (1989). *Science* 244:1288–1292.

Cariello N F (1988). *Am. J. Human Genetics* 42:726–734.

Chee M, et al. (1996). *Science* 274:610–614.

Chevray P M and Nathans D N (1992). *Proc. Natl. Acad. Sci. USA* 89:5789–5793.

Compton J (1991). *Nature* 350:91–92.

Conner B J, et al. (1983). *Proc. Nat. Acad. Sci. USA* 80:278–282.

Costantini F and Lacy E (1981). *Nature* 294:92–94.

Cotten M, et al. (1990). *Proc. Natl. Acad. Sci. USA* 87:4033–4037.

Cotton R G, et al. (1988). *Proc. Nat. Acad. Sci. USA* 85:4397–4401.

Culver K W, et al. (1992). *Science* 256:1550–1552.

Culver K (1996). *Gene Therapy: A Primer for Physicians*, 2nd Ed., Mary Ann Liebert.

Curiel D T, et al. (1991). *Proc. Natl. Acad Sci. USA* 88:8850–8854.

Curiel D T, et al. (1992). *Hum. Gene Ther.* 3:147–154.

DeRisi J, et al. (1996). *Nature Genetics* 14:457–460.

Deutscher M (1990). *Meth. Enzymology* 182:83–89 (Academic Press, San Diego).

Donehower L A, et al. (1992). *Nature* 356:215–221.

Dunaief J L, et al. (1994). *Cell* 79:119–130.

Editorial (1996). *Nature Genetics* 14:367–370.

Elghanian R, et al. (1997). *Science* 277:1078–1081.

*Enhancers and Eukaryotic Gene Expression*, Cold Spring Harbor Press, Cold Spring Harbor, N.Y. (1983).

Erickson J, et al. (1990). *Science* 249:527–533.

Ewen M E, et al. (1993). *Cell* 73:487–497.

Fahy E, eta). (1991). *PCR Methods Appl.* 1:25–33.

Feil R, et al. (1996). *Proc. Natl. Acad Sci. USA* 93:10887–10890.

Felgner P L, et al. (1987). *Proc. Natl. Acad. Sci. USA* 84:7413–7417.

Fields S and Song O K (1 989). *Nature* 340:245–246.

Fiers W, et al. (1978). *Nature* 273:113–120.

Fink D J, et al. (1992). *Hum. Gene Ther.* 3:11–19.

Fink D J, et al. (1996). *Ann. Rev. Neurosci.* 19:265–287.

Finkelstein J, et al. (1990). *Genomics* 7:167–172.

Fodor S P A (1997). *Science* 277:393–395.

Freese A, et al. (1990). *Biochem. Pharmacol.* 40:2189–2199.

Friedman T (1991). In *Therapy for Genetic Diseases*, T. Friedman, ed., Oxford University Press, pp. 105–121.

Gagneten S, et al. (1997). *Nucl. Acids Res.* 25:3326–3331.

Gao A C, et al. (1999). *Prostate* 38:46–54.

Glover D (1985). *DNA Cloning*, I and II (Oxford Press).

Goding (1986). *Monoclonal Antibodies: Principles and Practice*, 2d ed. (Academic Press, N.Y.).

Godowski P J, et al. (1988). *Science* 241:812–816.

Gordon J W, et al. (1980). *Proc. Natl. Acad. Sci. USA* 77:7380–7384.

Gorziglia M and Kapikian A Z (1992). *J. Virol.* 66:4407–4412.

Graham F L and van der Eb A J (1973). *Virology* 52:456–467.

Green E D and Olson M V (1990). *Science* 250:94–98.

Grompe M (1993). *Nature Genetics* 5:111–117.

Grompe M, et al. (1989). *Proc. Natl. Acad Sci. USA* 86:5855–5892.

Gruis N A, et al. (1995). *Am. J. Pathol.* 146:1–8.

Guthrie G and Fink G R (1991). *Guide to Yeast Genetics and Molecular Biology* (Academic Press).

Hacia J G, et al. (1996). *Nature Genetics* 14:441–447.

Hahn S A, et al. (1996). *Science* 271:350–353.

Hannon G J and Beach D (1994). *Nature* 371:257–261.

Harlow E and Lane D (1988). *Antibodies: A Laboratory Manual* (Cold Spring Harbor Laboratory, Cold Spring Harbor, N.Y.).

Hasty P, et al. (1991). *Nature* 350:243–246.

Helseth E, et al. (1990). *J. Virol.* 64:2416–2420.

Hodgson J (1991). *Bio/Technology* 9:19–21.

Huse W D, et al. (1989). *Science* 246:1275–1281.

Innis M A, et al. (1990). *PCR Protocols: A Guide to Methods and Applications*, (Academic Press, San Diego).

Jablonski E, et al. (1986). *Nucl. Acids Res.* 14:6115–6128.

Jakoby W B and Pastan I H (eds.) (1979). Cell Culture. Methods in Enzymology, volume 58 (Academic Press, Inc., Harcourt Brace Jovanovich (New York)).

Jiang P, et al. (1995). *J. Mol. Evol.* 41:795–802.

Johnson P A, et al. (1992). *J. Virol.* 66:2952–2965.

Johnson, et al. (1993). "Peptide Turn Mimetics" in *Biotechnology and Pharmacy*, Pezzuto et al., eds., Chapman and Hall, New York.

Kamb A, et al. (1994). *Science* 264:436–440.

Kaneda Y, et al. (1989). *J. Biol. Chem.* 264:12126–12129.

Kanehisa M (1984). *Nucl. Acids Res.* 12:203–213.

Khavari P A, et al. (1993). *Nature* 366:170–174.

Kinszler K W, et al. (1991). *Science* 251:1366–1370.

Knudson A G (1993). *Nature Genet.* 5:103–104.

Kohler G and Milstein C (1975). *Nature* 256:495–497.

Kraemer F B, et al. (1993). *J. Lipid Res.* 34:663–672.

Kubo T, et al. (1988). *FEBS Lett.* 241:119–125.

Kyte J and Doolittle R F (1982). *J. Mol. Biol.* 157:105–32.

Lammie G A, et al. (1991). *Oncogene* 6:439–444.

Landegren U, et al. (1988). *Science* 242:229–237.

Lee J E, et al. (1995). *Science* 268:836–844.

Li J, et al. (1997). *Science* 275:1943–1947.

Lim C S, et al. (1991). *Circulation* 83:2007–2011.

Lipshutz R J, et al. (1995). *Biotechniques* 19:442–447.

Liu Q, et al. (1995a). *Oncogene* 10:619–622.

Liu Q, et al. (1995b). *Oncogene* 10: 1061–1067.

Lobe C G and Nagy A (1998). *Bioessays* 20:200–208.

Lockhart D J, et al. (1996). *Nature Biotechnology* 14:1675–1680.

Madzak C, et al. (1992). *J. Gen. Virol.* 73:1533–1536.

Maniatis T, et al. (1982). *Molecular Cloning: A Laboratory Manual* (Cold Spring Harbor Laboratory, Cold Spring Harbor, N.Y.).

*Manipulating the Mouse Embryo; A Laboratory Manual*, 2nd edition (eds., Hogan, Beddington, Costantini and Long, Cold Spring Harbor Laboratory Press, 1994

Mann R and Baltimore D (1985). *J. Virol.* 54:401–407.

Margoiskee R F (1992). *Curr. Top. Microbiol. Immunol.* 158:67–95.

Martin R, et al. (1990). *BioTechniques* 9:762–768.

Marx J (1994). *Science* 263:319–321.

Matteucci M D and Caruthers M H (1981). *J. Am. Chem. Soc.* 103:3185.

Matthews J A and Kricka L J (1988). *Anal. Biochem.* 169:1–25.

Merrifield B (1963). *J. Am. Chem. Soc.* 85:2149–2156.

Metzger D, et al. (1988). *Nature* 334:31–36.

Mifflin T E (1989). *Clinical Chem.* 35:1819–1825.

Miller A D (1992). *Curr. Top. Microbiol. Immunol.* 158:1–24.

Miller A D, et al. (1985). *Mol Cell. Biol.* 5:431–437.

Miller A D, et al. (1988). *J. Virol* 62:4337–4345.

Modrich P (1991). *Ann. Rev. Genet.* 25:229–253.

Mombaerts P, et al. (1992). *Cell* 68:869–877.

Moss B (1992). *Curr. Top. Microbiol. Immunol.* 158:25–38.

Moss B (1996). *Proc. Natl. Acad Sci. USA* 93:11341–11348.

Motokura T, et al. (1991). *Nature* 350:512–515.

Muzyczka N (1992). *Curr. Top. Microbiol. Immunol.* 158:97–129.

Nabel E G, et al. (1990). *Science* 249:1285–1288.

Nabel (1992). *Hum. Gene Ther.* 3:399–410.

Naldini L, et al. (1996). *Science* 272:263–267.

Nasmyth K and Hunt T (1993). *Nature* 366:634–635.

Newton C R, et al. (1989). *Nucl. Acids Res.* 17:2503–2516.

Nguyen Q, et al. (1992). *BioTechniques* 13:116–123.

Novack D F, et al. (1986). *Proc. Nat. Acad. Sci. USA* 83:586–590.

Ohi S, et al. (1990). *Gene* 89:279–282.

Orita M, et al. (1989). *Proc. Nat. Acad Sci. USA* 86:2776–2770.

Osterrieder N and Wolf E (1998). *Rev. Sci. Tech.* 17:351–364.

Page K A, et al. (1990). *J. Virol.* 64:5270–5276.

Pellicer A, et al. (1980). *Science* 209:1414–1422.

Petropoulos C J, et al. (1992). *J. Virol.* 66:3391–3397.

Philpott K L, et al. (1992). *Science* 256:1448–1452.

Quantin B, et al. (1992). *Proc. Natl. Acad Sci. USA* 89:2581–2584.

Remington's Pharmaceutical Sciences, 18th Ed. (1990, Mack Publishing Co., Easton, Pa.).

Rigby P W J, et al. (1977). *J. Mol. Biol.* 113:237–251.

Rosenberg C L, et al. (1991). *Proc. Natl. Acad Sci. USA* 88:9638–9642.

Rosenfeld M A, et al. (1992). *Cell* 68:143–155.

Ruano G and Kidd K K (1989). *Nucl. Acids Res.* 17:8392.

Russell D and Hirata R (1998). *Nature Genetics* 18:323–328.

Sambrook J, et al. (1989). *Molecular Cloning: A Laboratory Manual*, 2nd Ed. (Cold Spring Harbor Laboratory, Cold Spring Harbor, N.Y.).

Scharf S J (1986). *Science* 233:1076–1078.

Schneider G, et al. (1998). *Nature Genetics* 18:180–183.

Scopes R (1982). *Protein Purification: Principles and Practice*, (Springer-Verlag, N.Y.).

Serrano M, et al. (1993). *Nature* 366:704–707.

Shastry B S (1995). *Experientia* 51:1028–1039.

Shastry B S (1998). *Mol. Cell. Biochem.* 181:163–179.

Sheffield V C, et al. (1989). *Proc. Natl. Acad. Sci. USA* 86:232–236.

Sheffield V C, et al. (1991). *Am. J. Hum. Genet.* 49:699–706.

Shenk T E, et al. (1975). *Proc. Natl. Acad Sci. USA* 72:989–993.

Shimada T, et al. (1991). *J. Clin. Invest.* 88:1043–1047.

Shinkai Y, et al. (1992). *Cell* 68:855–867.

Shoemaker D D, et al. (1996). *Nature Genetics* 14:450–456.

Snouwaert J N, et al. (1992). *Science* 257:1083–1088.

Sorge J, et al. (1984). *Mol. Cell. Biol.* 4:1730–1737.

Spargo C A, et al. (1996). *Mol. Cell. Probes* 10:247–256.

Steck P A, et al. (1997). *Nature Genet.* 15:356–362.

Stewart M J, et al. (1992). *Hum. Gene Ther.* 3:267–275.

Stone S, et al. (1995a). *Cancer Res.* 55:2988–2994.

Stone S, et al. (1995b). *Oncogene* 11:987–991.

Stratford-Perricaudet L D, et al. (1990). *Hum. Gene Ther.* 1:241–256.

Tavtigian S V, et al. (1996). *Nature Genet.* 12:333–337.

Valancius V and Smithies O (1991). *Mol Cell Biol.* 11:1402–1408.

Vollrath D, et al. (1992). *Science* 258:52–59.

Wagner E, et al. (1990). *Proc. Natl. Acad Sci. USA* 87:3410–3414.

Wagner E, et al. (1991). *Proc. Natl. Acad. Sci. USA* 88:4255–4259.

Walker G T, et al. (1992). *Nucl. Acids Res.* 20:1691–1696.

Wang C Y and Huang L (1989). *Biochemistry* 28:9508–9514.

Wartell R M, et al. (1990). *Nucl. Acids Res.* 18:2699–2705.

Wells J A (1991). *Methods Enzymol.* 202:390–411.

Wetmur J G and Davidson N (1968). *J. Mol. Biol.* 31:349–370.

White R and Lalouel J M (1988). *Annu. Rev. Genet.* 22:259–279.

White M B, et al. (1992). *Genomics* 12:301–306.

Wilkinson G W and Akrigg A (1992). *Nucleic Acids Res.* 20:2233–2239.

Withers D A, et al. (1991). *Mol. Cell Biol.* 11:4846–4853.

Wolff J A, et al. (1990). *Science* 247:1465–1468.

Wolff J A, et al. (1991). *BioTechniques* 11:474–485.

Wooster R, et al. (1995). *Nature* 378:789–792.

Wu D Y and Wallace R B (1989). *Genomics* 4:560–569.

Wu C H, et al. (1989). *J. Biol. Chem.* 264:16985–16987.

Wu G Y, et al. (1991). *J. Biol. Chem.* 266:14338–14342.

Zenke M, et al. (1990). *Proc. Natl. Acad. Sci. USA* 87:3655–3659.

List of Patents and Patent Applications:

U.S. Pat. No. 3,817,837
U.S. Pat. No. 3,850,752
U.S. Pat. No. 3,939,350
U.S. Pat. No. 3,996,345
U.S. Pat. No. 4,275,149
U.S. Pat. No. 4,277,437
U.S. Pat. No. 4,366,241
U.S. Pat. No. 4,376,110
U.S. Pat. No. 4,486,530
U.S. Pat. No. 4,554,101
U.S. Pat. No. 4,683,195
U.S. Pat. No. 4,683,202
U.S. Pat. No. 4,816,567
U.S. Pat. No. 4,868,105
U.S. Pat. No. 4,873,191
U.S. Pat. No. 5,252,479
U.S. Pat. No. 5,270,184
U.S. Pat. No. 5,409,818
U.S. Pat. No. 5,436,146
U.S. Pat. No. 5.455.166
U.S. Pat. No. 5,550,050
U.S. Pat. No. 5,691,198
U.S. Pat. No. 5,747,469
U.S. Pat. No. 5,753,500
EP 425,731 A
EPO Publication No. 225,807
European Patent Application Publication No. 0332435
Hitzeman et al., EP 73,675A
WO 84/03564
WO 90/07936
WO 92/19195
WO 93/07282
WO 94/25503
WO 95/01203
WO 95/05452
WO 96/02286
WO 96/02646
WO 96/11698
WO 96/40871
WO 96/40959
WO 97/02048
WO 97/12635

What is claimed is:

1. An isolated nucleic acid comprising SEQ ID NO:1.
2. The isolated nucleic acid of claim 1 wherein said isolated nucleic acid comprises a mutation at base 1835.
3. The isolated nucleic acid of claim 1 wherein said isolated nucleic acid comprises a deletion encompassing base 1835.
4. The isolated nucleic acid of claim 1 wherein said isolated nucleic acid comprises a mutation G→T at base 1835.
5. An isolated cDNA encoding a protein consisting of SEQ ID NO:2.

* * * * *